(12) United States Patent
Breslin et al.

(10) Patent No.: US 7,741,356 B2
(45) Date of Patent: Jun. 22, 2010

(54) COMPOUNDS AS OPIOID RECEPTOR MODULATORS

(75) Inventors: Henry J. Breslin, Lansdale, PA (US); Chaozhong Cai, N. Wales, PA (US); Wei He, Audubon, PA (US); Robert W. Kavash, Glenside, PA (US)

(73) Assignee: Janssen Pharmaceutica N.V., Beerse (BE)

( * ) Notice: Subject to any disclaimer, the term of this patent is extended or adjusted under 35 U.S.C. 154(b) by 1009 days.

(21) Appl. No.: 11/079,647

(22) Filed: Mar. 14, 2005

(65) Prior Publication Data

US 2005/0203143 A1    Sep. 15, 2005

Related U.S. Application Data

(60) Provisional application No. 60/553,342, filed on Mar. 15, 2004.

(51) Int. Cl.
A61K 31/4174    (2006.01)
A61K 31/4178    (2006.01)
C07D 233/64    (2006.01)

(52) U.S. Cl. .................. 514/396; 514/397; 548/335.5

(58) Field of Classification Search .......... 514/396, 514/397; 548/335.5
See application file for complete search history.

(56) References Cited

U.S. PATENT DOCUMENTS 6,013,658 A * 1/2000 Lau et al. .................. 514/364

FOREIGN PATENT DOCUMENTS

| EP | 1 055 665 A | 11/2000 |
|---|---|---|
| WO | WO 96/22997 A1 | 8/1996 |
| WO | WO 02/36116 A2 | 5/2002 |
| WO | WO 03/033486 A | 4/2003 |
| WO | WO 03/092688 A2 | 11/2003 |

OTHER PUBLICATIONS

Dufour E, et al; "Synthesis of amidrazones using an engineered papain nitrile hydratase", Elsevier Science Publishers, Amsterdam, NL, vol. 433, No. 1-2, Aug. 14, 1998, pp. 78-82.
Hipskind P, et al "3-Aryl-1,2-diacetamidopropane Derivatives as Novel and Potent NK-1 Receptor Antagonists", Belstein Institute For Organic Chemistry, Frankfurt-Main, DE; XP002330617, Database accession No. BRN: 7491912 abstract, J. Med. Chem., vol. 39, No. 3, 1996, pp. 736-748.
Tam J, et al, "Design and Synthesis of a Multi-Detachable Benzhydrylamine-Resin for Solid Phase Peptide Synthesis", Frankfurt-Main, DE: XP002330618, Database accession No. BRN: 5166497 abstract, Tetrahedron Lett., , vol. 22, No. 30, 1981, pp. 2851-2854.
Santi, D, "Tyrosyl Transfer Ribonucleic Acid Synthetase from *Escherichia coli* B. Analysis of Tyrosine and Adenosine 5-Triphospate Binding Sites", Belstein Institute For Organic Chemistry,, Frankfurt-Main, DE; XP002330619, Database accession No. BRN: 7278453 abstract, J. Med. Chem., vol. 16, No. 3, 1973, pp. 273-280.
Search report for International Appl. No. PCT/US2005/008339.

* cited by examiner

*Primary Examiner*—Rei-Tsang Shiao
*Assistant Examiner*—Joseph R Kosack

(57) ABSTRACT

The present invention is directed to novel opioid receptor modulators of Formula (I).

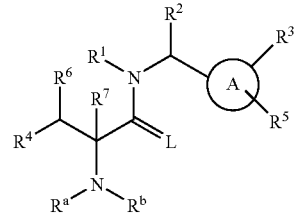

Formula (I)

The invention further relates to methods for preparing such compounds, pharmaceutical compositions containing them, and their use in the treatment of disorders that may be ameliorated or treated by the modulation of opioid receptors.

43 Claims, 3 Drawing Sheets

Recording

Zymosan treatment

** = $P < 0.01$ vs. Control 2
*** = $P < 0.001$ vs. Zymosan

US 7,741,356 B2

COMPOUNDS AS OPIOID RECEPTOR MODULATORS

CROSS-REFERENCE TO RELATED APPLICATIONS

This Application claims priority to U.S. Provisional Patent Application No. 60/553,342, filed Mar. 15, 2004, which is hereby incorporated by reference in its entirety.

STATEMENT REGARDING FEDERALLY SPONSORED RESEARCH OR DEVELOPMENT

The research and development of the invention described below was not federally sponsored.

FIELD OF THE INVENTION

The present invention is directed to novel opioid receptor modulators of Formula (I). The invention further relates to methods for preparing such compounds, pharmaceutical compositions containing them, and their use in the treatment of opioid modulated disorders.

BACKGROUND OF THE INVENTION

The opioid receptors were identified in the mid-1970's, and were quickly categorized into three sub-sets of receptors (mu, delta and kappa). More recently the original three types of receptors have been further divided into sub-types. Also known is that the family of opioid receptors are members of the G-protein coupled receptor (GPCR) super-family. More physiologically pertinent are the well established facts that opioid receptors are found throughout the central and peripheral nervous system of many mammalian species, including humans, and that modulation of the respective receptors can elicit numerous, albeit different, biological effects, both desirable and undesirable (D. S. Fries, "Analgesics", in *Principles of Medicinal Chemistry*, 4th ed.; W. O. Foye, T. L. Lemke, and D. A. Williams, Eds.; Williams and Wilkins: Baltimore, Md., 1995; pp. 247-269; J. V. Aldrich, "Analgesics", *Burger's Medicinal Chemistry and Drug Discovery*, 5th Edition, Volume 3: Therapeutic Agents, John Wiley & Sons, Inc., 1996, pp. 321-441). In the most current literature, the likelihood of heterodimerization of the sub-classes of opioid receptors has been reported, with respective physiological responses yet undetermined (Pierre J. M. Riviere and Jean-Louis Junien, "Opioid receptors: Targets for new gastrointestinal drug development", Drug Development 2000, pp. 203-238).

A couple biological effects identified for opioid modulators have led to many useful medicinal agents. Most significant are the many centrally acting mu opioid agonist modulators marketed as analgesic agents to attenuate pain (e.g., morphine), as well as peripherally acting mu agonists to regulate motility (e.g., loperamide). Currently, clinical studies are continuing to evaluate medicinal utility of selective delta, mu, and kappa modulators, as well as compounds possessing combined sub-type modulation. It is envisioned such explorations may lead to agents with new utilities, or agents with minimized adverse side effects relative to currently available agents (examples of side effects for morphine includes constipation, respiratory depression, and addiction potential). Some new GI areas where selective or mixed opioid modulators are currently being evaluated includes potential treatment for various diarrheic syndromes, motility disorders (post-operative ileus, constipation), and visceral pain (post operative pain, irritable bowel syndrome, and inflammatory bowel disorders) (Pierre J. M. Riviere and Jean-Louis Junien, "Opioid receptors: Targets for new gastrointestinal drug development" Drug Development, 2000, pp. 203-238).

Around the same time the opioid receptors were identified, the enkephalins were identified as a set of endogenous opioid ligands (D. S. Fries, "Analgesics", in *Principles of Medicinal Chemistry*, 4th ed.; W. O. Foye; T. L. Lemke, and D. A. Williams, Eds.; Williams and Wilkins: Baltimore, Md., 1995; pp. 247-269). Schiller discovered that truncating the original pentapeptide enkephalins to simplified dipeptides yielded a series of compounds that maintained opioid activity (Schiller, P. WO 96/06855). However one potential drawback cited for such compounds is the likelihood of their inherent instability (P. W. Schiller et al., Int. J. Pept. Protein Res. 1993, 41 (3), pp. 313-316).

More recently, a series of opioid pseudopeptides containing heteroaromatic or heteroaliphatic nuclei were disclosed, however this series is reported showing a different functional profile than that described in the Schiller works. (L. H. Lazarus et al., *Peptides* 2000, 21, pp. 1663-1671).

Most recently, works around morphine related structures were reported by Wentland, et al, where carboxamido morphine derivatives and it's analogs were prepared (M. P. Wentland et al., Biorg. Med. Chem. Letters 2001, 11, pp. 1717-1721; M. P. Wentland et al., *Biorg. Med. Chem. Letters* 2001, 11, pp. 623-626). Wentland found that substitution for the phenol moiety of the morphine related structures with a primary carboxamide led anywhere from equal activities up to 40 fold reduced activities, depending on the opioid receptor and the carboxamide. It was also revealed that any additional N-substitutions on the carboxamide significantly diminished the desired binding activity.

Compounds of the present invention have not been previously disclosed and are believed to provide advantages over related compounds by providing improved pharmacological profiles.

Opioid receptor modulators, agonists or antagonists are useful in the treatment and prevention of various mammalian disease states, for example pain and gastrointestinal disorders such as diarrheic syndromes, motility disorders including post-operative ileus and constipation, and visceral pain including post-operative pain, irritable bowel syndrome and inflammatory bowel disorders.

It is an object of the present invention to provide opioid receptor modulators. It is a further object of the invention to provide opioid receptor agonists and opioid receptor antagonists. It is an object of the present invention to provide opioid receptor ligands that are selective for each type of opioid receptor, mu, delta and kappa. It is a further object of the present invention to provide opioid receptor ligands that modulate two or three opioid receptor types, mu, delta and kappa, simultaneously. It is an object of the invention to provide certain instant compounds that are also useful as intermediates in preparing new opioid receptor modulators. It is also an object of the invention to provide a method of treating or ameliorating a condition mediated by an opioid receptor. And, it is an object of the invention to provide a useful pharmaceutical composition comprising a compound of the present invention useful as an opioid receptor modulator.

SUMMARY OF THE INVENTION

The present invention is directed to compounds of Formula (I)

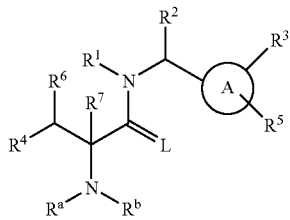

Formula (I)

wherein:
R¹ is selected from the group consisting of hydrogen, $C_{1-6}$alkyl, cycloalkyl, heterocyclyl, aryl($C_{1-6}$)alkyl, and heteroaryl($C_{1-6}$)alkyl; wherein aryl of aryl($C_{1-6}$)alkyl is optionally fused to a heterocyclyl or cycloalkyl;
and wherein the cycloalkyl and heterocyclyl of R¹ are optionally substituted with $C_{1-6}$alkyl, hydroxy($C_{1-6}$)alkyl, $C_{1-6}$alkoxy, hydroxy, cyano, amino, $C_{1-6}$alkylamino, ($C_{1-6}$alkyl)$_2$amino, halogen, carboxy, aryl($C_{1-6}$)alkoxycarbonyl, $C_{1-6}$alkoxycarbonyl, aminocarbonyl, $C_{1-6}$alkylaminocarbonyl, ($C_{1-6}$alkyl)$_2$aminocarbonyl, or aminosulfonyl;
and, wherein $C_{1-6}$alkyl of R¹ is optionally substituted with one to three substituents independently selected from the group consisting of $C_{1-6}$alkoxy, aryl, cycloalkyl, heterocyclyl, hydroxy, cyano, amino, $C_{1-6}$alkylamino, ($C_{1-6}$ alkyl)$_2$amino, halogen, and carboxy;
and wherein the aryl and heteroaryl portion of aryl($C_{1-6}$)alkyl and heteroaryl($C_{1-6}$)alkyl are optionally substituted with one to three R¹¹ substituents independently selected from the group consisting of $C_{1-6}$alkyl; hydroxy($C_{1-6}$)alkyl; $C_{1-6}$alkoxy; aryl($C_{1-6}$)alkyl; aryl($C_{1-6}$)alkoxy; aryl; heteroaryl optionally substituted with $C_{1-4}$alkyl; cycloalkyl; heterocyclyl; aryloxy; heteroaryloxy; cycloalkyloxy; heterocyclyloxy; amino; $C_{1-6}$alkylamino; ($C_{1-6}$alkyl)$_2$amino; $C_{3-6}$cycloalkylaminocarbonyl; hydroxy($C_{1-6}$) alkylaminocarbonyl; arylaminocarbonyl wherein aryl is optionally substituted with carboxy or $C_{1-8}$alkoxycarbonyl; heterocyclylcarbonyl; carboxy; $C_{1-6}$alkoxycarbonyl; $C_{1-6}$alkylcarbonyl; $C_{1-6}$alkylcarbonylamino; aminocarbonyl; $C_{1-6}$alkylaminocarbonyl; ($C_{1-6}$alkyl)$_2$aminocarbonyl; cyano; halogen; trifluoromethyl; trifluoromethoxy; or hydroxy;
R² is selected from the group consisting of hydrogen, $C_{1-8}$alkyl, hydroxy($C_{1-8}$) alkyl, aryl($C_{1-6}$)alkoxy($C_{1-6}$)alkyl, or aryl($C_{1-8}$)alkyl;
wherein the aryl portion of the aryl-containing substituents of R² are optionally substituted with one to two substituents independently selected from the group consisting of $C_{1-6}$alkyl, $C_{1-6}$alkoxy, hydroxy, amino, $C_{1-6}$alkylamino, ($C_{1-6}$alkyl)$_2$amino, aminocarbonyl, $C_{1-6}$alkylaminocarbonyl, ($C_{1-6}$alkyl)$_2$aminocarbonyl, cyano, fluoro, chloro, bromo, trifluoromethyl, and trifluoromethoxy;
and wherein alkyl and alkoxy substituents of aryl are optionally substituted with hydroxy, amino, $C_{1-6}$alkylamino, ($C_{1-6}$alkyl)$_2$amino, or aryl;
A is selected from the group consisting of aryl, ring system a-1, a-2, a-3, and a-4, optionally substituted with R³ and R⁵;

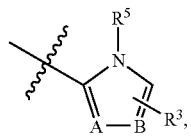

a-1

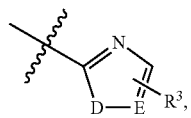

a-2

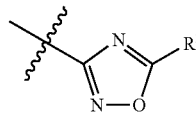

a-3 and

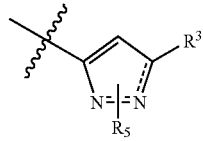

a-4 wherein
A-B is selected from the group consisting of N—C, C—N, N—N and C—C;
D-E is selected from the group consisting of O—C, S—C, and O—N;
R³ is one to two substituents independently selected from the group consisting of $C_{1-6}$alkyl, aryl, aryl($C_{1-6}$)alkyl, aryl($C_{2-6}$)alkenyl, aryl($C_{2-6}$)alkynyl, heteroaryl, heteroaryl($C_{1-6}$)alkyl, heteroaryl($C_{2-6}$)alkenyl, heteroaryl($C_{2-6}$)alkynyl, amino, $C_{1-6}$alkylamino, ($C_{1-6}$alkyl)$_2$amino, arylamino, heteroarylamino, aryloxy, heteroaryloxy, and halogen;
wherein the aryl and heteroaryl portion of R³ are optionally substituted with one to five substituents independently selected from the group consisting of $C_{1-6}$alkyl, hydroxy($C_{1-6}$)alkyl, $C_{1-6}$alkoxy, aryl($C_{1-6}$)alkyl, aryl($C_{1-6}$)alkoxy, aryl, aryloxy, heteroaryl($C_{1-6}$)alkyl, heteroaryl($C_{1-6}$)alkoxy, heteroaryl, heteroaryloxy, arylamino, heteroarylamino, amino, $C_{1-6}$alkylamino, ($C_{1-6}$alkyl)$_2$amino, carboxy($C_{1-6}$)alkylamino, carboxy, $C_{1-6}$alkylcarbonyl, $C_{1-6}$alkoxycarbonyl, $C_{1-6}$alkylcarbonylamino, aminocarbonyl, $C_{1-6}$alkylaminocarbonyl, ($C_{1-6}$alkyl)$_2$aminocarbonyl, carboxy($C_{1-6}$) alkylaminocarbonyl, cyano, halogen, trifluoromethyl, trifluoromethoxy, hydroxy, $C_{1-6}$alkylsulfonyl, $C_{1-6}$alkylsulfonylamino, —C(O)—NH—CH(—R$^c$)—C(O)—NH$_2$, and $C_{1-6}$alkyl;
wherein $C_{1-6}$alkyl of R³ is optionally substituted with a substituent selected from the group consisting of hydroxy, carboxy, $C_{1-4}$alkoxycarbonyl, amino, $C_{1-6}$alkylamino, ($C_{1-6}$ alkyl)$_2$amino, aminocarbonyl, ($C_{1-4}$)alkylaminocarbonyl, di($C_{1-4}$)alkylaminocarbonyl, aryl, heteroaryl, arylamino, heteroarylamino, aryloxy, heteroaryloxy, aryl($C_{1-4}$)alkoxy, and heteroaryl($C_{1-4}$)alkoxy;
R$^c$ is selected from the group consisting of hydrogen, $C_{1-6}$alkyl, $C_{1-6}$alkylcarbonyl, $C_{1-6}$alkoxycarbonyl, $C_{1-6}$alkylcarbonylamino, aryl($C_{1-6}$)alkyl, heteroaryl($C_{1-6}$)alkyl, aryl, and heteroaryl;
R⁴ is aryl or heteroaryl; wherein R⁴ is optionally substituted with one to five substituents independently selected from the group R⁴¹; wherein R⁴¹ is ($C_{1-6}$) alkyl, ($C_{1-6}$)alkoxy, aryl($C_{1-6}$)alkoxy, aryl($C_{1-6}$)alkylcarbonyloxy, heteroaryl ($C_{1-6}$)alkylcarbonyloxy, heteroaryl, hydroxy, halogen, aminosulfonyl, formylamino, aminocarbonyl, $C_{1-6}$alkylaminocarbonyl, ($C_{1-6}$alkyl)$_2$aminocarbonyl, heterocyclylcarbonyl, carboxy, or cyano; and wherein $C_{1-6}$alkyl is optionally substituted with amino, $C_{1-6}$alkylamino, or ($C_{1-6}$ alkyl)$_2$amino; and wherein the aryl portion of aryl ($C_{1-6}$)alkylcarbonyloxy is optionally substituted with one to four substituents independently selected from the group consisting of ($C_{1-6}$)alkyl, ($C_{1-6}$)alkoxy, halogen, cyano, amino, and hydroxy;

$R^5$ is a substituent on a nitrogen atom contained in ring A selected from the group consisting of hydrogen, $C_{1-4}$alkyl, and aryl;

$R^6$ is selected from the group consisting of hydrogen and $C_{1-6}$alkyl;

$R^7$ is selected from the group consisting of hydrogen and $C_{1-6}$alkyl;

$R^a$ and $R^b$ are substituents independently selected from the group consisting of hydrogen and $C_{1-6}$alkyl; or, when $R^a$ and $R^b$ are other than hydrogen, $R^a$ and $R^b$ are optionally taken together with the nitrogen to which they are both attached to form a five to eight membered monocyclic ring;

L is selected from the group consisting of O, S, and N($R^d$); wherein $R^d$ is hydrogen, $C_{1-6}$alkyl, or aryl;

and pharmaceutically acceptable enantiomers, diastereomers, racemates, and salts thereof.

The present invention is also directed to compounds of Formula (I)

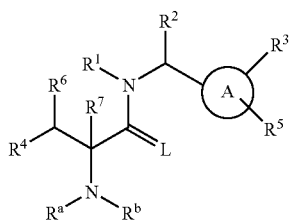

Formula (I)

wherein:
$R^1$ is selected from the group consisting of hydrogen, $C_{1-6}$alkyl, cycloalkyl, heterocyclyl, aryl($C_{1-6}$)alkyl, and heteroaryl($C_{1-6}$)alkyl; wherein when $R^1$ is phenyl($C_{1-6}$) alkyl, phenyl is optionally fused to a heterocyclyl or cycloalkyl;

wherein when $R^1$ is $C_{1-2}$alkyl, said $C_{1-2}$alkyl is optionally substituted with one to two substituents independently selected from the group consisting of $C_{1-6}$alkoxy, aryl, cycloalkyl, heterocyclyl, hydroxy, cyano, amino, $C_{1-6}$alkylamino, ($C_{1-6}$alkyl)$_2$amino, trifluoromethyl, and carboxy;

and further, wherein when $R^1$ is $C_{3-6}$alkyl, said $C_{3-6}$alkyl is optionally substituted with one to three substituents independently selected from the group consisting of $C_{1-6}$alkoxy, aryl, cycloalkyl, heterocyclyl, hydroxy, cyano, amino, $C_{1-6}$alkylamino, ($C_{1-6}$alkyl)$_2$amino, trifluoromethyl, and carboxy;

wherein the cycloalkyl and heterocyclyl of $C_{1-2}$alkyl and $C_{3-6}$alkyl are optionally substituted with one to two substituents independently selected from the group consisting of $C_{1-6}$alkyl, hydroxy($C_{1-6}$)alkyl, $C_{1-6}$alkoxy, hydroxy, cyano, amino, $C_{1-6}$alkylamino, ($C_{1-6}$alkyl)$_2$ amino, trifluoromethyl, carboxy, aryl($C_{1-6}$)alkoxycarbonyl, $C_{1-6}$alkoxycarbonyl, aminocarbonyl, $C_{1-6}$alkylaminocarbonyl, ($C_{1-6}$alkyl)$_2$aminocarbonyl, and aminosulfonyl;

furthermore, wherein the cycloalkyl and heterocyclyl of $R^1$ are optionally substituted with one to two substituents independently selected from the group consisting of $C_{1-6}$alkyl, hydroxy($C_{1-6}$)alkyl, $C_{1-6}$alkoxy, hydroxy, cyano, amino, $C_{1-6}$alkylamino, ($C_{1-6}$alkyl)$_2$amino, trifluoromethyl, carboxy, aryl($C_{1-6}$)alkoxycarbonyl, $C_{1-6}$alkoxycarbonyl, aminocarbonyl, $C_{1-6}$alkylaminocarbonyl, ($C_{1-6}$alkyl)$_2$aminocarbonyl, and aminosulfonyl;

furthermore, wherein the aryl and heteroaryl portion of the $R^1$ substituents aryl($C_{1-6}$)alkyl and heteroaryl($C_{1-6}$) alkyl, are optionally substituted with one to three $R^{11}$ substituents independently selected from the group consisting of $C_{1-6}$alkyl; hydroxy($C_{1-6}$)alkyl; $C_{1-6}$alkoxy; $C_{6-10}$aryl($C_{1-6}$)alkyl; $C_{6-10}$aryl($C_{1-6}$)alkoxy; $C_{6-10}$aryl; heteroaryl optionally substituted with one to two substituents independently selected from the group consisting of $C_{1-4}$alkyl, $C_{1-4}$alkoxy, and carboxy; cycloalkyl; heterocyclyl; $C_{6-10}$aryloxy; heteroaryloxy; cycloalkyloxy; heterocyclyloxy; amino; $C_{1-6}$alkylamino; ($C_{1-6}$ alkyl)$_2$amino; $C_{3-6}$cycloalkylaminocarbonyl; hydroxy ($C_{1-6}$) alkylaminocarbonyl; $C_{6-10}$arylaminocarbonyl wherein $C_{6-10}$aryl is optionally substituted with carboxy or $C_{1-4}$alkoxycarbonyl; heterocyclylcarbonyl; carboxy; $C_{1-6}$alkylcarbonyloxy; $Cr_{1-6}$alkoxycarbonyl; $C_{1-6}$alkylcarbonyl; $C_{1-6}$alkylcarbonylamino; aminocarbonyl; $C_{1-6}$alkylaminocarbonyl; ($C_{1-6}$alkyl)$_2$aminocarbonyl; cyano; halogen; trifluoromethyl; trifluoromethoxy; and hydroxy;

provided that no more than one $R^{11}$ substituent is selected from the group consisting of $C_{6-10}$aryl($C_{1-6}$)alkyl; $C_{6-10}$aryl($C_{1-6}$)alkoxy; $C_{6-10}$aryl; heteroaryl optionally substituted with one to two substituents independently selected from the group consisting of $C_{1-4}$alkyl, $C_{1-4}$alkoxy, and carboxy; cycloalkyl; heterocyclyl; $C_{6-10}$aryloxy; heteroaryloxy; cycloalkyloxy; $C_{6-10}$arylaminocarbonyl, heterocyclylcarbonyl; and heterocyclyloxy;

$R^2$ is hydrogen, $C_{1-8}$alkyl, hydroxy($C_{1-8}$)alkyl, $C_{6-10}$aryl ($C_{1-6}$)alkoxy($C_{1-6}$)alkyl, or $C_{6-10}$aryl($C_{1-8}$)alkyl;

wherein the $C_{6-10}$aryl group in the $C_{6-10}$aryl-containing substituents of $R^2$ are optionally substituted with one to two substituents independently selected from the group consisting of $C_{1-6}$alkyl, $C_{1-6}$alkoxy, hydroxy, amino, $C_{1-6}$alkylamino, ($C_{1-6}$alkyl)$_2$amino, aminocarbonyl, $C_{1-6}$alkylaminocarbonyl, ($C_{1-6}$alkyl)$_2$aminocarbonyl, cyano, fluoro, chloro, bromo, trifluoromethyl, and trifluoromethoxy; and, wherein the $C_{1-6}$alkyl and $C_{1-6}$alkoxy substituents of aryl are optionally substituted with hydroxy, amino, $C_{1-6}$alkylamino, ($C_{1-6}$alkyl)$_2$ amino, or C1-6 aryl;

A is selected from the group consisting of aryl, ring system a-1, a-2, a-3, and a-4, optionally substituted with $R^3$ and $R^5$;

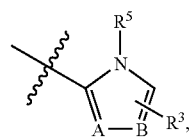

a-1

-continued

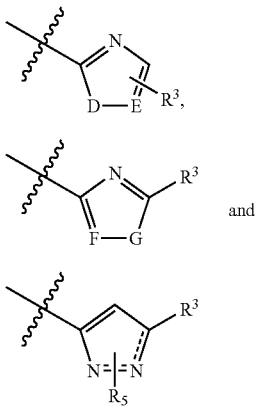

wherein
A-B is selected from the group consisting of N—C, C—N, N—N and C—C;
D-E is selected from the group consisting of O—C, S—C, and O—N;
F-G is selected from the group consisting of N—O and C—O;
$R^3$ is one to two substituents independently selected from the group consisting of $C_{1-6}$alkyl, aryl, aryl($C_{1-6}$)alkyl, aryl($C_{2-6}$)alkenyl, aryl($C_{2-6}$)alkynyl, heteroaryl, heteroaryl($C_{1-6}$)alkyl, heteroaryl($C_{2-6}$)alkenyl, heteroaryl($C_{2-6}$)alkynyl, amino, $C_{1-6}$alkylamino, ($C_{1-6}$alkyl)$_2$amino, arylamino, heteroarylamino, aryloxy, heteroaryloxy, trifluoromethyl, and halogen;
   wherein the aryl, heteroaryl and the aryl and heteroaryl of aryl($C_{1-6}$)alkyl, aryl($C_{2-6}$)alkenyl, aryl($C_{2-6}$)alkynyl, heteroaryl($C_{1-6}$)alkyl, heteroaryl($C_{2-6}$) alkenyl, heteroaryl($C_{2-6}$)alkynyl, arylamino, heteroarylamino, aryloxy, and heteroaryloxy, are optionally substituted with one to five fluoro substituents or one to three substituents independently selected from the group consisting of $C_{1-6}$alkyl, hydroxy($C_{1-6}$)alkyl, $C_{1-6}$alkoxy, $C_{6-10}$aryl ($C_{1-6}$) alkyl, $C_{6-10}$aryl($C_{1-6}$)alkoxy, $C_{6-10}$aryl, $C_{6-10}$aryloxy, heteroaryl($C_{1-6}$)alkyl, heteroaryl($C_{1-6}$)alkoxy, heteroaryl, heteroaryloxy, $C_{6-10}$arylamino, heteroarylamino, amino, $C_{1-6}$alkylamino, ($C_{1-6}$alkyl)$_2$amino, carboxy($C_{1-6}$) alkylamino, carboxy, $C_{1-6}$alkylcarbonyl, $C_{1-6}$alkoxycarbonyl, $C_{1-6}$alkylcarbonylamino, aminocarbonyl, $C_{1-6}$alkylaminocarbonyl, ($C_{1-6}$ alkyl)$_2$aminocarbonyl, carboxy($C_{1-6}$)alkylaminocarbonyl, cyano, halogen, trifluoromethyl, trifluoromethoxy, hydroxy, $C_{1-6}$alkylsulfonyl, and $C_{1-6}$alkylsulfonylamino; provided that no more than one such substituent on the aryl or heteroaryl portion of $R^3$ is selected from the group consisting of $C_{6-10}$aryl($C_{1-6}$)alkyl, $C_{6-10}$aryl ($C_{1-6}$)alkoxy, $C_{6-10}$aryl, $C_{6-10}$aryloxy, heteroaryl($C_{1-6}$) alkyl, heteroaryl($C_{1-6}$)alkoxy, heteroaryl, heteroaryloxy, $C_{6-10}$arylamino, and heteroarylamino;
   and wherein $C_{1-6}$alkyl, and $C_{1-6}$alkyl of aryl($C_{1-6}$)alkyl and heteroaryl($C_{1-6}$) alkyl is optionally substituted with a substituent selected from the group consisting of hydroxy, carboxy, $C_{1-4}$alkoxycarbonyl, amino, $C_{1-6}$alkylamino, ($C_{1-6}$alkyl)$_2$amino, aminocarbonyl, ($C_{1-4}$)alkylaminocarbonyl, di($C_{1-4}$)alkylaminocarbonyl, aryl, heteroaryl, arylamino, heteroarylamino, aryloxy, heteroaryloxy, aryl($C_{1-4}$)alkoxy, and heteroaryl ($C_{1-4}$)alkoxy;

$R^4$ is $C_{6-10}$aryl or a heteroaryl selected from the group consisting of furyl, thienyl, pyrrolyl, oxazolyl, thiazolyl, imidazolyl, pyrazolyl, pyridinyl, pyrimidinyl, pyrazinyl, indolyl, isoindolyl, indolinyl, benzofuryl, benzothienyl, benzimidazolyl, benzthiazolyl, benzoxazolyl, quinolizinyl, quinolinyl, isoquinolinyl and quinazolinyl;
   wherein $R^4$ is optionally substituted with one to three $R^{41}$ substituents independently selected from the group consisting of ($C_{1-6}$)alkyl optionally substituted with amino, $C_{1-6}$alkylamino, or ($C_{1-6}$alkyl)$_2$amino; ($C_{1-6}$)alkoxy; phenyl($C_{1-6}$)alkoxy; phenyl($C_{1-6}$)alkylcarbonyloxy wherein the C1-6 alkyl is optionally substituted with amino; a non fused 5-membered-heteroaryl ($C_1$-6)alkylcarbonyloxy; a non fused 5-membered-heteroaryl; hydroxy; halogen; aminosulfonyl; formylamino; aminocarbonyl; $C_{1-6}$alkylaminocarbonyl wherein $C_{1-6}$alkyl is optionally substituted with amino, $C_{1-6}$alkylamino, or ($C_{1-6}$alkyl)$_2$amino; ($C_{1-6}$alkyl)$_2$aminocarbonyl wherein each $C_{1-6}$alkyl is optionally substituted with amino, $C_{1-6}$alkylamino, or ($C_{1-6}$alkyl)$_2$amino; heterocyclylcarbonyl wherein heterocyclyl is a 5-7 membered nitrogen-containing ring and said heterocyclyl is attached to the carbonyl carbon via a nitrogen atom; carboxy; or cyano; and wherein the phenyl portion of phenyl($C_{1-6}$) alkylcarbonyloxy is optionally substituted with ($C_{1-6}$)alkyl ($C_{1-6}$)alkoxy, halogen, cyano, amino, or hydroxy;
   provided that no more than one $R^{41}$ is ($C_{1-6}$)alkyl substituted with $C_{1-6}$alkylamino or ($C_{1-6}$alkyl)$_2$amino; aminosulfonyl; formylamino; aminocarbonyl; $C_{1-6}$alkylaminocarbonyl; ($C_{1-6}$alkyl)$_2$aminocarbonyl; heterocyclylcarbonyl; hydroxy; carboxy; or a phenyl- or heteroaryl-containing substituent;
$R^5$ is a substituent on a nitrogen atom of ring A selected from the group consisting of hydrogen and $C_{1-4}$alkyl;
$R^6$ is hydrogen or $C_{1-6}$alkyl;
$R^7$ is hydrogen or $C_{1-6}$alkyl;
$R^a$ and $R^b$ are independently selected from the group consisting of hydrogen, $C_{1-6}$alkyl, and $C_{1-6}$alkoxycarbonyl; alternatively, when $R^a$ and $R^b$ are each other than hydrogen, $R^a$ and $R^b$ are optionally taken together with the nitrogen atom to which they are both attached to form a five to eight membered monocyclic ring;
L is selected from the group consisting of O, S, and N($R^d$) wherein $R^d$ is hydrogen or $C_{1-6}$alkyl;

and pharmaceutically acceptable enantiomers, diastereomers, racemates, and salts thereof.

Illustrative of the invention is a pharmaceutically acceptable carrier and any of the compounds described above.

The present invention is also directed to methods for producing the instant compounds of Formula (I) and pharmaceutical compositions and medicaments thereof.

The present invention is further directed to methods for treating opioid modulated disorders such as pain and gastrointestinal disorders. Compounds of the present invention are believed to provide advantages over related compounds by providing improved pharmacological profiles. Further specific embodiments of preferred compounds are provided hereinafter.

DETAILED DESCRIPTION OF THE INVENTION

Figure 1:
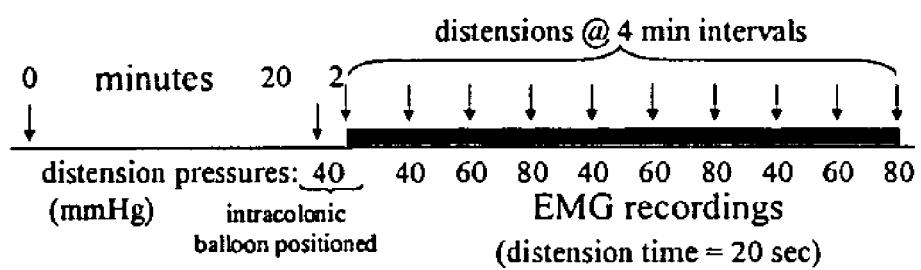
FIG. 1 shows a schematic of the protocol to determine visceral hyperalgesia in rats.
Figure 1:
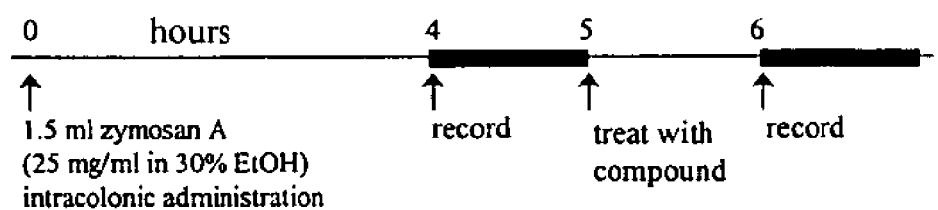

Embodiments of the present invention include those compounds wherein $R^1$ is selected from the group consisting of hydrogen, $C_{1-6}$alkyl, aryl($C_{1-4}$)alkyl, and heteroaryl($C_{1-4}$)alkyl;
wherein the aryl and heteroaryl portion of aryl($C_{1-4}$)alkyl and heteroaryl($C_{1-4}$)alkyl are optionally substituted with one to three $R^{11}$ substituents independently selected from the group consisting of $C_{1-6}$alkoxy; heteroaryl optionally substituted with one to two substituents independently selected from the group consisting of $C_{1-4}$alkyl, $C_{1-4}$alkoxy, and carboxy; carboxy; $C_{1-4}$alkoxycarbonyl; $C_{1-4}$alkoxycarbonyloxy; aminocarbonyl; $C_{1-4}$alkylaminocarbonyl; $C_{3-6}$cycloalkylaminocarbonyl; hydroxy($C_{1-6}$)alkylaminocarbonyl; $C_{6-10}$arylaminocarbonyl wherein $C_{6-10}$aryl is optionally substituted with carboxy or $C_{1-4}$alkoxycarbonyl; heterocyclylcarbonyl; cyano; halogen; trifluoromethoxy; or hydroxy; provided that no more than one $R^{11}$ is heteroaryl (optionally substituted with one to two $C_{1-4}$alkyl substituents); $C_{6-10}$arylaminocarbonyl wherein $C_{6-10}$aryl is optionally substituted with carboxy or $C_{1-4}$alkoxycarbonyl; or heterocyclylcarbonyl.

Embodiments of the present invention include those compounds wherein $R^1$ is selected from the group consisting of $C_{6-10}$aryl($C_{1-4}$)alkyl, pyridinyl($C_{1-4}$) alkyl, and furanyl($C_{1-4}$)alkyl; wherein $C_{6-10}$aryl, pyridinyl, and furanyl are optionally substituted with one to three $R^{11}$ substituents independently selected from the group consisting of $C_{1-3}$alkoxy; tetrazolyl; carboxy; $C_{1-4}$alkoxycarbonyl; aminocarbonyl; $C_{1-4}$alkylaminocarbonyl; $C_{3-6}$cycloalkylaminocarbonyl; hydroxy($C_{1-4}$)alkylaminocarbonyl; $C_{6-10}$arylaminocarbonyl wherein $C_{6-10}$aryl is optionally substituted with carboxy or $C_{1-4}$alkoxycarbonyl; morpholin-4-ylcarbonyl; cyano; halogen; and trifluoromethoxy; provided that that no more than one $R^{11}$ is $C_{6-10}$arylaminocarbonyl.

Embodiments of the present invention include those compounds wherein $R^1$ is selected from the group consisting of phenyl($C_{1-3}$)alkyl, pyridinyl($C_{1-3}$)alkyl, and furanyl($C_{1-3}$)alkyl; wherein phenyl, pyridinyl, and furanyl are optionally substituted with one to three $R^{11}$ substituents independently selected from the group consisting of $C_{1-3}$alkoxy; tetrazolyl; $C_{3-6}$cycloalkylaminocarbonyl; hydroxy($C_{1-4}$)alkylaminocarbonyl; $C_{6-10}$arylaminocarbonyl wherein $C_{6-10}$aryl is optionally substituted with carboxy or $C_{1-4}$alkoxycarbonyl; morpholin-4-ylcarbonyl; chloro; fluoro; trifluoromethoxy; $C_{1-4}$alkoxycarbonyl; and carboxy; provided that that no more than one $R^{11}$ is $C_{6-10}$arylaminocarbonyl.

Embodiments of the present invention include those compounds wherein $R^1$ is phenylmethyl, pyridinylmethyl, or furanylmethyl; wherein phenyl, pyridinyl, and furanyl are optionally substituted with one to three $R^{11}$ substituents independently selected from the group consisting of methoxy; tetrazolyl; cyclopropylaminocarbonyl; (2-hydroxyeth-1-yl)aminocarbonyl; methoxycarbonyl; phenylaminocarbonyl wherein phenyl is optionally substituted with carboxy; morpholin-4-ylcarbonyl; and carboxy; provided that that no more than one $R^{11}$ is phenylaminocarbonyl.

Embodiments of the present invention include those compounds wherein $R^2$ is a substituent selected from the group consisting of hydrogen, $C_{1-4}$alkyl, hydroxy($C_{1-4}$)alkyl, and phenyl($C_{1-6}$)alkoxy($C_{1-4}$)alkyl;

wherein said phenyl is optionally substituted with one to two substituents independently selected from the group consisting of $C_{1-3}$alkyl, $C_{1-3}$alkoxy, hydroxy, cyano, fluoro, chloro, bromo, trifluoromethyl, and trifluoromethoxy.

Embodiments of the present invention include those compounds wherein $R^2$ is selected from the group consisting of hydrogen and $C_{1-4}$alkyl.

Embodiments of the present invention include those compounds wherein $R^2$ is hydrogen or methyl.

Embodiments of the present invention include those compounds wherein ring A is a-1.

Embodiments of the present invention include those compounds wherein A-B of ring a-1 is selected from the group consisting of N—C and O—N.

Embodiments of the present invention include those compounds wherein A-B of ring a-1 is N—C.

Embodiments of the present invention include those compounds wherein $R^3$ is one to two substituents independently selected from the group consisting of $C_{1-6}$alkyl, halogen, and aryl; wherein aryl is optionally substituted with one to three substituents independently selected from the group consisting of halogen, carboxy, aminocarbonyl, $C_{1-3}$alkylsulfonylamino, cyano, hydroxy, amino, $C_{1-3}$alkylamino, and ($C_{1-3}$alkyl)$_2$amino.

Embodiments of the present invention include those compounds wherein $R^3$ is one to two substituents independently selected from the group consisting of $C_{1-3}$alkyl, bromo, and phenyl; wherein phenyl is optionally substituted with one to three substituents independently selected from the group consisting of chloro, fluoro, iodo, carboxy, aminocarbonyl, and cyano.

Embodiments of the present invention include those compounds wherein $R^3$ is one to two substituents independently selected from the group consisting of methyl and phenyl; wherein phenyl is optionally substituted with one to three substituents independently selected from the group consisting of chloro and carboxy.

Embodiments of the present invention include those compounds wherein at least one $R^3$ substituent is phenyl.

Embodiments of the present invention include those compounds wherein $R^3$ is a substituent selected from the group consisting of methyl and phenyl optionally substituted with one to two substituents independently selected from the group consisting of chloro and carboxy.

Embodiments of the present invention include those compounds wherein $R^4$ is $C_{6-10}$aryl optionally substituted with one to three $R^{41}$ substituents independently selected from the group consisting of ($C_{1-3}$)alkyl, ($C_{1-6}$)alkoxy, phenyl($C_{1-6}$)alkoxy; hydroxy; halogen; formylamino; aminocarbonyl; $C_{1-6}$alkylaminocarbonyl; ($C_{1-6}$alkyl)$_2$aminocarbonyl; heterocyclylcarbonyl wherein heterocyclyl is a 5-7 membered nitrogen-containing ring and said heterocyclyl is attached to the carbonyl carbon via a nitrogen atom; carboxy; and cyano; provided that no more than one $R^{41}$ substituent is formylamino, aminocarbonyl, $C_{1-6}$alkylaminocarbonyl, ($C_{1-6}$alkyl)$_2$ aminocarbonyl, heterocyclylcarbonyl, hydroxy, carboxy, or a phenyl-containing substituent.

Embodiments of the present invention include those compounds wherein $R^4$ is phenyl substituted with one to three $R^{41}$ substituents independently selected from the group consisting of ($C_{1-3}$)alkyl, ($C_{1-3}$)alkoxy, phenyl($C_{1-3}$) alkoxy, hydroxy, $C_{1-6}$alkylaminocarbonyl, and aminocarbonyl; provided that no more than one $R^{41}$ substitutent is aminocarbonyl, $C_{1-6}$alkylaminocarbonyl, hydroxy, or a phenyl-containing substituent.

Embodiments of the present invention include those compounds wherein $R^4$ is phenyl substituted at the 4-position with hydroxy, $C_{1-3}$alkylaminocarbonyl, or aminocarbonyl, and optionally substituted with one to two substituents independently selected from the group consisting of methyl, methoxy, and benzyloxy.

Embodiments of the present invention include those compounds wherein $R^4$ is phenyl substituted at the 4-position with hydroxy, $C_{1-3}$alkylaminocarbonyl, or aminocarbonyl, and optionally substituted with one to two methyl substituents.

Embodiments of the present invention include those compounds wherein $R^4$ is phenyl substituted at the 4-position with hydroxy, $C_{1-3}$alkylaminocarbonyl, or aminocarbonyl, and substituted at the 2- and 6-positions with methyl substituents.

Embodiments of the present invention include those compounds wherein $R^5$ is hydrogen or methyl.

Embodiments of the present invention include those compounds wherein $R^5$ is hydrogen.

Embodiments of the present invention include those compounds wherein $R^6$ is hydrogen or methyl.

Embodiments of the present invention include those compounds wherein $R^6$ is hydrogen.

Embodiments of the present invention include those compounds wherein $R^7$ is hydrogen or methyl.

Embodiments of the present invention include those compounds wherein $R^7$ is hydrogen.

Embodiments of the present invention include those compounds wherein $R^a$ and $R^b$ are independently selected from the group consisting of hydrogen and $C_{1-3}$alkyl; or, when $R^a$ and $R^b$ are each other than hydrogen or C1-6alkoxycarbonyl, $R^a$ and $R^b$ are optionally taken together with the nitrogen atom to which they are both attached to form a five to seven membered monocyclic ring.

Embodiments of the present invention include those compounds wherein $R^a$ and $R^b$ are independently hydrogen or methyl.

Embodiments of the present invention include those compounds wherein $R^a$ and $R^b$ are each hydrogen.

Embodiments of the present invention include those compounds wherein L is O.

Embodiments of the present invention include those compounds that are present in their RR, SS, RS, or SR configuration.

Embodiments of the present invention include those compounds that are present in their S,S configuration.

An aspect of the present invention includes compounds of Formula (Ia):

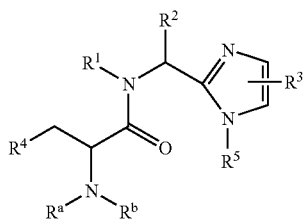

Formula (Ia)

wherein:
$R^1$ is selected from the group consisting of hydrogen, $C_{1-6}$alkyl, aryl($C_{1-4}$)alkyl, and heteroaryl($C_{1-4}$)alkyl;
wherein the aryl and heteroaryl portion of aryl($C_{1-4}$)alkyl and heteroaryl($C_{1-4}$) alkyl are optionally substituted with one to three $R^{11}$ substituents independently selected from the group consisting of $C_{1-6}$alkoxy; heteroaryl optionally substituted with one to two substituents independently selected from the group consisting of $C_{1-4}$alkyl, $C_{1-4}$alkoxy, and carboxy; carboxy; $C_{1-4}$alkoxycarbonyloxy; $C_{1-4}$alkoxycarbonyl; aminocarbonyl; $C_{1-4}$alkylaminocarbonyl; $C_{3-6}$cycloalkylaminocarbonyl; hydroxy($C_{1-6}$) alkylaminocarbonyl; $C_{6-10}$arylaminocarbonyl wherein $C_{6-10}$aryl is optionally substituted with carboxy or $C_{1-4}$alkoxycarbonyl; heterocyclylcarbonyl; cyano; halogen; trifluoromethoxy; and hydroxy; provided that no more than one $R^{11}$ is heteroaryl (optionally substituted with one to two $C_{1-4}$alkyl substituents); $C_{6-10}$arylaminocarbonyl wherein $C_{6-10}$aryl is optionally substituted with carboxy or $C_{1-4}$alkoxycarbonyl; or heterocyclylcarbonyl;
$R^2$ is selected from the group consisting of hydrogen, $C_{1-4}$alkyl, hydroxy($C_{1-4}$) alkyl, and phenyl($C_{1-6}$)alkoxy ($C_{1-4}$)alkyl;
wherein said phenyl is optionally substituted with one to two substituents independently selected from the group consisting of $C_{1-3}$alkyl, $C_{1-3}$alkoxy, hydroxy, cyano, fluorine, chlorine, bromine, trifluoromethyl, and trifluoromethoxy;
$R^3$ is one to two substituents independently selected from the group consisting of $C_{1-6}$alkyl, halogen, and aryl; wherein aryl is optionally substituted with one to three substituents independently selected from the group consisting of halogen, carboxy, aminocarbonyl, $C_{1-3}$alkylsulfonylamino, cyano, hydroxy, amino, $C_{1-3}$alkylamino, and $(C_{1-3}$alkyl)$_2$amino;
$R^4$ is $C_{6-10}$aryl optionally substituted with one to three $R^{41}$ substituents independently selected from the group consisting of $(C_{1-3})$alkyl, $(C_{1-6})$ alkoxy, phenyl($C_{1-6}$)alkoxy; hydroxy; halogen; formylamino; aminocarbonyl; $C_{1-6}$alkylaminocarbonyl; ($C_{1-6}$alkyl)$_2$aminocarbonyl; heterocyclylcarbonyl wherein heterocyclyl is a 5-7 membered nitrogen-containing ring and said heterocyclyl is attached to the carbonyl carbon via a nitrogen atom; carboxy; and cyano;

provided that no more than one $R^{41}$ substituent is formylamino, aminocarbonyl, $C_{1-6}$alkylaminocarbonyl, ($C_{1-6}$alkyl)$_2$aminocarbonyl, heterocyclylcarbonyl, hydroxy, carboxy, or a phenyl-containing substituent.

$R^5$ is hydrogen or methyl;
$R^a$ and $R^b$ are independently hydrogen or $C_{1-3}$alkyl; or, when $R^a$ and $R^b$ are each other than hydrogen, Ra and Rb are optionally taken together with the nitrogen atom to which they are both attached to form a five to seven membered monocyclic ring;

and pharmaceutically acceptable enantiomers, diastereomers, racemates, and salts thereof.

Another aspect of the present invention is directed to a compound of Formula (Ia) wherein:
$R^1$ is selected from the group consisting of $C_{6-10}$aryl($C_{1-4}$) alkyl, pyridinyl($C_{1-4}$) alkyl, and furanyl($C_{1-4}$)alkyl; wherein $C_{6-10}$aryl, pyridinyl, and furanyl are optionally substituted with one to three $R^{11}$ substituents independently selected from the group consisting of $C_{1-3}$alkoxy; tetrazolyl; carboxy; $C_{1-3}$alkoxycarbonyl; aminocarbonyl; $C_{1-4}$alkylaminocarbonyl; $C_{1-3}$alkylaminocarbonyl; $C_{3-6}$cycloalkylaminocarbonyl; hydroxy($C_{1-4}$) alkylaminocarbonyl; $C_{6-10}$arylaminocarbonyl wherein $C_{6-10}$aryl is optionally substituted with carboxy or $C_{1-4}$alkoxycarbonyl; morpholin-4-ylcarbonyl; cyano; halogen; and trifluoromethoxy; provided that no more than one $R^{11}$ is $C_{6-10}$arylaminocarbonyl;
$R^2$ is hydrogen or $C_{1-4}$alkyl;
$R^3$ is one to two substituents independently selected from the group consisting of $C_{1-3}$alkyl, bromo, and phenyl; wherein phenyl is optionally substituted with one to three substituents independently selected from the group consisting of chloro, fluoro, carboxy, aminocarbonyl, and cyano;
$R^4$ is phenyl substituted with one to three $R^{41}$ substituents independently selected from the group consisting of $(C_{1-3})$alkyl, $(C_{1-3})$alkoxy, phenyl($C_{1-3})$ alkoxy, hydroxy, $C_{1-6}$alkylaminocarbonyl, and aminocarbonyl; provided that no more than one $R^{41}$ is aminocarbonyl, $C_{1-6}$alkylaminocarbonyl, hydroxy, or a phenyl-containing substituent;

$R^5$ is hydrogen;

$R^a$ and $R^b$ are independently hydrogen or methyl;

and pharmaceutically acceptable enantiomers, diastereomers, racemates, and salts thereof.

Another aspect of the present invention is directed to a compound of Formula (Ia) wherein:

$R^1$ is selected from the group consisting of phenyl($C_{1-3}$)alkyl, pyridinyl($C_{1-3}$)alkyl, and furanyl($C_{1-3}$)alkyl; wherein phenyl, pyridinyl, and furanyl are optionally substituted with one to three $R^{11}$ substituents independently selected from the group consisting of $C_{1-3}$alkoxy; tetrazolyl; $C_{3-6}$cycloalkylaminocarbonyl; hydroxy($C_{1-4}$)alkylaminocarbonyl; $C_{6-10}$arylaminocarbonyl wherein $C_{6-10}$aryl is optionally substituted with carboxy or $C_{1-4}$alkoxycarbonyl; morpholin-4-ylcarbonyl; chloro; fluoro; trifluoromethoxy; and carboxy;

$R^2$ is hydrogen or methyl;

$R^3$ is one to two substituents independently selected from the group consisting of methyl and phenyl; wherein phenyl is optionally substituted with one to three substituents independently selected from the group consisting of chloro and carboxy;

$R^4$ is phenyl substituted at the 4-position with hydroxy, $C_{1-3}$alkylaminocarbonyl, or aminocarbonyl, and optionally substituted with one to two substituents independently selected from the group consisting of methyl, methoxy, and benzyloxy;

$R^5$ is hydrogen;

$R^a$ and $R^b$ are each hydrogen;

and pharmaceutically acceptable enantiomers, diastereomers, racemates, and salts thereof.

Another embodiment is directed to compounds of Formula (Ib):

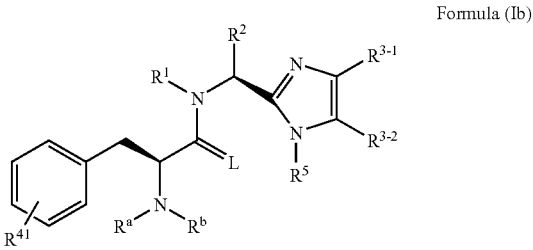

Formula (Ib)

wherein in one embodiment of this invention the variables are as previously defined. In another embodiment of the present invention L is oxygen and $R^1$, $R^2$, $R^{3-1}$, $R^{3-2}$, $R^5$, $R^a$, $R^b$, and $R^{41}$ are dependently selected from the group consisting of:

TABLE I

| Cpd | $R^1$ | $R^2$ | $R^{3-1}$ | $R^{3-2}$ | $R^5$ | $R^{41}$ | $R^a/R^b$ |
|---|---|---|---|---|---|---|---|
| 1 | 2-Aminocarbonyl-phenylmethyl | methyl | phenyl | H | H | 2,6-dimethyl-4-aminocarbonyl | H |
| 2 | 2-Cyano-phenyl methyl | methyl | phenyl | H | H | 2,6-dimethyl-4-aminocarbonyl | H |
| 3 | 2-Bromo-phenyl methyl | methyl | phenyl | H | H | 2,6-dimethyl-4-aminocarbonyl | H |
| 4 | 3-Carboxy-4-methoxy-phenyl methyl | methyl | phenyl | H | H | 4-aminocarbonyl | H |
| 5 | 3-Carboxy-4-methoxy-phenyl methyl | H | phenyl | H | H | 4-aminocarbonyl | H |
| 6 | 3-Carboxy-4-methoxy-phenyl methyl | H | phenyl | H | H | 2,6-dimethyl-4-aminocarbonyl | H |
| 7 | 3-Methoxycarbonyl-4-methoxy-phenylmethyl | H | phenyl | H | H | 2,6-dimethyl-4-aminocarbonyl | H |
| 8 | 3-(1H-tetrazol-5-yl)-4-methoxy-phenylmethyl | methyl | phenyl | H | H | 2,6-dimethyl-4-aminocarbonyl | H |
| 9 | 3-Methoxycarbonyl-phenylmethyl | methyl | phenyl | H | H | 2,6-dimethyl-4-aminocarbonyl | H |
| 10 | 3-Methoxy carbonyl-phenylmethyl | methyl | naphthalen-1-yl | H | H | 2,6-dimethyl-4-aminocarbonyl | H |
| 11 | 3-Carboxy-phenylmethyl | methyl | naphthalen-1-yl | H | H | 2,6-dimethyl-4-aminocarbonyl | H |
| 12 | 3-Carboxy-phenylmethyl | methyl | 4-chlorophenyl | Me | H | 2,6-dimethyl-4-aminocarbonyl | H |
| 13 | 4-Carboxy-phenylmethyl | methyl | naphthalen-1-yl | H | H | 2,6-dimethyl-4-aminocarbonyl | H |
| 14 | 3-Methoxy-4-carboxy-phenylmethyl | methyl | phenyl | H | H | 2,6-dimethyl-4-aminocarbonyl | H |
| 15 | 3,4-Dihydroxy-phenylmethyl | methyl | phenyl | H | H | 2,6-dimethyl-4-hydroxy | H |
| 16 | Piperidin-4-yl methyl | methyl | phenyl | H | H | 2,6-dimethyl-4-hydroxy | H |

TABLE I-continued

| Cpd | R¹ | R² | R³⁻¹ | R³⁻² | R⁵ | R⁴¹ | Rᵃ/Rᵇ |
|---|---|---|---|---|---|---|---|
| 17 | 3-Methoxy carbonyl-4-methoxy-phenylmethyl | methyl | phenyl | H | H | 2,6-dimethyl-4-aminocarbonyl | H |
| 18 | 3-Carboxy-4-methoxy-phenylmethyl | methyl | phenyl | H | H | 2,6-dimethyl-4-aminocarbonyl | H |
| 19 | 3,4-Dimethoxy-phenylmethyl | methyl | 3-bromophenyl | H | H | 2,6-dimethyl-4-aminocarbonyl | H |
| 20 | 3,4-Dimethoxy-phenylmethyl | methyl | 3-carboxyphenyl | H | H | 2,6-dimethyl-4-aminocarbonyl | H |
| 21 | 3,4-Dimethoxy-phenylmethyl | benzyloxy-methyl | phenyl | H | H | 2,6-dimethyl-4-hydroxy | H |
| 23 | 3,4-Dimethoxy-phenylmethyl | methyl | 3-aminocarbonyl phenyl | H | H | 2,6-dimethyl-4-aminocarbonyl | H |
| 24 | 3,4-Dimethoxy-phenylmethyl | methyl | 3-cyanophenyl | H | H | 2,6-dimethyl-4-aminocarbonyl | H |
| 25 | Isopropyl | H | quinoxalin-8-yl | Me | H | 2,6-dimethyl-4-hydroxy | H |
| 26 | 3,4-Dimethoxy-phenylmethyl | methyl | 2-bromophenyl | H | H | 2,6-dimethyl-4-aminocarbonyl | H |
| 27 | 3,4-Dimethoxy-phenylmethyl | methyl | 2-cyanophenyl | H | H | 2,6-dimethyl-4-aminocarbonyl | H |
| 28 | 3,4-Dimethoxy-phenylmethyl | methyl | 2-aminocarbonyl phenyl | H | H | 2,6-dimethyl-4-aminocarbonyl | H |
| 29 | 3,4-Dimethoxy-phenylmethyl | methyl | 2-carboxyphenyl | H | H | 2,6-dimethyl-4-aminocarbonyl | H |
| 30 | 3,4-Dibenzyloxy-phenylmethyl | methyl | phenyl | H | H | 2,6-dimethyl-4-hydroxy | H |
| 31 | [1,3]benzo dioxal-5-yl | methyl | phenyl | H | H | 2,6-dimethyl, 4-hydroxy | H |
| 32 | 4-Methoxy-phenylmethyl | methyl | phenyl | H | H | 2,6-dimethyl-4-hydroxy | H |
| 33 | 3-Methoxy-phenylmethyl | methyl | phenyl | H | H | 2,6-dimethyl-4-hydroxy | H |
| 34 | 2,4-Dimethoxy-phenylmethyl | methyl | phenyl | H | H | 2,6-dimethyl-4-hydroxy | H |
| 35 | 3,4-Dimethoxy-phenylmethyl | H | phenyl | H | H | 2,6-dimethyl-4-hydroxy | H |
| 36 | Isopropyl | H | 4-methylcarbonyl phenyl | H | H | 2,6-dimethyl-4-hydroxy | H |
| 37 | Isopropyl | H | 3-fluoro, 4-carboxy-phenyl | Me | H | 2,6-dimethyl-4-hydroxy | H |
| 38 | Isopropyl | H | 2-phenyl-ethylen-1-yl | Me | H | 2,6-dimethyl-4-hydroxy | H |
| 39 | Isopropyl | H | 4-hydroxymethyl phenyl | Me | H | 2,6-dimethyl-4-hydroxy | H |
| 40 | Benzhydryl | H | phenyl | H | H | 2,6-dimethyl-4-hydroxy | H |
| 41 | Isopropyl | H | 4-cyanophenyl | Me | H | 2,6-dimethyl-4-hydroxy | H |
| 42 | Benzyl | methyl | 4-trifluoromethyl phenyl | H | H | 2,6-dimethyl-4-aminocarbonyl | H |
| 43 | Isopropyl | H | 3-trifluoromethoxy phenyl | Me | H | 2,6-dimethyl-4-hydroxy | H |
| 44 | Isopropyl | H | 4-trifluoromethoxy phenyl | Me | H | 2,6-dimethyl-4-hydroxy | H |
| 45 | Isopropyl | H | 3-methanesulfonyl aminophenyl | Me | H | 2,6-dimethyl-4-hydroxy | H |
| 46 | Isopropyl | H | 4-(2-carboxyethyl) phenyl | Me | H | 2,6-dimethyl-4-hydroxy | H |
| 47 | Isopropyl | H | 3-amino-5-carboxyphenyl | Me | H | 2,6-dimethyl-4-hydroxy | H |
| 48 | 3-Carboxy-phenylmethyl | methyl | phenyl | H | H | 2,6-dimethyl-4-hydroxy | H |
| 49 | 4-Carboxy-phenylmethyl | methyl | phenyl | H | H | 2,6-dimethyl-4-carboxy | H |
| 50 | 4-Carboxy-phenylmethyl | methyl | phenyl | H | H | 2,6-dimethyl-4-aminocarbonyl | H |
| 51 | 4-Methoxy carbonyl-phenylmethyl | methyl | phenyl | H | H | 2,6-dimethyl-4-aminocarbonyl | H |
| 52 | 3-Methoxy carbonyl-phenylmethyl | methyl | phenyl | H | H | 2,6-dimethyl-4-hydroxy | H |
| 53 | 1-Benzyloxy carbonyl- | methyl | phenyl | H | H | 2,6-dimethyl-4-hydroxy | H |

TABLE I-continued

| Cpd | R¹ | R² | R³⁻¹ | R³⁻² | R⁵ | R⁴¹ | Rᵃ/Rᵇ |
|---|---|---|---|---|---|---|---|
|  | piperadin-4-yl methyl |  |  |  |  |  |  |
| 54 | Furan-2-yl methyl | methyl | phenyl | H | H | 2,6-dimethyl-4-hydroxy | H |
| 55 | Furan-3-yl methyl | methyl | phenyl | H | H | 2,6-dimethyl-4-hydroxy | H |
| 56 | Cyclohexyl methyl | methyl | phenyl | H | H | 2,6-dimethyl-4-hydroxy | H |
| 57 | Pyridin-4-yl methyl | methyl | phenyl | H | H | 2,6-dimethyl-4-hydroxy | H |
| 58 | Benzyl | methyl | 4-chlorophenyl | Me | H | 2,6-dimethyl-4-aminocarbonyl | H |
| 59 | Benzyl | methyl | 3-fluorophenyl | H | H | 2,6-dimethyl-4-aminocarbonyl | H |
| 60 | Isopropyl | H | 3-cyanophenyl | Me | H | 2,6-dimethyl-4-hydroxy | H |
| 61 | Isopropyl | H | 2,5-difluorophenyl | Me | H | 2,6-dimethyl-4-hydroxy | H |
| 62 | Isopropyl | H | 4-methanesulfonyl phenyl | Me | H | 2,6-dimethyl-4-hydroxy | H |
| 64 | Benzyl | benzyloxy methyl | phenyl | H | H | 2,6-dimethyl-4-aminocarbonyl | H |
| 65 | Isopropyl | H | Br | Me | H | 2,6-dimethyl-4-hydroxy | H |
| 66 | Isopropyl | H | 4-dimethylamino phenyl | Me | H | 2,6-dimethyl-4-hydroxy | H |
| 67 | Isopropyl | H | 3-dimethylamino carbonylphenyl | Me | H | 2,6-dimethyl-4-hydroxy | H |
| 68 | Isopropyl | H | 3-hydroxyphenyl | Me | H | 2,6-dimethyl-4-hydroxy | H |
| 69 | Isopropyl | H | 4-aminocarbonyl phenyl | Me | H | 2,6-dimethyl-4-hydroxy | H |
| 70 | Isopropyl | H | 3-chlorophenyl | Me | H | 2,6-dimethyl-4-hydroxy | H |
| 71 | Isopropyl | H | 2,4-difluorophenyl | Me | H | 2,6-dimethyl-4-hydroxy | H |
| 72 | Isopropyl | H | 3-methanesulfonyl phenyl | Me | H | 2,6-dimethyl-4-hydroxy | H |
| 73 | Isopropyl | H | 3-aminocarbonyl phenyl | Me | H | 2,6-dimethyl-4-hydroxy | H |
| 74 | Benzyl | methyl | 4-trifluoromethyl phenyl | Me | H | 2,6-dimethyl-4-aminocarbonyl | H |
| 75 | 3,4-Dimethoxy-phenylmethyl | methyl | phenyl | H | H | 2,6-dimethyl-4-aminocarbonyl | H |
| 76 | Benzyl | methyl | 4-fluorophenyl | H | H | 2,6-dimethyl-4-aminocarbonyl | H |
| 77 | 4-Dimethylamino-phenylmethyl | methyl | phenyl | H | Me | 2,6-dimethyl-4-hydroxy | H |
| 78 | 4-Methylamino-phenylmethyl | methyl | phenyl | H | H | 2,6-dimethyl-4-hydroxy | H |
| 79 | 4-Methylcarbonyl amino-phenyl methyl | methyl | phenyl | H | H | 2,6-dimethyl-4-hydroxy | H |
| 80 | 4-Carboxy-phenylmethyl | methyl | phenyl | H | H | 2,6-dimethyl-4-hydroxy | H |
| 81 | 4-Hydroxy-phenylmethyl | methyl | phenyl | H | H | 2,6-dimethyl-4-hydroxy | H |
| 83 | Benzyl | methyl | 4-fluorophenyl | H | H | 2,6-dimethyl-4-hydroxy | H |
| 84 | Isopropyl | methyl | 4-fluorophenyl | H | H | 2,6-dimethyl-4-hydroxy | H |
| 85 | Isopropyl | hydroxy methyl | phenyl | H | H | 2,6-dimethyl-4-aminocarbonyl | H |
| 86 | Isopropyl | H | phenyl | H | H | 2,6-dimethyl, 4-aminocarbonyl | H |
| 87 | 3,4-Dichloro-phenylmethyl | H | phenyl | H | H | 2,6-dimethyl-4-hydroxy | H |
| 88 | 4-Methylcarbonyl oxy-phenyl methyl | methyl | phenyl | H | H | 2,6-dimethyl-4-hydroxy | H |
| 89 | 4-Methoxy carbonyl-phenylmethyl | methyl | phenyl | H | H | 2,6-dimethyl-4-hydroxy | H |
| 90 | 3-Aminocarbonyl-phenylmethyl | methyl | phenyl | H | H | 2,6-dimethyl-4-hydroxy | H |
| 91 | 3-Cyano-phenyl methyl | methyl | phenyl | H | H | 2,6-dimethyl-4-hydroxy | H |

TABLE I-continued

| Cpd | R¹ | R² | R³⁻¹ | R³⁻² | R⁵ | R⁴¹ | Rᵃ/Rᵇ |
|---|---|---|---|---|---|---|---|
| 92 | Pyridin-3-yl methyl | methyl | phenyl | H | H | 2,6-dimethyl-4-hydroxy | H |
| 93 | Pyridin-2-yl methyl | methyl | phenyl | H | H | 2,6-dimethyl-4-hydroxy | H |
| 94 | 1-(R)-Phenylethyl | H | phenyl | H | H | 2,6-dimethyl-4-aminocarbonyl | H |
| 95 | 1-(S)-Phenylethyl | H | phenyl | H | H | 2,6-dimethyl-4-aminocarbonyl | H |
| 96 | 2-Methoxy-phenylmethyl | methyl | phenyl | H | H | 2,6-dimethyl-4-hydroxy | H |
| 97 | 2,6-Dichloro-phenylmethyl | methyl | phenyl | H | H | 2,6-dimethyl-4-hydroxy | H |
| 98 | 3-Phenoxy-phenylmethyl | methyl | phenyl | H | H | 2,6-dimethyl-4-hydroxy | H |
| 99 | Naphthalen-1-yl-methyl | methyl | phenyl | H | H | 2,6-dimethyl-4-hydroxy | H |
| 100 | Naphthalen-2-yl-methyl | methyl | phenyl | H | H | 2,6-dimethyl-4-hydroxy | H |
| 101 | 3-Bromo-phenyl methyl | methyl | phenyl | H | H | 2,6-dimethyl-4-hydroxy | H |
| 102 | 3,4-Dimethoxy-phenylmethyl | methyl | phenyl | H | H | 2,6-dimethyl-4-hydroxy | H |
| 103 | 2,4-Dichloro-phenylmethyl | methyl | phenyl | H | H | 2,6-dimethyl-4-hydroxy | H |
| 104 | Benzyl | isobutyl | phenyl | H | H | 2,6-dimethyl-4-hydroxy | H |
| 105 | Benzyl | benzyl | phenyl | H | H | 2,6-dimethyl-4-hydroxy | H |
| 106 | Benzyl | isopropyl | phenyl | H | H | 2,6-dimethyl-4-hydroxy | H |
| 107 | Benzyl | H | phenyl | H | H | 2,6-dimethyl-4-aminocarbonyl | H |
| 108 | 3-Phenyl prop-1-yl | methyl | phenyl | H | H | 2,6-dimethyl-4-aminocarbonyl | H |
| 109 | 2-Phenylethyl | methyl | phenyl | H | H | 2,6-dimethyl-4-aminocarbonyl | H |
| 111 | 1-Phenylethyl diastereomer A | methyl | phenyl | H | H | 2,6-dimethyl-4-aminocarbonyl | H |
| 112 | 1-Phenylethyl diasteromer B | methyl | phenyl | H | H | 2,6-dimethyl-4-aminocarbonyl | H |
| 114 | Benzyl | methyl | phenyl | H | H | 2,6-dimethyl-4-aminocarbonyl | H |
| 115 | Isopropyl | H | 4-biphenyl | Me | H | 2,6-dimethyl-4-hydroxy | H |
| 116 | Isopropyl | H | 3-fluorophenyl | Me | H | 2,6-dimethyl-4-hydroxy | H |
| 117 | Isopropyl | H | 2-fluorophenyl | Me | H | 2,6-dimethyl-4-hydroxy | H |
| 118 | Isopropyl | hydroxy methyl | phenyl | H | H | 2,6-dimethyl-4-hydroxy | H |
| 119 | H | hydroxy methyl | phenyl | H | H | 2,6-dimethyl-4-hydroxy | H |
| 120 | Isopropyl | 3-(amino methyl) phenyl methyl | phenyl | H | H | 2,6-dimethyl-4-hydroxy | H |
| 121 | Isopropyl | 3-amino carbonyl phenyl methyl | phenyl | H | H | 2,6-dimethyl-4-hydroxy | H |
| 122 | Isopropyl | 3-cyano phenyl methyl | phenyl | H | H | 2,6-dimethyl-4-hydroxy | H |
| 123 | Isopropyl | H | 4-carboxyphenyl | Me | H | 2,6-dimethyl-4-hydroxy | H |
| 124 | Isopropyl | H | pyridin-3-yl | Me | H | 2,6-dimethyl-4-hydroxy | H |
| 125 | Isopropyl | H | 4-methoxyphenyl | Me | H | 2,6-dimethyl-4-hydroxy | H |
| 126 | Isopropyl | H | 3,5-difluorophenyl | Me | H | 2,6-dimethyl-4-hydroxy | H |
| 127 | Cyclohexyl | methyl | phenyl | H | H | 2,6-dimethyl-4-aminocarbonyl | H |
| 129 | Carboxymethyl | H | phenyl | H | H | 2,6-dimethyl-4-hydroxy | H |
| 130 | Isopropyl | H | 3-hydroxymethyl phenyl | Me | H | 2,6-dimethyl-4-hydroxy | H |

TABLE I-continued

| Cpd | R¹ | R² | R³⁻¹ | R³⁻² | R⁵ | R⁴¹ | Rᵃ/Rᵇ |
|---|---|---|---|---|---|---|---|
| 131 | Isopropyl | H | pyrimidin-5-yl | Me | H | 2,6-dimethyl-4-hydroxy | H |
| 132 | Isopropyl | H | pyrimidin-5-yl | Me | H | 4-hydroxy | H |
| 133 | Isopropyl | H | 3-carboxyphenyl | Me | H | 2,6-dimethyl-4-hydroxy | H |
| 134 | Isopropyl | H | 3-biphenyl | Me | H | 2,6-dimethyl-4-hydroxy | H |
| 135 | Isopropyl | H | 2-methoxyphenyl | Me | H | 2,6-dimethyl-4-hydroxy | H |
| 136 | Isopropyl | benzyl | phenyl | H | H | 3-aminocarbonyl | H |
| 137 | Isopropyl | isopropyl | phenyl | H | H | 3-aminocarbonyl | H |
| 138 | Isopropyl | benzyloxymethyl | phenyl | H | H | 2,6-dimethyl-4-hydroxy | H |
| 139 | Isopropyl | isobutyl | phenyl | H | H | 2,6-dimethyl-4-[2-(2,6-dimethyl-4-hydroxyphenyl)-1-amino-ethylcarbonxyloxy]phenyl | H |
| 140 | Isopropyl | isobutyl | phenyl | H | H | 2,6-dimethyl-4-hydroxy | H |
| 141 | Isopropyl | H | 3,5-dichlorophenyl | Me | H | 2,6-dimethyl-4-hydroxy | H |
| 142 | Isopropyl | H | 3-methoxyphenyl | Me | H | 2,6-dimethyl-4-hydroxy | H |
| 143 | Isopropyl | methyl | phenyl | H | H | 2,6-dimethyl-4-aminocarbonyl | H |
| 145 | Isopropyl | H | 2-biphenyl | Me | H | 2,6-dimethyl-4-hydroxy | H |
| 146 | Isopropyl | H | thiophen-3-yl | Me | H | 2,6-dimethyl-4-hydroxy | H |
| 147 | Isopropyl | H | 4-chlorophenyl | Me | H | 2,6-dimethyl-4-hydroxy | H |
| 148 | Isopropyl | H | 3-methylcarbonyl aminophenyl | Me | H | 2,6-dimethyl-4-hydroxy | H |
| 149 | Isopropyl | H | 4-trifluoromethyl phenyl | Me | H | 2,6-dimethyl-4-hydroxy | H |
| 150 | Isopropyl | H | naphthalen-2-yl | Me | H | 2,6-dimethyl-4-hydroxy | H |
| 151 | Isopropyl | H | 2-trifluoromethyl phenyl | Me | H | 2,6-dimethyl-4-hydroxy | H |
| 152 | Isopropyl | H | thiophen-3-yl | Me | H | 4-hydroxy | H |
| 153 | Isopropyl | H | pyridin-3-yl | Me | H | 4-hydroxy | H |
| 154 | Isopropyl | H | phenyl | Me | H | 4-hydroxy | H |
| 155 | Isopropyl | H | 2-chlorophenyl | Me | H | 2,6-dimethyl-4-hydroxy | H |
| 156 | Isopropyl | H | naphthalen-1-yl | Me | H | 2,6-dimethyl-4-hydroxy | H |
| 157 | Isopropyl | benzyl | phenyl | H | H | 3-cyano | H |
| 158 | Isopropyl | benzyl | phenyl | H | H | 4-hydroxy | H |
| 159 | Isopropyl | benzyl | phenyl | H | H | 2,6-dimethyl-4-hydroxy | H |
| 160 | Isopropyl | isopropyl | phenyl | H | H | 3-cyano | H |
| 161 | Isopropyl | isopropyl | phenyl | H | H | 4-hydroxy | H |
| 162 | Isopropyl | isopropyl | phenyl | H | H | 2,6-dimethyl-4-hydroxy | H |
| 163 | Isopropyl | H | 4-fluorophenyl | Me | H | 2,6-dimethyl-4-hydroxy | H |
| 164 | Isopropyl | H | 3,5-bis-trifluoromethyl phenyl | Me | H | 2,6-dimethyl-4-hydroxy | H |
| 165 | Isopropyl | H | 2-methylphenyl | Me | H | 2,6-dimethyl-4-hydroxy | H |
| 166 | Isopropyl | H | phenyl | Me | H | 2,6-dimethyl-4-hydroxy | H |
| 167 | 2-Dimethylamino-1-methyl-eth-1-yl | H | phenyl | H | H | 2,6-dimethyl-4-hydroxy | H |
| 168 | Methyl | isobutyl | phenyl | H | H | 3-aminocarbonyl | H |
| 169 | Methyl | isobutyl | phenyl | H | H | 3-cyano | H |
| 170 | Ethyl | isopropyl | phenyl | H | H | 2,6-dimethyl-4-hydroxy | H |
| 171 | Methyl | isopropyl | phenyl | H | H | 4-hydroxy | H |
| 172 | H | 3-aminocarbonyl phenyl methyl | phenyl | H | H | 2,6-dimethyl-4-hydroxy | H |

TABLE I-continued

| Cpd | R¹ | R² | R³⁻¹ | R³⁻² | R⁵ | R⁴¹ | Rᵃ/Rᵇ |
|---|---|---|---|---|---|---|---|
| 173 | H | 3-cyano phenyl methyl | phenyl | H | H | 2,6-dimethyl-4-hydroxy | H |
| 174 | Methyl | isobutyl | phenyl | H | H | 2,6-dimethyl-4-hydroxy | H |
| 175 | H | benzyloxy methyl | phenyl | H | H | 2,6-dimethyl-4-hydroxy | H |
| 176 | H | isobutyl | phenyl | H | H | 2,6-dimethyl-4-hydroxy | H |
| 177 | H | benzyl | phenyl | H | H | 2,6-dimethyl-4-hydroxy | H |
| 178 | Isopropyl | H | phenyl | H | H | 2,6-dimethyl-4-aminocarbonyl | H |
| 179 | Methyl | methyl | phenyl | H | H | 2,6-dimethyl-4-morpholin-1-ylcarbonyl | H |
| 181 | Methyl | methyl | phenyl | H | H | 2,6-dimethyl-4-ethyl aminocarbonyl | H |
| 183 | Methyl | methyl | phenyl | H | H | 2,6-dimethyl-4-methyl aminocarbonyl | H |
| 185 | H | isopropyl | phenyl | H | H | 3-aminocarbonyl | H |
| 186 | H | isopropyl | phenyl | H | H | 3-cyano | H |
| 187 | H | isopropyl | phenyl | H | H | 2,6-dimethyl-4-hydroxy | H |
| 188 | H | isopropyl | phenyl | H | H | 4-hydroxy | H |
| 189 | Methyl | methyl | phenyl | H | H | 4-aminosulfonyl | H |
| 190 | Cyclohexyl | H | phenyl | H | H | 2,6-dimethyl-4-hydroxy | H |
| 191 | Cyclohexyl | H | phenyl | H | H | 4-hydroxy | H |
| 192 | Cyclopropyl methyl | H | phenyl | H | H | 2,6-dimethyl-4-hydroxy | H |
| 193 | Cyclopropyl methyl | H | phenyl | H | H | 4-hydroxy | H |
| 194 | Isopropyl | H | phenyl | H | H | 2,6-dimethyl-4-hydroxy | H |
| 195 | Isopropyl | H | phenyl | H | H | 4-hydroxy | H |
| 196 | Methyl | methyl | phenyl | H | H | 2,6-dimethyl-4-aminocarbonyl | H |
| 197 | Ethyl | methyl | phenyl | H | H | 2,6-dimethyl-4-aminocarbonyl | H |
| 198 | Methyl | H | phenyl | H | H | 4-hydroxy | H |
| 199 | Methyl | H | phenyl | H | H | 2,6-dimethyl-4-hydroxy | H |
| 202 | Methyl | methyl | phenyl | H | H | 4-aminocarbonyl | H |
| 204 | Methyl | methyl | benzyl | H | H | 4-hydroxy | H |
| 205 | Methyl | methyl | benzyl | H | H | 2,6-dimethyl-4-hydroxy | H |
| 207 | Methyl | methyl | phenyl | H | H | 2,6-dimethyl-4-hydroxy | H |
| 209 | H | methyl | phenyl | H | H | 2,6-dimethyl-4-hydroxy | H |
| 211 | Methyl | methyl | phenyl | H | H | 4-hydroxy | H |
| 213 | H | methyl | phenyl | H | H | 4-hydroxy | H |
| 215 | Ethyl | methyl | phenyl | H | H | 4-hydroxy | H |
| 216 | Ethyl | methyl | phenyl | H | H | 2,6-dimethyl-4-hydroxy | H |
| 218 | Benzyl | methyl | phenyl | H | H | 2,6-dimethyl-4-hydroxy | H |
| 219 | Benzyl | methyl | phenyl | H | H | 4-hydroxy | H |
| 224 | Isopropyl | methyl | phenyl | H | H | 2,6-dimethyl-4-hydroxy | H |
| 225 | Isopropyl | methyl | phenyl | H | H | 4-hydroxy | H |
| 226 | 2-Carboxy-phenyl methyl | methyl | phenyl | H | H | 2,6-dimethyl-4-aminocarbonyl | H |
| 227 | 3-Carboxy-phenyl methyl | methyl | phenyl | H | H | 2,6-dimethyl-4-aminocarbonyl | H |
| 229 | 2-Bromo-4,5-dimethoxy-phenylmethyl | methyl | phenyl | H | H | 2,6-dimethyl-4-aminocarbonyl | H |
| 230 | 2-Carboxy-4,5-dimethoxy-phenylmethyl | methyl | phenyl | H | H | 2,6-dimethyl-4-aminocarbonyl | H |
| 231 | 3-Carboxy-4-methoxy-phenyl methyl | methyl | phenyl | H | H | H | H |

TABLE I-continued

| Cpd | R¹ | R² | R³⁻¹ | R³⁻² | R⁵ | R⁴¹ | Rᵃ/Rᵇ |
|---|---|---|---|---|---|---|---|
| 232 | 3-Carboxy-4-methoxy-phenyl methyl | methyl | phenyl | H | H | 2,6-dimethyl | H |
| 233 | 3-Methoxycarbonyl-4-methoxy-phenylmethyl | methyl | phenyl | H | H | 2,6-dimethyl | H |
| 234 | 3,4-Dimethoxy-phenylmethyl | methyl | phenyl | H | H | 2,6-dimethyl-4-imidazol-2-yl | H |
| 236 | 3,4-Dimethoxy-phenylmethyl | methyl | phenyl | H | H | 2,6-dimethyl | H |
| 237 | 3-Carboxy-4-methoxy-phenyl methyl | methyl | 4-chloropheny | H | H | 2,6-dimethyl-4-aminocarbonyl | H |
| 238 | 3-Carboxy, 4-methoxy-phenyl methyl | methyl | 4-fluorophenyl | H | H | 2,6-dimethyl-4-aminocarbonyl | H |
| 239 | 3-Carboxy-4-methoxy-phenyl methyl | methyl | 4-chlorophenyl | Me | H | 2,6-dimethyl-4-aminocarbonyl | H |
| 240 | 4-Carboxy-phenyl methyl | methyl | 4-chlorophenyl | Me | H | 2,6-dimethyl-4-aminocarbonyl | H |
| 241 | 3-Carboxy-4-methoxy-phenyl methyl | methyl | 4-chlorophenyl | Cl | H | 2,6-dimethyl-4-aminocarbonyl | H |
| 242 | 3-(1H-tetrazol-5-yl)-phenylmethyl | methyl | phenyl | H | H | 2,6-dimethyl-4-aminocarbonyl | H |
| 243 | 3-Carboxy-4-trifluoromethoxy-phenylmethyl | methyl | phenyl | H | H | 2,6-dimethyl-4-aminocarbonyl | H |
| 244 | Bis-3,4-trifluoromethoxy-phenylmethyl | methyl | phenyl | H | H | 2,6-dimethyl-4-aminocarbonyl | H |
| 245 | 3-Carboxy-phenyl methyl | methyl | phenyl | H | H | 2,6-dimethyl-4-aminocarbonyl | H |
| 246 | Quinolin-4-yl methyl | methyl | phenyl | H | H | 2,6-dimethyl-4-hydroxy | H |
| 247 | 4-Methoxy naphthalen-1-yl methyl | methyl | phenyl | H | H | 2,6-dimethyl-4-hydroxy | H |
| 248 | 4-Trifluoromethoxy-phenylmethyl | methyl | phenyl | H | H | 2,6-dimethyl-4-hydroxy | H |
| 249 | 4-Trifluoromethyl-phenylmethyl | methyl | phenyl | H | H | 2,6-dimethyl-4-hydroxy | H |
| 250 | 4-Isopropyloxy-phenylmethyl | methyl | phenyl | H | H | 2,6-dimethyl-4-hydroxy | H |
| 251 | 3-Ethoxyphenyl-methyl | methyl | phenyl | H | H | 2,6-dimethyl-4-hydroxy | H |
| 252 | 5-Methoxycarbonyl-pyridin-2-ylmethyl | methyl | phenyl | H | H | 2,6-dimethyl-4-aminocarbonyl | H |
| 253 | 5-Carboxy-pyridin-2-ylmethyl | methyl | phenyl | H | H | 2,6-dimethyl-4-aminocarbonyl | H |
| 254 | 6-Carboxy-pyridin-3-ylmethyl | methyl | phenyl | H | H | 2,6-dimethyl-4-aminocarbonyl | H |
| 255 | 6-Methoxycarbonyl-pyridin-3-ylmethyl | methyl | phenyl | H | H | 2,6-dimethyl-4-aminocarbonyl | H |
| 256 | 5-Carboxy-furan-2-ylmethyl | methyl | phenyl | H | H | 2,6-dimethyl-4-aminocarbonyl | H |
| 257 | 5-Methoxycarbonyl-furan-2-ylmethyl | methyl | phenyl | H | H | 2,6-dimethyl-4-aminocarbonyl | H |
| 258 | 3,4-Dimethoxy-phenylmethyl | hydroxy methyl | phenyl | H | H | 2,6-dimethyl-4-aminocarbonyl | H |
| 259 | Benzyl | hydroxy methyl | phenyl | H | H | 2,6-dimethyl-4-aminocarbonyl | H |
| 260 | 3-Carboxy-4-methoxy-phenyl methyl | methyl | phenyl | H | H | 2,6-dimethyl-4-hydroxy | H |
| 261 | 3-Carboxy-4-methoxy-phenyl methyl | methyl | phenyl | H | H | 4-hydroxy | H |
| 262 | 3-Carboxy-4-methoxy-phenyl methyl | methyl | phenyl | H | H | 4-hydroxy | H/Me |
| 263 | 3-Carboxy-4-methoxy-phenyl methyl | H | phenyl | H | H | 4-hydroxy | H |

TABLE I-continued

| Cpd | R$^1$ | R$^2$ | R$^{3-1}$ | R$^{3-2}$ | R$^5$ | R$^{41}$ | R$^a$/R$^b$ |
|---|---|---|---|---|---|---|---|
| 264 | 3-Carboxy-4-methoxy-phenyl methyl | H | phenyl | H | H | 4-hydroxy | H/Me |
| 265 | 3-Carboxy-4-methoxy-phenyl methyl | H | phenyl | H | H | 2,6-dimethyl-4-hydroxy | H |
| 266 | 3-Methoxycarbonyl-4-methoxy-phenylmethyl | methyl | phenyl | H | H | H | H |
| 267 | 3-(1H-tetrazol-5-yl)-phenylmethyl | methyl | phenyl | H | H | 4-aminocarbonyl | H |
| 268 | 3-Methoxycarbonyl-4-methoxy-phenylmethyl | methyl | phenyl | H | H | 2,6-dimethyl-4-hydroxy | H |
| 269 | 3-Methoxycarbonyl | methyl | phenyl | H | H | 4-aminocarbonyl | H |
| 270 | 3-Carboxy | methyl | phenyl | H | H | 4-aminocarbonyl | H |
| 271 | 3-Methoxycarbonyl | H | phenyl | H | H | 2,6-dimethyl-4-aminocarbonyl | H |
| 272 | 3-Carboxy | H | phenyl | H | H | 2,6-dimethyl-4-aminocarbonyl | H |
| 274 | 3-Carboxy-4-methoxy-phenylmethyl | methyl | phenyl | H | H | 4-benzyloxy | H/Me |
| 275 | 3-Carboxy-4-methoxy-phenylmethyl | methyl | phenyl | H | H | 4-aminocarbonyl | H |
| 277 | 3-Carboxy-phenyl | methyl | 4-chlorophenyl | Me | H | 4-aminocarbonyl | H |
| 279 | 3-Methoxycarbonyl-4-methoxy-phenylmethyl | methyl | phenyl | H | H | 4-hydroxy | H |
| 286 | 5-Methoxycarbonyl-furan-2-ylmethyl | methyl | phenyl | H | H | 2,6-dimethyl-4-hydroxy | H |
| 287 | 5-Carboxy-furan-2-ylmethyl | methyl | phenyl | H | H | 2,6-dimethyl-4-hydroxy | H |
| 288 | 3-Carboxy-4-methoxy-phenylmethyl | methyl | 3-bromophenyl | H | H | 2,6-dimethyl-4-aminocarbonyl | H |
| 289 | 3-Carboxy-4-methoxy-phenylmethyl | methyl | 4-iodophenyl | H | H | 2,6-dimethyl-4-aminocarbonyl | H |
| 290 | 3-Carboxy-4-methoxy-phenylmethyl | methyl | 2-bromophenyl | H | H | 2,6-dimethyl-4-aminocarbonyl | H |
| 291 | 3-Carboxy-4-methoxy-phenylmethyl | methyl | 4-bromophenyl | H | H | 2,6-dimethyl-4-aminocarbonyl | H |
| 292 | 3-Carboxy-4-methoxy-phenylmethyl | methyl | phenyl | H | H | 2,6-dimethyl | H |
| 293 | 3-Carboxy-4-methoxy-phenylmethyl | methyl | 4-chlorophenyl | methyl | H | 4-hydroxy | H |
| 295 | 3-Aminocarbonyl-4-methoxy phenylmethyl | methyl | phenyl | H | H | 2,6-dimethyl-4-aminocarbonyl | H |
| 296 | 3-(Morpholin-4-ylcarbonyl)-4-methoxy phenylmethyl | methyl | phenyl | H | H | 2,6-dimethyl-4-aminocarbonyl | H |
| 297 | -3-Aminocarbonyl-4-methoxy-phenylmethyl | methyl | phenyl | H | H | 4-hydroxy | H |
| 298 | 3-(Morpholin-4-ylcarbonyl)-4-methoxy-phenylmethyl | methyl | phenyl | H | H | 4-hydroxy | H |
| 299 | 3-(2-Hydroxy eth-1-yl-aminocarbonyl)-4-methoxy phenylmethyl | methyl | phenyl | H | H | 2,6-dimethyl-4-aminocarbonyl | H |
| 300 | 3-(Cyclopropyl aminocarbonyl)-4-methoxy-phenylmethyl | methyl | phenyl | H | H | 2,6-dimethyl-4-aminocarbonyl | H |
| 301 | 3-(Phenylamino carbonyl)-4- | methyl | phenyl | H | H | 2,6-dimethyl-4-aminocarbonyl | H |

TABLE I-continued

| Cpd | $R^1$ | $R^2$ | $R^{3-1}$ | $R^{3-2}$ | $R^5$ | $R^{41}$ | $R^a/R^b$ |
|---|---|---|---|---|---|---|---|
|  | methoxy-phenylmethyl |  |  |  |  |  |  |
| 303 | 5-Methoxycarbonyl-furan-2-ylmethyl | methyl | phenyl | H | H | 4-aminocarbonyl | H |
| 304 | 5-Carboxy-furan-2-ylmethyl | methyl | phenyl | H | H | 4-aminocarbonyl | H |
| 305 | 3-(Phenylamino carbonyl)-4-methoxy-phenylmethyl | methyl | phenyl | H | H | 2,6-dimethyl-4-hydroxy | H |
| 306 | 3-(3-carboxyphenyl aminocarbonyl)-4-methoxy-phenylmethyl | methyl | phenyl | H | H | 2,6-dimethyl-4-hydroxy | H |
| 307 | 3-(1H-Tetrazol-5-yl)-4-methoxy-phenylmethyl | methyl | phenyl | H | H | 2,6-dimethyl-4-hydroxy | H |
| 308 | 3-(4-Carboxyphenyl aminocarbonyl)-4-methoxy-phenylmethyl | methyl | phenyl | H | H | 2,6-dimethyl-4-hydroxy | H |
| 309 | 3-(2-t-Butyl-tetrazol-5-yl)-4-methoxy-phenylmethyl | methyl | phenyl | H | H | 2,6-dimethyl-4-aminocarbonyl | H |
| 310 | 3-Methoxycarbonyl-4-methoxy-phenylmethyl | methyl | phenyl | H | H | 2,6-dimethyl-4-aminocarbonyl | Methoxy carbonyl |
| 311 | 2-Methoxycarbonyl-pyridin-4-ylmethyl | methyl | phenyl | H | H | 2,6-dimethyl-4-aminocarbonyl | H |
| 312 | 4-Methoxycarbonyl-pyridin-2-ylmethyl | methyl | phenyl | H | H | 2,6-dimethyl-4-aminocarbonyl | H |
| 313 | 6-Methoxycarbonyl-pyridin-2-ylmethyl | methyl | phenyl | H | H | 2,6-dimethyl-4-aminocarbonyl | H |
| 315 | 3-Methoxycarbonyl-4-methoxy-phenylmethyl | methyl | phenyl | H | H | 2,6-dimethyl-4-aminocarbonyl | Methoxy carbonyl |
| 316 | 2-Carboxy-pyridin-4-ylmethyl | methyl | phenyl | H | H | 2,6-dimethyl-4-aminocarbonyl | H |
| 317 | 6-Carboxy-pyridin-2-ylmethyl | methyl | phenyl | H | H | 2,6-dimethyl-4-aminocarbonyl | H |

Exemplified compounds of the present invention include compounds of Formula (Ic):

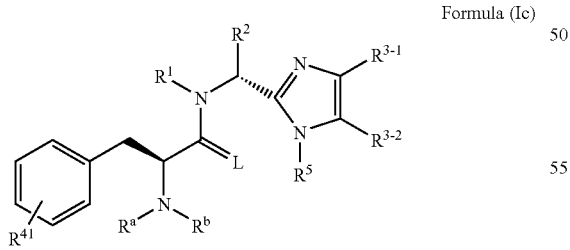

Formula (Ic)

wherein in one embodiment of this invention the variables are as previously defined. In another embodiment of the present invention L is O and $R^1$, $R^2$, $R^{3-1}$, $R^{3-2}$, $R^5$, $R^a$, $R^b$, and $R^{41}$ are dependently selected from the group consisting of:

TABLE II

| Cpd | R$^1$ | R$^2$ | R$^{3-1}$ | R$^{3-2}$ | R$^5$ | R$^{41}$ | R$^a$/R$^b$ |
|---|---|---|---|---|---|---|---|
| 22 | 3,4-Dimethoxy-phenylmethyl | benzyloxymethyl | phenyl | H | H | 2,6-dimethyl-4-hydroxy | H |
| 63 | Isopropyl | hydroxymethyl | phenyl | H | H | 2,6-dimethyl-4-hydroxy | H |
| 82 | Isopropyl | methyl | 4-fluorophenyl | H | H | 2,6-dimethyl-4-hydroxy | H |
| 110 | 2-Phenylethyl | methyl | phenyl | H | H | 2,6-dimethyl-4-aminocarbonyl | H |
| 113 | Benzyl | methyl | phenyl | H | H | 2,6-dimethyl-4-aminocarbonyl | H |
| 128 | Cyclohexyl | methyl | phenyl | H | H | 2,6-dimethyl-4-aminocarbonyl | H |
| 144 | Methyl | methyl | phenyl | H | H | 2,6-dimethyl-4-aminocarbonyl | H |
| 180 | Methyl | methyl | phenyl | H | H | 2,6-dimethyl-4-(morpholin-4-ylcarbonyl) | H |
| 182 | Methyl | methyl | phenyl | H | H | 2,6-dimethyl-4-ethylaminocarbonyl | H |
| 184 | Methyl | methyl | phenyl | H | H | 2,6-dimethyl-4-methylaminocarbonyl | H |
| 203 | Methyl | methyl | phenyl | H | H | 4-aminocarbonyl | H |
| 206 | Methyl | methyl | phenyl | H | H | 2,6-dimethyl-4-hydroxy | H |
| 208 | H | methyl | phenyl | H | H | 2,6-dimethyl-4-hydroxy | H |
| 210 | Methyl | methyl | phenyl | H | H | 4-hydroxy | H |
| 212 | H | methyl | phenyl | H | H | 4-hydroxy | H |
| 214 | Ethyl | methyl | phenyl | H | H | 4-hydroxy | H |
| 217 | Ethyl | methyl | phenyl | H | H | 2,6-dimethyl-4-hydroxy | H |
| 220 | Benzyl | methyl | phenyl | H | H | 2,6-dimethyl-4-hydroxy | H |
| 221 | Benzyl | methyl | phenyl | H | H | 4-hydroxy | H |
| 222 | Isopropyl | methyl | phenyl | H | H | 4-hydroxy | H |
| 223 | Isopropyl | methyl | phenyl | H | H | 2,6-dimethyl-4-hydroxy | H |
| 228 | 3-Carboxy-phenylmethyl | methyl | 4-chlorophenyl | Me | H | 2,6-dimethyl-4-aminocarbonyl | H |
| 276 | 3-Carboxy-phenyl | methyl | 4-chlorophenyl | Me | H | 4-aminocarbonyl | H |
| 278 | 3-Carboxy-4-methoxy-phenylmethyl | methyl | 4-chlorophenyl | Me | H | 2,6-dimethyl-4-aminocarbonyl | H |
| 280 | 3-Methoxycarbonyl-4-methoxy-phenylmethyl | methyl | phenyl | H | H | 2,6-dimethyl-4-aminocarbonyl | H |
| 281 | 3-Methoxycarbonyl-4-methoxy-phenylmethyl | methyl | phenyl | H | H | 4-aminocarbonyl | H |
| 282 | 3-Carboxy-4-methoxy-phenylmethyl | methyl | phenyl | H | H | 2,6-dimethyl-4-aminocarbonyl | H |
| 283 | 3-Carboxy-4-methoxy-phenylmethyl | methyl | phenyl | H | H | 4-aminocarbonyl | H |
| 294 | 3-Carboxy-4-methoxy-phenylmethyl | methyl | 4-chlorophenyl | Me | H | 4-hydroxy | H |
| 314 | 6-Methoxycarbonyl-pyridin-2-ylmethyl | methyl | phenyl | H | H | 2,6-dimethyl-4-aminocarbonyl | H |
| 318 | 3-Carboxy-4-methoxy-phenylmethyl | methyl | 4-chlorophenyl | H | H | 4-aminocarbonyl | H |

Another embodiment is directed to compositions comprised of a compound of Formula (Id):

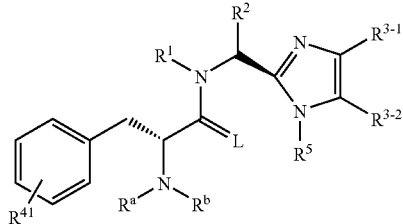

Formula (Id)

wherein in one embodiment of this invention the variables are as previously defined. In another embodiment of the present invention L is oxygen and $R^1$, $R^2$, $R^{3-1}$, $R^{3-2}$, $R^5$, $R^a$, $R^b$, and $R^{41}$ are dependently selected from the group consisting of:

TABLE III

| Cpd | $R^1$ | $R^2$ | $R^{3-1}$ | $R^{3-2}$ | $R^5$ | $R^{41}$ | $R^a/R^b$ |
|---|---|---|---|---|---|---|---|
| 273 | 3-Carboxy-4-methoxyphenylmethyl | methyl | phenyl | H | H | 4-aminocarbonyl | H |

Exemplified compounds of the present invention include compounds of Formula (Ie):

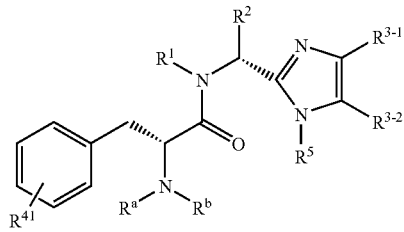

Formula (Ie)

wherein in one embodiment of this invention the variables are as previously defined. In another embodiment of the present invention L is O and $R^1$, $R^2$, $R^{3-1}$, $R^{3-2}$, $R^5$, $R^a$, $R^b$, and $R^{41}$ are dependently selected from the group consisting of:

TABLE IV

| Cpd | $R^1$ | $R^2$ | $R^{3-1}$ | $R^{3-2}$ | $R^5$ | $R^{41}$ | $R^a/R^b$ |
|---|---|---|---|---|---|---|---|
| 284 | 3-Methoxycarbonyl-4-methoxyphenylmethyl | methyl | phenyl | H | H | 4-aminocarbonyl | H |
| 285 | 3-Carboxy-4-methoxyphenylmethyl | methyl | phenyl | H | H | 4-aminocarbonyl | H |

A further embodiment of the present invention includes representative compounds shown in Table V:

TABLE V

| Cpd | |
|---|---|
| 4 | 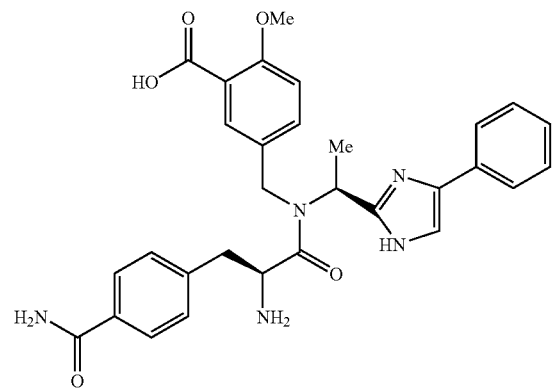 |
| 6 | 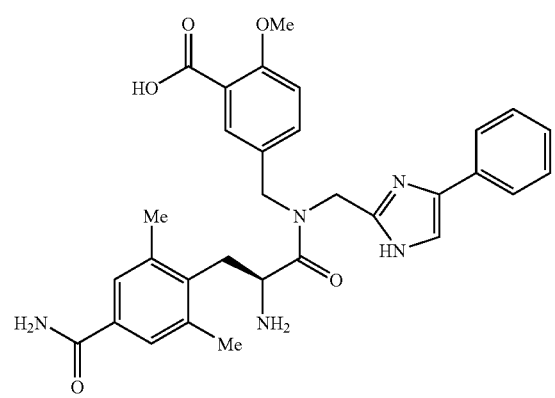 |

TABLE V-continued

| Cpd | |
|---|---|
| 8 | (structure) |
| 12 | (structure) |
| 18 | (structure) |
| 20 | (structure) |

TABLE V-continued

| Cpd | |
|---|---|
| 75 | (structure: 3,4-dimethoxybenzyl group attached to N, linked to 1-(4-phenyl-1H-imidazol-2-yl)ethyl; amide with α-amino-CH2-[2,6-dimethyl-4-carbamoylphenyl]) |
| 227 | (structure: 3-carboxybenzyl group attached to N, linked to 1-(4-phenyl-1H-imidazol-2-yl)ethyl; amide with α-amino-CH2-[2,6-dimethyl-4-carbamoylphenyl]) |

The compounds of the present invention may also be present in the form of pharmaceutically acceptable salts. For use in medicine, the salts of the compounds of this invention refer to non-toxic "pharmaceutically acceptable salts" (Ref. International J. Pharm., 1986, 33, 201-217; J. Pharm. Sci., 1997 (January), 66, 1, 1). Other salts may, however, be useful in the preparation of compounds according to this invention or of their pharmaceutically acceptable salts. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic acid. Representative organic or inorganic bases include, but are not limited to, basic or cationic salts such as benzathine, chloroprocaine, choline, diethanolamine, ethylenediamine, meglumine, procaine, aluminum, calcium, lithium, magnesium, potassium, sodium and zinc.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the subject. Conventional procedures for the selection and preparation of suitable prodrug derivatives are described, for example, in "Design of Prodrugs", ed. H. Bundgaard, Elsevier, 1985.

Where the compounds according to this invention have at least one chiral center, they may accordingly exist as enantiomers. Where the compounds possess two or more chiral centers, they may additionally exist as diastereomers. Where the processes for the preparation of the compounds according to the invention give rise to mixtures of stereoisomers, these isomers may be separated by conventional techniques such as preparative chromatography. The compounds may be prepared in racemic form or as individual enantiomers or diastereomers by either stereospecific synthesis or by resolution. The compounds may, for example, be resolved into their component enantiomers or diastereomers by standard techniques, such as the formation of stereoisomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of stereoisomeric esters or amides, followed by chromatographic separation and removal of the chiral auxiliary. Alternatively, the compounds may be resolved using a chiral HPLC column. It is to be understood that all stereoisomers, racemic mixtures, diastereomers and enantiomers thereof are encompassed within the scope of the present invention.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known in the art.

Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

In general, under standard nomenclature rules used throughout this disclosure, the terminal portion of the designated side chain is described first followed by the adjacent functionality toward the point of attachment. Thus, for example, a "phenylC$_1$-C$_6$alkylamidoC$_1$-C$_6$alkyl" substituent refers to a group of the formula:

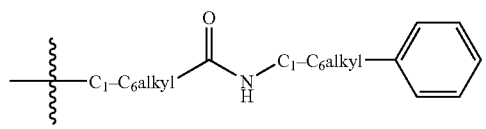

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

An "independently" selected substituent refers to a group of substituents, wherein the substituents may be different. Therefore, designated numbers of carbon atoms (e.g. C$_{1-8}$) shall refer independently to the number of carbon atoms in an alkyl or cycloalkyl moiety or to the alkyl portion of a larger substituent in which alkyl appears as its prefix root.

As used herein, unless otherwise noted, "alkyl" whether used alone or as part of a substituent group refers to straight and branched carbon chains having 1 to 8 carbon atoms or any number within this range. The term "alkoxy" refers to an —Oalkyl substituent group, wherein alkyl is as defined supra. Similarly, the terms "alkenyl" and "alkynyl" refer to straight and branched carbon chains having 2 to 8 carbon atoms or any number within this range, wherein an alkenyl chain has at least one double bond in the chain and an alkynyl chain has at least one triple bond in the chain. An alkyl and alkoxy chain may be substituted on a carbon atom. In substituent groups with multiple alkyl groups such as (C$_{1-6}$alkyl)$_2$amino- the C$_{1-6}$alkyl groups of the dialkylamino may be the same or different.

The term "cycloalkyl" refers to saturated or partially unsaturated, moncyclic or polycyclic hydrocarbon rings of from 3 to 14 carbon atom members. Examples of such rings include, and are not limited to cyclopropyl, cyclobutyl, cyclopentyl, cyclohexyl, cycloheptyl and adamantyl. Alternatively, the cycloalkyl ring may be fused to a benzene ring (benzo fused cycloalkyl), a 5 or 6 membered heteroaryl ring (containing one of O, S or N and, optionally, one additional nitrogen) to form a heteroaryl fused cycloalkyl.

The term "heterocyclyl" refers to a nonaromatic cyclic ring of 5 to 7 members in which 1 to 2 members are nitrogen, or a nonaromatic cyclic ring of 5 to 7 members in which zero, one or two members are nitrogen and up to two members are oxygen or sulfur; wherein, optionally, the ring contains zero to one unsaturated bonds, and, optionally, when the ring is of 6 or 7 members, it contains up to two unsaturated bonds. The term "heterocyclyl" includes a 5 to 7 membered monocyclic heterocyclic ring fused to a benzene ring (benzo fused heterocyclyl), a 5 or 6 membered heteroaryl ring (containing one of O, S or N and, optionally, one additional nitrogen), a 5 to 7 membered cycloalkyl or cycloalkenyl ring, a 5 to 7 membered heterocyclyl ring (of the same definition as above but absent the option of a further fused ring) or fused with the carbon of attachment of a cycloalkyl, cycloalkenyl or heterocyclyl ring to form a spiro moiety. For instant compounds of the invention, the carbon atom ring members that form the heterocyclyl ring are fully saturated. Other compounds of the invention may have a partially saturated heterocyclyl ring. The term "heterocyclyl" also includes a 5 to 7 membered monocyclic heterocycle bridged to form bicyclic rings. Such compounds are not considered to be fully aromatic and are not referred to as heteroaryl compounds. Examples of heterocyclyl groups include, and are not limited to, pyrrolinyl (including 2H-pyrrole, 2-pyrrolinyl or 3-pyrrolinyl), pyrrolidinyl, 2-imidazolinyl, imidazolidinyl, 2-pyrazolinyl, pyrazolidinyl, piperidinyl, morpholinyl, thiomorpholinyl and piperazinyl.

The term "aryl" refers to an unsaturated, aromatic monocyclic ring of 6 carbon members or to an unsaturated, aromatic polycyclic ring of from 10 to 14 carbon members. Examples of such aryl rings include, and are not limited to, phenyl, naphthalenyl or anthracenyl. Preferred aryl groups for the practice of this invention are phenyl and naphthalenyl.

The term "heteroaryl" refers to an aromatic ring of 5 or 6 members wherein the ring consists of carbon atoms and has at least one heteroatom member. Suitable heteroatoms include nitrogen, oxygen or sulfur. In the case of 5 membered rings, the heteroaryl ring contains one member of nitrogen, oxygen or sulfur and, in addition, may contain up to three additional nitrogens. In the case of 6 membered rings, the heteroaryl ring may contain from one to three nitrogen atoms. For the case wherein the 6 membered ring has three nitrogens, at most two nitrogen atoms are adjacent. Optionally, the heteroaryl ring is fused to a benzene ring (benzo fused heteroaryl), a 5 or 6 membered heteroaryl ring (containing one of O, S or N and, optionally, one additional nitrogen), a 5 to 7 membered cycloalkyl ring or a 5 to 7 membered heterocyclo ring (as defined supra but absent the option of a further fused ring). Examples of heteroaryl groups include, and are not limited to, furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl or pyrazinyl; fused heteroaryl groups include indolyl, isoindolyl, indolinyl, benzofuryl, benzothienyl, indazolyl, benzimidazolyl, benzthiazolyl, benzoxazolyl, benzisoxazolyl, benzothiadiazolyl, benzotriazolyl, quinolizinyl, quinolinyl, isoquinolinyl or quinazolinyl.

The term "arylalkyl" means an alkyl group substituted with an aryl group (e.g., benzyl, phenethyl). Similarly, the term "arylalkoxy" indicates an alkoxy group substituted with an aryl group (e.g., benzyloxy).

The term "halogen" refers to fluorine, chlorine, bromine and iodine. Substituents that are substituted with multiple halogens are substituted in a manner that provides compounds, which are stable.

Whenever the term "alkyl" or "aryl" or either of their prefix roots appear in a name of a substituent (e.g., arylalkyl, alkylamino) it shall be interpreted as including those limitations given above for "alkyl" and "aryl." Designated numbers of carbon atoms (e.g., C$_1$-C$_6$) shall refer independently to the number of carbon atoms in an alkyl moiety or to the alkyl portion of a larger substituent in which alkyl appears as its prefix root. For alkyl, and alkoxy substituents the designated number of carbon atoms includes all of the independent member included in the range specified individually and all the combination of ranges within in the range specified. For example $C_{1-6}$ alkyl would include methyl, ethyl, propyl, butyl, pentyl and hexyl individually as well as sub-combinations thereof (e.g. $C_{1-2}$, $C_{1-3}$, $C_{1-4}$, $C_{1-5}$, $C_{2-6}$, $C_{3-6}$, $C_{4-6}$, $C_{5-6}$, $C_{2-5}$, etc.).

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

The novel compounds of the present invention are useful opioid receptor modulators. In particular, certain compounds are opioid receptor agonists useful in the treatment or amelioration of conditions such as pain and gastrointestinal disorders. Examples of pain intended to be within the scope of the present invention include, but are not limited to, centrally mediated pain, peripherally mediated pain, structural or soft tissue injury related pain, pain related to inflammation, progressive disease related pain, neuropathic pain and acute pain such as caused by acute injury, trauma or surgery and chronic pain such as caused by neuropathic pain conditions, diabetic peripheral neuropathy, post-herpetic neuralgia, trigeminal neuralgia, post-stroke pain syndromes or cluster or migraine headaches. Examples of gastrointestinal disorders intended to be within the scope of this invention include, but are not limited to, diarrheic syndromes, motility disorders such as diarrhea-predominant, or alternating irritable bowel syndrome, and visceral pain and diarrhea associated with inflammatory bowel disease including ulcerative colitis and Crohn's disease.

Examples of gastrointestinal disorders where opioid receptor ("OR") antagonists are useful include constipation-predominant irritable bowel syndrome, post-operative ileus and constipation, including but not limited to the constipation associated with treatment of chronic pain with opiates. Modulation of more than one opioid receptor subtype is also useful as follows: a compound that is a mixed mu OR agonist and delta OR antagonist could have antidiarrheal properties without being profoundly constipating. A compound that is a mixed mu OR agonist and delta OR agonist are useful in cases of severe diarrhea that are refractory to treatment with pure mu OR agonists, or has additional utility in treating visceral pain associated with inflammation and diarrhea.

Accordingly, a compound of the present invention may be administered by any conventional route of administration including, but not limited to oral, nasal, pulmonary, sublingual, ocular, transdermal, rectal, vaginal and parenteral (i.e. subcutaneous, intramuscular, intradermal, intravenous etc.). It is currently preferred that the compounds of the present invention be administered via modes of administration other than pulmonary or parenteral administration. However, the preferred compounds provided in Table IV may be administered via pulmonary or parenteral modes of administration.

To prepare the pharmaceutical compositions of this invention, one or more compounds of Formula (I) or salt thereof as the active ingredient, is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

In preparing a pharmaceutical composition of the present invention in liquid dosage form for oral, topical and parenteral administration, any of the usual pharmaceutical media or excipients may be employed. Thus, for liquid dosage forms, such as suspensions (i.e. colloids, emulsions and dispersions) and solutions, suitable carriers and additives include, but are not limited to, pharmaceutically acceptable wetting agents, dispersants, flocculation agents, thickeners, pH control agents (i.e. buffers), osmotic agents, coloring agents, flavors, fragrances, preservatives (i.e. to control microbial growth, etc.) and a liquid vehicle may be employed. Not all of the components listed above will be required for each liquid dosage form.

In solid oral preparations such as, for example, dry powders for reconstitution or inhalation, granules, capsules, caplets, gelcaps, pills and tablets (each including immediate release, timed release and sustained release formulations), suitable carriers and additives include but are not limited to diluents, granulating agents, lubricants, binders, glidants, disintegrating agents and the like. Because of their ease of administration, tablets and capsules represent the most advantageous oral dosage unit form, in which case solid pharmaceutical carriers are obviously employed. If desired, tablets may be sugar coated, gelatin coated, film coated or enteric coated by standard techniques.

The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.01 mg/kg to about 300 mg/kg (preferably from about 0.01 mg/kg to about 100 mg/kg; and, more preferably, from about 0.01 mg/kg to about 30 mg/kg) and may be given at a dosage of from about 0.01 mg/kg/day to about 300 mg/kg/day (preferably from about 0.01 mg/kg/day to about 100 mg/kg/day and more preferably from about 0.01 mg/kg/day to about 30 mg/kg/day). Preferably, the method for the treatment of conditions that may be mediated by opioid receptors described in the present invention using any of the compounds as defined herein, the dosage form will contain a pharmaceutically acceptable carrier containing between from about 0.01 mg to about 100 mg; and, more preferably, from about 5 mg to about 50 mg of the compound, and may be constituted into any form suitable for the mode of administration selected. The dosages, however, may be varied depending upon the requirement of the subjects, the severity of the condition being treated and the compound being employed. The use of either daily administration or post-periodic dosing may be employed.

Preferably these compositions are in unit dosage forms from such as tablets, pills, capsules, dry powders for reconstitution or inhalation, granules, lozenges, sterile solutions or suspensions, metered aerosol or liquid sprays, drops, or suppositories for administration by oral, intranasal, sublingual, intraocular, transdermal, rectal, vaginal, dry powder inhaler or other inhalation or insufflation means.

For preparing solid pharmaceutical compositions such as tablets, the principal active ingredient is mixed with a pharmaceutical carrier, e.g. conventional tableting ingredients such as diluents, binders, adhesives, disintegrants, lubricants, antiadherents and gildants. Suitable diluents include, but are not limited to, starch (i.e. corn, wheat, or potato starch, which may be hydrolized), lactose (granulated, spray dried or anhydrous), sucrose, sucrose-based diluents (confectioner's sugar; sucrose plus about 7 to 10 weight percent invert sugar; sucrose plus about 3 weight percent modified dextrins; sucrose plus invert sugar, about 4 weight percent invert sugar, about 0.1 to 0.2 weight percent cornstarch and magnesium stearate), dextrose, inositol, mannitol, sorbitol, microcrystalline cellulose (i.e. AVICEL™ microcrystalline cellulose available from FMC Corp.), dicalcium phosphate, calcium sulfate dihydrate, calcium lactate trihydrate and the like. Suitable binders and adhesives include, but are not limited to acacia gum, guar gum, tragacanth gum, sucrose, gelatin, glucose, starch, and cellulosics (i.e. methylcellulose, sodium carboxymethylcellulose, ethylcellulose, hydroxypropylmethylcellulose, hydroxypropylcellulose, and the like), water soluble or dispersible binders (i.e. alginic acid and salts thereof, magnesium aluminum silicate, hydroxyethylcellulose [i.e. TYLOSE™ available from Hoechst Celanese], polyethylene glycol, polysaccharide acids, bentonites, polyvinylpyrrolidone, polymethacrylates and pregelatinized starch) and the like. Suitable disintegrants include, but are not limited to, starches (corn, potato, etc.), sodium starch glycolates, pregelatinized starches, clays (magnesium aluminum silicate), celluloses (such as crosslinked sodium carboxymethylcellulose and microcrystalline cellulose), alginates, pregelatinized starches (i.e. corn starch, etc.), gums (i.e. agar, guar, locust bean, karaya, pectin, and tragacanth gum), crosslinked polyvinylpyrrolidone and the like. Suitable lubricants and antiadherents include, but are not limited to, stearates (magnesium, calcium and sodium), stearic acid, talc waxes, stearowet, boric acid, sodium chloride, DL-leucine, carbowax 4000, carbowax 6000, sodium oleate, sodium benzoate, sodium acetate, sodium lauryl sulfate, magnesium lauryl sulfate and the like. Suitable gildants include, but are not limited to, talc, cornstarch, silica (i.e. CAB-O-SIL™ silica available from Cabot, SYLOID™ silica available from W. R. Grace/Davison, and AEROSIL™ silica available from Degussa) and the like. Sweeteners and flavorants may be added to chewable solid dosage forms to improve the palatability of the oral dosage form. Additionally, colorants and coatings may be added or applied to the solid dosage form for ease of identification of the drug or for aesthetic purposes. These carriers are formulated with the pharmaceutical active to provide an accurate, appropriate dose of the pharmaceutical active with a therapeutic release profile.

Generally these carriers are mixed with the pharmaceutical active to form a solid preformulation composition containing a homogeneous mixture of the pharmaceutical active of the present invention, or a pharmaceutically acceptable salt thereof. Generally the preformulation will be formed by one of three common methods: (a) wet granulation, (b) dry granulation and (c) dry blending. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from about 0.1 mg to about 500 mg of the active ingredient of the present invention. The tablets or pills containing the novel compositions may also be formulated in multilayer tablets or pills to provide a sustained or provide dual-release products. For example, a dual release tablet or pill can comprise an inner dosage and an outer dosage component, the latter being in the form of an envelope over the former. The two components can be separated by an enteric layer, which serves to resist disintegration in the stomach and permits the inner component to pass intact into the duodenum or to be delayed in release. A variety of materials can be used for such enteric layers or coatings, such materials including a number of polymeric materials such as shellac, cellulose acetate (i.e. cellulose acetate phthalate, cellulose acetate trimetllitate), polyvinyl acetate phthalate, hydroxypropyl methylcellulose phthalate, hydroxypropyl methylcellulose acetate succinate, methacrylate and ethylacrylate copolymers, methacrylate and methyl methacrylate copolymers and the like. Sustained release tablets may also be made by film coating or wet granulation using slightly soluble or insoluble substances in solution (which for a wet granulation acts as the binding agents) or low melting solids a molten form (which in a wet granulation may incorporate the active ingredient). These materials include natural and synthetic polymers waxes, hydrogenated oils, fatty acids and alcohols (i.e. beeswax, carnauba wax, cetyl alcohol, cetylstearyl alcohol, and the like), esters of fatty acids metallic soaps, and other acceptable materials that can be used to granulate, coat, entrap or otherwise limit the solubility of an active ingredient to achieve a prolonged or sustained release product.

The liquid forms in which the novel compositions of the present invention may be incorporated for administration orally or by injection include, but are not limited to aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable suspending agents for aqueous suspensions, include synthetic and natural gums such as, acacia, agar, alginate (i.e. propylene alginate, sodium alginate and the like), guar, karaya, locust bean, pectin, tragacanth, and xanthan gum, cellulosics such as sodium carboxymethylcellulose, methylcellulose, hydroxymethylcellulose, hydroxyethylcellulose, hydroxypropyl cellulose and hydroxypropyl methylcellulose, and combinations thereof, synthetic polymers such as polyvinyl pyrrolidone, carbomer (i.e. carboxypolymethylene), and polyethylene glycol; clays such as bentonite, hectorite, attapulgite or sepiolite; and other pharmaceutically acceptable suspending agents such as lecithin, gelatin or the like. Suitable surfactants include but are not limited to sodium docusate, sodium lauryl sulfate, polysorbate, octoxynol-9, nonoxynol-10, polysorbate 20, polysorbate 40, polysorbate 60, polysorbate 80, polyoxamer 188, polyoxamer 235 and combinations thereof. Suitable deflocculating or dispersing agent include pharmaceutical grade lecithins. Suitable flocculating agent include but are not limited to simple neutral electrolytes (i.e. sodium chloride, potassium, chloride, and the like), highly charged insoluble polymers and polyelectrolyte species, water soluble divalent or trivalent ions (i.e. calcium salts, alums or sulfates, citrates and phosphates (which can be used jointly in formulations as pH buffers and flocculating agents). Suitable preservatives include but are not limited to parabens (i.e. methyl, ethyl, n-propyl and n-butyl), sorbic acid, thimerosal, quaternary ammonium salts, benzyl alcohol, benzoic acid, chlorhexidine gluconate, phenylethanol and the like. There are many liquid vehicles that may be used in liquid pharmaceutical dosage forms, however, the liquid vehicle that is used in a particular dosage form must be compatible with the suspending agent(s). For example, nonpolar liquid vehicles such as fatty esters and oils liquid vehicles are best used with suspending agents such as low HLB (Hydrophile-Lipophile Balance) surfactants, stearalkonium hectorite, water insoluble resins, water insoluble film forming polymers and the like. Conversely, polar liquids such as water, alcohols, polyols and glycols are best used with suspending agents such as higher HLB surfactants, clays silicates, gums, water soluble cellulosics, water soluble polymers and the like.

Furthermore, compounds of the present invention can be administered in an intranasal dosage form via topical use of suitable intranasal vehicles or via transdermal skin patches, the composition of which are well known to those of ordinary skill in that art. To be administered in the form of a transdermal delivery system, the administration of a therapeutic dose will, of course, be continuous rather than intermittent throughout the dosage regimen.

Compounds of this invention may be administered in any of the foregoing compositions and dosage regimens or by means of those compositions and dosage regimens established in the art whenever treatment of disorders that may be mediated or ameliorated by opioid receptors for a subject in need thereof.

The daily dose of a pharmaceutical composition of the present invention may be varied over a wide range from about 0.1 mg to about 7000 mg per adult human per day; most preferably the dose will be in the range of from about 0.7 mg to about 2100 mg per adult human per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the subject to be treated. An effective amount of the drug is ordinarily supplied at a dosage level of from about 0.01 mg/kg to about 300 mg/kg of body weight per day. Preferably, the range is from about 0.01 mg/kg to about 100 mg/kg of body weight per day; and, most preferably, from about 0.01 mg/kg to about 30 mg/kg of body weight per day. Advantageously, a compound of the present invention may be administered in a single daily dose or the total daily dosage may be administered in divided doses of two, three or four times daily.

Optimal dosages to be administered may be readily determined by those skilled in the art, and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level.

Representative IUPAC names for the compounds of the present invention were derived using the AutoNom version 2.1 nomenclature software program provided by Beilstein Informationssysteme.

Abbreviations used in the instant specification, particularly the Schemes and Examples, are as follows:
BOC=tert-butoxycarbonyl
BuLi=n-butyllithium
CBZ=benzyloxycarbonyl
Cpd or Cmpd=compound
d=day/days
DIPEA diisopropylethylamine
DPPF=1,1'-bis(diphenylphosphino)ferrocene
DPPP=1,3-Bis(diphenylphosphino)propane
EDCI or EDC=1-[3-(dimethylamino)propyl]-3-ethylcarbodiimide hydrochloride
EtOAc=ethyl acetate
EtOH=ethanol
h=hour/hours
HMDS=1,1,3,3-Hexamethyldisilazane
HOBt/HOBT=hydroxybenzotiazole
M=molar
MeCN=acetonitrile
MeOH=methanol
min=minutes
PyBOP=Benzotriazol-1-yl-oxy-tris-pyrrolidinophosphonium hexafluorophosphate
rt/RT=room temperature
TFA=trifluoroacetic acid
OTf=triflate
Ts=tosyl

SYNTHETIC METHODS

Representative compounds of the present invention can be synthesized in accordance with the general synthetic methods described below and are illustrated more particularly in the schemes that follow. Since the schemes are an illustration, the invention should not be construed as being limited by the chemical reactions and conditions expressed. The preparation of the various starting materials used in the schemes is well within the skill of persons versed in the art.

The following schemes describe general synthetic methods whereby intermediate and target compounds of the present invention may be prepared. Additional representative compounds and stereoisomers, racemic mixtures, diasteromers and enantiomers thereof can be synthesized using the intermediates prepared in accordance to the general schemes and other materials, compounds and reagents known to those skilled in the art. All such compounds, stereoisomers, racemic mixtures, diasteromers and enantiomers thereof are intended to be encompassed within the scope of the present invention.

Certain intermediates and compounds of the present invention may be prepared according to the process outlined in Scheme A below.

Scheme A

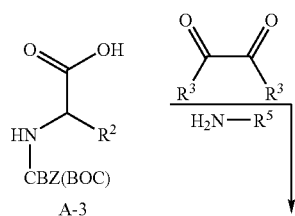

A-3

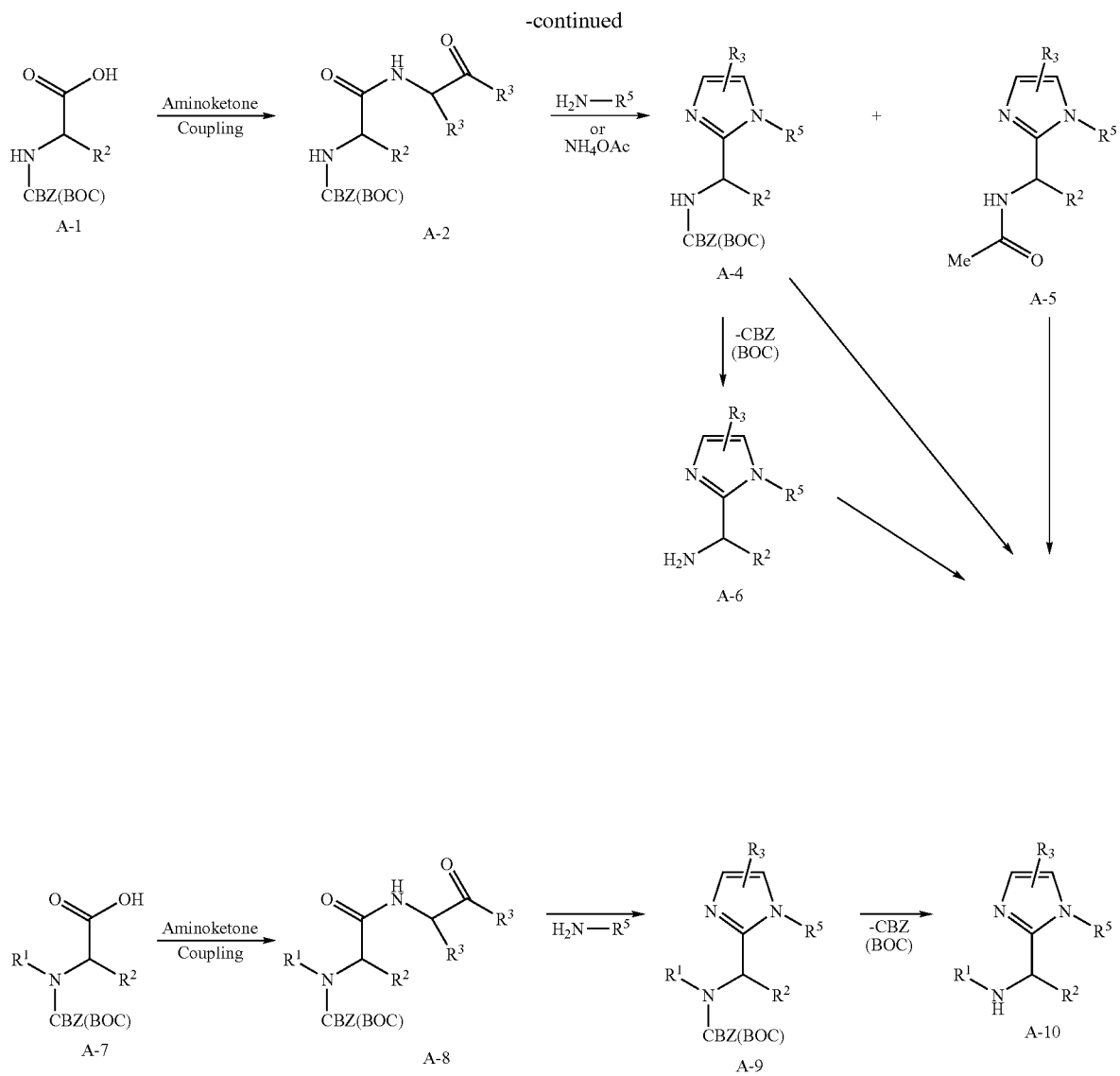

A carboxylic acid of the formula A-1, available either commercially or prepared by reported protocols in the scientific literature, may be coupled to an α-aminoketone using standard peptide coupling conditions with a coupling agent such as EDCI and an additive such as HOBt to provide a compound of formula A-2. Compound A-2 may be condensed with an amine of the formula $H_2N-R_5$ or ammonium acetate and cyclized upon heating in acetic acid to a compound of formula A-4.

The protecting group of compound A-4 may be removed using conditions known to those skilled in the art that are appropriate for the particular protecting group to afford a compound of the formula A-6. For instance, hydrogenation in the presence of a palladium catalyst is one method for the removal of a CBZ protecting group, whereas treatment with an acid such as TFA is effective for a BOC group deprotection.

A compound of formula A-6 may be substituted using reductive amination with an appropriately substituted aldehyde or ketone in the presence of a hydride source, such as sodium borohydride or sodium triacetoxyborohydride, provide compounds of formula A-10.

Alternatively, a compound of formula A-3 may be condensed with a dicarbonyl compound of the formula $R_3(C=O)_2R_3$ and an amine of the formula $H_2N-R_5$ upon heating in acetic acid to afford a compound of the formula A-4. When compound A-3 is protected with a BOC group, a by-product of formula A-5 may be produced. Compounds of formula A-4 or A-5 may be treated with a hydride source such as lithium aluminum hydride to give certain compounds of formula A-10.

Similarly, a compound of formula A-7 may be coupled to an α-aminoketone as described above for compounds of formula A-1 to yield the corresponding compounds of formula A-8. A compound of formula A-8 may then be cyclized in the presence of an amine of formula $H_2N-R_5$ or ammonium acetate and subsequently deprotected as described above to arrive at compounds of formula A-10.

Certain compounds of the present invention may be prepared according to the process outlined in Scheme B below.

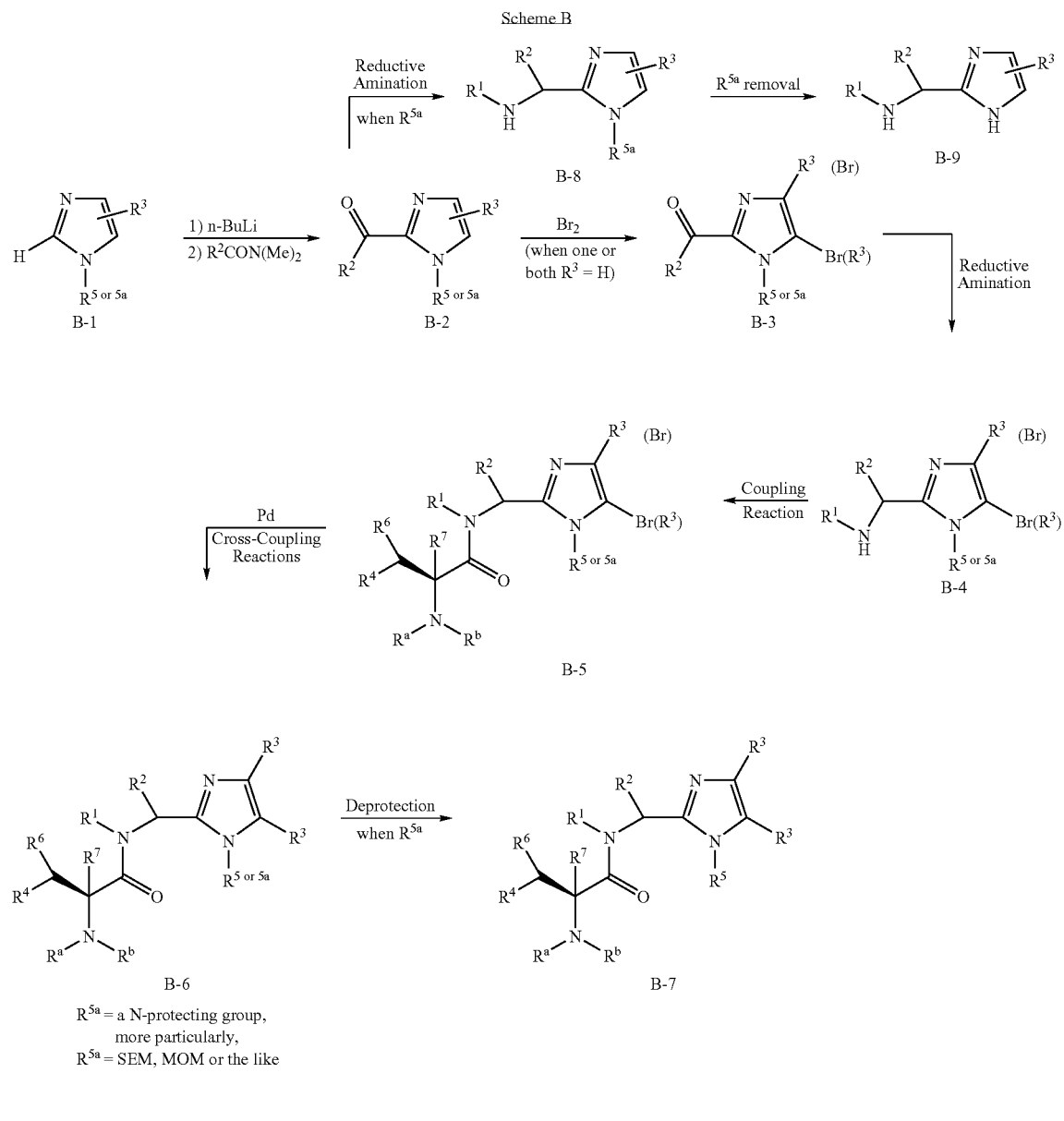

Scheme B $R^{5a}$ = a N-protecting group, more particularly,
$R^{5a}$ = SEM, MOM or the like More specifically, a compound of formula B-1 (wherein the imidazole nitrogen is substituted with $R^5$, as defined herein, or $R^{5a}$, a nitrogen protecting group such as SEM, MOM, or the like) may be deprotonated with an organometallic base such as n-butyllithium and then treated with a suitably substituted amide to yield a compound of formula B-2.

Compound B-2 may be brominated to yield a mixture of regioisomers of formula B-3. A compound of formula B-3 may be further elaborated via a reductive amination with an amine of the formula $H_2N-R^1$ in the presence of a hydride source as described in Scheme A to afford a compound of formula B-4.

The amine of a compound of formula B-4 may be coupled with a suitable carboxylic acid under standard peptide coupling conditions with a coupling agent such as EDCI and an additive such as HOBt to yield compounds of formula B-5.

Certain $R^3$ substituents of the present invention in which a carbon atom is the point of attachment may be introduced into a compound of formula B-5 through a transition metal-catalyzed cross coupling reaction to afford compounds of formula B-6. Suitable palladium catalysts include palladium tetrakis triphenylphosphine and the like. Suitable Lewis acids for the reaction include boronic acids and the like. Compounds protected with $R^{5a}$ may be deprotected under acidic conditions to yield compounds of formula B-7.

In a similar manner, an intermediate B-2 when optionally protected with. $R^{5a}$ may be reductively alkylated using methods described above to give a compound of formula B-8, followed by removal of protecting group $R^{5a}$ using conditions described herein to yield a compound of formula B-9.

One skilled in the art will recognize that substituent L (depicted as O in the formulae of Scheme B) may be further elaborated to S or $N(R^d)$ of the present invention using conventional, known chemical methods.

Certain compounds of the present invention may be prepared according to the process outlined in Scheme C below.

Scheme C

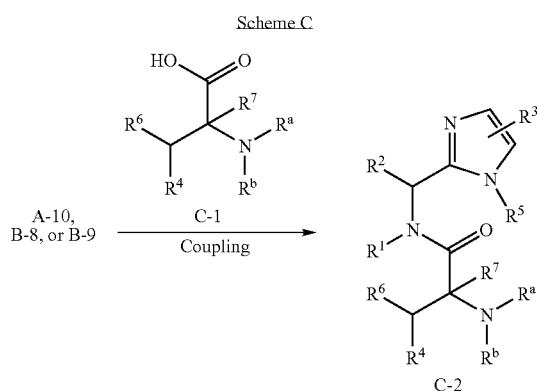

More specifically, a compound of formula A-10, B-8, or B-9 may be elaborated to a compound of formula C-2 through coupling with a suitable carboxylic acid under standard peptide coupling conditions as described above. One skilled in the art will recognize that substituent L in a compound of formula C-2 (depicted as O) may be converted to S or N($R^d$) of the present invention using conventional, known chemical methods.

Suitably substituted carboxylic acids of the present invention may either be commercially available or prepared by reported protocols in the scientific literature. Several chemical routes for preparing certain compounds of formula C-1 are outlined below in Schemes D and E.

Specifically, a compound of formula D-1 may be treated with trifluoromethanesulfonic anhydride to afford the triflate compound of formula D-2. A compound of formula D-2 may be converted to a compound of formula D-4 by a variety of chemical routes which utilize conventional chemical methods known to those skilled in the art. For example, the bromo group of a compound of formula D-2 may undergo a carboxylation reaction via an initial carbonylation under a carbon monoxide atmosphere in the presence of an appropriate palladium catalyst and DPPF, followed by an aqueous basic workup to afford a compound of formula D-3. Subsequently, the carboxyl group may be converted to a substituent of $R^{41a}$ of formula D-4 using standard peptide coupling conditions. Alternatively, a compound of formula D-4 may be directly prepared via a carbonylation of compound of formula D-2, followed by treatment with HMDS, or a primary or secondary amine.

The compound of formula D-5, known or prepared by known methods, may be treated with EDC in the presence of copper (I) chloride to afford the corresponding alkene of formula D6. A compound of formula D-6 may then undergo a Heck reaction with a compound of formula D-4 in the presence of an appropriate palladium catalyst and phosphino ligand to afford a compound of formula D7. Subsequent hydrogenation of the alkenyl substituent using standard hydrogen reduction methods affords a compound of formula D-8.

Scheme E demonstrates an alternative method for preparing intermediate D-7 of the present invention. A compound of formula E-1 may be elaborated to a compound of formula E-4 using the appropriately adapted synthetic steps described in Scheme D. One skilled in the art will recognize that this

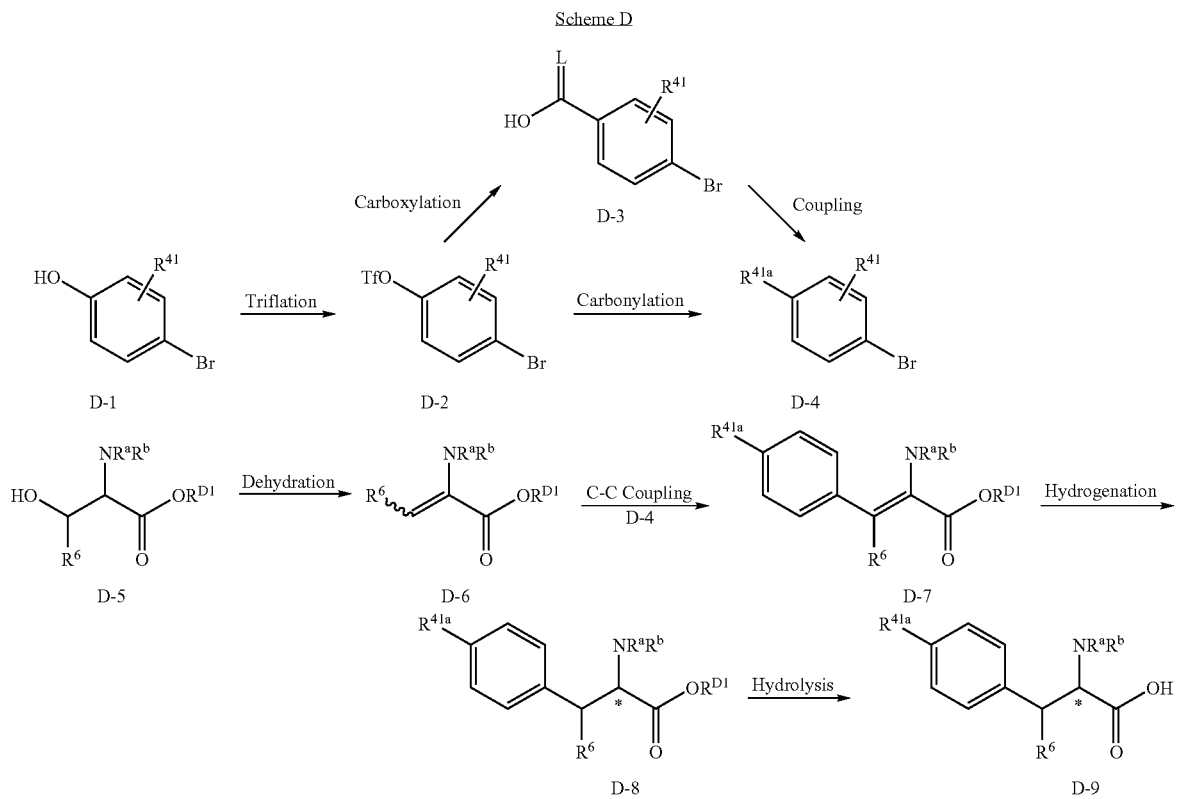

$R^{41a}$ = aminocarbonyl, $C_{1-6}$alkylaminocarbonyl, or ($C_{1-6}$alkyl)$_2$aminocarbonyl;
$R^{D1}$ = H, $C_{1-6}$alkyl, or aryl($C_{1-6}$)alkyl transformation may be achieved by manipulation of the reaction sequence. A compound of formula E-4 may be converted to its corresponding nitrile via an aromatic nucleophilic displacement reaction with cyanide anion. One skilled in the art will recognize that a nitrile substituent is a viable synthon for a substituent of $R^{41a}$.

A compound of formula E-4 may participate in a Horner-Wadsworth-Emmons reaction with a compound of formula E-7 in the presence of an organometallic base such as n-butyllithiium to afford a compound of formula D-7. This intermediate may be further elaborated as described in Scheme D, herein.

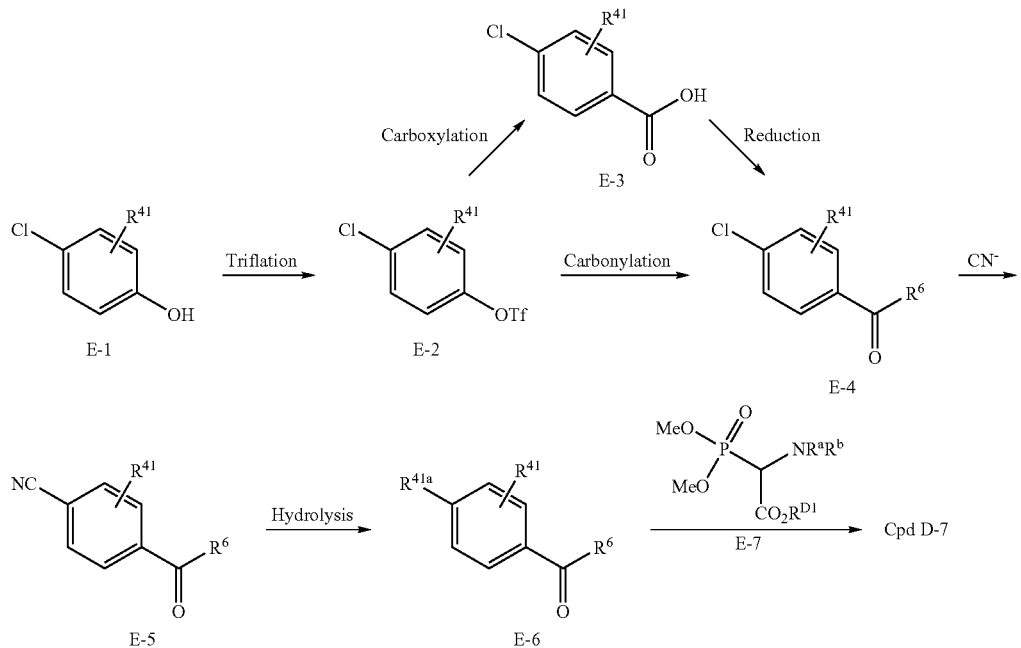

Certain compounds of the present invention may be prepared according to the process outlined in Scheme F below.

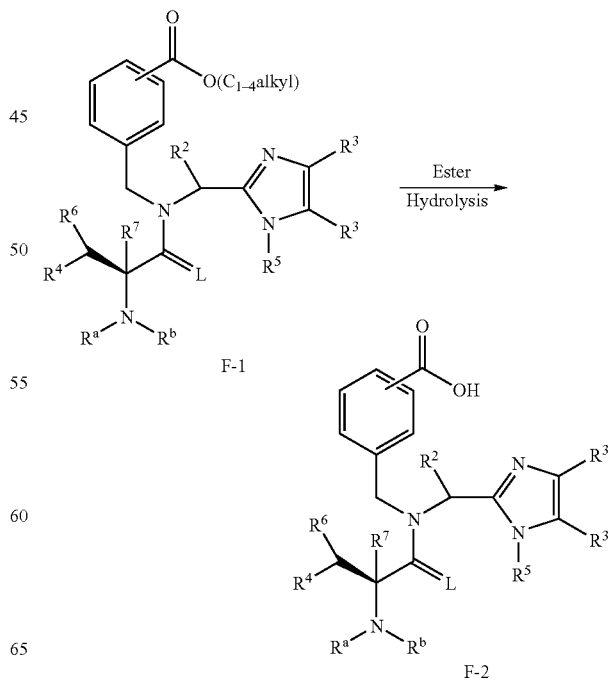

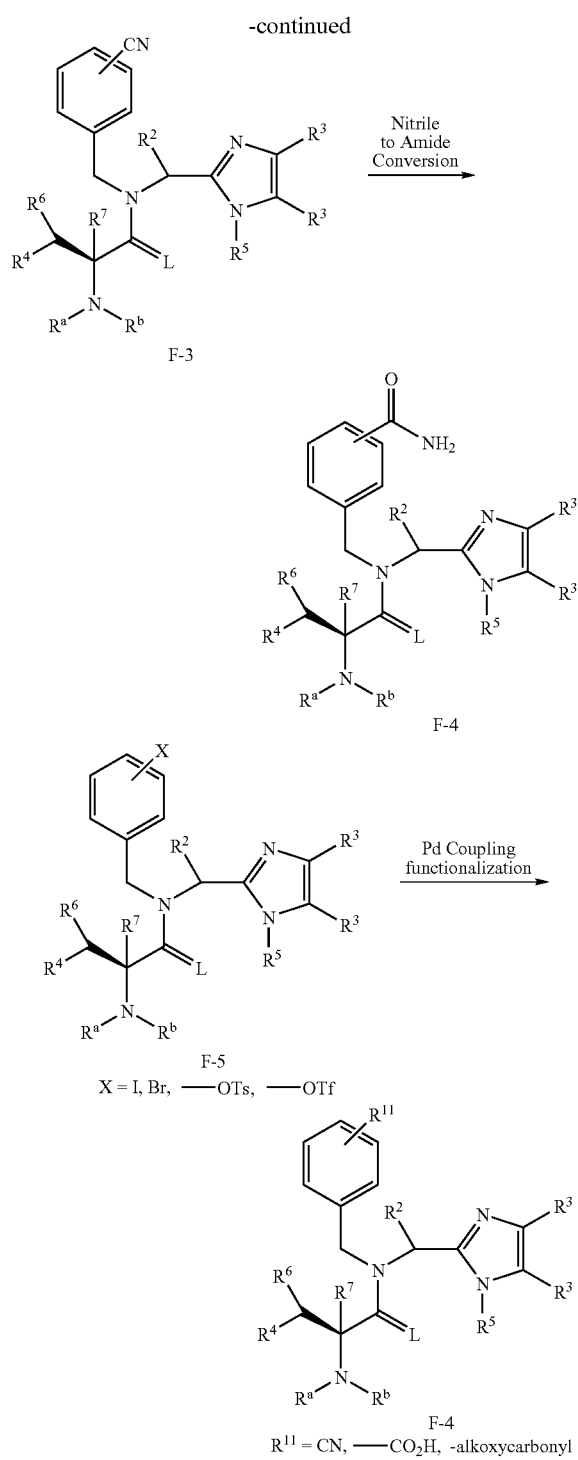

X = I, Br, —OTs, —OTf

F-5

$R^{11}$ = CN, —CO$_2$H, -alkoxycarbonyl

F-4

More specifically, a compound of formula F-1, wherein $R^{11}$ is an alkoxycarbonyl as defined above, may be saponified to its corresponding acid, a compound of formula F-2.

A compound of formula F-3 wherein $R^{11}$ is a cyano substituent may be elaborated to its corresponding aminocarbonyl, compound F-4 by treatment with hydrogen peroxide in the presence of hydroxide anion. Similarly, when $R^3$ is a cyano-substituted aryl ring, it may be treated as described above to form an aminocarbonyl-substituted aryl ring.

Certain substitutents of $R^{11}$ may be installed via a palladium catalyzed coupling reaction with an X-substituted precursor. For example, a compound of formula F-5 wherein X is iodide, bromide, tosylate, triflate, or the like may be treated with $Zn(CN)_2$ in the presence of palladium tetrakis triphenylphosphine to give a compound of formula F-6 wherein $R^{11}$ is cyano.

Treatment of a compound of formula F-5 with $Pd(OAc)_2$ and a ligand such as 1,1-bis(diphenylphosphino)ferrocene under a carbon monoxide atmosphere provides a compound of formula F-6 wherein $R^{11}$ is a carboxy substituent.

The palladium catalyzed couplings described above may also be used to install cyano, carboxy, and alkoxycarbonyl substituents onto an aryl ring at $R^3$.

SPECIFIC EXAMPLES

Specific compounds which are representative of this invention were prepared as per the following examples and reaction sequences; the examples and the diagrams depicting the reaction sequences are offered by way of illustration, to aid in the understanding of the invention and should not be construed to limit in any way the invention set forth in the claims which follow thereafter. The instant compounds may also be used as intermediates in subsequent examples to produce additional compounds of the present invention. No attempt has been made to optimize the yields obtained in any of the reactions. One skilled in the art would know how to increase such yields through routine variations in reaction times, temperatures, solvents and/or reagents.

Reagents were purchased from commercial sources. Nuclear magnetic resonance (NMR) spectra for hydrogen atoms were measured in the indicated solvent with (TMS) as the internal standard on a Bruker Biospin, Inc. DPX-300 (300 MHz) spectrometer. The values are expressed in parts per million down field from TMS. The mass spectra (MS) were determined on a Micromass Platform LC spectrometer or an Agilent LC spectrometer using electrospray techniques. Microwave accelerated reactions were performed using either a CEM Discover or a Personal Chemistry Smith Synthesizer microwave instrument. Stereoisomeric compounds may be characterized as racemic mixtures or as separate diastereomers and enantiomers thereof using X-ray crystallography and other methods known to one skilled in the art. Unless otherwise noted, the materials used in the examples were obtained from readily available commercial suppliers or synthesized by standard methods known to one skilled in the art of chemical synthesis. The substituent groups, which vary between examples, are hydrogen unless otherwise noted.

Example 1

2-Amino-3-(4-hydroxy-2,6-dimethyl-phenyl)-N-isopropyl-N-[1-(4-phenyl-1H-imidazol-2-yl)-ethyl]-propionamide

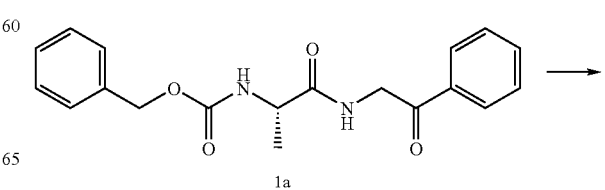

1a

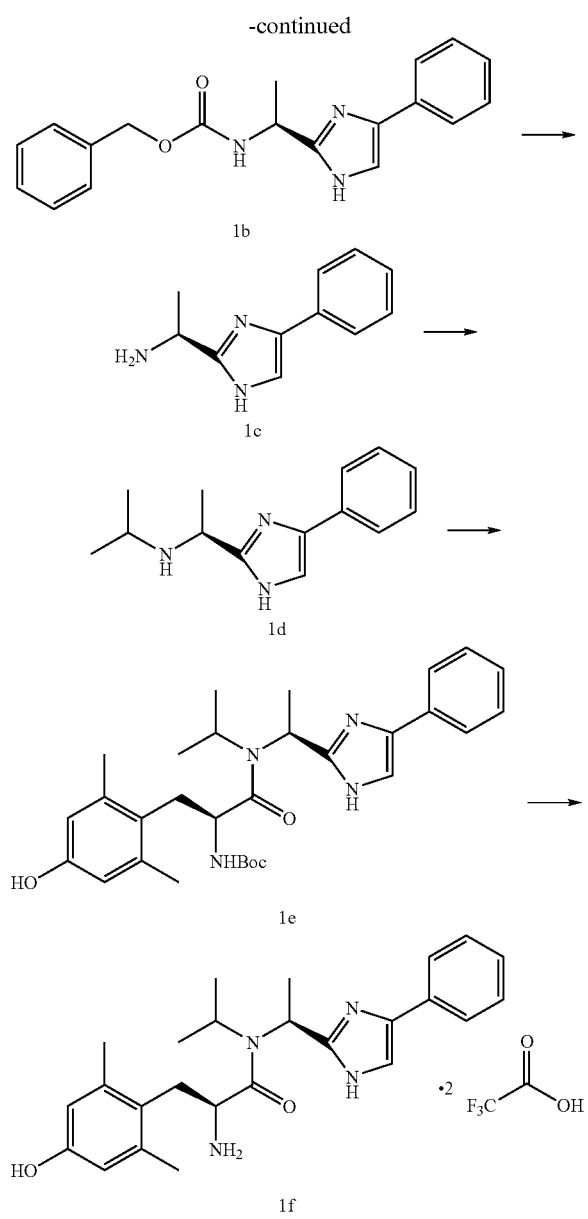

A. [1-(2-Oxo-2-phenyl-ethylcarbamoyl)-ethyl]-carbamic acid benzyl ester. To a solution of commercially available N-α-CBZ-L-alanine (2.11 g, 9.5 mmol) in dichloromethane (50 mL) was added 2-aminoacetophenone hydrochloride (1.62 g, 9.5 mmol). The resulting solution was cooled to 0° C. and N-methylmorpholine (1.15 g, 11 mmol), 1-hydroxybenzotriazole (2.55 g, 18.9 mmol) and 1-[3-(dimethylamino)propyl]-3-ethylcarbodiimide hydrochloride (2.35 g, 12.3 mmol) in that order were added under an Argon atmosphere. The reaction mixture was warmed to room temperature and stirred overnight. The reaction was quenched by addition of saturated aqueous NaHCO$_3$ solution; the separated organic phase was washed with 2N citric acid, saturated NaHCO$_3$ solution and brine, then dried over MgSO$_4$ overnight. After filtration and concentration, the residue was purified by column chromatography on silica gel (eluent, EtOAc:hexane-1:1) to give the pure product: [1-(2-oxo-2-phenyl-ethylcarbamoyl)-ethyl]-carbamic acid benzyl ester (2.68 g, 83%). $^1$H NMR (300 MHz, CDCl$_3$): δ 1.46 (3H, d), 4.39 (1H, m), 4.75 (2H, d), 5.13 (2H, d), 5.40 (1H, m), 7.03 (1H, m), 7.36 (5H, m), 7.50 (2H, m), 7.63 (1H, m), 7.97(2H, m).

MS(ES$^+$): 341.1 (100%).

B. [1-(4-Phenyl-1H-imidazol-2-yl)-ethyl]-carbamic acid benzyl ester. To a suspension of [1-(2-oxo-2-phenyl-ethylcarbamoyl)-ethyl]-carbamic acid benzyl ester (2.60 g, 7.64 mmol) in xylene (60 mL) was added NH$_4$OAc (10.3 g, 134 mmol) and HOAc (5 mL). The resulting mixture was heated at reflux for 7 h. After being cooled to room temperature, brine was added and the mixture was separated. The aqueous phase was extracted with EtOAc, and the combined organic phases were dried over Na$_2$SO$_4$ overnight. After filtration and concentration, the residue was purified by column chromatography on silica gel (eluent, EtOAc:hexane-1:1) to give the title compound (2.33 g, 95%). $^1$H NMR (300 MHz, CDCl$_3$): δ 1.65 (3H, d), 5.06 (1H, m), 5.14 (2H, q), 5.94 (1H, d), 7.32 (10H, m), 7.59 (2H, d). MS(ES$^+$): 322.2 (100%).

C. 1-(4-Phenyl-1H-imidazol-2-yl)-ethylamine. To a solution of [1-(4-phenyl-1H-imidazol-2-yl)-ethyl]-carbamic acid benzyl ester (1.5 g, 4.67 mmol) in methanol (25 mL) was added 10% palladium on carbon (0.16 g). The mixture was shaken in a hydrogenation apparatus at rt under a hydrogen atmosphere (10 psi) for 8 h. Filtration followed by evaporation to dryness under reduced pressure gave the crude product 1-(4-Phenyl-1H-imidazol-2-yl)-ethylamine (0.88 g, 100%). $^1$H NMR (300 MHz, CDCl$_3$): δ 1.53 (3H, d), 4.33 (1H, q), 7.23 (3H, m), 7.37 (2H, m), 7.67 (2H, m). MS(ES$^+$): 188.1 (38%).

D. Isopropyl-[1-(4-phenyl-1H-imidazol-2-yl)-ethyl]-amine. 1-(4-Phenyl-1H-imidazol-2-yl)-ethylamine (0.20 g, 1.07 mmol) and acetone (0.062 g, 1.07 mmol) were mixed in 1,2-dichloroethane (4 mL), followed by the addition of NaBH(OAc)$_3$ (0.34 g, 1.61 mmol). The resulting mixture was stirred at rt for 3 h. The reaction was quenched with saturated NaHCO$_3$ solution. The mixture was extracted with EtOAc and the combined extracts were dried over Na$_2$SO$_4$. Filtration followed by evaporation to dryness under reduced pressure gave the crude isopropyl-[1-(4-phenyl-1H-imidazol-2-yl)-ethyl]-amine (0.23 g, 100%) which was used for the next reaction without further purification. $^1$H NMR (300 MHz, CDCl$_3$): δ 1.10 (3H, d), 1.18 (3H, d), 1.57 (3H, d), 2.86 (1H, m), 4.32 (1H, m), 7.24 (2H, m), 7.36 (2H, m), 7.69 (2H, m). MS(ES$^+$): 230.2 (100%).

E. (2-(4-Hydroxy-2,6-dimethyl-phenyl)-1-{isopropyl-[1-(4-phenyl-1H-imidazol-2-yl)-ethyl]-carbamoyl}-ethyl)-carbamic acid tert-butyl ester. Into a solution of 2-tert-Butoxycarbonylamino-3-(4-hydroxy-2,6-dimethyl-phenyl)-propionic acid (0.18 g, 0.6 mmol) in DMF (7 mL) was added isopropyl-[1-(4-phenyl-1H-imidazol-2-yl)-ethyl]-amine (0.11 g, 0.5 mmol), 1-hydroxybenzotriazole (0.22 g, 1.6 mmol) and 1-[3-(dimethylamino)propyl]-3-ethylcarbodiimide hydrochloride (0.12 g, 0.6 mmol). The resulting mixture was stirred under an Argon atmosphere at rt overnight. The reaction mixture was extracted with EtOAc and the combined organic extracts were washed sequentially with saturated aqueous NaHCO$_3$ solution, 1N HCl, saturated aqueous NaHCO$_3$ solution, and brine. The organic phase was then dried over MgSO$_4$, filtered, and the filtrate was concentrated under reduced pressure. The resulting residue was purified by flash column chromatography (eluent: EtOAc) to afford the product (2-(4-hydroxy-2,6-dimethyl-phenyl)-1-{isopropyl-[1-(4-phenyl-1H-imidazol-2-yl)-ethyl]-carbamoyl}-ethyl)-carbamic acid tert-butyl ester (0.13 g, 50%). MS(ES$^+$): 521.5 (100%).

F. 2-Amino-3-(4-hydroxy-2,6-dimethyl-phenyl)-N-isopropyl-N-[1-(4-phenyl-1H-imidazol-2-yl)-ethyl]-propionamide. A solution of (2-(4-hydroxy-2,6-dimethyl-phenyl)-1-

{isopropyl-[1-(4-phenyl-1H-imidazol-2-yl)-ethyl]-carbamoyl}-ethyl)-carbamic acid tert-butyl ester (0.13 g, 0.25 mmol) in trifluoroacetic acid (5 mL) was stirred at rt for 2 h. Upon removal of the solvents, the residue was purified by preparative LC and lyophilized to give the TFA salt of the title compound as a white powder (0.042 g). $^1$H NMR (300 MHz, $CDCl_3$): δ 0.48 (3H, d), 1.17 (3H, d), 1.76 (3H, d), 2.28 (6H, s), 3.19 (2H, m), 3.74 (1H, m), 4.70 (1H, m), 4.82 (1H, q), 6.56 (2H, s), 7.45 (4H, m), 7.74 (2H, m). MS(ES$^+$): 421.2 (100%).

Example 2

Methyl-[2-methyl-1-(4-phenyl-1H-imidazol-2-yl)-propyl]-amine and

Ethyl-[2-methyl-1-(4-phenyl-1H-imidazol-2-yl)-propyl]-amine 1-(2-oxo-2-phenyl-ethylcarbamoyl)-propyl]-carbamic acid tert-butyl ester (Cpd 2a), 1.89 g (50%) of [2-methyl-1-(4-phenyl-1-H-imidazol-2-yl)-propyl]-carbamic acid tert-butyl ester (Cpd 2b), and 0.60 g of a mixture of N-[2-methyl-1-(4-phenyl-1H-imidazol-2-yl)-propyl]-acetamide (Cpd 2c) and acetamide.

Cpd 2c was purified by dissolving it in hot $CH_3CN$ and cooling to 0° C. Collection of the precipitate by suction filtration afforded 0.21 g (7%) of N-[2-methyl-1-(4-phenyl-1H-imidazol-2-yl)-propyl]-acetamide, Cpd 2c, as a white powder (HPLC: 100% @254 nm and 214 nm). $^1$H NMR (300 MHz, $CDCl_3$): δ 7.63 (2H, br s), 7.33 (2H, t, J=7.5 Hz), 7.25-7.18 (2H, m), 4.78 (1H, br s), 2.35 (1H, br m), 2.02 (3H, s), 1.03 (3H, d, J=6.7 Hz), 0.87 (3H, d, J=6.7 Hz); MS (ES$^+$) (relative intensity): 258.3 (100) (M+1).

C. Methyl-[2-methyl-1-(4-phenyl-1H-imidazol-2-yl)-propyl]-amine. A solution of [2-methyl-1-(4-phenyl-1-H-imidazol-2-yl)-propyl]-carbamic acid tert-butyl ester (0.095g, 0.30

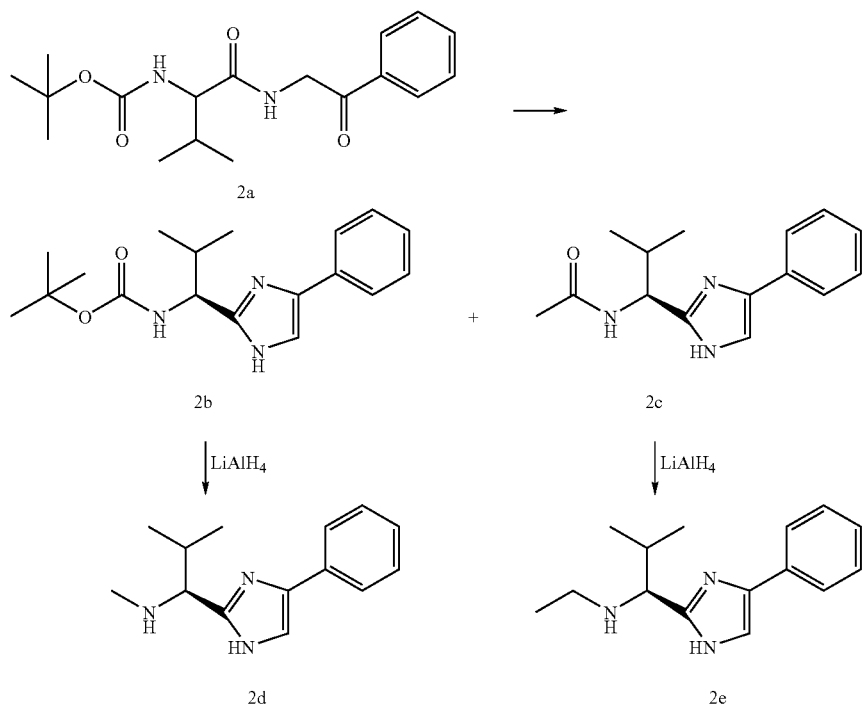

A. [2-Methyl-1-(2-oxo-2-phenyl-ethylcarbamoyl)-propyl]-carbamic acid tert-butyl ester. Compound 2a was prepared according to Example 1 using the appropriate reagents, starting materials and methods known to those skilled in the art.

B. [2-Methyl-1-(4-phenyl-1-H-imidazol-2-yl)-propyl]-carbamic acid tert-butyl ester. Following the procedure described in Example 1 for the conversion of Compound 1a to Compound 1b, and using the appropriate reagents and methods known to those skilled in the art, [2-methyl-1-(4-phenyl-1-H-imidazol-2-yl)-propyl]-carbamic acid tert-butyl ester, Cpd 2b, was prepared.

Subsequent to workup, the crude product mixture was subjected to flash silica gel chromatography (eluents: $CH_2Cl_2$, followed by 4:1 $CH_2Cl_2/Et_2O$, then EtOAc). Processing of the fractions afforded 1.08 g (27%) of recovered [2-methylmmol) in THF (2.0 mL) was added dropwise over 10 min to a refluxing 1.0 M solution of $LiAlH_4$ in THF (3.0 mL). The reaction was maintained at reflux for 2 h, cooled to room temperature, and quenched by sequential treatment with 0.11 mL of cold water (5° C.), 0.11 mL of 15% NaOH in aqueous solution, and 0.33 mL of cold water (5° C.). The resultant solid was removed by suction filtration and the filtrate (pH 8-9) was extracted three times with EtOAc. The combined organic fractions were dried over $MgSO_4$, filtered, and concentrated to afford 0.58 g (84%) of methyl-[2-methyl-1-(4-phenyl-1H-imidazol-2-yl)-propyl]-amine as a light yellow oil (HPLC: 97% @254 nm and 214 nm). $^1$H NMR (300 MHz, $CDCl_3$): δ 7.69 (2H, d, J=7.4 Hz), 7.36 (2H, t, J=7.6 Hz), 7.26 (1H, s), 7.25-7.20 (1H, m), 3.62 (1H, d, J=6.3 Hz), 2.35 (3H, s), 2.06 (1H, m), 0.99 (3H, d, J=6.7 Hz), 0.89 (3H, d, J=6.7 Hz);

MS (ES$^+$) (relative intensity): 230.2 (100) (M+1).

D. Ethyl-[2-methyl-1-(4-phenyl-1H-imidazol-2-yl)-propyl]-amine. A solution of N-[2-methyl-1-(4-phenyl-1H-imidazol-2-yl)-propyl]-acetamide (0.077g, 0.30 mmol) in THF (2.0 mL) was added dropwise over 10 min to a refluxing 1.0 M solution of LiAlH$_4$ in THF (3.0 mL). The reaction was maintained at reflux for 11 h, cooled to rt, and quenched by sequential treatment with 0.11 mL of cold water (5° C.), 0.11 mL of 15% NaOH in aqueous solution, and 0.33 mL of cold water (5° C.). The resultant solid was removed by suction filtration and the filtrate (pH 8-9) was extracted three times with EtOAc. The combined organic fractions were dried over MgSO$_4$, filtered, and concentrated to afford 0.069 g of a 5:1 mixture (determined by $^1$H NMR) of ethyl-[2-methyl-1-(4-phenyl-1H-imidazol-2-yl)-propyl]-amine and recovered Cpd 2c as a colorless oil (HPLC: peaks overlap). $^1$H NMR (300 MHz, CDCl$_3$): δ 7.67 (2H, br s), 7.35 (2H, t, J=7.6 Hz), 7.26-7.17 (2H, m), 3.72 (1H, d, J=6.0 Hz), 2.56 (2H, dq, J=13.0, 7.1 Hz), 2.05 (1H, m), 1.08 (3H, t, J=7.1 Hz), 0.97 (3H,d, J=6.7 Hz), 0.89 (3H, d, J=6.7 Hz); MS (ES$^+$) (relative intensity): 244.2 (100) (M+1). This sample was of sufficient quality to use in the next reaction without further purification.

Methyl-[2-methyl-1-(4-phenyl-1H-imidazol-2-yl)-propyl]-amine and ethyl-[2-methyl-1-(4-phenyl-1H-imidazol-2-yl)-propyl]-amine may be substituted for Cpd 1d of Example 1 and elaborated to compounds of the present invention with the appropriate reagents, starting materials and purification methods known to those skilled in the art.

Example 3

(3,4-Dimethoxy-benzyl)-[1-(4-phenyl-1H-imidazol-2-yl)-ethyl]-amine

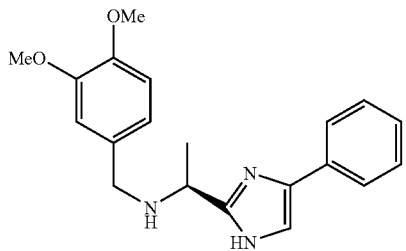

A solution of 1-(4-phenyl-1H-imidazol-2-yl)-ethylamine (0.061 g, 0.33 mmol) of Example 1, and 0.55 g (0.33 mmol) of 3,4-dimethoxybenzaldehyde in 5 mL of anhydrous methanol was stirred at room temperature for 1 h and then cooled to about 0-10° C. in an ice bath for 1 h. The reaction was treated carefully with 0.019 g (0.49 mmol) of sodium borohydride in one portion and maintained at about 0-10° C. for 21 h. Cold 2M aqueous HCl was added dropwise (30 drops), the mixture was stirred for 5 min, and then partially concentrated in vacuo unheated. The residual material was taken up in EtOAc to yield a suspension that was treated with 5 mL of cold 3M aqueous NaOH and stirred vigorously until clear. The phases were separated and the aqueous layer was extracted three times additional with EtOAc. The combined extracts were dried over MgSO$_4$, filtered, and concentrated to afford 0.11 g of (3,4-dimethoxy-benzyl)-[1-(4-phenyl-1H-imidazol-2-yl)-ethyl]-amine as a light yellow oil (HPLC: 87% @254 nm and 66% @214 nm). MS (ES$^+$) (relative intensity): 338.1 (100) (M+1). This sample was of sufficient quality to use in the next reaction without further purification. The title compound may be substituted for Cpd 1 d of Example 1 and elaborated to compounds of the present invention with the appropriate reagents, starting materials and purification methods known to those skilled in the art.

Example 4

1-[4-(4-Fluoro-phenyl)-1H-imidazol-2-yl]-ethylamine

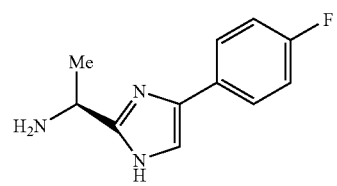

A. {1-[4-(4-Fluoro-phenyl)-1H-imidazol-2-yl]-ethyl}-carbamic acid tert-butyl ester. A mixture of ammonium acetate (19.3 g, 250 mmol) and glacial HOAc (35 mL) was stirred mechanically and heated to about 100° C. to give a colorless solution in 5-10 min. After cooling to rt, a solid mixture of N-t-BOC-L-Alaninal (commercially available from Aldrich) and 4-fluorophenyl glyoxal hydrate was added in portions while stirring to give a yellow mixture. The resulting mixture was heated at 100° C. for approximately 2 h before cooling to rt. The mixture was cooled to 0-5C, then basified by dropwise addition of conc. NH$_4$OH (25 mL), H$_2$O (25 mL), and EtOAc (40 mL), and additional conc. NH$_4$OH (50 mL) to render the mixture alkaline. The phases were separated and the aqueous phase was re-extracted with EtOAc. The combined organic phases were filtered through dicalite to remove an orange solid and were washed with saturated aqueous NaCl. The organic phase was then dried over MgSO$_4$, filtered, and concentrated under reduced pressure to give 4.27 g of an orange-brown residue. The residue was dissolved in a solution of MeCN (22 mL) and DMSO (3 mL) then purified by preparative HPLC on a Kromasil 10u C18 250×50 mm column, eluting with a 35:65 MeCN:H$_2$O gradient. The pure fractions were combined and lyophilized to give 1.77 g of the product as a yellow-white powder (42%; TFA salt). MS: m/z 306.1 (MH$^+$).

B. 1-[4-(4-Fluoro-phenyl)-1H-imidazol-2-yl]-ethylamine. {1-[4-(4-Fluoro-phenyl)-1H-imidazol-2-yl]-ethyl}-carbamic acid tert-butyl ester may be BOC-deprotected using the procedure described in Example 1 for the conversion of Cpd 1e to Cpd 1f. Upon completion of the BOC-deprotection, the resulting amine may be substituted for Cpd 1c of Example 1 and elaborated to compounds of the present invention with the appropriate reagents, starting materials and purification methods known to those skilled in the art.

Example 5

Isopropyl-[4(5)-phenyl-1-(2-trimethylsilanyl-ethoxymethyl)-1H-imidazol-2-ylmethyl]-amine (mixture of regioisomers)

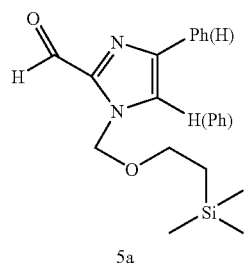

5a
Mixture of regioisomers

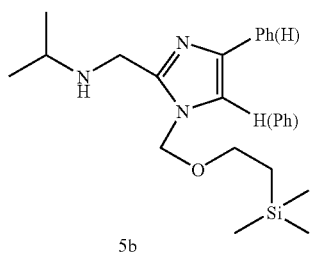

5b

A. Cpd 5a Regioisomers. Into a cooled solution of 4(5)-phenyl-1-(2-trimethylsilanyl-ethoxymethyl)-1H-imidazole (*Tet. Lett.* 1986, 27(35), 4095-8) (7.70 g, 28.1 mmol) in dry THF (60 mL) was added n-butyllithium (2.5 M in hexane, 22.5 mL, 56.2 mmol) at −78° C. under $N_2$. The resulting mixture was stirred at −78° C. for 1 h, followed by the addition of DMF (4.35 mL, 56.2 mmol). After being stirred at −78° C. for an additional hour, the reaction was warmed to room temperature and stirred overnight. The reaction was quenched by the addition of saturated aqueous $NaHCO_3$ solution and extracted with EtOAc. The combined organic extracts were dried over $Na_2SO_4$. After filtration and evaporation, the residue was purified by flash column chromatography (eluent: EtOAc:hexane, 1:9) to give 4(5)-phenyl-1-(2-trimethylsilanyl-ethoxymethyl)-1H-imidazole-2-carbaldehyde (5.11 g, 60%) as a mixture of regioisomers. $^1$H NMR (300 MHz, $CDCl_3$): δ 0.00 (9H, s), 2.98 (2H, t), 3.62 (2H, t), 5.83 (2H, s), 7.36 (1H, m), 7.44 (2H, m), 7.65 (1H, s), 7.86 (2H, m). MS(ES$^+$): 303.0 (42%).

B. Cpd 5b Regioisomers. Isopropylamine (0.18 g, 3 mmol) and a regioisomeric mixture of 4(5)-phenyl-1-(2-trimethylsilanyl-ethoxymethyl)-1H-imidazole-2-carbaldehyde (0.91 g, 3 mmol) were mixed in 1,2-dichloroethane (10 mL), followed by addition of sodium triacetoxyborohydride (0.95 g, 4.5 mmol). The resulting mixture was stirred at room temperature for 5 h. The reaction was quenched with saturated aqueous $NaHCO_3$ solution. The resultant mixture was extracted with EtOAc and the combined organic phases were dried over $Na_2SO_4$. After filtration and concentration, the residue was purified by flash column chromatography (eluent: $CH_2Cl_2$:$CH_3OH$, 7:3) to give isopropyl-[4(5)-phenyl-1-(2-trimethylsilanyl-ethoxymethyl)-1H-imidazol-2-ylmethyl]-amine (0.70 g, 68%) as a mixture of regioisomers. $^1$H NMR (300 MHz, $CDCl_3$): δ 0.00 (9H, s), 0.94 (2H, t), 1.11 (6H, d), 2.89 (1H, m), 3.56 (2H, t), 3.94 (2H, s), 5.39 (2H, s), 7.25 (2H, m), 7.37 (2H, m), 7.76 (2H, d). MS(ES$^+$): 346.6 (75%).

Compound 5b may be substituted for Cpd 1d of Example 1 and elaborated to compounds of the present invention with the appropriate reagents, starting materials and purification methods known to those skilled in the art.

Example 6

2-Amino-3-(4-hydroxy-phenyl)-N-isopropyl-N-(5-methyl-4-phenyl-1H-imidazol-2-ylmethyl)-propionamide Trifluoroacetate (1:2)

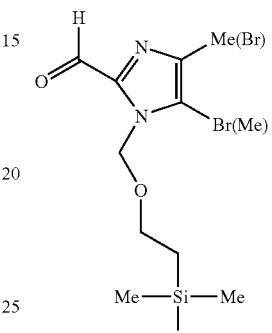

6a
Mixtures of regioisomers

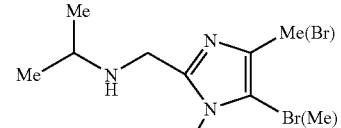

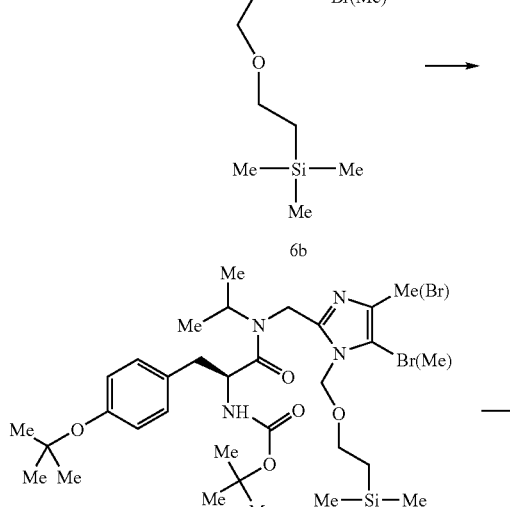

6b

6c

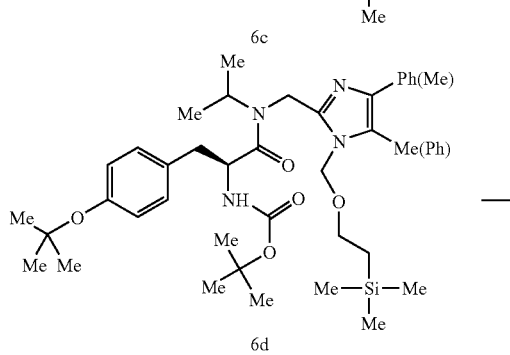

6d

-continued

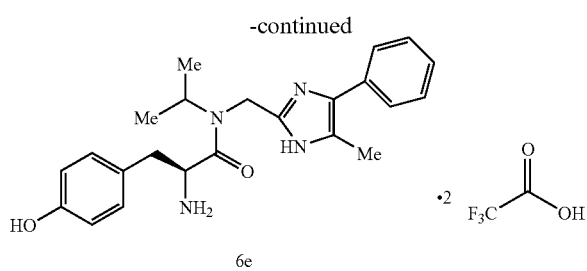

6e

A. Cpd 6a Regioisomers. Bromine (1.17 mL, 22.76 mmol) was added slowly to an ice cooled regioisomeric mixture of 4(5)-methyl-1-(2-trimethylsilanyl-ethoxymethyl)-1H-imidazole-2-carbaldehyde (5.47 g, 22.76 mmol; JOC, 1986, 51 (10), 1891-4) in CHCl₃ (75 mL). The reaction was warmed to rt after 1.5 h, and then was stirred an additional 1 h. The reaction mixture was then extracted with saturated aqueous NaHCO₃, and the organic phase was then dried over Na₂SO₄, filtered, and concentrated under reduced pressure to give 7.46 g of crude material. This material was vacuum distilled (bp 127-135° C.; 1 mm Hg) to yield 3.16 g (43%) of a regioisomeric mixture, Cpd 6a, as a yellow liquid, which was used without further purification. $^1$H NMR (CDCl₃) δ 0 (S, 9H), 0.9-1.0 (t, 2H), 2.35 (s, 3H), 3.5-3.6 (t, 2H), 5.8 (s, 2H), 9.75 (s,1H).

B. Cpd 6b Regioisomers. Isopropyl amine (0.30 g, 5 mmol) in 1,2-dichloroethane (2 mL) was added to a 5° C. solution of regioisomers Cpd 6a (0.96 g, 3 mmol) in 1,2-dichloroethane (70 mL). After stirring for 5 min, sodium triacetoxyborohydride (1.80 g, 8.5 mmol) was added neat to the reaction mixture. The mixture was gradually warmed to rt and stirred for 24 h. At this time, an additional portion of sodium triacetoxyborohydride (0.60g, 2.8 mmol) was added and the reaction was stirred an additional 16 h. The reaction was then cooled to approximately 10° C. and treated while stirring with saturated aqueous NaHCO₃. After stirring for 15 min, the layers were separated and the organic phase was dried over Na₂SO₄, filtered, and concentrated under reduced pressure to give 1.20 g (T.W. 1.09 g) of a regioisomeric mixture, Cpd 6b, as a yellow oil which was used directly without further purification.

C. Cpd 6c Regioisomers. Isobutyl chloroformate (0.43 g, 3.15 mmol) was added neat to a 0° C. solution containing 2-tert-butoxycarbonylamino-3-(4-tert-butoxy-phenyl)-propionic acid (1.21 g, 3.6 mmol; Advanced Chem Tech), N-methylmorpholine (362 μL, 3.3 mmol), and CH₂Cl₂ (60 mL). After stirring 1.5 h, Cpd 6b (1.09 g, 3 mmol) was added to the reaction mixture. The reaction mixture was then warmed to room temperature and stirred for 16 h. The reaction mixture was then adsorbed on silica gel, and flash chromatographed on a silica gel column eluting with 25% ethyl acetate/hexane. The desired fractions were combined and concentrated under reduced pressure to give 715 mg (35%) of regioisomers of Cpd 6c as a clear oil (TLC: 25% EtOAc/hexane $R_{f=b}$ 0.3, homogeneous; HPLC: 100% at 254 and 214 nm, 7.51 min).

D. Cpd 6d Regioisomers. To the regioisomers of Cpd 6c (90 mg, 0.132 mmol) in 1,2-dimethoxyethane (2 mL) was added phenyl boronic acid (32.2 mg, 0.26 mmol) followed by 2M Na₂CO₃(aq) (0.53 mL, 1.06 mmol). The resulting mixture was degassed with N₂ for 5 min and then palladium tetrakis triphenylphosphine (53 mg, 0.046 mmol) was added neat. The reaction vessel was capped and warmed to 80° C. for 14 h with rapid stirring. After cooling to room temperature the mixture was dried over MgSO₄, filtered through dicalite, and concentrated under a stream of N₂. The residue was dissolved in a small amount of EtOAc and flash chromatographed on a silica gel column (Eluent: 5%-25% EtOAc/hexane). The desired fractions were concentrated under reduced pressure to yield 55 mg (61%) as regioisomeric mixture of Cpd 6d, which was used without further purification (TLC: 25% EtOAc/hexane $R_f$=0.3; HPLC: 100% at 254 nm; 88% at 214 nm, 6.50 min).

E. 2-Amino-3-(4-hydroxy-phenyl)-N-isopropyl-N-(5-methyl-4-phenyl-1H-imidazol-2-ylmethyl)-propionamide Trifluoroacetate (1:2). Trifluoroacetic acid (1 mL) was added to the Cpd 6d regioisomers (55 mg, 0.081 mmol) at room temperature. After 6 h, the excess TFA was removed under a stream of N₂. The residue was dissolved in a small amount of acetonitrile and purified by preparative HPLC on a YMC C18 100×20 mm column. The purest fractions were combined and lyophilized to give 37 mg (74%) of the title compound as a white lyophil (TLC: 5:1 CHCl₃:MeOH $R_f$=0.55, homogeneous; HPLC: 100% at 214 nm; HPLC/MS: m/z 393 (MH⁺)). $^1$H NMR (MeOH-d₄) δ 0.85-0.9 (d, 3H), 1.2-1.25 (d, 3H), 2.45 (s, 3H), 3.05-3.1 (t, 2H), 4.0-4.15 (m, 1H), 4.55-4.6 (d, 1H), 4.7-4.85 (m, 2H), 6.65-6.7 (d, 2H), 6.95-7.0 (d, 2H), 7.45-7.6 (m, 5H).

Example 7

(3,4-Dichloro-benzyl)-(4-phenyl-1H-imidazol-2-ylmethyl)-amine Trifluoroacetate (1:2)

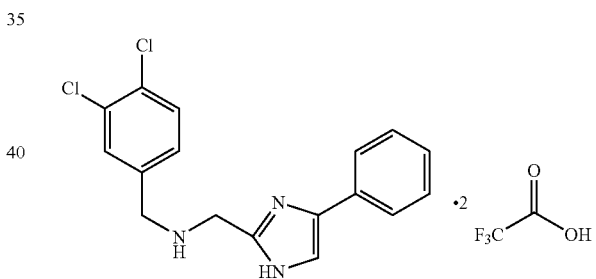

Using the procedure described in Example 5 and substituting 3,4-dichloro-benzylamine for isopropylamine, (3,4-dichloro-benzyl)-[4(5)-phenyl-1-(2-trimethylsilanyl-ethoxymethyl)-1H-imidazol-2-ylmethyl]-amine was prepared as a pair of regioisomers. A sample (95 mg, 0.21 mmol) of this compound was dissolved in TFA (3 mL) at room temperature. After 2 h the mixture was concentrated under a stream of nitrogen. The residue was purified by reverse phase HPLC, the purest fractions were combined and lyophilized to yield desired product (3,4-dichloro-benzyl)-(4-phenyl-1H-imidazol-2-ylmethyl)-amine as an off white lyophil.

Following the procedure described in Example 1, substituting (3,4-dichloro-benzyl)-(4(5)-phenyl-1H-imidazol-2-ylmethyl)-amine for Cpd 1 d, compounds of the present invention may be synthesized with the appropriate reagents, starting materials, and purification methods known to those skilled in the art.

Example 8

(S)-2-tert-Butoxycarbonylamino-3-(2,6-dimethyl-4-trifluoromethanesulfonylphenyl)-propionic acid methyl ester

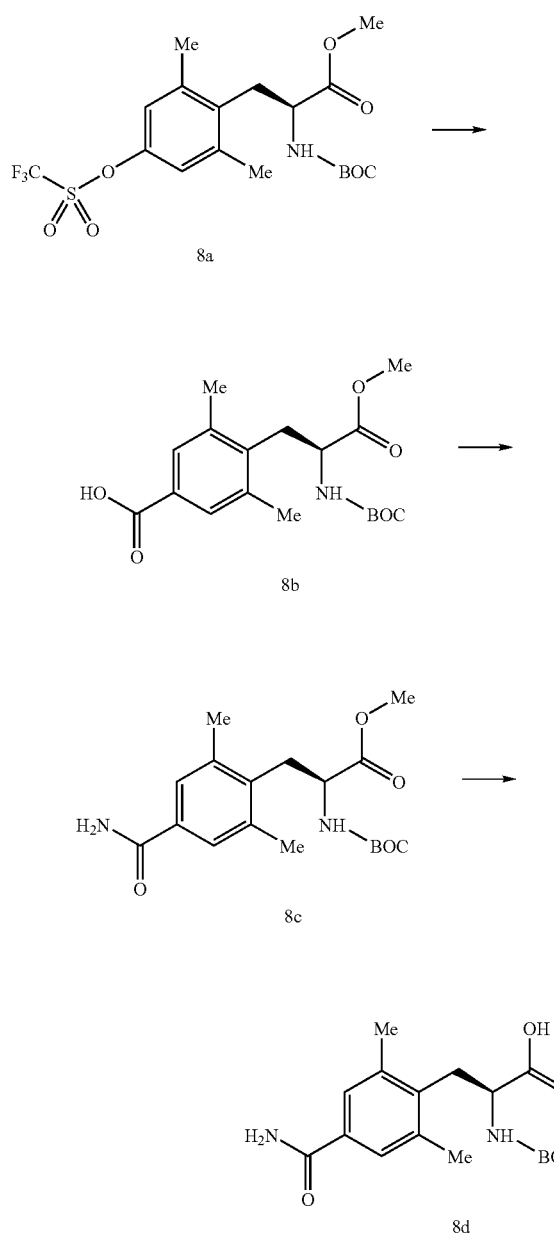

A. (S)-2-tert-Butoxycarbonylamino-3-(2,6-dimethyl-4-trifluoromethanesulfonylphenyl)-propionic acid methyl ester. Into a cool solution of Boc-L-(2,6-diMe)Tyr-OMe (7.0 g, 21.6 mmol; Sources: Chiramer or RSP AminoAcidAnalogues) and N-phenyltrifluoromethanesulfonimide (7.9 g, 22.0 mmol) in dichloromethane (60 mL) was added triethylamine (3.25 mL, 23.3 mmol). The resulting solution was stirred at 0° C. for 1 h and slowly warmed to rt. Upon completion, the reaction was quenched by addition of water. The separated organic phase was washed with 1 N NaOH aqueous solution, water and dried over $Na_2SO_4$ overnight. After filtration and evaporation, the residue was purified by flash column chromatography (eluent: EtOAc-hexane: 3:7) to give the desired product (9.74 g, 99%) as a clear oil; $^1$H NMR (300 MHz, $CDCl_3$): δ 1.36 (9H, s), 2.39 (6H, s), 3.06 (2H, d, J=7.7 Hz), 3.64 (3H, s), 4.51-4.59 (1H, m), 5.12 (1H, d, J=8.5 Hz), 6.92 (2H, s); MS (ES+) (relative intensity): 355.8 (100) (M−Boc)$^+$.

B. (S)$_4$-(2-tert-Butoxycarbonylamino-2-methoxycarbonylethyl)-3,5-dimethylbenzoic acid. To a suspension of (S)-2-tert-butoxycarbonylamino-3-(2,6-dimethyl-4-trifluoromethanesulfonylphenyl)-propionic acid methyl ester (9.68 g, 21.3 mmol), $K_2CO_3$ (14.1 g, 0.102 mol), Pd(OAc)$_2$ (0.48 g, 2.13 mmol) and 1,1'-bis(diphenylphosphino)ferrocene (2.56 g, 4.47 mmol) in DMF (48 mL) was bubbled in gaseous CO for 15 min. The mixture was heated to 60° C. for 8 h with a CO balloon. The cool mixture was partitioned between $NaHCO_3$ and EtOAc, and filtered. The aqueous layer was separated, acidified with 10% citric acid aqueous solution, extracted with EtOAc, and finally dried over $Na_2SO_4$. Filtration and concentration of the filtrate resulted in a residue. The residue was recrystallized from EtOAc-hexanes to afford the desired product (7.05 g, 94%); $^1$H NMR (300 MHz, $CDCl_3$): δ 1.36 (9H, s), 2.42 (6H, s), 3.14 (2H, J=7.4 Hz), 3.65 (3H, s), 4.57-4.59 (1H, m), 5.14 (1H, d, J=8.6 Hz), 7.75 (2H, s); MS(ES+) (relative intensity): 251.9 (100) (M−Boc)$^+$.

C. (S)-2-tert-Butoxycarbonylamino-3-(4-carbamoyl-2,6-dimethylphenyl)propionic acid methyl ester. Into a stirring solution of (S)-4-(2-tert-butoxycarbonylamino-2-methoxycarbonylethyl)-3,5-dimethyl benzoic acid (3.00 g, 8.54 mmol), PyBOP (6.68 g, 12.8 mmol) and HOBt (1.74 g, 12.8 mmol) in DMF (36 mL) was added DIPEA (5.96 mL, 34.2 mmol) and $NH_4Cl$ (0.92 g, 17.1 mmol). The resulting mixture was stirred at rt for 40 min before being partitioned between aqueous $NH_4Cl$ solution and EtOAc. The separated organic phase was washed sequentially with 2N citric acid aqueous solution, saturated aqueous $NaHCO_3$ solution, and brine, then dried over $Na_2SO_4$ overnight. After filtration and concentration, the residue was purified by flash column chromatography (eluent: EtOAc) to give the product. (3.00 g, 100%); $^1$H NMR (300 MHz, $CDCl_3$): δ 1.36 (9H, s), 2.39 (6H, s), 3.11 (2H, J=7.2 Hz), 3.65 (3H, s), 4.53-4.56 (1H, m), 5.12 (1H, d, J=8.7 Hz), 5.65 (1H, brs), 6.09 (1H, br s), 7.46 (2H, s); MS(ES+) (relative intensity): 250.9 (100) (M−Boc)$^+$.

D. (S)-2-tert-Butoxycarbonylamino-3-(4-carbamoyl-2,6-dimethylphenyl)propionic acid. Into an ice-cooled solution of methyl ester from Step C (2.99 g, 8.54 mmol) in THF (50 mL) was added an aqueous LiOH solution (1N, 50 mL) and stirred at 0° C. Upon consumption of the starting materials, the organic solvents were removed and the aqueous phase was neutralized with cooled 1N HCl at 0° C., and extracted with EtOAc, and dried over $Na_2SO_4$ overnight. Filtration and evaporation to dryness led to the title acid (S)-2-tert-butoxycarbonylamino-3-(4-carbamoyl-2,6-dimethylphenyl)propionic acid (2.51 g, 87%); $^1$H NMR (300 MHz, DMSO-d$_6$): δ 1.30 (9H, s), 2.32 (6H, s), 2.95 (1H, dd, J=8.8, 13.9 Hz), 3.10 (1H, dd, J=6.2, 14.0 Hz), 4.02-4.12 (1H, m), 7.18-7.23 (2H, m), 7.48 (2H, s), 7.80 (1H, s);

MS(ES+) (relative intensity): 236.9 (6) (M−Boc)$^+$.

Example 9

5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid

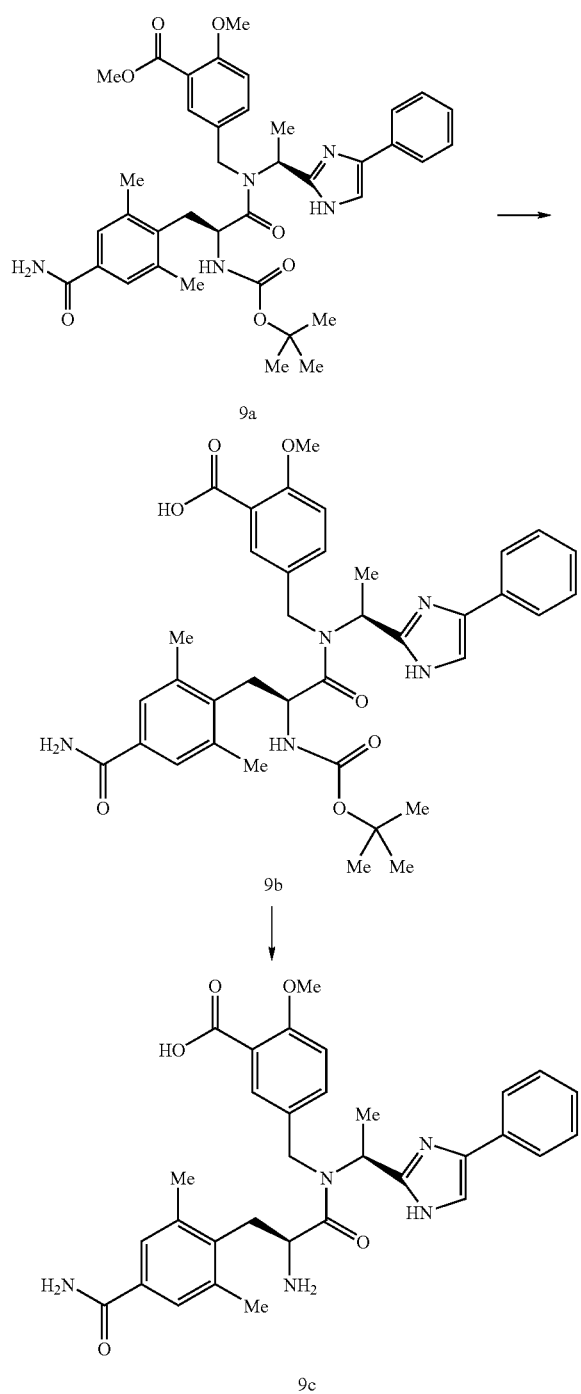

A. 2-Methoxy-5{[1-(4-phenyl-1 H-imidazol-2-yl)-ethylamino]-methyl}-benzoic acid methyl ester. Using the procedures described for Example 3, substituting 5-formyl-2-methoxy-benzoic acid methyl ester (WO 02/22612) for 3,4-dimethoxybenzaldehyde, 2-methoxy-5-{[1-(4-phenyl-1H-imidazol-2-yl)-ethylamino]-methyl}-benzoic acid methyl ester was prepared.

B. 5-({[2-tert-Butoxycarbonyl methyl-3-(4-carbamoyl-2,6-dimethyl-phenyl)-propionyl]-[1-(4-phenyl-1H-imidazol-2-yl)-ethyl]-amino}-methyl)-2-methoxy-benzoic acid methyl ester. Using the procedure of Example 1 for the conversion of Cpd 1d to Cpd 1e, substituting 2-methoxy-5-{[1-(4-phenyl-1H-imidazol-2-yl)-ethylamino]-methyl}-benzoic acid methyl ester for Cpd 1 d and substituting 2-tert-Butoxycarbonylamino-3-(4-carbamoyl-2,6-dimethyl-phenyl-propionic acid of Example 8 for 2-tert-Butoxycarbonylamino-3-(4-hydroxy-2,6-dimethyl-phenyl)-propionic acid, Cpd 9a was prepared.

C. 5-({[2-tert-butoxycarbonylamino-3-(4-carbamoyl-2,6-dimethyl-phenyl)-propionyl]-[1-(4-phenyl-1H-imidazol-2-yl)-ethyl]-amino}-methyl)-2-methoxy-benzoic acid. 5-({[2-tert-Butoxycarbonyl methyl-3-(4-carbamoyl-2,6-dimethyl-phenyl)-propionyl]-[1-(4-phenyl-1H-imidazol-2-yl)-ethyl]-amino}-methyl)-2-methoxy-benzoic acid methyl ester was dissolved in an ice-chilled (0-10° C.), mixed solvent system of THF (10 mL) and MeOH (5 mL). A LiOH.H$_2$O/water suspension (2.48 M; 3.77 mL) was added dropwise, then the reaction was allowed to warm to room temperature and stirred overnight. The resulting mixture was cooled in an ice bath and the basic solution was neutralized with 2N citric acid until slightly acidic. The mixture was concentrated under reduced pressure to remove the volatile materials, after which time the remaining aqueous phase was extracted with EtOAc (3×26 mL). These combined organic phases were dried over MgSO$_4$, filtered, and concentrated under reduced pressure to give 2.26 g (146% of theory) of pale yellowish white solid. This crude material was dissolved in a 10% MeOH/CH$_2$Cl$_2$ solution and adsorbed onto 30 g of silica. The adsorbed material was divided and chromatographed on an ISCO normal phase column over two runs, using a 40 g Redi-Sep column for both runs. The solvent system was a gradient MeOH/CH$_2$Cl$_2$ system as follows: Initial 100% CH$_2$Cl$_2$, 98%-92% over 40 min; 90% over 12 min, and then 88% over 13 min. The desired product eluted cleanly between 44-61 min. The desired fractions were combined and concentrated under reduced pressure to yield 1.74 g (113% of theory) of 5-({[2-tert-butoxycarbonylamino-3-(4-carbamoyl-2,6-dimethyl-phenyl)-propionyl]-[1-(4-phenyl-1H-imidazol-2-yl)-ethyl]-amino}-methyl)-2-methoxy-benzoic acid, Cpd 9b, as a white solid.

D. 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid. A portion of Cpd 9b (0.27g, 0.41 mmol) was dissolved in EtOAc (39 mL)/THF (5 mL), filtered, and subsequently treated with gaseous HCl for 15 min. After completion of the HCl addition, the reaction was slowly warmed to room temperature and a solid precipitate formed. After 5 h the reaction appeared >97% complete by LC (@214 nm; 2.56 min.). The stirring was continued over 3 d, then the solid was collected and rinsed with a small amount of EtOAc. The resulting solid was dried under high vacuum under refluxing toluene for 2.5 h to yield 0.19 g (71%) of desired Cpd 9c as a white solid di-HCl salt.

Example 10

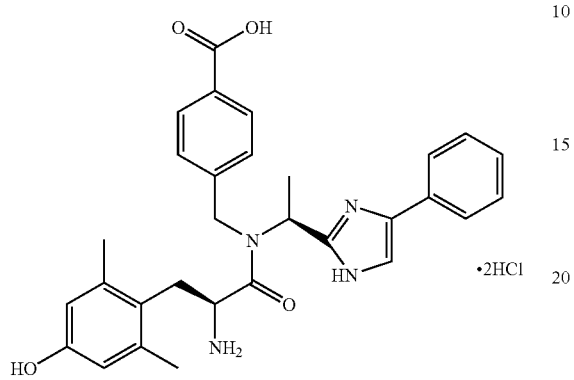

A. 4-{[1-(4-Phenyl-1H-imidazol-2-yl)-ethylamino]-methyl}-benzoic acid methyl ester. Using the procedure described for Example 3, substituting 4-formyl-benzoic acid methyl ester for 3,4-dimethoxybenzaldehyde, 4-{[1-(4-phenyl-1H-imidazol-2-yl)-ethylamino]-methyl}-benzoic acid methyl ester was prepared.

B. 4-({[2-Amino-3-(4-hydroxy-2,6-dimethyl-phenyl)-propionyl]-[1-(4-phenyl-1H-imidazol-2-yl)-ethyl]-amino}-methyl)-benzoic acid methyl ester. 4-{[1-(4-phenyl-1H-imidazol-2-yl)-ethylamino]-methyl}-benzoic acid methyl ester was substituted for Cpd 1d of Example 1 and elaborated according to the procedure of Example 1 to prepare the product.

C. 4-({[2-Amino-3-(4-hydroxy-2,6-dimethyl-phenyl)-propionyl]-[1-(4-phenyl-1H-imidazol-2-yl)-ethyl]-amino}-methyl)-benzoic acid. A solution of 4-({[2-amino-3-(4-hydroxy-2,6-dimethyl-phenyl)-propionyl]-[1-(4-phenyl-1H-imidazol-2-yl)-ethyl]-amino}-methyl)-benzoic acid methyl ester (TFA salt), (0.043 g, 0.067 mmol) in 5 mL of THF was cooled in an ice bath. A cold (5-10° C.) 3M aqueous solution of LiOH (5 mL) was added and the reaction mixture was stirred vigorously while cold. Chilled (5-10C) 2M aqueous HCl (7.5 mL) was added dropwise to neutralize the mixture was stirred for 5 min, and then partially concentrated in vacuo unheated. The resultant aqueous suspension was extracted seven times with EtOAc. The extracts were dried over $Na_2SO_4$, filtered, and concentrated to afford 0.030 g of 4-({[2-amino-3-(4-hydroxy-2,6-dimethyl-phenyl)-propionyl]-[1-(4-phenyl-1H-imidazol-2-yl)-ethyl]-amino}-methyl)-benzoic acid as a white powder. The material was taken up in EtOH and treated with 1 M HCl in $Et_2O$. The solution was concentrated and the residue was triturated with $CH_3CN$. A 0.021 g (53%) sample of 4-({[2-amino-3-(4-hydroxy-2,6-dimethyl-phenyl)-propionyl]-[1-(4-phenyl-1H-imidazol-2-yl)-ethyl]-amino}-methyl)-benzoic acid was collected as its HCl salt. MS (ES$^+$) (relative intensity): 513.2 (100) (M+1).

Example 11

3-({[2-Amino-3-(4-hydroxy-2,6-dimethyl-phenyl)-propionyl]-[1-(4-phenyl-1H-imidazol-2-yl)-ethyl]-amino}-methyl)-benzamide

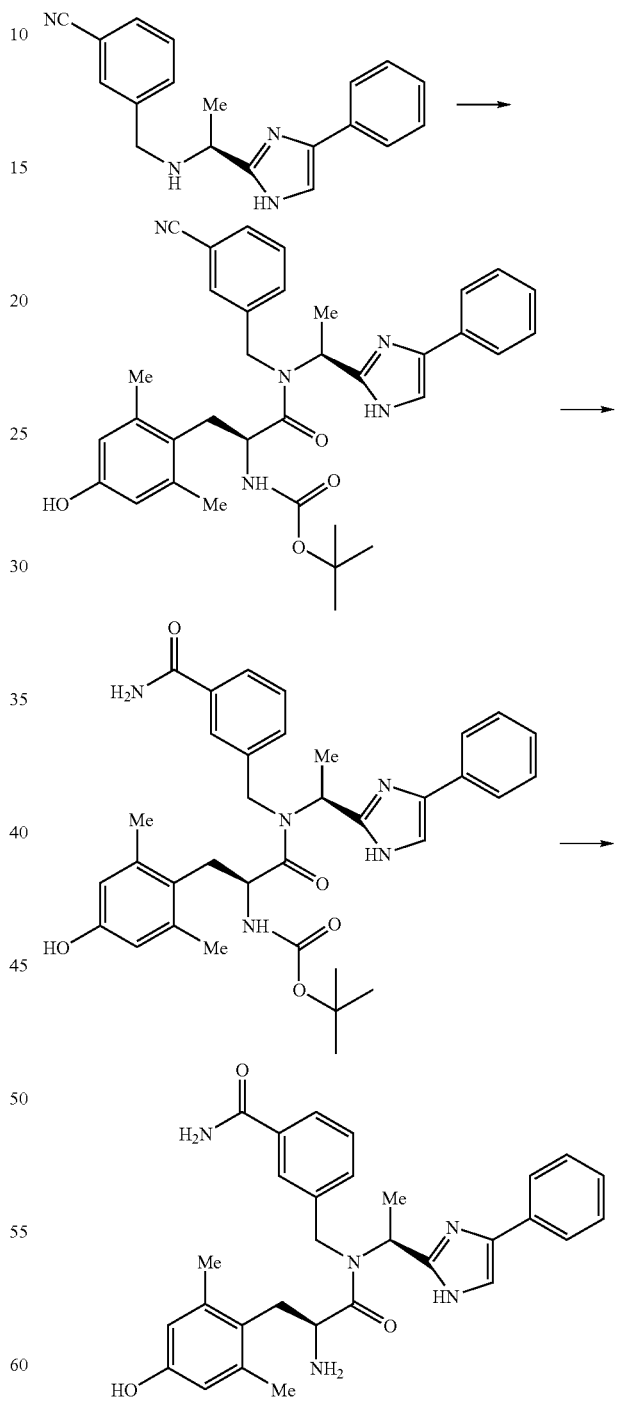

A. 3-{[1-(4-phenyl-1H-imidazol-2-yl)-ethylamino]-methyl}-benzonitrile. Using the procedure described for Example 3, substituting 3-formyl-benzonitrile for 3,4-dimethoxybenzaldehyde, the product was prepared.

B. [1-{(3-Cyano-benzyl)-[1-(4-phenyl-1H-imidazol-2-yl)-ethyl]-carbamoyl}-2-(4-hydroxy-2,6-dimethyl-phenyl)-ethyl]-carbamic acid tert-butyl ester. 3-{[1-(4-phenyl-1H-imidazol-2-yl)-ethylamino]-methyl}-benzonitrile was substituted for Cpd 1d of Example 1 and elaborated according to the procedure of Example 1 to prepare the product.

C. [1-{(3-Carbamoyl-benzyl)-[1-(4-phenyl-1H-imidazol-2-yl)-ethyl]-carbamoyl}-2-(4-hydroxy-2,6-dimethyl-phenyl)-ethyl]-carbamic acid tert-butyl ester. A solution of [1-{(3-cyano-benzyl)-[1-(4-phenyl-1H-imidazol-2-yl)-ethyl]-carbamoyl}-2-(4-hydroxy-2,6-dimethyl-phenyl)-ethyl]-carbamic acid tert-butyl ester (0.070 g, 0.12 mmol) in 3 mL of EtOH was treated with 1.0 mL of 30% hydrogen peroxide followed immediately by 0.1 mL of a 6M aqueous solution of NaOH. The reaction mixture was stirred vigorously for 18 h and quenched by pouring into chilled (5-10C) water. The aqueous solution was extracted five times with $Et_2O$ and the combined extracts were dried over $MgSO_4$, filtered, and concentrated to provide 0.051 g of [1-{(3-carbamoyl-benzyl)-[1-(4-phenyl-1H-imidazol-2-yl)-ethyl]-carbamoyl}-2-(4-hydroxy-2,6-dimethyl-phenyl)-ethyl]-carbamic acid tert-butyl ester as a colorless residue (HPLC: 84% @254 nm and 77% @214 nm). MS ($ES^+$) (relative intensity): 612.5 (100) (M+1). This sample was of sufficient quality to use in the next reaction without further purification.

D. 3-({[2-Amino-3-(4-hydroxy-2,6-dimethyl-phenyl)-propionyl]-[1-(4-phenyl-1H-imidazol-2-yl)-ethyl]-amino}-methyl)-benzamide. [1-{(3-carbamoyl-benzyl)-[1-(4-phenyl-1H-imidazol-2-yl)-ethyl]-carbamoyl}-2-(4-hydroxy-2,6-dimethyl-phenyl)-ethyl]-carbamic acid tert-butyl ester may be BOC-deprotected using the procedure described in Example 1 for the conversion of Cpd 1e to Cpd 1f to provide the title compound.

Example 12

4-{2-Amino-2-[{1-[4-(2-cyano-phenyl)-1H-imidazol-2-yl]-ethyl}-(3,4-dimethoxy-benzyl)-carbamoyl]-ethyl}-3,5-dimethyl-benzamide

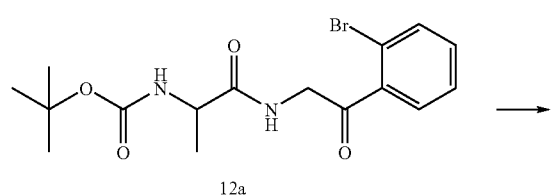

12a

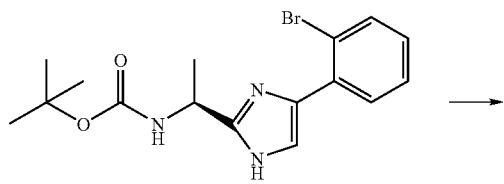

12b

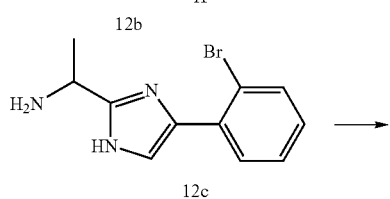

12c

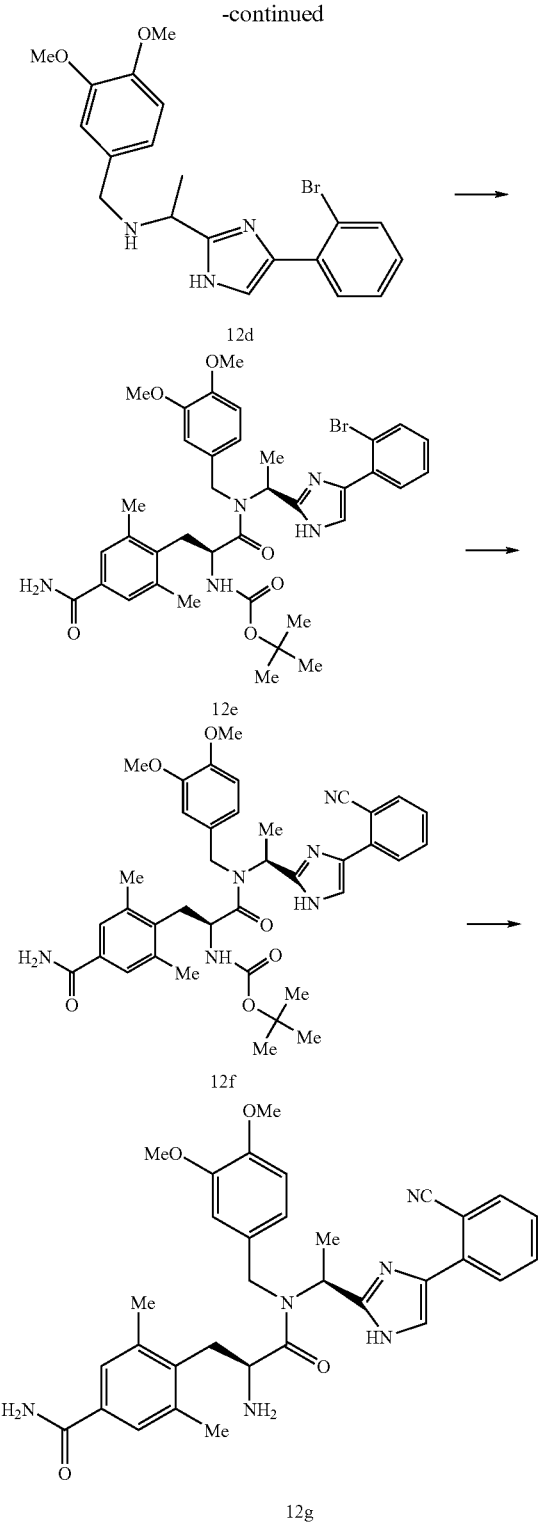

A. {1-[2-(2-Bromo-phenyl)-2-oxo-ethylcarbamoyl]-ethyl}-carbamic acid tert-butyl ester. Compound 2a was prepared according to Example 1 using the appropriate reagents, starting materials and methods known to those skilled in the art.

B. {1-[4-(2-Bromo-phenyl)-1H-imidazol-2-yl]-ethyl}-carbamic acid tert-butyl ester. Following the procedure described in Example 1 for the conversion of Compound 1a to Compound 1b, and using the appropriate reagents and methods known to those skilled in the art, Cpd 12b, was prepared.

C. 1-[4-(4-Bromo-phenyl)-1H-imidazol-2-yl]-ethylamine. Using the procedure described for the conversion of Cpd 1e to 1f, Compound 12c was prepared.

D. [1-[{1-[4-(2-Bromo-phenyl)-1H-imidazol-2-yl]-ethyl}-(3,4-dimethoxy-benzyl)-carbamoyl]-2-(4-carbamoyl-2,6-dimethyl-phenyl)-ethyl]-carbamic acid tert-butyl ester. Using the procedure described in Example 9, Step D, and substituting 1-[4-(4-bromo-phenyl)-1H-imidazol-2-yl]-ethylamine for 1-(4-phenyl-1H-imidazol-2-yl)-ethylamine, the product was prepared.

E. {2-(4-Carbamoyl-2,6-dimethyl-phenyl)-1-[{1-[4-(2-cyano-phenyl)-1H-imidazol-2-yl]-ethyl}-(3,4-dimethoxy-benzyl)-carbamoyl]-ethyl}-carbamic acid tert-butyl ester. To a solution of [1-[{1-[4-(2-bromo-phenyl)-1H-imidazol-2-yl]-ethyl}-(3,4-dimethoxy-benzyl)-carbamoyl]-2-(4-carbamoyl-2,6-dimethyl-phenyl)-ethyl]-carbamic acid tert-butyl ester (294 mg; 0.4 mmol) in DMF (2 mL) was added $Zn(CN)_2$ (28 mg; 0.24 mmol). The resulting mixture was degassed with Argon for 5 min, then $Pd(PPh_3)_4$ (92 mg; 0.08 mmol) was added neat, and the system was immediately warmed to 100° C. After heating for 6 h, the reaction was cooled to rt and partitioned between EtOAc and water. The organic phase was dried over $Na_2SO_4$, filtered, and concentrated under reduced pressure. The crude material was subjected to reverse phase HPLC (water/acetonitrile/0.1% TFA). The fractions of interest were combined, basified with saturated aqueous $NaHCO_3$ and extracted twice with EtOAc. The EtOAc extracts were combined, dried over $Na_2SO_4$, filtered, and concentrated to afford 146 mg (54%) of desired {2-(4-carbamoyl-2,6-dimethyl-phenyl)-1-[{1-[4-(2-cyano-phenyl)-1H-imidazol-2-yl]-ethyl}-(3,4-dimethoxy-benzyl)-carbamoyl]-ethyl}-carbamic acid tert-butyl ester (HPLC: 96% @ 254 nm and 97% @ 214 nm). This sample was of sufficient quality to use in the next reaction without further purification.

F. 4-{2-Amino-2-[{1-[4-(2-cyano-phenyl)-1H-imidazol-2-yl]-ethyl}-(3,4-dimethoxy-benzyl)-carbamoyl]-ethyl}-3,5-dimethyl-benzamide. {2-(4-carbamoyl-2,6-dimethyl-phenyl)-1-[{1-[4-(2-cyano-phenyl)-1H-imidazol-2-yl]-ethyl}-(3,4-dimethoxy-benzyl)-carbamoyl]-ethyl}-carbamic acid tert-butyl ester may be BOC-deprotected using the procedure described in Example 1 for the conversion of Cpd 1e to Cpd 1f to give the title compound.

Example 13

3-(2-{1-[[2-Amino-3-(4-carbamoyl-2,6-dimethyl-phenyl)-propionyl]-(3,4-dimethoxy-benzyl)-amino]-ethyl}-1H-imidazol-4-yl)-benzoic acid

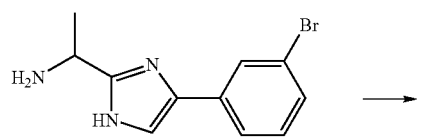

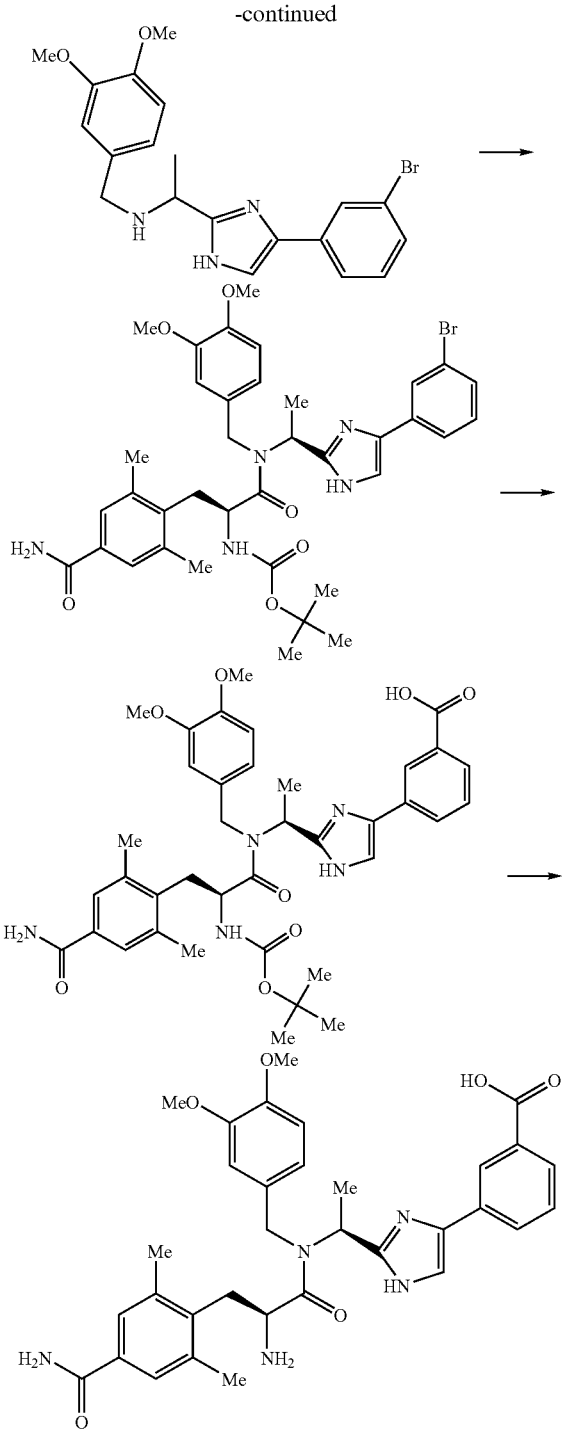

A. 1-[4-(3-Bromo-phenyl)-1H-imidazol-2-yl]-ethylamine. Using the procedure described in Example 12, and the appropriately substituted starting materials and reagents, 1-[4-(3-bromo-phenyl)-1H-imidazol-2-yl]-ethylamine was prepared.

B. {1-[4-(3-Bromo-phenyl)-1H-imidazol-2-yl]-ethyl}-(3,4-dimethoxy-benzyl)-amine-. Using the procedure described in Example 3, and substituting 1-[4-(3-bromo-phenyl)-1H-imidazol-2-yl]-ethylamine for 1-(4-phenyl-1H-imidazol-2-yl)-ethylamine, the product was prepared.

C. [1-[{1-[4-(3-Bromo-phenyl)-1H-imidazol-2-yl]-ethyl}-(3,4-dimethoxy-benzyl)-carbamoyl]-2-(4-carbamoyl-2,6-dimethyl-phenyl)-ethyl]-carbamic acid tert-butyl ester. Using the procedure of Example 1 for the conversion of Cpd 1d to Cpd 1e, substituting {1-[4-(3-Bromo-phenyl)-1H-imidazol-2-yl]-ethyl}-(3,4-dimethoxy-benzyl)-amine for Cpd 1d and substituting 2-tert-Butoxycarbonylamino-3-(4-carbamoyl-2,6-dimethyl-phenyl-propionic acid of Example 8 for 2-tert-Butoxycarbonylamino-3-(4-hydroxy-2,6-dimethyl-phenyl)-propionic acid, the product was prepared.

D. 3-(2-{1-[[2-tert-Butoxycarbonylamino-3-(4-carbamoyl-2,6-dimethyl-phenyl)-propionyl]-(3,4-dimethoxy-benzyl)-amino]-ethyl}-1H-imidazol-4-yl)-benzoic acid. To a solution of [1-[{1-[4-(3-bromo-phenyl)-1H-imidazol-2-yl]-ethyl}-(3,4-dimethoxy-benzyl)-carbamoyl]-2-(4-carbamoyl-2,6-dimethyl-phenyl)-ethyl]-carbamic acid tert-butyl ester (290 mg; 0.40 mmol) in DMF (5 mL) was added $K_2CO_3$ (262 mg; 1.9 mmol) and the resulting mixture was degassed with Argon for 5 min. At this time, $Pd(OAc)_2$ (8.9 mg; 0.04 mmol) and 1,1-bis(diphenylphosphino) ferrocene (46 mg; 0.083 mmol) were added. Carbon monoxide was then bubbled through the resulting mixture for 10 min at rt, the reaction was capped, and warmed to 100° C. for 6 h. After cooling to rt the mixture was partitioned between EtOAc and water, filtered through Celite, and then separated. The aqueous phase was then washed with a second portion of EtOAc. The aqueous phase was then acidified to pH 5 with 2N citric acid and the resulting aqueous solution extracted with EtOAc (4×). These latter EtOAc extracts were combined, dried over $Na_2SO_4$, filtered, and concentrated under reduced pressure to give the crude product (HPLC: 87% at 254 nm).

E. 3-(2-{1-[[2-Amino-3-(4-carbamoyl-2,6-dimethyl-phenyl)-propionyl]-(3,4-dimethoxy-benzyl)-amino]-ethyl}-1H-imidazol-4-yl)-benzoic acid. 3-(2-{1-[[2-tert-Butoxycarbonylamino-3-(4-carbamoyl-2,6-dimethyl-phenyl)-propionyl]-(3,4-dimethoxy-benzyl)-amino]-ethyl}-1H-imidazol-4-yl)-benzoic acid may be BOC-deprotected using the procedure described in Example 1 for the conversion of Cpd 1e to Cpd 1f to give the title compound.

Example 14

4-(2-Amino-2-{[2-hydroxy-1-(4-phenyl-1H-imidazol-2-yl)-ethyl]-isopropyl-carbamoyl}-ethyl)-3,5-dimethyl-benzamide

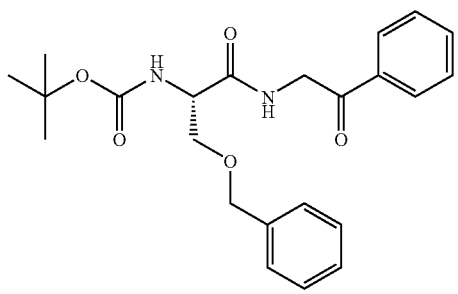

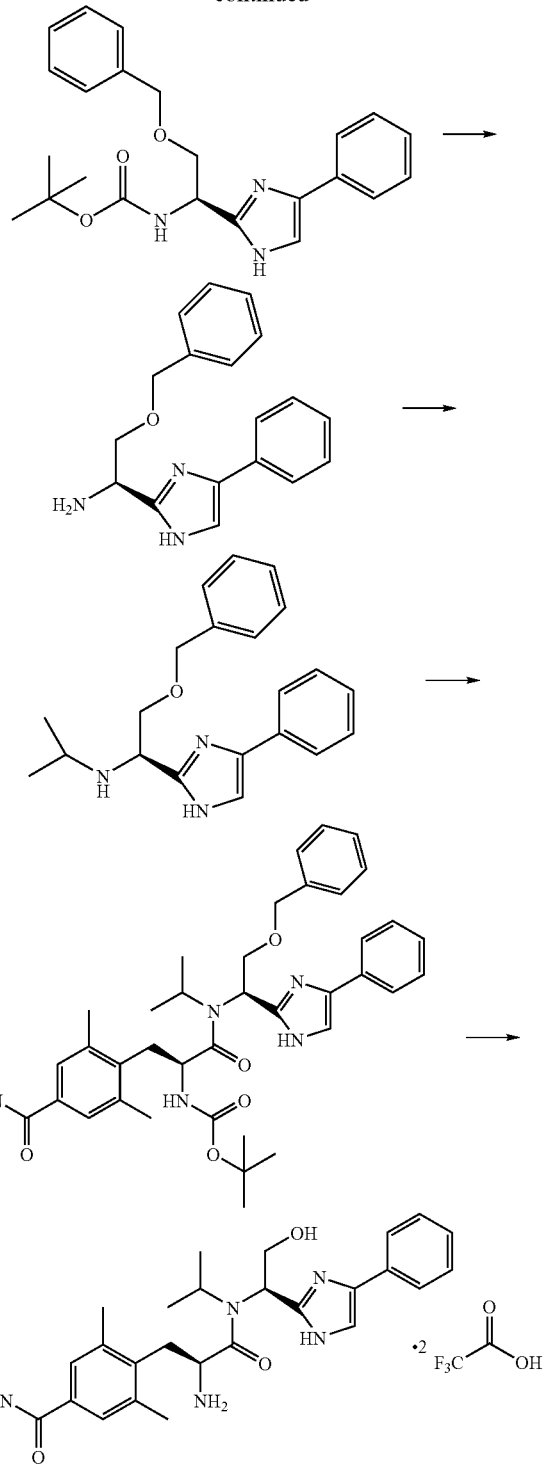

A. [2-Benzyloxy-1-(2-oxo-2-phenyl-ethylcarbamoyl-ethyl]-carbamic acid tert butyl ester. The product was prepared using the procedure described in Example 1 and substituting N-α-BOC-L-serine benzyl ester for N-α-CBZ-L-alanine.

B. [2-Benzyloxy-1-(4-phenyl-1H-imidazol-2-yl-ethyl]-carbamic acid tert butyl ester. By the procedure described in Example 1 for the conversion of Cpd 1a to Cpd 1b, [2-benzyloxy-1-(2-oxo-2-phenyl-ethylcarbamoyl-ethyl]-carbamic acid tert butyl ester was converted to the product.

C. [2-Benzyloxy-1-(4-phenyl-1H-imidazol-2-yl-ethylamine. [2-benzyloxy-1-(4-phenyl-1H-imidazol-2-yl-ethyl]-carbamic acid tert butyl ester may be BOC-deprotected using the procedure described in Example 1 for the conversion of Cpd 1e to Cpd 1f to give the product.

D. [2-Benzyloxy-1-(4-phenyl-1H-imidazol-2-yl-ethyl]-isopropyl-amine. By the procedure described in Example 1 for the conversion of Cpd 1c to Cpd 1d, [2-benzyloxy-1-(4-phenyl-1H-imidazol-2-yl-ethylamine was converted to the product.

E. [1-{[2-Benzyloxy-1-(4-phenyl-1H-imidazol-2-yl)-ethyl]-isopropyl-carbamoyl}-2-(4-carbamoyl-2,6-dimethyl-phenyl)-ethyl]-carbamic acid tert-butyl ester. Using the procedure of Example 1 for the conversion of Cpd 1d to Cpd 1e, substituting [2-benzyloxy-1-(4-phenyl-1H-imidazol-2-yl-ethyl]-isopropyl-amine for Cpd 1d and substituting 2-tert-Butoxycarbonylamino-3-(4-carbamoyl-2,6-dimethyl-phenyl-propionic acid of Example 8 for 2-tert-butoxycarbonylamino-3-(4-hydroxy-2,6-dimethyl-phenyl)-propionic acid, the product was prepared.

F. 4-(2-Amino-2-{[2-hydroxy-1-(4-phenyl-1H-imidazol-2-yl)-ethyl]-isopropyl-carbamoyl}-ethyl)-3,5-dimethyl-benzamide (TFA salt). A solution of [1-{[2-benzyloxy-1-(4-phenyl-1H-imidazol-2-yl)-ethyl]-isopropyl-carbamoyl}-2-(4-carbamoyl-2,6-dimethyl-phenyl)-ethyl]-carbamic acid tert-butyl ester, (0.287 g, 0.439 mmol), in chloroform (10 mL) was cooled in an ice bath and treated with 0.62 mL (4.4 mmol) of iodotrimethylsilane. The reaction, which immediately clouded, was warmed slowly to room temperature while stirring. After 16 h, the reaction was cooled in an ice bath to 5-10° C. and treated with 100 mL of MeOH. The quenched mixture was stirred at 5-10° C. for 30 min, removed from the ice bath and stirred for an additional 30 min, and concentrated in vacuo to obtain 0.488 g of orange residue that was subjected to reverse phase HPLC (water/acetonitrile/0.1% TFA). The fractions of interest were combined and the sample was lyophilized to afford 0.150 g (59%) of 4-(2-amino-2-{[2-hydroxy-1-(4-phenyl-1H-imidazol-2-yl)-ethyl]-isopropyl-carbamoyl}-ethyl)-3,5-dimethyl-benzamide (TFA salt) as a white powder (HPLC: 99% @ 254 nm and 100% @ 214 nm). MS (ES$^+$) (relative intensity): 464.1 (100)(M+1).

Example 15

(S)-2-tert-Butoxycarbonylamino-3-(4-carbamoyl-2,6-dimethyl-phenyl)-propionic acid

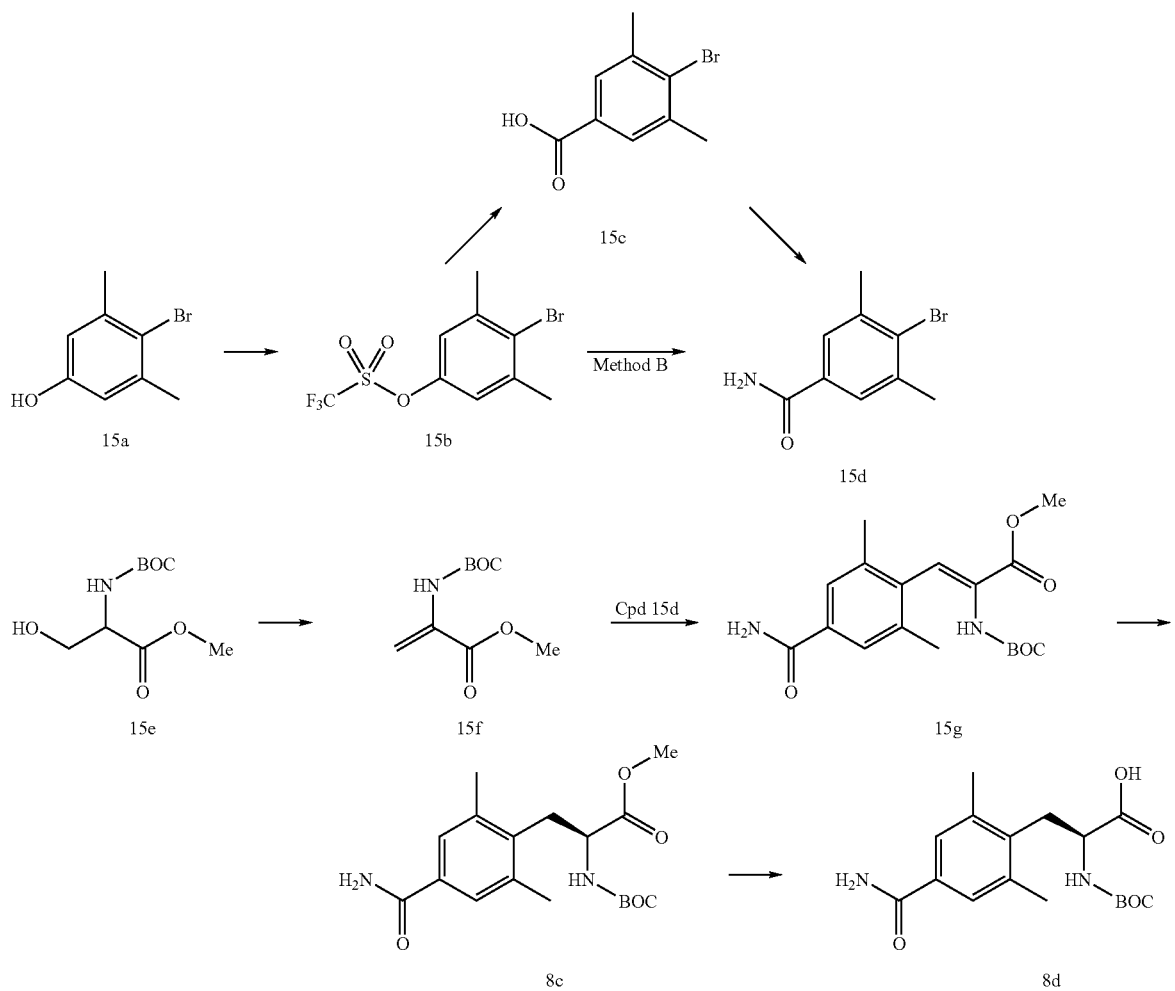

A. Trifluoromethanesulfonic acid 4-bromo-3,5-dimethyl-phenyl ester. To a cooled (0° C.) solution of 4-bromo-3,5-dimethylphenol (3.05 g, 15.2 mmol) in pyridine (8 mL) was added trifluoromethanesulfonic anhydride (5.0 g, 17.7 mmol) dropwise. After completion of addition, the resulting mixture was stirred at 0° C. for 15 min, and then at rt overnight. The reaction was quenched by addition of water, and then extracted with EtOAc. The organic extracts were washed sequentially with water, 2N HCl (2×), brine, and then dried over $MgSO_4$. Filtration and evaporation to dryness afforded Compound 15b (5.30 g, 95%) as a colorless oil. $^1$H NMR (300 MHz, $CDCl_3$): δ 2.45 (6H, s), 7.00 (2H, s).

B. 4-Bromo-3,5-dimethylbenzoic acid. To a solution of Compound 15b (6.57 g, 19.7 mmol) in DMF (65 mL) were added $K_2CO_3$ (13.1 g, 94.7 mmol), $Pd(OAc)_2$ (0.44 g, 1.97 mmol) and 1,1'-bis(diphenylphosphino)ferrocene (2.29 g, 4.14 mmol). The resulting mixture was bubbled in gaseous CO for 10 min and was heated to 60° C. for 7.5 h with a $CO_{(g)}$ balloon. The cooled mixture was partitioned between aqueous $NaHCO_3$ and EtOAc, and filtered. The aqueous phase was separated, acidified with aqueous 6N HCl, extracted with EtOAc, and finally dried over $Na_2SO_4$. Filtration and concentration of the filtrate resulted in the crude Compound 15c as a brown residue, which was used in the next step without further purification.

C. 4-Bromo-3,5-dimethyl-benzamide. A suspension of Compound 15c in DCM (40 mL) was added $SOCl_2$ (3.1 mL, 42 mmol) and the mixture was heated at reflux for 2 h. Upon removal of the solvent by evaporation, the residue was dissolved in DCM (40 mL) and ammonium hydroxide (28% $NH_3$ in water, 2.8 mL) was added. The mixture was heated at 50° C. for 2 h and concentrated. The residue was diluted with $H_2O$, extracted with EtOAc, and the organic portion was dried over $Na_2SO_4$. After filtration and evaporation, the residue was purified by flash column chramotagraphy (eluent: EtOAc) to give the Compound 15d (2.90 g, 65% for 2 steps) as an off-white solid. $^1$H NMR (300 MHz, $CD_3CN$): δ 2.45 (6H, s), 5.94 (1H, br s), 6.71 (1H, br s), 7.57 (2H, s); MS(ES$^+$)(relative intensity): 228.0 (100%) (M+1).

Method B: A mixture of Compound 15b (3.33 g, 10 mmol), $PdCl_2$ (0.053 g, 0.3 mmol), hexamethyldisilazane (HMDS, 8.4 mL, 40 mmol), and dppp (0.12 g, 0.3 mmol) was bubbled with a gaseous CO for 5 min and then stirred in a CO balloon at 80° C. for 4 h. To the reaction mixture was added MeOH (5 mL). The mixture was stirred for 10 min, diluted with 2N $H_2SO_4$ (200 mL), and then extracted with EtOAc. The EtOAc extract was washed with saturated aqueous $NaHCO_3$, brine, and then dried over $Na_2SO_4$. Filtration and evaporation of the resultant filtrate gave a residue, which was purified by flash column chromatography (eluent: EtOAc) to give Compound 15d (1.60 g, 70%) as a white solid.

D. 2-tert-Butoxycarbonylaminoacrylic acid methyl ester. To a suspension of N-Boc-serine methyl ester (Cpd 15e, 2.19 g, 10 mmol) and EDC (2.01 g, 10.5 mmol) in DCM (70 mL) was added CuCl (1.04 g, 10.5 mmol). The reaction mixture was stirred at rt for 72 h. Upon removal of the solvent, the residue was diluted with EtOAc, washed sequentially with water and brine and then dried over $MgSO_4$. The crude product was purified by flash column chromatography (eluent: EtOAc:hexane~1:4) to give Compound 15e (1.90 g, 94%) as a colorless oil. $^1$H NMR (300 MHz, $CDCl_3$): δ 1.49 (9H, s), 3.83 (3H, s), 5.73 (1H, d, J=1.5 Hz), 6.16 (1H, s), 7.02 (1H, s).

E. (Z)-2-tert-Butoxycarbonylamino-3-(4-carbamoyl-2,6-dimethyl-phenyl)acrylic acid methyl ester. A flask charged with Compound 15d (0.46 g, 2.0 mmol), Compound 15f (0.80 g, 4.0 mmol), tri-o-tolylphosphine (0.098 g, 0.32 mmol), DMF (8 mL) was purged with $N_{2\,(g)}$ 3 times. After the addition of tris(dibenzylideneacetone)dipalladium (0) (0.074 g, 0.08 mmol) and TEA (0.31 mL, 2.2 mol), the reaction mixture was heated at 110° C. for 24 h. At that time, the reaction was quenched by addition of water, and then extracted with EtOAc. The organic phase was washed with 1 N HCl, saturated aqueous $NaHCO_3$, brine, and dried over $MgSO_4$. The mixture was concentrated to a residue, which was purified by flash column chromatography (eluent: EtOAc:hexane~1:1 to EtOAc only) to give Compound 15g (0.40 g, 57%) as a white solid. $^1$H NMR (300 MHz, $CD_3OD$): δ 1.36 (9H, s), 2.26 (6H, s), 3.83 (3H, s), 7.10 (1H, s), 7.56 (2H, s); $^{13}$C NMR (75 MHz, DMSO-$d_6$): δ 17.6, 25.7, 50.2, 78.7, 124.9, 126.4, 128.3, 131.2, 135.2, 135.5, 152.8, 164.3,169.6; MS (ES$^+$) (relative intensity): 349.1 (38%)(M+1).

F. (S)-2-tert-Butoxycarbonylamino-3-(4-carbamoyl-2,6-dimethyl-phenyl)propionic acid methyl ester. Into a reactor charged with a solution of Compound 15g (0.56 g, 1.6 mmol) in degassed MeOH (80 mL) was added [Rh(cod)(R,R-DIPAMP)]$^+$BF$_4^-$ under a stream of argon. The reactor was sealed and flushed with $H_2$, stirred at 60° C. under 1000 psi of $H_2$ for 14 d. The crude product was purified by flash column chromatography (eluent: EtOAc:hexane~1:1) to afford Compound 8c (0.54 g, 96%) as a white solid. ee: >99%; $^1$H NMR (300 MHz, $CDCl_3$): δ 1.36 (9H, s), 2.39 (6H, s), 3.11 (2H, J=7.2 Hz), 3.65 (3H, s), 4.53-4.56 (1H, m), 5.12 (1H, d, J=8.7 Hz), 5.65 (1H, br s), 6.09 (1H, br s), 7.46 (2H, s); MS(ES$^+$) (relative intensity): 250.9 (100) (M–Boc)$^+$.

G. (S)-2-tert-Butoxycarbonylamino-3-(4-carbamoyl-2,6-dimethyl-phenyl)propionic acid. Into an ice-cooled solution of Compound 8c (0.22 g, 0.63 mmol) in THF (3.5 mL) was added an aqueous LiOH solution (1 N, 3.5 mL) and stirred at 0° C. Upon completion of the reaction, the reaction was concentrated and the aqueous phase was neutralized with cooled aqueous 1 N HCl at 0° C., and extracted with EtOAc. The combined extracts were dried over $Na_2SO_4$ overnight. Filtration and evaporation of the filtrate to dryness led to Compound 8d (0.20 g, 94%) as a white solid. $^1$H NMR (300 MHz, DMSO-$d_6$): δ 1.30 (9H, s), 2.32 (6H, s), 2.95 (1H, dd, J=8.8, 13.9 Hz), 3.10 (1H, dd, J=6.2, 14.0 Hz), 4.02-4.12 (1H, m), 7.18-7.23 (2H, m), 7.48 (2H, s), 7.80 (1H, s); MS(ES$^+$) (relative intensity): 236.9 (6) (M–Boc)$^+$.

Example 16

Racemic 2-tert-Butoxycarbonylamino-3-(4-carbamoyl-2,6-dimethyl-phenyl)-propionic acid

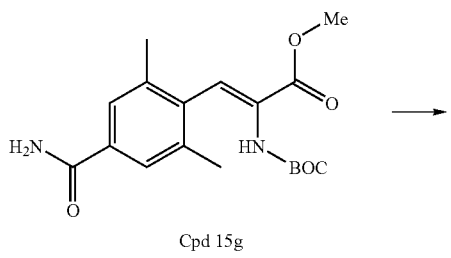

Cpd 15g

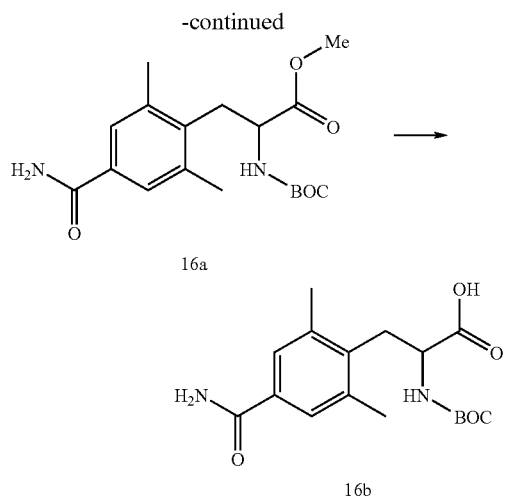

16a

16b

A. Racemic 2-tert-butoxycarbonylamino-3-(4-carbamoyl-2,6-dimethyl-phenyl)propionic acid methyl ester. To a reactor charged with a solution of Compound 15g (0.68 g, 1.95 mmol) in MeOH (80 mL) was added 10% Pd-C (0.5 g). The reactor was connected to a hydrogenator and shaken under 51 psi of $H_2$ overnight. The mixture was filtered through a pad of Celite and the filtrate was concentrated to dryness to give Compound 16a (0.676 g, 99%) as a white solid. The $^1H$ NMR spectrum was identical to that of (S)-2-tert-butoxycarbonylamino-3-(4-carbamoyl-2,6-dimethyl-phenyl)propionic acid methyl ester, Compound 8c.

B. Racemic 2-tert-butoxycarbonylamino-3-(4-carbamoyl-2,6-dimethyl-phenyl)propionic acid. Using the procedure described for Example 15, for the preparation of (S)-2-tert-Butoxycarbonylamino-3-(4-carbamoyl-2,6-dimethyl-phenyl)propionic acid, racemic 2-tert-butoxycarbonylamino-3-(4-carbamoyl-2,6-dimethyl-phenyl)propionic acid, Compound 16b, was prepared.

Using the procedures of the Examples above and the appropriate reagents, starting materials and purification methods known to those skilled in the art, other compounds of the present invention may be prepared including but not limited to:

TABLE VI

Mass Spectral Data for Selected Compounds

| Cpd | Theoretical MW | Measured MW (MH+) |
|---|---|---|
| 1 | 538 | 539 |
| 2 | 520 | 521 |
| 3 | 573 | 574 |
| 4 | 541 | 542 |
| 5 | 527 | 528 |
| 6 | 555 | 556 |
| 7 | 569 | 570 |
| 8 | 593 | 594 |
| 9 | 553 | 554 |
| 10 | 603 | 604 |
| 11 | 589 | 590 |
| 12 | 587.2 | 588.3 |
| 13 | 589.3 | 590.2 |
| 14 | 569.3 | 570.2 |
| 15 | 500.2 | 499.2 |
| 16 | 475.3 | 476.1 |
| 17 | 583.28 | 584.5 |
| 18 | 569.26 | 570.2 |
| 19 | 633.2 | 634.0 |
| 20 | 599.3 | 600.2 |
| 21 | 634.3 | 635.2 |
| 22 | 634.3 | 635.2 |
| 23 | 598.3 | 599.2 |
| 24 | 580.3 | 581.1 |
| 25 | 471.26 | 472.4 |
| 26 | 633.2 | 634.0 |
| 27 | 580.3 | 581.1 |
| 28 | 598.3 | 599.2 |
| 29 | 599.3 | 600.0 |
| 30 | 680.3 | 681.2 |
| 31 | 512.2 | 513 |
| 32 | 498.3 | 499.1 |
| 33 | 498.3 | 499.1 |
| 34 | 528.3 | 529.2 |
| 35 | 514.3 | 515.1 |
| 36 | 462.26 | 463.4 |
| 37 | 482.23 | 483.4 |
| 38 | 446.27 | 447.5 |
| 39 | 450.26 | 451.5 |
| 40 | 530.3 | 531.2 |
| 41 | 445.3 | 446.1 |
| 42 | 563.3 | 564.2 |
| 43 | 504.23 | 505.3 |
| 44 | 504.23 | 505.3 |
| 45 | 513.24 | 514.3 |
| 46 | 492.27 | 493.2 |
| 47 | 479.25 | 480.1 |
| 48 | 512.2 | 513.2 |
| 49 | 540.2 | 541 |
| 50 | 539.25 | 540.2 |
| 51 | 553.3 | 554.1 |
| 52 | 526.3 | 527.1 |
| 53 | 609.3 | 610.2 |
| 54 | 458.2 | 459 |
| 55 | 458.2 | 459 |
| 56 | 474.3 | 475.2 |
| 57 | 469.25 | 470.1 |
| 58 | 543.2 | 544.3 |
| 59 | 513.3 | 514.2 |
| 60 | 445.3 | 446.2 |
| 61 | 456.2 | 457.1 |
| 62 | 498.2 | 499.1 |
| 63 | 436.3 | 437.1 |
| 64 | 601.3 | 602.2 |
| 65 | 422.1 | 423.1 |
| 66 | 463.3 | 464.5 |
| 67 | 491.3 | 492.1 |
| 68 | 436.3 | 437.1 |
| 69 | 463.3 | 464.1 |
| 70 | 454.2 | 455.0 |
| 71 | 456.2 | 457.0 |
| 72 | 498.2 | 499.1 |
| 73 | 463.3 | 464.2 |
| 74 | 577.3 | 578.6 |
| 75 | 555.3 | 555.8 |
| 76 | 513.3 | 514.2 |
| 77 | 525.3 | 526.3 |
| 78 | 497.3 | 498.3 |
| 79 | 525.3 | 526.2 |
| 80 | 512.2 | 513.2 |
| 81 | 484.2 | 485.4 |
| 82 | 438.24 | 439.2 |
| 83 | 486.24 | 487.5 |
| 84 | 438.24 | 439.0 |
| 85 | 463.3 | 464.2 |
| 86 | 433.2 | 434.2 |
| 87 | 522.2 | 523 |
| 88 | 526.3 | 527.4 |
| 89 | 526.3 | 527.4 |
| 90 | 511.3 | 512.4 |
| 91 | 493.2 | 494.4 |
| 92 | 469.2 | 470.2 |

TABLE VI-continued

Mass Spectral Data for Selected Compounds

| Cpd | Theoretical MW | Measured MW (MH+) |
|---|---|---|
| 93 | 469.2 | 470.4 |
| 94 | 495.3 | 496.2 |
| 95 | 495.3 | 496.2 |
| 96 | 498.3 | 499.2 |
| 97 | 536.2 | 537.2 |
| 98 | 560.3 | 561.2 |
| 99 | 518.3 | 519.2 |
| 100 | 518.3 | 519.2 |
| 101 | 546.2 | 547.2 |
| 102 | 528.3 | 529.2 |
| 103 | 536.2 | 537.2 |
| 104 | 510.3 | 511.2 |
| 105 | 544.3 | 545.3 |
| 106 | 496.3 | 497.2 |
| 107 | 481.3 | 482.3 |
| 108 | 523.3 | 524.8 |
| 109 | 509.3 | 510.4 |
| 110 | 509.3 | 510.3 |
| 111 | 509.3 | 510 |
| 112 | 509.3 | 510 |
| 113 | 495.3 | 496.4 |
| 114 | 495.3 | 496.1 |
| 115 | 496.28 | 497.4 |
| 115 | 496.28 | 497.4 |
| 116 | 438.24 | 439.4 |
| 117 | 438.24 | 439.4 |
| 118 | 436.2 | 437.3 |
| 119 | 394.2 | 395.2 |
| 120 | 525.3 | 526.2 |
| 121 | 539.3 | 540.3 |
| 122 | 521.3 | 522.3 |
| 123 | 464 | 465 |
| 124 | 421 | 422 |
| 125 | 450.26 | 451.5 |
| 126 | 456.23 | 457.3 |
| 127 | 487.3 | 488.5 |
| 128 | 487.3 | 488.6 |
| 129 | 422.2 | 423.3 |
| 130 | 450 | 451 |
| 131 | 422.2 | 423.3 |
| 132 | 394.2 | 395.2 |
| 133 | 464.2 | 465.3 |
| 134 | 496.3 | 497.4 |
| 135 | 450.26 | 451.37 |
| 136 | 495.3 | 496.4 |
| 137 | 447.3 | 448.4 |
| 138 | 526.3 | 527.4 |
| 139 | 653.4 | 654.5 |
| 140 | 462.3 | 463.4 |
| 141 | 488.17 | 489.16 |
| 142 | 450.26 | 451.40 |
| 143 | 447.3 | 448.4 |
| 144 | 419.2 | 420.3 |
| 145 | 496.28 | 497.32 |
| 146 | 426.21 | 427.39 |
| 147 | 454.21 | 455.22 |
| 148 | 477.3 | 478 |
| 149 | 488.2 | 489 |
| 150 | 470.3 | 471 |
| 151 | 488.2 | 489 |
| 152 | 398.2 | 399 |
| 153 | 393 | 394 |
| 154 | 392 | 393 |
| 155 | 454.21 | 455.21 |
| 156 | 470.27 | 471.36 |
| 157 | 477.2 | 478.4 |
| 158 | 468.2 | 469.4 |
| 159 | 496.3 | 497.4 |
| 160 | 429.2 | 430.4 |
| 161 | 420.2 | 421.4 |
| 162 | 448.3 | 449.4 |
| 163 | 438.24 | 439.1 |
| 164 | 556.23 | 557.1 |
| 165 | 434.27 | 435.1 |
| 166 | 420.25 | 421.1 |
| 167 | 449.3 | 450.2 |
| 168 | 433.3 | 434.2 |
| 169 | 415.2 | 416.2 |
| 170 | 434.3 | 435.3 |
| 171 | 392.2 | 393.3 |
| 172 | 497.2 | 498.3 |
| 173 | 479.2 | 480.3 |
| 174 | 434.3 | 435.3 |
| 175 | 484.2 | 485.2 |
| 176 | 420.2 | 421.4 |
| 177 | 454.2 | 455.3 |
| 178 | 433.3 | 434.1 |
| 179 | 489.3 | 490.1 |
| 180 | 489.3 | 489.9 |
| 181 | 447.3 | 448.1 |
| 182 | 447.3 | 448.3 |
| 183 | 433.3 | 434.2 |
| 184 | 433.3 | 434.2 |
| 185 | 405.2 | 406.2 |
| 186 | 387.2 | 388.2 |
| 187 | 406.2 | 407.2 |
| 188 | 378.2 | 379.2 |
| 189 | 427.2 | 428 |
| 190 | 446.3 | 447.4 |
| 191 | 418.2 | 419.4 |
| 192 | 418.2 | 419.3 |
| 193 | 390.2 | 391.3 |
| 194 | 406.2 | 407.5 |
| 195 | 378.2 | 379.3 |
| 196 | 419.2 | 420.4 |
| 197 | 433.3 | 434.1 |
| 198 | 350.2 | 351.1 |
| 199 | 378.2 | 379.2 |
| 202 | 391.2 | 392 |
| 203 | 391.2 | 391.9 |
| 204 | 378.2 | 379 |
| 205 | 406.2 | 407 |
| 206 | 392.2 | 393.3 |
| 207 | 392.2 | 393.2 |
| 208 | 378.2 | 379.3 |
| 209 | 378.2 | 379.2 |
| 210 | 364.2 | 365.2 |
| 211 | 364.2 | 365.2 |
| 212 | 350.2 | 351.2 |
| 213 | 350.2 | 351.1 |
| 214 | 378.2 | 379.1 |
| 215 | 378.2 | 379.1 |
| 216 | 406.2 | 407.2 |
| 217 | 406.2 | 407.1 |
| 218 | 468.3 | 469.4 |
| 219 | 440.2 | 441.3 |
| 220 | 468.3 | 469.4 |
| 221 | 440.2 | 441.2 |
| 222 | 392.2 | 393.2 |
| 223 | 420.3 | 421.2 |
| 224 | 420.3 | 421.1 |
| 225 | 392.2 | 393.2 |
| 226 | 539 | 540 |
| 227 | 539 | 540 |
| 228 | 587 | 588 |
| 229 | 633 | 634 |
| 230 | 599.3 | 599.8 |
| 231 | 512.2 | 513.2 |
| 239 | 617.2 | 618.2 |
| 242 | 563.3 | 564.2 |
| 246 | 519.3 | 520.0 |
| 247 | 548.3 | 549.2 |
| 248 | 552.2 | 553.2 |
| 249 | 536.2 | 537.0 |
| 250 | 526.3 | 527.2 |
| 251 | 512.3 | 513.2 |
| 252 | 554.3 | 555.3 |
| 253 | 540.2 | 541.2 |

TABLE VI-continued

Mass Spectral Data for Selected Compounds

| Cpd | Theoretical MW | Measured MW (MH+) |
|---|---|---|
| 254 | 540.2 | 541.2 |
| 255 | 554.3 | 555.3 |
| 256 | 529.2 | 530.2 |
| 257 | 543.2 | 543.9 |
| 260 | 542.2 | 543.2 |
| 261 | 514.2 | 515.1 |
| 262 | 528.2 | 529.1 |
| 266 | 512.2 | 513.2 |
| 267 | 535.2 | 536.0 |
| 268 | 556.3 | 557.2 |
| 269 | 525.2 | 526.0 |
| 270 | 511.2 | 512.2 |
| 271 | 539.2 | 540.2 |
| 272 | 525.2 | 526.0 |
| 273 | 541.2 | 542.4 |
| 274 | 618.2 | 619.2 |
| 275 | 589.2 | 590.2 |
| 276 | 559.2 | 560.2 |
| 277 | 559.2 | 560.2 |
| 278 | 617.2 | 618.2 |
| 279 | 528.2 | 528.9 |
| 280 | 583.3 | 584.4 |
| 281 | 555.2 | 556.2 |
| 282 | 569.3 | 570.2 |
| 283 | 541.2 | 542.2 |
| 284 | 555.2 | 556.3 |
| 285 | 541.2 | 542.4 |
| 286 | 516.2 | 517.0 |
| 287 | 502.2 | 503.1 |
| 288 | 648.6 | 648.0 |
| 289 | 695.2 | 695.7 |
| 290 | 648.6 | 648.0 |
| 291 | 648.6 | 648.0 |
| 292 | 526.3 | 527.4 |
| 293 | 562.2 | 563.2 |
| 294 | 562.2 | 563.2 |
| 295 | 568.3 | 569.3 |
| 296 | 638.3 | 638.8 |
| 297 | 513.2 | 513.7 |
| 298 | 583.3 | 583.8 |
| 299 | 612.3 | 613.3 |
| 300 | 608.3 | 609.3 |
| 301 | 644.3 | 644.7 |
| 303 | 515.2 | 515.8 |
| 304 | 501.2 | 502.2 |
| 305 | 617.3 | 617.8 |
| 306 | 661.3 | 661.8 |
| 307 | 566.3 | 566.8 |
| 308 | 661.3 | 661.8 |
| 309 | 649.3 | 650.0 |
| 310 | 641.3 | 642.3 |
| 311 | 554.3 | 555.3 |
| 312 | 554.3 | 555.3 |
| 313 | 554.3 | 555.3 |
| 314 | 554.3 | 555.3 |
| 315 | 627.3 | 628.3 |
| 316 | 540.2 | 541.3 |
| 317 | 540.2 | 541.3 |
| 318 | 589.2 | 590.2 |

BIOLOGICAL EXAMPLES

Opioid receptor binding affinity of the compounds of the present invention was determined according to the following procedures and the indicated results were obtained.

Example 1

Rat Brain Delta Opioid Receptor Binding Assay

Male, Wistar rats (150-250 g, VAF, Charles River, Kingston, N.Y.) are killed by cervical dislocation, and their brains removed and placed immediately in ice cold Tris HCl buffer (50 mM, pH 7.4). The forebrains are separated from the remainder of the brain by a coronal transection, beginning dorsally at the colliculi and passing ventrally through the midbrain-pontine junction. After dissection, the forebrains are homogenized in Tris buffer in a Teflone® glass homogenizer. The homogenate is diluted to a concentration of 1 g of forebrain tissue per 80 mL Tris and centrifuged at 39,000×g for 10 min. The pellet is resuspended in the same volume of Tris buffer containing 5 mM $MgCl_2$ with several brief pulses from a Polytron homogenizer. This particulate preparation is used for the delta opioid binding assays. Following incubation with the delta selective peptide ligand ~4 nM [$^3$H]DPDPE at 25° C. for 2.5 h in a 96-well plate with total volume of 1 mL, the plate contents are filtered through Wallac filtermat B sheets on a Tomtec 96-well harvester. The filters are rinsed three times with 2 mL of 10 mM HEPES (pH 7.4), and dried in a microwave oven 2 min twice. To each sample area 2×50 µL of Betaplate Scint scintillation fluid (LKB) is added and analyzed on a LKB (Wallac) 1205 BetaPlate liquid scintillation counter.

The data are used to calculate either the % inhibition compared to control binding (when only a single concentration of test compound is evaluated) or a $K_i$ value (when a range of concentrations is tested). % inhibition is calculated as: [(total dpm-test compound dpm)/(total dpm-nonspecific dpm)]*100. Kd and Ki values were calculated using GraphPad PRISM data analysis program. The biological activity of the compounds of the present invention is shown in Table VII.

Example 1a

Rat Brain Delta Opioid Receptor Binding Assay-Version 1a

Male, Wistar rats (150-250 g, VAF, Charles River, Kingston, N.Y.) were killed by cervical dislocation, and their brains removed and placed immediately in ice-cold Tris HCl buffer (50 mM, pH 7.4). The forebrains were separated from the remainder of the brain by a coronal transection, beginning dorsally at the colliculi and passing ventrally through the midbrain-pontine junction. After dissection, the forebrains were homogenized in Tris buffer in a Teflon®-glass homogenizer. The homogenate was diluted to a concentration of 1 g of forebrain tissue per 80 mL Tris and centrifuged at 39,000×g for 10 min. The pellet was resuspended in the same volume of Tris buffer containing 5 mM $MgCl_2$ with several brief pulses from a Polytron homogenizer. This particulate preparation was used for the delta opioid binding assay. Following incubation with 0.1 nM of the delta selective ligand [$^3$H]naltrindole at 25° C. for 2.5 h in a 96-well plate with total 1 mL, the plate contents were filtered through Wallac filtermat B sheets on a Tomtec 96-well harvester. The filters were rinsed three times with 2 mL of 10 mM HEPES (pH 7.4) and dried in a microwave oven. To each sample area, Betaplate Scint scintillation fluid (LKB) was added and the resulting radioactivity quantified on a LKB (Wallac) 1205 BetaPlate liquid scintillation counter. Kd and Ki values were calculated using the GraphPad PRISM data analysis program. The biological activity of the compounds of the present invention is shown in Table VII.

Example 2

Rat Brain Mu Opioid Receptor Binding Assay

Male, Wistar rats (150-250 g, VAF, Charles River, Kingston, N.Y.) are killed by cervical dislocation, and their brains removed and placed immediately in ice cold Tris HCl buffer (50 mM, pH 7.4). The forebrains are separated from the remainder of the brain by a coronal transection, beginning dorsally at the colliculi and passing ventrally through the midbrain-pontine junction. After dissection, the forebrains are homogenized in Tris buffer in a Teflon® glass homogenizer. The homogenate is diluted to a concentration of 1 g of forebrain tissue per 80 mL Tris and centrifuged at 39,000×g for 10 min. The pellet is resuspended in the same volume of Tris buffer containing 5 mM $MgCl_2$ with several brief pulses from a Polytron homogenizer. This particulate preparation is used for the mu-opioid binding assays. Following incubation with the mu selective peptide ligand .about. 0.8 nM [$^3$H] DAMGO at 25° C. for 2.5 h in a 96-well plate with total 1 mL, the plate contents are filtered through Wallac filtermat B sheets on a Tomtec 96-well harvester. The filters are rinsed three times with 2 mL of 10 mM HEPES (pH7.4), and dried in a microwave oven 2 min twice. To each sample area 2×50 μL of Betaplate Scint scintillation fluid (LKB) is added and analyzed on a LKB (Wallac) 1205 BetaPlate liquid scintillation counter.

The data are used to calculate either the % inhibition compared to control binding (when only a single concentration of test compound is evaluated) or a $K_i$ value (when a range of concentrations is tested). % inhibition is calculated as: [(total dpm-test compound dpm)/(total dpm-nonspecific dpm)]*100. Kd and Ki values were calculated using GraphPad PRISM data analysis program. The biological activity of the compounds of the present invention is shown in Table VII.

Example 2a

Rat Brain Mu Opioid Receptor Binding Assay-Version 2a

Male, Wistar rats (150-250 g, VAF, Charles River, Kingston, N.Y.) were killed by cervical dislocation, and their brains removed and placed immediately in ice-cold Tris HCl buffer (50 mM, pH 7.4). The forebrains were separated from the remainder of the brain by a coronal transection, beginning dorsally at the colliculi and passing ventrally through the midbrain-pontine junction. After dissection, the forebrains were homogenized in Tris buffer in a Teflon®-glass homogenizer. The homogenate was diluted to a concentration of 1 g of forebrain tissue per 80 mL Tris and centrifuged at 39,000×g for 10 min. The pellet was resuspended in the same volume of Tris buffer containing 5 mM $MgCl_2$ with several brief pulses from a Polytron homogenizer. This particulate preparation was used for the mu opioid binding assay. Following incubation with 0.8 nM of the mu selective ligand [$^3$H]DAMGO at 25° C. for 2.5 h in a 96-well plate with total 1 mL, the plate contents were filtered through Wallac filtermat B sheets on a Tomtec 96-well harvester. The filters were rinsed three times with 2 mL of 10 mM HEPES (pH 7.4), and dried in a microwave oven. To each sample area, Betaplate Scint scintillation fluid (LKB) was added and the resulting radioactivity quantified on a LKB (Wallac) 1205 BetaPlate liquid scintillation counter. Kd and Ki values were calculated using the GraphPad PRISM data analysis program.

TABLE VII

| Cpd | r Ki δ* (nM) | r Ki δ* Ver. 1a (nM) | r Ki μ* (nM) |
|---|---|---|---|
| 1 | 13.2 | | 1.1 |
| 2 | | | |
| 3 | | | |
| 4 | 11, 17 | | 2.41 |
| 5 | 630, 183 | | 1.19 |
| 6 | 1.7 | | |
| 7 | | | |
| 8 | 0.43, 0.15 | | 0.51 |
| 9 | 0.11 | | 0.16 |
| 10 | | | |
| 11 | 0.54 | | 0.23 |
| 12 | 0.08 | | |
| 13 | | | |
| 14 | 0.36 | | |
| 15 | | | |
| 16 | | | |
| 17 | 60 | | 0.22 |
| 18 | 0.38-14.4 | | 0.75, 1.1 |
| 19 | | | |
| 20 | | | |
| 21 | | | |
| 22 | | | |
| 23 | | | |
| 24 | | | |
| 25 | | | |
| 26 | | | |
| 27 | | | |
| 28 | | | |
| 29 | 28 | | 25 |
| 30 | | | |
| 31 | | | |
| 32 | | | |
| 33 | | | |
| 34 | | | |
| 35 | | | |
| 36 | | | |
| 37 | | | |
| 38 | | | |
| 39 | | | |
| 40 | | | |
| 41 | | | |
| 42 | | | |
| 43 | | | |
| 44 | | | |
| 45 | | | |
| 46 | | | |
| 47 | | | |
| 48 | | 0.24 | 0.14 |
| 49 | | | |
| 50 | 0.58 | | 1.68 |
| 51 | | | |
| 52 | | | |
| 53 | | | |
| 54 | | | |
| 55 | | | |
| 56 | | | |
| 57 | | | |
| 58 | | | |
| 59 | | | |
| 60 | | | |
| 61 | | | |
| 62 | | | |
| 63 | | | |
| 64 | | | |
| 65 | | | |
| 66 | | | |
| 67 | | | |
| 68 | | | |

TABLE VII-continued

| Cpd | r Ki δ* (nM) | r Ki δ* Ver. 1a (nM) | r Ki μ* (nM) |
|---|---|---|---|
| 69 | | | |
| 70 | | | |
| 71 | | | |
| 72 | | | |
| 73 | | | |
| 74 | | | |
| 75 | 0.66 | | 0.51 |
| 76 | | | |
| 77 | | | |
| 78 | | | |
| 79 | | | |
| 80 | | | |
| 81 | | | |
| 82 | | | |
| 83 | | | |
| 84 | | | |
| 85 | | | |
| 86 | | | |
| 87 | | | |
| 88 | | | |
| 89 | | | |
| 90 | | | |
| 91 | | | |
| 92 | | | |
| 93 | | | |
| 94 | | | |
| 95 | | | |
| 96 | | | |
| 97 | | | |
| 98 | | | |
| 99 | | | |
| 100 | | | |
| 101 | | | |
| 102 | | | |
| 103 | | | |
| 104 | | | |
| 105 | | | |
| 106 | | | |
| 107 | | | |
| 108 | | | |
| 109 | | | |
| 110 | | | |
| 111 | | | |
| 112 | | | |
| 113 | | | |
| 114 | 12 | | 0.26 |
| 115 | | | |
| 116 | | | |
| 117 | | | |
| 118 | | | |
| 119 | | | |
| 120 | | | |
| 121 | | | |
| 122 | | | |
| 123 | | | |
| 124 | | | |
| 125 | | | |
| 126 | | | |
| 127 | | | |
| 128 | | | |
| 129 | | | |
| 130 | | | |
| 131 | | | |
| 132 | | | |
| 133 | | | |
| 134 | | | |
| 135 | | | |
| 136 | | | |
| 137 | | | |
| 138 | | | |
| 139 | | | |
| 140 | | | |
| 141 | | | |
| 142 | | | |
| 143 | | | |
| 144 | | | |
| 145 | | | |
| 146 | | | |
| 147 | | | |
| 149 | | | |
| 150 | | | |
| 151 | | | |
| 152 | | | |
| 153 | | | |
| 154 | | | |
| 155 | | | |
| 156 | | | |
| 157 | | | |
| 158 | | | |
| 159 | | | |
| 160 | | | |
| 161 | | | |
| 162 | | | |
| 163 | 4.51 | | 0.03 |
| 164 | 120 | | 0.38 |
| 165 | 23.6 | | 0.07 |
| 166 | 5.58, 12.03 | | 0.03, 0.07 |
| 167 | 10000 | | 3.15 |
| 168 | 8867 | | 5322 |
| 169 | 10000 | | 853 |
| 170 | 32.6 | | 0.48 |
| 171 | 10000 | | 141 |
| 172 | 10000 | | 150 |
| 173 | 5069 | | 45.7 |
| 174 | | | |
| 175 | 166 | | 3.60 |
| 176 | 10000 | | 156 |
| 177 | 255 | | 13.4 |
| 178 | 104 | | 0.6 |
| 179 | 10000 | | 7116 |
| 180 | 5221 | | 1209 |
| 181 | 341 | | 1.3 |
| 182 | 1859 | | 7 |
| 183 | 604 | | 4 |
| 184 | 10000 | | 19.5 |
| 185 | 182 | | 6716 |
| 186 | 515 | | 5314 |
| 187 | 5198 | | 121 |
| 188 | 541 | | 307 |
| 189 | 360 | | 277 |
| 190 | 13.8 | | 2.61 |
| 191 | 727.3 | | 189 |
| 192 | 7.64 | | 0.09 |
| 193 | 182.1 | | 21.1 |
| 194 | 14.8 | | 0.06 |
| 195 | 306.2 | | 9.29 |
| 196 | | | |
| 197 | 4.27 | | 0.9 |
| 198 | 5178 | | 152 |
| 199 | 26.3 | | 0.3 |
| 202 | 31.5 | | 5.9 |
| 203 | 49.3 | | 29.1 |
| 204 | | | |
| 205 | 4.44 | | 0.14 |
| 206 | 5.8 | | 0.2 |
| 207 | 5.3, 5.37, 14.7 | | 0.05, 0.08, 0.1 |
| 208 | 33 | | 1.3 |
| 209 | 708 | | 17 |
| 210 | 1862 | | 420.3 |
| 211 | 180 | | 5.9 |
| 212 | 1278 | | 103 |
| 213 | 5658 | | 1263 |
| 214 | 308 | | 44 |
| 215 | 126 | | 0.43 |
| 216 | 1.14 | | 0.04 |
| 217 | 5.4 | | 1.08 |
| 218 | 1.45 | | 0.03 |
| 219 | 87.83 | | 0.87 |
| 220 | 6921 | | 157.2 |
| 221 | 9.58 | | 0.36 |

TABLE VII-continued

| Cpd | r Ki δ * (nM) | r Ki δ * Ver. 1a (nM) | r Ki μ * (nM) |
|---|---|---|---|
| 222 | 394 | | 91.2 |
| 223 | 2.6 | | 0.87 |
| 224 | 1.41 | | 0.03 |
| 225 | 112 | | 0.73 |
| 226 | 48 | | |
| 227 | 0.08, 0.46 | | 0.96 |
| 228 | 27.8 | | 0.35 |
| 229 | | | |
| 230 | 10 | | 5 |
| 231 | 1070 | | 6.19 |
| 239 | 0.1 | | 0.44 |
| 242 | 0.18 | | 0.59 |
| 246 | 0.035 | | 0.15 |
| 247 | 0.4 | | 0.61 |
| 248 | 0.44 | | 0.11 |
| 249 | 0.18 | | 0.12 |
| 250 | 0.21 | | 0.06 |
| 249 | 0.18 | | 0.12 |
| 250 | 0.21 | | 0.06 |
| 251 | 0.26 | | 0.08 |
| 249 | 0.18 | | 0.12 |
| 250 | 0.21 | | 0.06 |
| 251 | 0.26 | | 0.08 |
| 256 | 3.82 | | 7.08 |
| 257 | | 14.0 | 1.22 |
| 260 | 0.13 | | 0.24 |
| 261 | 8.01 | | 0.79 |
| 262 | 17.5 | | 1.1 |
| 266 | | | |
| 267 | 0.46 | | 1.53 |
| 268 | | | |
| 269 | 0.61 | 6.24 | 0.37 |
| 270 | 1.03 | 4.47 | 1.37 |
| 271 | 12.2 | | 0.27 |
| 272 | 15.6 | | 1.1 |
| 273 | 1140 | | 754 |
| 274 | | | |
| 275 | 0.47 | | 0.69 |
| 276 | 115 | | 47 |
| 277 | 0.14 | | 0.44 |
| 278 | 49 | | 12 |
| 279 | 5.2 | | 0.137 |
| 280 | 32 | | 3 |
| 281 | 721 | | 399 |
| 282 | 907 | | 185 |
| 283 | 6735 | | 3572 |
| 284 | 1526 | | 1033 |
| 285 | 2897 | | 1868 |
| 286 | 0.11 | | 0.05 |
| 287 | 0.14 | | 0.13 |
| 288 | 0.17 | | 0.43 |
| 288 | 0.17 | | 0.43 |
| 289 | 0.1, 3.8 | | 0.25 |
| 290 | 0.69 | | 0.43 |
| 291 | 0.12 | | 0.47 |
| 292 | 100 | | 0.65 |
| 293 | 3175 | | 646 |
| 295 | 3.95 | | 0.18 |
| 296 | 2.2 | | 0.49 |
| 297 | 44 | | 0.11 |
| 298 | 44 | | 0.3 |
| 299 | 1.16 | | 0.44 |
| 300 | 0.29 | | 0.09 |
| 301 | 0.76 | | 0.09 |
| 303 | | 24.5 | 3.87 |
| 304 | | 119 | 161 |
| 305 | | 1.24 | 0.2 |
| 306 | | 0.18 | 0.9 |
| 307 | | 0.07 | 0.4 |
| 308 | | 0.48 | 1.2 |
| 318 | 1220 | | 357 |

* The binding assays described above may be associated with a margin of error between 10-20%.

Example 3

Human Mu Opioid Receptor Binding Assay

Membranes from Chinese Hamster Ovary cells expressing the human μopioid receptor (Perkin Elmer #RBHOMM400UA) are homogenized in assay buffer (50 mM Tris, pH 7.5 with 5 mM $MgCl_2$) using a glass tissue grinder, Teflon pestle and a Steadfast Stirrer (Fisher Scientific). The concentration of membranes is adjusted to 300 μg/mL in assay buffer and 100 μL is dispensed into each well of the assay plate, a 96 well round bottom polypropylene plate. Compounds to be tested are solubilized in DMSO (Pierce), 10 mM, then diluted in assay buffer to 6× the desired final concentration. The ligand, $^3$H-Damgo (Perkin Elmer #NET-902) is also diluted in assay buffer to 3.6 nM. In a second 96 well round bottom polypropylene plate, known as the premix plate, 60 μL of the 6× compound is combined with 60 μL of 3.6 nM $^3$H-Damgo. From this premix plate 50 μL is transferred to the assay plate containing the membranes, in duplicate. The assay plate is incubated for 2 h at room temperature. A GF/C 96 well filter plate (Perkin Elmer #6005174) is pretreated with 0.3% polyethylenimine for 30 min. The contents of the assay plate are filtered through the filter plate using a Packard Filtermate Harvester, and washed 3 times with 0.9% saline that is 4° C. The filter plate is dried, the underside sealed, and 30 μL Microscint20 (Packard #6013621) added to each well. A Topcount-NXT Microplate Scintillation Counter (Packard) is used to measure emitted energies in the range of 2.9 to 35 KeV. Results are compared to maximum binding, wells receiving no inhibitors. Nonspecific binding is determined in the presence of 1 μM unlabelled Damgo (Tocris #1171). The biological activity of the compounds of the present invention is shown in Table VIII.

The biological activity of the compounds of the present invention may also be measured in a human delta opioid receptor binding assay using the following example.

Example 4

Human Delta Opioid Receptor Binding Assay

This assay is designed to test the ability of a compound to interfere with the binding of tritiated Naltrindole to the human delta subtype 2 opioid receptor. Membranes from Chinese Hamster Ovary cells expressing the human delta subtype 2 opioid receptor (Perkin Elmer #RBHODM400UA) are homogenized in assay buffer (50 mM Tris, pH 7.5 with 5 mM $MgCl_2$) using a glass tissue grinder, Teflon pestle and a Steadfast Stirrer (Fisher Scientific). The concentration of membranes is adjusted to 100 μg/mL in assay buffer and 100 μL is dispensed into each well of the assay plate, a 96 well round bottom polypropylene plate. Compounds to be tested are solubilized in DMSO (Pierce), 10 mM, then diluted in assay buffer to 6× the desired final concentration. The ligand, $^3$H-Naltrindole (Perkin Elmer #NET-1065) is also diluted in assay buffer to 6 nM. In a second 96 well round bottom polypropylene plate, known as the premix plate, 60 μL of the 6× compound is combined with 60 μL of 6 nM $^3$H-Naltrindole. From this premix plate 50 μL is transferred to the assay plate containing the membranes, in duplicate. The assay plate is incubated for 30 min at room temperature. A GF/C 96 well filter plate (Perkin Elmer #6005174) is pretreated with 0.3% polyethylenimine for 30 min. The contents of the assay plate are filtered through the filter plate using a Packard Filtermate Harvester, and washed 3 times with 0.9% saline that is 4° C. The filter plate is dried, the underside sealed, and 30 μL Microscint20 (Packard #6013621) added to each well. A Topcount-NXT Microplate Scintillation Counter (Packard) is used to measure emitted energies in the range of 2.9 to 35 KeV. Results are compared to maximum binding, wells receiving no inhibitors. Nonspecific binding is determined in the presence of 1 μM unlabelled Naltrindole (Sigma #N115).

Biological activity measured for select compounds of the present invention are listed in Table VIII below, including δ- and μ-opioid receptor binding ($K_i$), as determined using the procedures outlined above.

TABLE VIII

| Cpd | hKi δ * (nM) | hKi μ * (nM) |
|---|---|---|
| 1 | | 3.6 |
| 2 | | 2.9 |
| 3 | | 13 |
| 4 | | 5.5 |
| 5 | | 3.9 |
| 6 | | 2 |
| 7 | | 6.8 |
| 8 | | 2.5, 4.4 |
| 9 | | 10.9 |
| 10 | | 15.5 |
| 11 | | 5.1 |
| 12 | | 4.1 |
| 13 | | 4.8 |
| 14 | | 4.7 |
| 15 | | 285 |
| 16 | | 16 |
| 17 | | 2.2 |
| 18 | | 1.7 |
| 19 | | 18.2 |
| 20 | | 63 |
| 21 | | 37.6 |
| 22 | | ~200 |
| 23 | | 34.3 |
| 24 | | 9.3 |
| 26 | | 17 |
| 27 | | 30 |
| 28 | | 44 |
| 29 | | 38 |
| 30 | | 34 |
| 31 | | 19 |
| 32 | | 6.8 |
| 33 | | 6.9 |
| 34 | | 19 |
| 35 | | 2.8 |
| 36 | | 5.6 |
| 37 | | 183 |
| 38 | | 19 |
| 39 | | 0.9 |
| 40 | | 152 |
| 41 | | 1.6 |
| 42 | | 5.8 |
| 43 | | 6.9 |
| 44 | | 8.7 |
| 45 | | 1.2 |
| 46 | | 35 |
| 47 | | 22 |
| 48 | | 0.4 |
| 49 | | 48 |
| 50 | | 1.4 |
| 51 | 113 | 2.7 |
| 52 | 66 | 12.1 |
| 53 | 96 | 13.1 |
| 54 | 172 | 1.1 |
| 55 | 44 | 1.8 |
| 56 | 225 | 65.3 |
| 57 | 2.2 | 0.66 |
| 58 | 70 | 8.5 |
| 59 | 120 | 5.1 |
| 60 | 114 | 2 |
| 61 | 243 | 3 |
| 62 | 69 | 2.4 |
| 63 | 473 | 58 |
| 64 | 1108 | 117 |
| 65 | 517 | 0.36 |
| 66 | 550 | 6.5 |
| 67 | 438 | 4.5 |
| 68 | 59 | 0.6 |
| 69 | 272 | 4.4 |
| 70 | 85 | 2.6 |
| 71 | 102 | 0.57 |
| 72 | 71 | 1.03 |
| 73 | 151 | 1.9 |
| 74 | 63 | 9.8 |
| 75 | 8.5 | 2.6 |
| 76 | 43.1 | 1.6 |
| 77 | 13.5 | 1.8 |
| 78 | 28.9 | 2.4 |
| 79 | 11.5 | 1.7 |
| 80 | 0.95 | 1.09 |
| 81 | 15.7 | 1.7 |
| 82 | 46 | 2.39 |
| 83 | 48 | 4.67 |
| 84 | 9.6 | 1.1 |
| 85 | 1175 | 5.4 |
| 86 | 400 | 1 |
| 87 | 38.9 | 12.6 |
| 88 | 16.2 | 5.8 |
| 89 | 19.3 | 9.2 |
| 90 | 6.6 | 0.7 |
| 91 | 15 | 4.8 |
| 92 | 5.4 | 0.25 |
| 93 | 9.5 | 0.9 |
| 94 | 403 | 4.1 |
| 95 | 278 | 7.8 |
| 96 | 14.6 | 9.7 |
| 97 | 6.3 | 19.2 |
| 98 | 54 | 48 |
| 99 | 19.3 | 16 |
| 100 | 88 | 20 |
| 101 | 47 | 24 |
| 102 | 5.2 | 3.5 |
| 103 | 9.7 | 23 |
| 104 | 484 | 100 |
| 105 | 742 | 410 |
| 106 | 279 | 150 |
| 107 | 584 | 2.95 |
| 108 | 43.3 | 23.5 |
| 109 | 77 | 8.2 |
| 110 | 1402 | 191 |
| 111 | 307 | 6.4 |
| 112 | 135 | 9.5 |
| 113 | | 16 |
| 114 | 49 | 1.39 |
| 115 | 321 | 68 |
| 116 | 30.3 | 0.54 |
| 117 | 118 | 0.24 |
| 118 | 316, 212 | 1.04 |
| 119 | >10,000 | 185 |
| 120 | 740 | 20.8 |
| 121 | 182 | 25.3 |
| 122 | 107 | 12.8 |
| 123 | 84 | 47 |
| 124 | 1279 | 1.7 |
| 125 | 237 | 8.6 |
| 126 | 164 | 7.8 |
| 127 | 710 | 47 |
| 128 | | 58 |
| 129 | | 25.3 |
| 130 | 712 | 1.6 |
| 131 | 675 | 3.1 |
| 132 | | 166 |
| 133 | 108 | 11.5 |
| 134 | 463 | 121 |
| 135 | 1040 | 7 |
| 136 | 1607 | 726 |
| 137 | | 445 |
| 138 | 1183 | 104 |
| 139 | 1263 | 58 |
| 140 | 985 | 79 |

TABLE VIII-continued

| Cpd | hKi δ * (nM) | hKi μ * (nM) |
|---|---|---|
| 141 | 252 | 52 |
| 142 | 454 | 8.2 |
| 143 | 69 | 1.6 |
| 144 | 251 | 1.3 |
| 145 | 267 | |
| 146 | 71 | |
| 147 | 241 | |
| 149 | 408 | |
| 150 | 992 | |
| 151 | 1295 | |
| 152 | >10,000 | |
| 153 | >10,000 | |
| 154 | >10,000 | 1 |
| 155 | 345 | |
| 156 | 380 | 0.59 |
| 157 | >10,000 | 2.2 |
| 158 | >10,000 | 0.23 |
| 159 | 400 | 8.6 |
| 160 | >10000 | >1000 |
| 161 | >10000 | >1000 |
| 162 | 173 | 7.6 |
| 163 | 301, 63 | 0.67 |
| 164 | | 16.3 |
| 165 | 322 | 0.45 |
| 166 | 300, 375 | 0.39, 0.5 |
| 167 | | 4.2 |
| 190 | 285 | |
| 191 | >10,000 | |
| 192 | | 0.62 |
| 193 | >10,000 | |
| 194 | 103 | 0.13 |
| 195 | >10,000 | 9.8 |
| 196 | | |
| 197 | | |
| 198 | >10,000 | 140 |
| 199 | 209 | 0.29 |
| 203 | 501 | 13.7 |
| 204 | | 7.7 |
| 205 | | |
| 206 | 275.4 | |
| 207 | 132.2 | |
| 208 | | 1.2 |
| 209 | | 23 |
| 210 | | 0.29 |
| 211 | | |
| 212 | | 55 |
| 213 | | >1000 |
| 214 | | 29 |
| 215 | | 1.5 |
| 216 | | |
| 217 | 506 | |
| 218 | 189 | 3.92 |
| 219 | | 16.2 |
| 220 | | 377 |
| 221 | | 0.42 |
| 222 | | 185 |
| 223 | | |
| 224 | 81.3 | 0.65 |
| 225 | | 1.4 |
| 226 | | 7.91 |
| 227 | | 1.92 |
| 228 | | 15.9 |
| 229 | | 12 |
| 231 | | 28 |
| 239 | | |
| 242 | | 2.35 |
| 246 | | 5.63 |
| 256 | | 2 |
| 257 | | 3.4 |
| 260 | | 0.58 |
| 261 | | 2.58, 1.3 |
| 262 | | 3.24 |
| 266 | | 69 |
| 267 | | 6.88 |
| 268 | | 5.79 |
| 269 | | 21.5 |
| 270 | | 3.27 |
| 271 | | 15.5 |
| 272 | | 1.93 |
| 273 | | 325 |
| 274 | | >1000 |
| 289 | | 2.2 |
| 303 | | 3.8 |
| 304 | | 41 |

Example 5

Delta Opioid Receptor Functional Assay: [$^{35}$S]GTPγS Binding Assay in CHO-hδ Cell Membranes, Version 1

Preparation of Membranes

CHO-hδ cell membranes were purchased from Receptor Biology, Inc. (Baltimore, Md.). 10 mg/ml of membrane protein suspended in 10 mM TRIS-HC pH 7.2, 2 mM EDTA, 10% sucrose.

Membranes were maintained at 4-8° C. A portion (1 ml) of membranes was added into 15 mL cold binding assay buffer. The assay buffer contained 50 mM HEPES, pH 7.6, 5 mM MgCl$_2$, 100 mM NaCl, 1 mM DTT and 1 mM EDTA. The membrane suspension was homogenized with a Polytron for 2 times and centrifuged at 3000 rpm for 10 min. The supernent was then centrifuged at 18,000 rpm for 20 min. The pellet was saved in a tube and 10 ml assay buffer was added into the tube. The pellet and buffer were mixed with a Polytron.

Incubation Procedure

The pellet membranes (20 μg/ml) were preincubated with SPA (10 mg/ml) at 25° C. for 45 min in the assay buffer. The SPA (5 mg/ml) coupled with membranes (10 μg/ml) was then incubated with 0.5 nM [$^{35}$S]GTPγS in the same HEPES buffer containing 50 μM GDP in total volume of 200 μl. Increasing concentrations of receptor agonists were used to stimulate [$^{35}$S]GTPγS binding. The basal binding was tested in the absent agonists and no specific binding was tested in the present 10 μM unlabeled GTPγS. The data were analyzed on a Top counter.

Data

The % of Basal=(stimulate−non specific)*100/(basal−non specific). EC50 values were calculated using a Prism program.

Example 6

Delta Opioid Receptor Functional Assay: [$^{35}$S]GTPγS Binding Assay in NG108-15 Cell Membranes, Version 2

Preparation of Membranes

NG108-15 cell membranes were purchased from Applied Cell Sciences (Rockville, Md.). 8 mg/ml of membrane protein suspended in 10 mM TRIS-HC pH 7.2, 2 mM EDTA, 10% sucrose.

Membranes were maintained at 4-8° C. A portion (1 ml) of membranes was added into 10 ml cold binding assay buffer. The assay buffer contained 50 mM Tris, pH 7.6, 5 mM MgCl$_2$, 100 mM NaCl, 1 mM DTT and 1 mM EGTA. The membrane suspension was homogenized with a Polytron for 2 times and centrifuged at 3000 rpm for 10 min. The supernent was then centrifuged at 18,000 rpm for 20 min. The pellet was saved in a tube and 10 ml assay buffer was added into the tube. The pellet and buffer were mixed with a Polytron.

Incubation Procedure

The pellet membranes (75 µg/ml) were preincubated with SPA (10 mg/ml) at 25° C. for 45 min in the assay buffer. The SPA (5 mg/ml) coupled with membranes (37.5 µg/ml) was then incubated with 0.1 nM [$^{35}$S] GTPγS in the same Tris buffer containing 100 µM GDP in total volume of 200 µl. Increasing concentrations of receptor agonists were used to stimulate [$^{35}$S] GTPγS binding. The basal binding was tested in the absent agonists and no specific binding was tested in the present 10 µM unlabeled GTPγS. The data were analyzed on a Top counter.

Data Analysis

The following parameters were calculated:

$$\% \text{ Stimulation} = \frac{(\text{test compound } cpm - \text{non-specific } cpm)}{(\text{Basal } cpm - \text{non-specific } cpm)} \times 100$$

% Inhibition = (% stimulation by 1 µM SNC80 −

% stimulation by 1 µM SNC80 in presence of test compound) ×

100/(% Stimulation by 1 µM SNC80 − 100)

% of Basal=(stimulate−non specific)*100/(basal−non specific).

$EC_{50}$ values were calculated using GraphPad Prism.

Example 7

Mu Opioid Receptor Functional Assay: [$^{35}$S]GTPγS Binding Assays in CHO-hMOR cell membranes, Versions 1 and 2

CHO-hMOR cell membranes were purchased from Receptor Biology, Inc. (Baltimore, Md.). About 10 mg/ml of membrane protein was suspended in 10 mM TRIS-HCl pH 7.2, 2 mM EDTA, 10% sucrose, and the suspension kept on ice. One ml of membranes was added to 15 ml cold binding assay buffer containing 50 mM HEPES, pH 7.6, 5 mM $MgCl_2$, 100 mM NaCl, 1 mM DTT and 1 mM EDTA. The membrane suspension was homogenized with a Polytron and centrifuged at 3,000 rpm for 10 min. The supernatant was then centrifuged at 18,000 rpm for 20 min. The pellet was resuspended in 10 ml assay buffer with a Polytron.

The membranes were preincubated with wheat germ agglutinin coated SPA beads (Amersham) at 25° C. for 45 min in the assay buffer. The SPA bead (5 mg/ml) coupled membranes (10 µg/ml) were then incubated with 0.5 nM [$^{35}$S] GTPγS in the assay buffer. The basal binding is that taking place in the absence of added test compound; this unmodulated binding is considered as 100%, with agonist stimulated binding rising to levels significantly above this value. A range of concentrations of receptor agonists was used to stimulate [$^{35}$S]GTPγS binding. Both basal and non-specific binding was tested in the absence of agonist; non-specific binding determination included 10 µM unlabeled GTPγS.

Compounds were tested for function as antagonists by evaluating their potential to inhibit agonist-stimulated GTPγS binding. Radioactivity was quantified on a Packard Top-Count. The following parameters were calculated:

$$\% \text{ Stimulation} = \frac{(\text{test compound } cpm - \text{non-specific } cpm)}{(\text{Basal } cpm - \text{non-specific } cpm)} \times 100$$

% Inhibition = (% stimulation by 1 µM SNC80 −

% stimulation by 1 µM SNC80 in presence of test compound) ×

100/(% Stimulation by 1 µM SNC80 − 100)

$EC_{50}$ values were calculated using GraphPad Prism.

Biological activity measured for select compounds of the present invention are listed in Table VIII below, including δ- and µ-opioid receptor functional data (% I and EC50), as determined from a single set of experiments using the procedures outlined above.

TABLE IX

| Cpd No. | DOR GTP-binding Assay_v1 EC50 (nM) | DOR GTP-binding Assay_v2_ EC50 (nM) | DOR GTP-binding Assay v2 (% I) | MOR GTP binding assay v2 EC50 (nM) | MOR GTP binding assay_v2 (% I) | MOR GTP assay_v1 % of Basal | MOR GTP binding assay_v1 (% I) |
|---|---|---|---|---|---|---|---|
| 1 |  | 88 | 22.10 |  |  |  |  |
| 4 |  | 46 | 66.12 |  |  |  |  |
| 5 |  | >10,000 | 47.12 | 71 | 7.87 |  |  |
| 8 |  | >10,000 | 94.03 | 1.2 | 13.95 |  |  |
| 9 |  | 3.4 | 67.13 |  |  |  |  |
| 14 |  | 0.6 | 59.70 |  |  |  |  |
| 17 |  | 1.3 | 68.64 | 2.5 | 8.71 |  |  |
| 18 |  | >10,000 | 100 |  |  |  |  |
| 18 |  |  |  | 1.0 | 7.54 |  |  |
| 20 |  | >10,000 | 78.74 |  |  |  |  |
| 29 |  | >10,000 | 79.05 |  |  |  |  |
| 48 |  | >10,000 | 108.36 | 2.2 | 24.53 |  |  |
| 50 |  | 1.4 | 60.27 |  |  |  |  |
| 51 |  | 27 | 66.04 |  |  |  |  |
| 75 |  | 1.4 | 65.35 |  |  |  |  |
| 114 | 35 |  |  |  |  | 717.59 | 13.20 |
| 117 | 37 |  |  |  |  | 816.16 | 3.31 |
| 122 |  |  |  |  |  | 278.08 | 41.93 |
| 130 | 16 |  |  |  |  | 866.39 | 1.62 |
| 131 | 99 |  |  |  |  | 391.98 | 28.64 |

TABLE IX-continued

| Cpd No. | DOR GTP-binding Assay_v1 EC50 (nM) | DOR GTP-binding Assay_v2 EC50 (nM) | DOR GTP-binding Assay v2 (% I) | MOR GTP binding assay v2 EC50 (nM) | MOR GTP binding assay_v2 (% I) | MOR GTP assay_v1 % of Basal | MOR GTP binding assay_v1 (% I) |
|---|---|---|---|---|---|---|---|
| 146 | 27 | | | | | 740.77 | 2.79 |
| 147 | 51 | | | | | 779.35 | 1.00 |
| 149 | 44 | | | | | 753.53 | 1.00 |
| 150 | 49 | | | | | 476.63 | 53.35 |
| 151 | 350 | | | | | 606.38 | 24.19 |
| 155 | 150 | | | | | 655.93 | 14.32 |
| 163 | 21 | | | | | 1286.00 | 1.00 |
| 164 | 2500 | | | | | 1077.00 | 1.00 |
| 165 | 231 | | | | | 1182.00 | 1.00 |
| 166 | 21 | | | | | 1448.00 | 1.00 |
| 166 | 71 | | | | | 1425.00 | 1.00 |
| 167 | | | | | | 780.00 | 17.00 |
| 170 | 115 | | | | | 1031.00 | 26.00 |
| 173 | | | | | | 147.00 | 85.00 |
| 174 | 20 | | | | | 864.00 | 42.00 |
| 175 | | | | | | 471.00 | 53.00 |
| 177 | | | | | | 625.00 | 23.00 |
| 178 | | | | | | 1059.00 | 10.00 |
| 181 | | | | | | 1304.00 | 1.00 |
| 182 | | | | | | 1091.00 | 6.00 |
| 183 | 2320 | | | | | 962.00 | 27.00 |
| 184 | | | | | | 862.00 | 13.00 |
| 190 | 3830 | | | | | 109, 194 | 70.00 |
| 192 | 76 | | | | | 383.00 | 30.00 |
| 193 | | | | | | 182.00 | 54.00 |
| 194 | 189 | | | | | 558.00 | 1.00 |
| 195 | | | | | | 378.00 | 34.00 |
| 196 | 24 | | | | | 620.00 | 1.00 |
| 197 | 140 | | | | | 582.00 | 1.00 |
| 199 | 217 | | | | | 465.00 | 11.00 |
| 202 | 1580 | | | | | 529.00 | 1.00 |
| 203 | 515 | | | | | 331.00 | 20.00 |
| 205 | 32 | | | | | 566.00 | 1.00 |
| 206 | 37 | | | | | 446.00 | 1.00 |
| 207 | 8.65 | | | | | 432, 1160 | 40.00 |
| 207 | 12 | | | | | 1183.00 | 21.00 |
| 208 | | | | | | 475.00 | 1.00 |
| 209 | | | | | | 295.00 | 10.00 |
| 210 | | | | | | 414.00 | 10.00 |
| 211 | | | | | | 371.00 | 10.00 |
| 214 | 26000 | | | | | 295.00 | 3.00 |
| 215 | 1060 | | | | | 606.00 | 1.00 |
| 216 | 16 | | | | | 666.00 | 1.00 |
| 217 | 82 | | | | | 599.00 | 1.00 |
| 218 | 20 | | | | | 599.00 | 1.00 |
| 219 | 3560 | | | | | 611.00 | 1.00 |
| 221 | 308 | | | | | 427.00 | 13.00 |
| 223 | 56 | | | | | 495.00 | 1.00 |
| 224 | 103 | | | | | 694.00 | 1.00 |
| 225 | 2190 | | | | | 657.00 | 1.00 |
| 226 | | >10,000 | 19.71 | | | | |
| 227 | | >10,000 | 66.56 | 60.8 | 36.00 | | |
| 230 | | | 48.93 | | | | |
| 239 | | >10,000 | | | | | |
| 242 | | >10,000 | 91.45 | | | | |
| 246 | | 0.3 | 47.01 | 4.5 | 21.30 | | |
| 247 | | 44 | 41.89 | | | | |
| 248 | | 15 | 31.72 | | | | |
| 249 | | 8 | 20.14 | | | | |
| 250 | | 10 | 34.93 | | | | |
| 251 | | 18 | 53.94 | | | | |
| 252 | | 32.1 | 66.00 | 4.15 | 24.00 | | |
| 253 | | 1.35 | 52.00 | 251 | 28.00 | | |
| 254 | | 6.27 | 62.00 | 316 | 42.00 | | |
| 255 | | 13.1 | 54.00 | 3.48 | 33.00 | | |
| 256 | | >10,000 | 89.19 | 13 | 29.40 | | |
| 257 | | 7.4 | 48.88 | 3.9 | 10.96 | | |
| 260 | | >10,000 | 100.97 | 1.5 | 2.89 | | |
| 261 | | 21 | 30.04 | 17 | 5.88 | | |
| 267 | | 6 | 31.76 | | | | |
| 269 | | 86 | 21.18 | 48 | 1.00 | | |
| 270 | | 1000 | 63.51 | 56 | 6.61 | | |
| 275 | | 3 | 72.08 | | | | |
| 286 | | 2.6 | 34.65 | | | | |

TABLE IX-continued

| Cpd No. | DOR GTP-binding Assay_v1 EC50 (nM) | DOR GTP-binding Assay_v2 EC50 (nM) | DOR GTP-binding Assay v2 (% I) | MOR GTP binding assay v2 EC50 (nM) | MOR GTP binding assay_v2 (% I) | MOR GTP assay_v1 % of Basal | MOR GTP binding assay_v1 (% I) |
|---|---|---|---|---|---|---|---|
| 287 | | >10,000 | 84.50 | | | | |
| 288 | | >10,000 | 74.54 | | | | |
| 289 | | >10,000 | 86.27 | | | | |
| 290 | | >10,000 | 52.41 | | | | |
| 291 | | >10,000 | 96.52 | | | | |
| 295 | | 2.2 | 71.66 | 1.4 | 8.21 | | |
| 296 | | 7.9 | 69.41 | 2.2 | 9.35 | | |
| 299 | | 2.3 | | 1.0 | 12.11 | | |
| 300 | | 32 | | 2.6 | 15.40 | | |
| 301 | | >10,000 | 109.56 | 2.6 | 76.20 | | |
| 303 | | 95 | 23.85 | 30 | 1.00 | | |
| 309 | | | | 23.0 | 47.00 | | |
| 310 | | | | 3920 | 51.00 | | |
| 311 | | 1.02 | 41.00 | | | | |
| 312 | | | | 58.7 | 35.00 | | |
| 313 | | 5.03 | 49 | 50.6 | 29.00 | | |
| 316 | | | | 24.1 | 76 | | |

Example 8

In Vivo Assay-Stress-induced Fecal Output (fecal output for 1 hr)

This assay evaluates the fecal output in novel environment-stressed mice to that of acclimated controls.

Methods: Adult, male, Crl:CD-1 (ICR) mice, weighing ~30-35 g were used in these studies, with a minimum of 10 mice per dose group. One group of mice was assigned as acclimated, or "non-stressed" controls. These control mice were transported from colony housing, where they were housed 3/cage in polycarbonate cages with access to food and water ad lib. to the procedure room. The mice were removed from their home cages and individually housed in 20 cm wide×20 cm deep×15 cm tall cages, equipped with a wire mesh bottom where they remained for a 16-18 hr period of acclimation to their novel environment. Mice were allowed access to food and water ad lib. during acclimation. The other groups of mice were assigned as non-acclimated, or "stressed" treatment groups. Each mouse in each group was weighed and vehicle, or test compound, was intragastrically administered by oral intubation in 0.5% methylcellulose. Mice were allowed access to water only ad lib. during the test period. After compound administrations, acclimated (control) as well as non-acclimated (stressed) mice were individually housed in a 20 cm wide×20 cm deep×15 cm tall cage, with a wire mesh bottom. An absorbent cardboard is placed beneath the cages. The number of fecal pellets excreted by each mouse was determined at hourly intervals following placement of the mice in the individual cages. Raw Data=# of fecal pellets/mouse/hr. The mean fecal pellet output for each test group was calculated and the results expressed as a percent of mean fecal pellet output of the control group (the acclimated, non-stressed group, to which vehicle only was administered). ANOVA was performed and Tukey's Multiple Comparison Test used to compare the means, which were considered significantly different when P<0.05. Data is shown in Table X, XI, and XII.

TABLE X

Fecal Output (# pellets)

| Cpd No. | dose (mg/kg) | control | NES | cpd | NES % ctrl | cpd % control | cpd % NES |
|---|---|---|---|---|---|---|---|
| 18 | 30 | 2.3 | 3.8 | 3.1 | 166.7 | 137.8 | 82.7 |
| 50 | 30 | 2.3 | 7.0 | 3.3 | 304.3 | 143.5 | 47.1 |
| 55 | 30 | 3.9 | 14.1 | 8.3 | 361.5 | 212.8 | 58.9 |
| 57 | 30 | 3.9 | 14.1 | 7.6 | 361.5 | 194.9 | 53.9 |
| 58 | 30 | 2.3 | 7.0 | 3.9 | 304.3 | 169.6 | 55.7 |
| 75 | 30 | 3.1 | 9.1 | 6.4 | 293.5 | 206.5 | 70.3 |
| 75 | 30 | 1.9 | 3.9 | 1.4 | 206.7 | 73.3 | 35.5 |
| 78 | 30 | 3.6 | 7.3 | 3.3 | 202.8 | 91.7 | 45.2 |
| 79 | 30 | 3.6 | 7.3 | 7.1 | 202.8 | 197.2 | 97.3 |
| 80 | 30 | 3.6 | 7.3 | 5.5 | 202.8 | 152.8 | 75.3 |
| 80 | 30 | 3.9 | 13.1 | 10.3 | 335.9 | 264.1 | 78.6 |
| 85 | 30 | 5.4 | 12.0 | 7.9 | 222.2 | 146.3 | 65.8 |
| 87 | 30 | 7.3 | 12.9 | 10.3 | 176.7 | 141.1 | 79.8 |
| 89 | 30 | 5.0 | 11.6 | 6.4 | 232.0 | 128.0 | 55.2 |
| 90 | 30 | 3.1 | 12.9 | 10.3 | 416.1 | 332.3 | 79.8 |
| 91 | 30 | 3.1 | 12.9 | 8.9 | 416.1 | 287.1 | 69.0 |
| 92 | 30 | 3.6 | 11.1 | 9.2 | 308.3 | 255.6 | 82.9 |
| 93 | 30 | 3.6 | 11.1 | 5.0 | 308.3 | 138.9 | 45.0 |
| 94 | 30 | 2.7 | 9.1 | 9.4 | 337.0 | 348.1 | 103.3 |
| 95 | 30 | 2.7 | 9.1 | 8.5 | 337.0 | 314.8 | 93.4 |

TABLE X-continued

Fecal Output (# pellets)

| Cpd No. | dose (mg/kg) | control | NES | cpd | NES % ctrl | cpd % control | cpd % NES |
|---|---|---|---|---|---|---|---|
| 97 | 30 | 7.3 | 12.9 | 4.8 | 176.7 | 65.8 | 37.2 |
| 102 | 30 | 5.7 | 15.0 | 3.4 | 263.2 | 59.6 | 22.7 |
| 103 | 30 | 7.3 | 12.9 | 10.2 | 176.7 | 139.7 | 79.1 |
| 107 | 30 | 5.7 | 15.0 | 13.1 | 263.2 | 229.8 | 87.3 |
| 111 | 30 | 7.2 | 10.3 | 4.4 | 143.1 | 60.8 | 42.5 |
| 112 | 30 | 7.2 | 10.3 | 7.2 | 143.1 | 100.0 | 69.9 |
| 114 | 30 | 7.2 | 10.3 | 7.8 | 143.1 | 108.3 | 75.7 |
| 118 | 30 | 5.4 | 12.0 | 7.2 | 222.2 | 133.7 | 60.2 |
| 133 | 30 | 5.5 | 12.1 | 9.9 | 220.0 | 180.0 | 81.8 |
| 143 | 10 | 3.7 | 13.6 | 9.1 | 367.6 | 245.9 | 66.9 |
| 143 | 30 | 7.5 | 9.2 | 5.2 | 122.7 | 69.3 | 56.5 |
| 144 | 30 | 3.7 | 13.6 | 11.5 | 367.6 | 310.8 | 84.6 |
| 178 | 30 | 3.2 | 8.8 | 5.5 | 275.0 | 171.9 | 62.5 |
| 192 | 10 | 5.4 | 12.5 | 10.5 | 231.5 | 194.4 | 84.0 |
| 194 | 10 | 5.4 | 12.5 | 11.8 | 231.5 | 218.5 | 94.4 |
| 194 | 30 | 8.1 | 11.0 | 4.2 | 135.8 | 51.9 | 38.2 |
| 194 | 30 | 3.1 | 4.8 | 4.9 | 154.3 | 157.5 | 102.1 |
| 194 | 30 | 3.7 | 14.0 | 6.2 | 378.4 | 167.6 | 44.3 |
| 196 | 10 | 3.7 | 14.0 | 9.2 | 378.4 | 248.6 | 65.7 |
| 196 | 30 | 1.1 | 9.5 | 4.3 | 863.6 | 390.9 | 45.3 |
| 199 | 10 | 2.7 | 10.5 | 9.1 | 388.9 | 337.0 | 86.7 |
| 199 | 10 | 3.8 | 13.1 | 10.8 | 344.7 | 284.2 | 82.4 |
| 205 | 30 | 3.3 | 9.5 | 2.3 | 287.9 | 70.7 | 24.6 |
| 206 | 10 | 3.8 | 13.1 | 8.6 | 344.7 | 226.3 | 65.6 |
| 207 | 10 | 5.6 | 9.4 | 8.3 | 167.9 | 148.2 | 88.3 |
| 207 | 10 | 7.7 | 13.0 | 5.0 | 168.8 | 64.9 | 38.5 |
| 207 | 10 | 5.7 | 12.8 | 6.6 | 225.9 | 116.5 | 51.6 |
| 207 | 10 | 2.9 | 12.8 | 5.3 | 441.4 | 182.8 | 41.4 |
| 207 | 30 | 3.5 |  | 3.2 |  | 91.4 |  |
| 207 | 30 | 3.5 | 13.0 | 6.4 | 371.4 | 184.1 | 49.6 |
| 216 | 10 | 3.6 | 10.3 | 4.9 | 286.1 | 136.1 | 47.6 |
| 218 | 30 | 2.7 | 10.5 | 3.7 | 388.9 | 137.6 | 35.4 |
| 223 | 30 | 3.1 | 4.8 | 5.0 | 154.3 | 160.7 | 104.2 |
| 224 | 10 | 3.6 | 6.9 | 3.5 | 191.7 | 97.2 | 50.7 |
| 225 | 30 | 3.1 | 4.8 | 7.3 | 154.3 | 234.7 | 152.1 |

TABLE XI

Dose-dependent Mouse Fecal Pellet Output Test

| Cpd No. | # of pellets control | NES | NES (% ctrl) | Compound (mg) 0.3 | 0.5 | 1.0 | 3.0 | 5.0 | 6.0 | 10.0 | 30.0 |
|---|---|---|---|---|---|---|---|---|---|---|---|
| 75 |  |  | 235.7 |  |  |  |  |  |  |  |  |
| 93 | 2.7 | 8.3 | 307.4 |  |  |  | 6.2 |  |  | 5.5 | 3.2 |
| 97 | 6.1 | 11.6 | 190.2 |  |  |  | 14 |  |  | 7.5 | 3.5 |
| 97 | 4.8 | 10.1 | 210.4 |  |  |  | 9.1 |  |  | 10.4 | 2.3 |
| 102 | 5.3 | 10.7 | 201.9 |  |  |  | 6.9 |  |  | 4.5 | 2.22 |
| 114 | 3.4 | 10 | 294.1 |  |  |  | 9.6 |  |  | 7.7 | 5.4 |
| 200 | 3.556 | 8.8 | 247.5 |  |  |  | 8.1 |  |  | 8.2 | 5.8 |
| 207 | 5.2 | 11.4 | 219.2 | 11.4 |  |  | 12 |  |  | 4.9 |  |
| 207 | 4.8 | 8.6 | 179.2 |  | 9.4 |  |  | 8.6 |  | 6.7 |  |
| 207 | 3.4 | 10.8 | 317.6 |  |  |  |  |  | 7.5 | 5.5 | 3.5 |
| 207 | 3.6 | 6.5 | 180.6 |  |  |  | 7.3 |  |  | 4.8 | 3.4 |
| 224 | 2.2 | 9.6 | 436.4 |  | 7.6 | 7.2 |  |  |  | 4.2 |  |

TABLE XII

Dose-dependent Mouse Fecal Pellet Output Test: Computed Results

| Cpd No. | Compound (% control) | | | | | | | | Compound (% NES) | | | | | | | |
|---|---|---|---|---|---|---|---|---|---|---|---|---|---|---|---|---|
|  | 0.3 | 0.5 | 1.0 | 3.0 | 5.0 | 6.0 | 10.0 | 30.0 | 0.3 | 0.5 | 1.0 | 3.0 | 5.0 | 6.0 | 10.0 | 30 |
| 75 |  |  |  | 223.8 |  |  | 188.1 | 100 |  |  |  |  |  |  |  |  |
| 93 |  |  |  | 229.6 |  |  | 203.7 | 119 |  |  |  | 74.7 |  |  | 66.27 | 38.55 |
| 97 |  |  |  | 226.2 |  |  | 123.0 | 57 |  |  |  | 119 |  |  | 64.66 | 30.17 |
| 97 |  |  |  | 189.6 |  |  | 216.7 | 48 |  |  |  | 90.1 |  |  | 103 | 22.77 |

TABLE XII-continued

Dose-dependent Mouse Fecal Pellet Output Test: Computed Results

| Cpd No. | Compound (% control) | | | | | | | | Compound (% NES) | | | | | | | |
|---|---|---|---|---|---|---|---|---|---|---|---|---|---|---|---|---|
| | 0.3 | 0.5 | 1.0 | 3.0 | 5.0 | 6.0 | 10.0 | 30.0 | 0.3 | 0.5 | 1.0 | 3.0 | 5.0 | 6.0 | 10.0 | 30 |
| 102 | | | | 130.2 | | | 84.9 | 42 | | | | 64.5 | | | 42.06 | 20.77 |
| 114 | | | | 282.4 | | | 226.5 | 159 | | | | 96 | | | 77 | 54 |
| 200 | | | | 227.8 | | | 230.6 | 163 | | | | 92.05 | | | 93.18 | 65.91 |
| 207 | 219.2 | | | 228.8 | | | 94.2 | | 100 | | | 104.4 | | | 42.98 | |
| 207 | | 195.8 | | | 179.2 | | 139.6 | | | 109 | | | 100 | | 77.91 | |
| 207 | | | | | | 220.6 | 161.8 | 103 | | | | | | 69.44 | 50.93 | 32.41 |
| 207 | | | | 202.8 | | | 133.3 | 94 | | | | 112.3 | | | 73.85 | 52.31 |
| 224 | | | 345.5 | 327.3 | | | 190.9 | | | | 79.17 | 75 | | | 43.75 | |

Example 9

In Vivo Assay: Stress-Induced Entire GI Tract Transit (6 Hour Transit Time Test)

Methods: The animals used in these studies are male CD-1 mice, ave. wt. ~30 g. Procedure: Mice were housed in LAM under 12h/12h light/dark cycle, food & water ad lib. On the day before the experiments, the mice assigned to the "acclimated" (non-stressed) control group were placed into individual wire mesh-bottomed cages, provided food and water ad lib. The acclimated control group was in this new environment for 16-18 hrs prior to beginning the test. On the day of the experiment, mice assigned to experimental groups were housed in home cages were transported to procedure room and remain in their home cages until the start of the transit portion of the study. Mice were intragastrically dosed with compounds (volume remains constant at 0.1 mL/10 g body wt) by oral gavage 30 minutes before carmine (a red vital dye that does not have the drug-adsorbing properties of charcoal) is administered (0.25 mL, 6% carmine in 0.5% methylcellulose). After the carmine marker was administered each mouse was placed in the novel environment cage. One hour after administration of carmine, the fecal pellet output of each animal was recorded. At one-hour intervals thereafter the fecal pellets were examined for the presence of carmine-dye. The number of mice that excreted a carmine-containing fecal pellet at the end of each hour post carmine administration was recorded, until all mice had excreted carmine in a fecal pellet or the end of 6 hrs post carmine administration, whichever occurred first. A variant of this novel environment stress (NES) paradigm is to use the same procedures of dye and compound administrations, but to use restraint (confinement in a small plastic tube for 3 hr) as a stressor (RS=restraint stress), followed by two hours in an individual cage (total of 5 hr fecal transit time). Data is shown in Table XIII. The original data are quantal, i.e. a mouse in the treatment group either did, or did not exhibit entire GI tract transit (excrete colored feces). The mouse entire GI tract (MEGIT) transit test can thus be done in mice that are all acclimated (non-stressed), in which case the data are expressed as % control (vehicle only), or in mice that are exposed to NES or RS, in which cases the data are expressed as % of the vehicle treated NES or RS group. Data is shown in Table XIII.

TABLE XIII

Mouse entire GI tract transit test (MEGIT or MEGIT-NES or MEGIT-RS*

| Cpd No. | dose (mg) | route | MEGIT-NES Entire GI transit 6 hr (% NES) | MEGIT entire GI transit 6 hr % ctrl | MEGIT-RS entire GI transit 5 hr (% RS) |
|---|---|---|---|---|---|
| 4 | 20 | p.o. | | | 100 |
| 18 | 30 | p.o. | 80 | | |
| 75 | 30 | p.o. | | 125 | |
| 75 | 60 | p.o. | | 0 | |
| 75 | 100 | p.o. | | 0 | |
| 227 | 20 | p.o. | | | 100 |
| 242 | 20 | p.o. | | | 100 |
| 261 | 20 | p.o. | | | 103.6 |
| 270 | 20 | p.o. | | | 112.5 |
| 289 | 20 | p.o. | | | 14.1 |

*RS = restraint stress;
NES = novel environment stress

Example 10

In Vivo Assay: Upper GI tract transit

Methods: The animals used in these studies were male CD-1 mice, ave. wt. ~30 g. Mice were housed under 12h/12h light/dark cycle, food & water ad lib. On the day of the experiment mice were assigned to experimental groups, including one vehicle-only group (=control). At 30 min before administration of carmine dye, animals were dosed with vehicle or vehicle-plus-compound, mice were returned to their home cages after drug administration. After administration of carmine, the animals were either returned to their home cages (non-stressed) or individually placed in the same metal cages as used in the fecal output or entire GI tract transit to induce a novel environment stress. One hour after administration of carmine, mice were sacrificed by cervical dislocation, the abdomen opened midventrally, the small intestine from pylorus to cecum was removed, the mesentery divided in order to lay the intestine straight & flat—without stretching. The total length of intestine and the length of carmine-dyed intestine were measured in order to determine the percent of the upper GI tract over which transit had occurred as follows: {(Length of carmine-dyed intestine)/(Total length of intestine)}×100=% upper GI transit. The data expressed were group means±SD (or s.e.m.) and data expressed as % of control. Statistics: ANOVA with the Tukey-Kramer post-hoc test and means were considered significantly different when $P<0.05$. Data is presented in Table XIV.

TABLE XIV

Mouse Upper GI Transit Test (MUGIT)

| Cpd No. | dose (mg) | route | upper GI transit (% ctrl) |
|---|---|---|---|
| 8 | 30 | p.o. | 77.3 |
| 17 | 30 | p.o. | 37.3 |
| 18 | 10 | p.o. | 99.6 |
| 18 | 50 | p.o. | 69.9 |
| 18 | 5 | p.o. | 94.2 |
| 18 | 25 | p.o. | 83.0 |
| 18 | 100 | p.o. | 41.2 |
| 18 | 30 | p.o. | 37.5 |
| 18 | 30 | p.o. | 53.1 |
| 48 | 30 | p.o. | 102.1 |
| 75 | 30 | p.o. | 71.1 |
| 75 | 60 | p.o. | 56.0 |
| 75 | 100 | p.o. | 45.6 |
| 227 | 30 | p.o. | 93.9 |
| 256 | 30 | p.o. | 89.7 |
| 261 | 30 | p.o. | 87.7 |
| 270 | 30 | p.o. | 96.5 |
| 287 | 30 | p.o. | 66.4 |
| 289 | 30 | p.o. | 76.4 |
| 315 | 30 | p.o. | 94.5 |

Example 11

Visceral Hyperalgesia Testing

Method: Rats were chronically instrumented with EMG electrodes in the muscles of the anterior abdominal wall. Distention of an intracolonic balloon, using a barostat apparatus, evoked increases in the EMG recordings that are related to the pressure. Control responses are compared with repeat stimulation 4 hours after zymosan is administered to the colon (FIG. 1). Animals with 10% higher visceromotor responses for at least two distending pressures are considered to exhibit visceral hyperalgesia.

Figure 2:
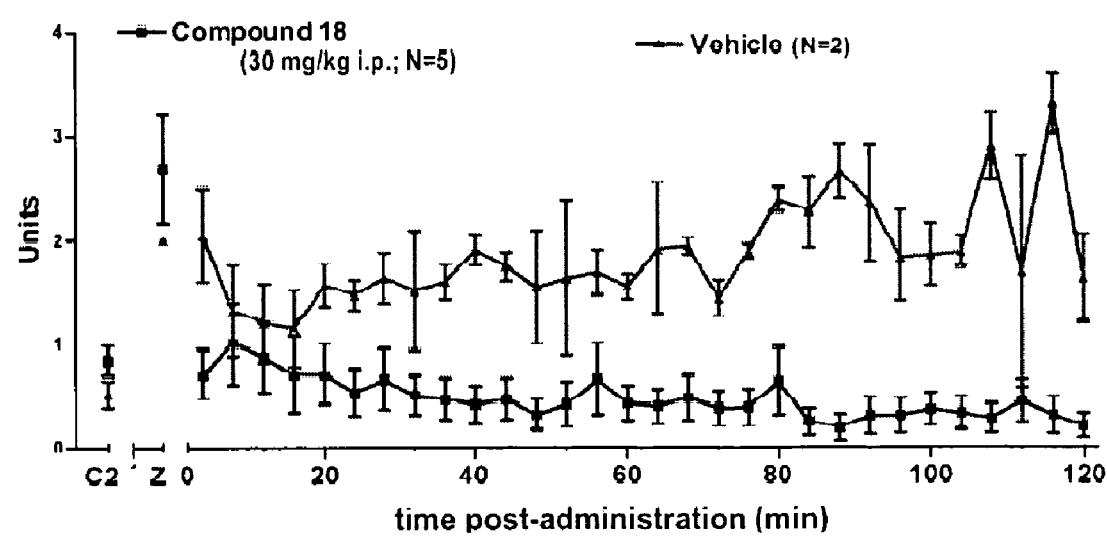
FIG. 2 and FIG. 3 each show the effect in rat of Cpd 18 on the hyperalgesic response to colorectal balloon distention following zymosan.
Figure 3:
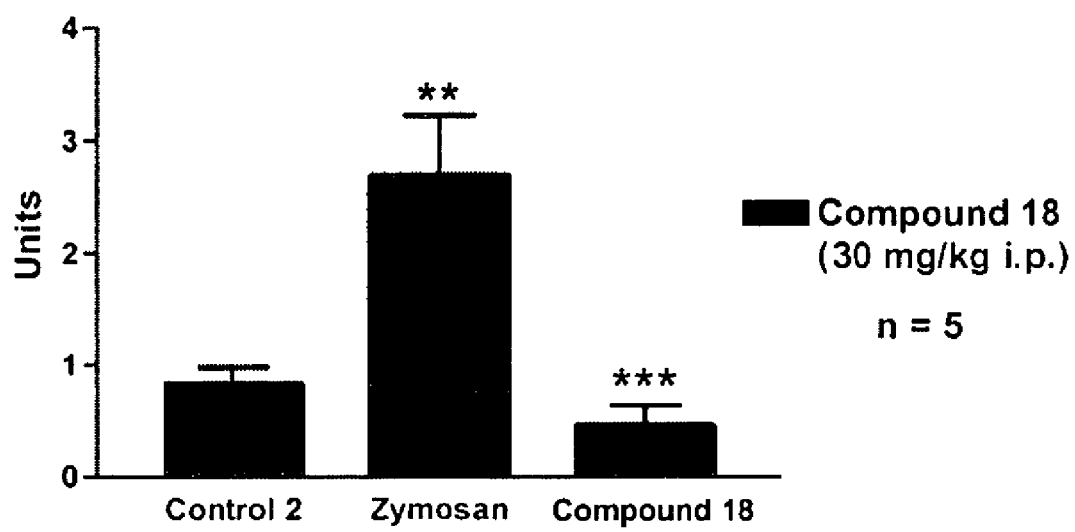

Compound 18 in 5 rats at repeated distentions of 40 mmHg administered at 30 mg/kg, i.p., blocked the hyperalgesic response to colorectal balloon distention following zymosan (FIG. 2 and FIG. 3).

The agonistic or antagonistic activity of the compounds of the invention at the kappa opioid receptor can be determined by known methods, for example, by the procedure described in S. Giuliani, A. Lecci, M. Tramontana, C. A. Maggi, Role of kappa opioid receptors in modulating cholinergic twitches in the circular muscle of guinea-pig colon. *Brit J Pharmacol* 119, 985-9 (November, 1996).

What is claimed is:

1. A compound of Formula (I)

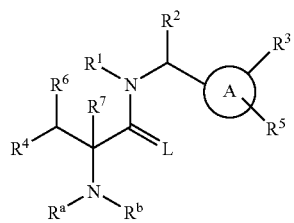

Formula (I)

wherein:

$R^1$ is selected from the group consisting of hydrogen, $C_{1-6}$alkyl, cycloalkyl, heterocyclyl, aryl($C_{1-6}$)alkyl, and heteroaryl($C_{1-6}$)alkyl; wherein when $R^1$ is phenyl($C_{1-6}$) alkyl, phenyl is optionally fused to a heterocyclyl or cycloalkyl;

wherein when $R^1$ is $C_{1-2}$alkyl, said $C_{1-2}$alkyl is optionally substituted with one to two substituents independently selected from the group consisting of $C_{1-6}$alkoxy, aryl, cycloalkyl, heterocyclyl, hydroxy, cyano, amino, $C_{1-6}$alkylamino, ($C_{1-6}$alkyl)$_2$amino, trifluoromethyl, and carboxy;

and further, wherein when $R^1$ is $C_{3-6}$alkyl, said $C_{3-6}$alkyl is optionally substituted with one to three substituents independently selected from the group consisting of $C_{1-6}$alkoxy, aryl, cycloalkyl, heterocyclyl, hydroxy, cyano, amino, $C_{1-6}$alkylamino, ($C_{1-6}$alkyl)$_2$amino, trifluoromethyl, and carboxy;

wherein the cycloalkyl and heterocyclyl of $C_{1-2}$alkyl and $C_{3-6}$alkyl are optionally substituted with one to two substituents independently selected from the group consisting of $C_{1-6}$alkyl, hydroxy($C_{1-6}$)alkyl, $C_{1-6}$alkoxy, hydroxy, cyano, amino, $C_{1-6}$alkylamino, ($C_{1-6}$alkyl)$_2$amino, trifluoromethyl, carboxy, aryl ($C_{1-6}$)alkoxycarbonyl, $C_{1-6}$alkoxycarbonyl, aminocarbonyl, $C_{1-6}$alkylaminocarbonyl, ($C_{1-6}$alkyl)$_2$ aminocarbonyl, and aminosulfonyl;

furthermore, wherein the cycloalkyl and heterocyclyl of $R^1$ are optionally substituted with one to two substituents independently selected from the group consisting of $C_{1-6}$alkyl, hydroxy($C_{1-6}$)alkyl, $C_{1-6}$alkoxy, hydroxy, cyano, amino, $C_{1-6}$alkylamino, ($C_{1-6}$alkyl)$_2$amino, trifluoromethyl, carboxy, aryl($C_{1-6}$)alkoxycarbonyl, $C_{1-6}$alkoxycarbonyl, aminocarbonyl, $C_{1-6}$alkylaminocarbonyl, ($C_{1-6}$alkyl)$_2$aminocarbonyl, and aminosulfonyl;

furthermore, wherein the aryl and heteroaryl portion of the $R^1$ substituents aryl($C_{1-6}$)alkyl and heteroaryl($C_{1-6}$) alkyl, are optionally substituted with one to three $R^{11}$ substituents independently selected from the group consisting of $C_{1-6}$alkyl; hydroxy($C_{1-6}$)alkyl; $C_{1-6}$alkoxy; $C_{6-10}$aryl($C_{1-6}$)alkyl; $C_{6-10}$aryl($C_{1-6}$) alkoxy; $C_{6-10}$aryl; heteroaryl optionally substituted with one to two substituents independently selected from the group consisting of $C_{1-4}$alkyl, $C_{1-4}$alkoxy, and carboxy; cycloalkyl; heterocyclyl; $C_{6-10}$aryloxy; heteroaryloxy; cycloalkyloxy; heterocyclyloxy; amino; $C_{1-6}$alkylamino; ($C_{1-6}$alkyl)$_2$amino; $C_{3-6}$cycloalkylaminocarbonyl; hydroxy ($C_{1-6}$) alkylaminocarbonyl; $C_{6-10}$arylaminocarbonyl wherein $C_{6-10}$aryl is optionally substituted with carboxy or $C_{1-4}$alkoxycarbonyl; heterocyclylcarbonyl; carboxy; $C_{1-6}$alkoxycarbonyl; $C_{1-6}$alkoxycarbonyloxy; $C_{1-6}$alkylcarbonyl; $C_{1-6}$alkylcarbonylamino; aminocarbonyl; $C_{1-6}$alkylaminocarbonyl; ($C_{1-6}$alkyl)$_2$aminocarbonyl; cyano; halogen; trifluoromethyl; trifluoromethoxy; and hydroxy;

provided that no more than one $R^{11}$ substituent is selected from the group consisting of $C_{6-10}$aryl($C_{1-6}$)alkyl; $C_{6-10}$aryl($C_{1-6}$)alkoxy; $C_{6-10}$aryl; heteroaryl optionally substituted with one to two substituents independently selected from the group consisting of $C_{1-4}$alkyl, $C_{1-4}$alkoxy, and carboxy; cycloalkyl; heterocyclyl; $C_{6-10}$aryloxy; heteroaryloxy; cycloalkyloxy; $C_{6-10}$arylaminocarbonyl wherein $C_{6-10}$aryl is optionally substituted with carboxy or $C_{1-4}$alkoxycarbonyl; heterocyclylcarbonyl; and heterocyclyloxy;

$R^2$ is hydrogen, $C_{1-8}$alkyl, hydroxy($C_{1-8}$)alkyl, $C_{6-10}$aryl ($C_{1-6}$)alkoxy($C_{1-6}$)alkyl, or $C_{6-10}$aryl($C_{1-8}$)alkyl;

wherein the $C_{6-10}$aryl group in the $C_{6-10}$aryl-containing substituents of $R^2$ are optionally substituted with one to two substituents independently selected from the group consisting of $C_{1-6}$alkyl, $C_{1-6}$alkoxy, hydroxy, amino, $C_{1-6}$alkylamino, $(C_{1-6}$alkyl$)_2$amino, aminocarbonyl, $C_{1-6}$alkylaminocarbonyl, $(C_{1-6}$alkyl$)_2$aminocarbonyl, cyano, fluoro, chloro, bromo, trifluoromethyl, and trifluoromethoxy; and, wherein the $C_{1-6}$alkyl and $C_{1-6}$alkoxy substituents of aryl are optionally substituted with hydroxy, amino, $C_{1-6}$alkylamino, $(C_{1-6}$alkyl$)_2$amino, or aryl;

A is a-1, optionally substituted with $R^3$ and $R^5$;

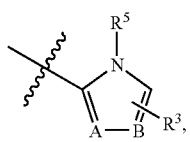

a-1 wherein

A-B is N—C;

$R^3$ is one to two substituents independently selected from the group consisting of $C_{1-6}$alkyl, aryl, aryl($C_{1-6}$)alkyl, aryl($C_{2-6}$)alkenyl, aryl($C_{2-6}$)alkynyl, heteroaryl, heteroaryl($C_{1-6}$)alkyl, heteroaryl($C_{2-6}$)alkenyl, heteroaryl($C_{2-6}$)alkynyl, amino, $C_{1-6}$alkylamino, $(C_{1-6}$alkyl$)_2$amino, arylamino, heteroarylamino, aryloxy, heteroaryloxy, trifluoromethyl, and halogen;

wherein the aryl, heteroaryl, and the aryl and heteroaryl of aryl($C_{1-6}$)alkyl, aryl($C_{2-6}$)alkenyl, aryl($C_{2-6}$)alkynyl, heteroaryl($C_{1-6}$)alkyl, heteroaryl($C_{2-6}$)alkenyl, heteroaryl($C_{2-6}$)alkynyl, arylamino, heteroarylamino, aryloxy, and heteroaryloxy, are optionally substituted with one to five fluoro substituents or one to three substituents independently selected from the group consisting of $C_{1-6}$alkyl, hydroxy($C_{1-6}$)alkyl, $C_{1-6}$alkoxy, $C_{6-10}$aryl($C_{1-6}$)alkyl, $C_{6-10}$aryl($C_{1-6}$)alkoxy, $C_{6-10}$aryl, $C_{6-10}$aryloxy, heteroaryl($C_{1-6}$)alkyl, heteroaryl($C_{1-6}$)alkoxy, heteroaryl, heteroaryloxy, $C_{6-10}$arylamino, heteroarylamino, amino, $C_{1-6}$alkylamino, $(C_{1-6}$alkyl$)_2$amino, carboxy($C_{1-6}$)alkylamino, carboxy, $C_{1-6}$alkylcarbonyl, $C_{1-6}$alkoxycarbonyl, $C_{1-6}$alkylcarbonylamino, aminocarbonyl, $C_{1-6}$alkylaminocarbonyl, $(C_{1-6}$alkyl$)_2$aminocarbonyl, carboxy($C_{1-6}$)alkylaminocarbonyl, cyano, halogen, trifluoromethyl, trifluoromethoxy, hydroxy, $C_{1-6}$alkylsulfonyl, and $C_{1-6}$alkylsulfonylamino; provided that no more than one such substituent on the aryl or heteroaryl portion of $R^3$ is selected from the group consisting of $C_{6-10}$aryl($C_{1-6}$)alkyl, $C_{6-10}$aryl($C_{1-6}$)alkoxy, $C_{6-10}$aryl, $C_{6-10}$aryloxy, heteroaryl($C_{1-6}$)alkyl, heteroaryl($C_{1-6}$)alkoxy, heteroaryl, heteroaryloxy, $C_{6-10}$arylamino, heteroarylamino;

and wherein $C_{1-6}$alkyl and $C_{1-6}$alkyl of aryl($C_{1-6}$)alkyl and heteroaryl($C_{1-6}$)alkyl are optionally substituted with a substituent selected from the group consisting of hydroxy, carboxy, $C_{1-4}$alkoxycarbonyl, amino, $C_{1-6}$alkylamino, $(C_{1-6}$alkyl$)_2$amino, aminocarbonyl, $(C_{1-4}$)alkylaminocarbonyl, di($C_{1-4}$)alkylaminocarbonyl, aryl, heteroaryl, arylamino, heteroarylamino, aryloxy, heteroaryloxy, aryl($C_{1-4}$)alkoxy, and heteroaryl($C_{1-4}$)alkoxy;

$R^4$ is $C_{6-10}$aryl or a heteroaryl selected from the group consisting of furyl, thienyl, pyrrolyl, oxazolyl, thiazolyl, imidazolyl, pyrazolyl, pyridinyl, pyrimidinyl, pyrazinyl, indolyl, isoindolyl, indolinyl, benzofuryl, benzothienyl, benzimidazolyl, benzthiazolyl, benzoxazolyl, quinolizinyl, quinolinyl, isoquinolinyl and quinazolinyl;

wherein $R^4$ is optionally substituted with one to three $R^{41}$ substituents independently selected from the group consisting of ($C_{1-6}$)alkyl optionally substituted with amino, $C_{1-6}$alkylamino, or $(C_{1-6}$alkyl$)_2$amino; ($C_{1-6}$)alkoxy; phenyl($C_{1-6}$)alkoxy; phenyl($C_{1-6}$)alkylcarbonyloxy wherein C1-6 alkyl is optionally substituted with amino; a non fused 5-membered-heteroaryl($C_{1-6}$)alkylcarbonyloxy; a non fused 5-membered-heteroaryl; hydroxy; halogen; aminosulfonyl; formylamino; aminocarbonyl; $C_{1-6}$alkylaminocarbonyl wherein ($C_{1-6}$)alkyl is optionally substituted with amino, $C_{1-6}$alkylamino, or $(C_{1-6}$alkyl$)_2$amino; $(C_{1-6}$alkyl$)_2$aminocarbonyl wherein each ($C_{1-6}$)alkyl is optionally substituted with amino, $C_{1-6}$alkylamino, or $(C_{1-6}$alkyl$)_2$amino; heterocyclylcarbonyl wherein heterocyclyl is a 5-7 membered nitrogen-containing ring and said heterocyclyl is attached to the carbonyl carbon via a nitrogen atom; carboxy; or cyano; and wherein the phenyl portion of phenyl($C_{1-6}$)alkylcarbonyloxy is optionally substituted with ($C_{1-6}$)alkyl ($C_{1-6}$) alkoxy, halogen, cyano, amino, or hydroxy;

provided that no more than one $R^{41}$ is $C_{1-6}$alkyl substituted with $C_{1-6}$alkylamino or $(C_{1-6}$alkyl$)_2$amino; aminosulfonyl; formylamino; aminocarbonyl; $C_{1-6}$alkylaminocarbonyl; $(C_{1-6}$alkyl$)_2$aminocarbonyl; heterocyclylcarbonyl; hydroxy; carboxy; or a phenyl- or heteroaryl-containing substituent;

$R^5$ is a substituent on a nitrogen atom of ring A selected from the group consisting of hydrogen and $C_{1-4}$alkyl;

$R^6$ is hydrogen or $C_{1-6}$alkyl;

$R^7$ is hydrogen or $C_{1-6}$alkyl;

$R^a$ and $R^b$ are independently selected from the group consisting of hydrogen, $C_{1-6}$alkyl, and $C_{1-6}$alkoxycarbonyl; alternatively, when $R^a$ and $R^b$ are each other than hydrogen, $R^a$ and $R^b$ are optionally taken together with the nitrogen atom to which they are both attached to form a five to eight membered monocyclic ring;

L is O;

and pharmaceutically acceptable enantiomers, diastereomers, racemates, and salts thereof.

2. The compounds of claim 1 wherein $R^1$ is selected from the group consisting of hydrogen, $C_{1-6}$alkyl, aryl($C_{1-4}$)alkyl, and heteroaryl($C_{1-4}$)alkyl;

wherein the aryl and heteroaryl portion of aryl($C_{1-4}$)alkyl and heteroaryl($C_{1-4}$) alkyl are optionally substituted with one to three $R^{11}$ substituents independently selected from the group consisting of $C_{1-6}$alkoxy; heteroaryl optionally substituted with one to two substitutents independently selected from the group consisting of $C_{1-4}$alkyl, $C_{1-4}$alkoxy, and carboxy; carboxy; $C_{1-4}$alkoxycarbonyl; $C_{1-4}$alkoxycarbonyloxy; aminocarbonyl; $C_{1-4}$alkylaminocarbonyl; $C_{3-6}$cycloalkylaminocarbonyl; hydroxy($C_{1-6}$) alkylaminocarbonyl; $C_{6-10}$arylaminocarbonyl wherein $C_{6-10}$aryl is optionally substituted with carboxy or $C_{1-4}$alkoxycarbonyl; heterocyclylcarbonyl; cyano; halogen; trifluoromethoxy; and hydroxy; provided that no more than one $R^{11}$ is heteroaryl (optionally substituted with one to two $C_{1-4}$alkyl substituents); $C_{6-10}$arylaminocarbonyl wherein $C_{6-10}$aryl is optionally substituted with carboxy or $C_{1-4}$alkoxycarbonyl; or heterocyclylcarbonyl.

3. The compounds of claim 1 wherein $R^1$ is selected from the group consisting of $C_{6-10}$aryl($C_{1-4}$)alkyl, pyridinyl($C_{1-4}$) alkyl, and furanyl($C_{1-4}$)alkyl; wherein $C_{6-10}$aryl, pyridinyl, and furanyl are optionally substituted with one to three $R^{11}$ substituents independently selected from the group consisting of $C_{1-3}$alkoxy; tetrazolyl; carboxy; $C_{1-4}$alkoxycarbonyl; aminocarbonyl; $C_{1-4}$alkylaminocarbonyl; $C_{1-3}$alkylaminocarbonyl; $C_{3-6}$cycloalkylaminocarbonyl; hydroxy($C_{1-4}$) alkylaminocarbonyl; $C_{6-10}$arylaminocarbonyl wherein $C_{6-10}$aryl is optionally substituted with carboxy or $C_{1-4}$alkoxycarbonyl; morpholin-4-ylcarbonyl; cyano; halogen; and trifluoromethoxy; provided that no more than one $R^{11}$ is $C_{6-10}$arylaminocarbonyl.

4. The compounds of claim 1 wherein $R^1$ is selected from the group consisting of phenyl($C_{1-3}$)alkyl, pyridinyl($C_{1-3}$) alkyl, and furanyl($C_{1-3}$)alkyl; wherein phenyl, pyridinyl, and furanyl are optionally substituted with one to three $R^{11}$ substituents independently selected from the group consisting of $C_{1-3}$alkoxy; tetrazolyl, $C_{3-6}$cycloalkylaminocarbonyl; hydroxy($C_{1-4}$) alkylaminocarbonyl; $C_{6-10}$arylaminocarbonyl wherein $C_{6-10}$aryl is optionally substituted with carboxy or $C_{1-4}$alkoxycarbonyl; morpholin-4-ylcarbonyl; chloro; fluoro; trifluoromethoxy; $C_{1-4}$alkoxycarbonyl; and carboxy; provided that no more than one $R^{11}$ is $C_{6-10}$arylaminocarbonyl.

5. The compounds of claim 1 wherein $R^1$ is phenylmethyl, pyridinylmethyl, or furanylmethyl; wherein phenyl, pyridinyl, and furanyl are optionally substituted with one to three $R^{11}$ substituents independently selected from the group consisting of methoxy; tetrazolyl; cyclopropylaminocarbonyl, (2-hydroxyeth-1-yl)aminocarbonyl; methoxycarbonyl; phenylaminocarbonyl wherein phenyl is optionally substituted with carboxy; morpholin-4-ylcarbonyl; and carboxy.

6. The compounds of claim 1 wherein $R^2$ is a substituent selected from the group consisting of hydrogen, $C_{1-4}$alkyl, hydroxy($C_{1-4}$)alkyl, and phenyl($C_{1-6}$) alkoxy($C_{1-4}$)alkyl; wherein said phenyl is optionally substituted with one to two substituents independently selected from the group consisting of $C_{1-3}$alkyl, $C_{1-3}$alkoxy, hydroxy, cyano, fluoro, chloro, bromo, trifluoromethyl, and trifluoromethoxy.

7. The compounds of claim 1 wherein $R^2$ is a substituent selected from the group consisting of hydrogen and $C_{1-4}$alkyl.

8. The compounds of claim 1 wherein $R^2$ is hydrogen or methyl.

9. The compounds of claim 1 wherein $R^3$ is one to two substituents independently selected from the group consisting of $C_{1-6}$alkyl, halogen, and aryl; wherein aryl is optionally substituted with one to three substituents independently selected from the group consisting of halogen, carboxy, aminocarbonyl, $C_{1-3}$alkylsulfonylamino, cyano, hydroxy, amino, $C_{1-3}$alkylamino, and ($C_{1-3}$alkyl)$_2$amino.

10. The compounds of claim 1 wherein $R^3$ is one to two substituents independently selected from the group consisting of $C_{1-3}$alkyl, bromo, and phenyl; wherein phenyl is optionally substituted with one to three substituents independently selected from the group consisting of chloro, fluoro, iodo, carboxy, aminocarbonyl, and cyano.

11. The compounds of claim 1 wherein $R^3$ is one to two substituents independently selected from the group consisting of methyl and phenyl; wherein phenyl is optionally substituted with one to three substituents independently selected from the group consisting of chloro and carboxy.

12. The compounds of claim 1 wherein at least one $R^3$ substituent is phenyl.

13. The compounds of claim 1 wherein $R^3$ is a substituent selected from the group consisting of methyl and phenyl; wherein phenyl is optionally substituted with one to two substituents independently selected from the group consisting of chloro and carboxy.

14. The compounds of claim 1 wherein $R^4$ is $C_{6-10}$aryl optionally substituted with one to three $R^{41}$ substituents independently selected from the groupconsisting of ($C_{1-3}$)alkyl, ($C_{1-6}$)alkoxy, phenyl($C_{1-6}$)alkoxy; hydroxy; halogen; formylamino; aminocarbonyl; $C_{1-6}$alkylaminocarbonyl; ($C_{1-6}$alkyl)$_2$aminocarbonyl; heterocyclylcarbonyl wherein heterocyclyl is a 5-7 membered nitrogen-containing ring and said heterocyclyl is attached to the carbonyl carbon via a nitrogen atom; carboxy; and cyano;
provided that no more than one $R^{41}$ substituent is formylamino, aminocarbonyl, $C_{1-6}$alkylaminocarbonyl, ($C_{1-6}$alkyl)$_2$aminocarbonyl, heterocyclylcarbonyl, hydroxy, carboxy, or a phenyl-containing substituent.

15. The compounds of claim 1 wherein $R^4$ is phenyl substituted with one to three $R^{41}$ substituents independently selected from the group consisting of ($C_{1-3}$)alkyl, ($C_{1-3}$)alkoxy, phenyl($C_{1-3}$)alkoxy, hydroxy, $C_{1-6}$alkylaminocarbonyl, and aminocarbonyl; provided that no more than one $R^{41}$ substituent is aminocarbonyl, $C_{1-6}$alkylaminocarbonyl, hydroxy, or a phenyl-containing substituent.

16. The compounds of claim 1 wherein $R^4$ is phenyl substituted at the 4-position with hydroxy, $C_{1-3}$alkylaminocarbonyl, or aminocarbonyl, and optionally substituted with one to two substituents independently selected from the group consisting of methyl, methoxy, and benzyloxy.

17. The compounds of claim 1 wherein $R^4$ is phenyl substituted at the 4-position with hydroxy, $C_{1-3}$alkylaminocarbonyl, or aminocarbonyl, and optionally substituted with one to two methyl substituents.

18. The compounds of claim 1 wherein $R^4$ is phenyl substituted at the 4-position with hydroxy, $C_{1-3}$alkylaminocarbonyl, or aminocarbonyl, and substituted at the 2- and 6-positions with methyl substituents.

19. The compounds of claim 1 wherein $R^5$ is hydrogen or methyl.

20. The compounds of claim 1 wherein $R^5$ is hydrogen.

21. The compounds of claim 1 wherein $R^6$ is hydrogen or methyl.

22. The compounds of claim 1 wherein $R^6$ is hydrogen.

23. The compounds of claim 1 wherein $R^7$ is hydrogen or methyl.

24. The compounds of claim 1 wherein $R^7$ is hydrogen.

25. The compounds of claim 1 wherein $R^a$ and $R^b$ are independently selected from the group consisting of hydrogen and $C_{1-3}$alkyl; or, when $R^a$ and $R^b$ are each other than hydrogen, $R^a$ and $R^b$ are optionally taken together with the nitrogen atom to which they are both attached to form a five to seven membered monocyclic ring.

26. The compounds of claim 1 wherein $R^a$ and $R^b$ are independently hydrogen or methyl.

27. The compounds of claim 1 wherein $R^a$ and $R^b$ are each hydrogen.

28. The compounds of claim 1 that are present in their RR, SS, RS, and SR configurations.

29. The compounds of claim 1 in their S,S configuration.

30. A compound of Formula (Ia):

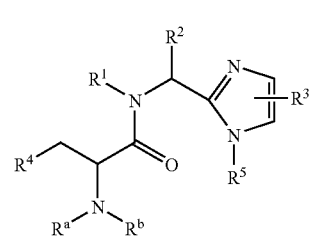

Formula (Ia)

wherein:
R$^1$ is selected from the group consisting of hydrogen, C$_{1-6}$alkyl, aryl(C$_{1-4}$)alkyl, and heteroaryl(C$_{1-4}$)alkyl;
wherein the aryl and heteroaryl portion of aryl(C$_{1-4}$)alkyl and heteroaryl(C$_{1-4}$) alkyl are optionally substituted with one to three R$^{11}$ substituents independently selected from the group consisting of C$_{1-6}$alkoxy; heteroaryl optionally substituted with one to two substituents independently selected from the group consisting of C$_{1-4}$alkyl, C$_{1-4}$alkoxy, and carboxy; carboxy; C$_{1-4}$alkoxycarbonyl; C$_{1-4}$alkoxycarbonyloxy; aminocarbonyl; C$_{1-4}$alkylaminocarbonyl; C$_{3-6}$cycloalkylaminocarbonyl; hydroxy(C$_{1-6}$) alkylaminocarbonyl; C$_{6-10}$arylaminocarbonyl wherein C$_{6-10}$aryl is optionally substituted with carboxy or C$_{1-4}$alkoxycarbonyl; heterocyclylcarbonyl; cyano; halogen; trifluoromethoxy; and hydroxy; provided that no more than one R$^{11}$ is heteroaryl (optionally substituted with one to two C$_{1-4}$alkyl substituents); C$_{6-10}$arylaminocarbonyl wherein C$_{6-10}$aryl is optionally substituted with carboxy or C$_{1-4}$alkoxycarbonyl; or heterocyclylcarbonyl;
R$^2$ is selected from the group consisting of hydrogen, C$_{1-4}$alkyl, hydroxy(C$_{1-4}$) alkyl, and phenyl(C$_{1-6}$)alkoxy (C$_{1-4}$)alkyl;
wherein said phenyl is optionally substituted with one to two substituents independently selected from the group consisting of C$_{1-3}$alkyl, C$_{1-3}$alkoxy, hydroxy, cyano, fluoro, chloro, bromo, trifluoromethyl, and trifluoromethoxy;
R$^3$ is one to two substituents independently selected from the group consisting of C$_{1-6}$alkyl, halogen, and aryl; wherein aryl is optionally substituted with one to three substituents independently selected from the group consisting of halogen, carboxy, aminocarbonyl, C$_{1-3}$alkylsulfonylamino, cyano, hydroxy, amino, C$_{1-3}$alkylamino, and (C$_{1-3}$alkyl)$_2$amino;
R$^4$ is C$_{6-10}$aryl optionally substituted with one to three R$^{41}$ substituents independently selected from the group consisting of (C$_{1-3}$)alkyl, (C$_{1-6}$) alkoxy, phenyl(C$_{1-6}$) alkoxy; hydroxy; halogen; formylamino; aminocarbonyl; C$_{1-6}$alkylaminocarbonyl; (C$_{1-6}$alkyl)$_2$ aminocarbonyl; heterocyclylcarbonyl wherein heterocyclyl is a 5-7 membered nitrogen-containing ring and said heterocyclyl is attached to the carbonyl carbon via a nitrogen atom; carboxy; and cyano;
provided that no more than one R$^{41}$ substituent is formylamino, aminocarbonyl, C$_{1-6}$alkylaminocarbonyl, (C$_{1-6}$ alkyl)$_2$aminocarbonyl, heterocyclylcarbonyl, hydroxy, carboxy, or a phenyl-containing substituent.
R$^5$ is hydrogen or methyl;
R$^a$ and R$^b$ are independently hydrogen or C$_{1-3}$alkyl; or, when R$^a$ and R$^b$ are each other than hydrogen, R$^a$ and R$^b$ are optionally taken together with the nitrogen atom to which they are both attached to form a five to seven membered monocyclic ring;
and pharmaceutically acceptable enantiomers, diastereomers, racemates, and salts thereof.

31. A compound of Formula (Ia) wherein:
R$^1$ is selected from the group consisting of C$_{6-10}$aryl(C$_{1-4}$) alkyl, pyridinyl(C$_{1-4}$) alkyl, and furanyl(C$_{1-4}$)alkyl; wherein C$_{6-10}$aryl, pyridinyl, and furanyl are optionally substituted with one to three R$^{11}$ substituents independently selected from the group consisting of C$_{1-3}$alkoxy; tetrazolyl; carboxy; C$_{1-3}$alkoxycarbonyl; aminocarbonyl; C$_{1-4}$alkylaminocarbonyl; C$_{1-3}$alkylaminocarbonyl; C$_{3-6}$cycloalkylaminocarbonyl; hydroxy(C$_{1-4}$) alkylaminocarbonyl; C$_{6-10}$arylaminocarbonyl wherein C$_{6-10}$aryl is optionally substituted with carboxy or C$_{1-4}$alkoxycarbonyl; morpholin-4-ylcarbonyl; cyano; halogen; trifluoromethoxy; C$_{1-4}$alkoxycarbonyl; or carboxy; provided that no more than one R$^{11}$ is C$_{6-10}$arylaminocarbonyl;
R$^2$ is hydrogen or C$_{1-4}$alkyl;
R$^3$ is one to two substituents independently selected from the group consisting of C$_{1-3}$alkyl, bromo, and phenyl; wherein phenyl is optionally substituted with one to three substituents independently selected from the group consisting of chloro, fluoro, carboxy, aminocarbonyl, and cyano;
R$^4$ is phenyl substituted with one to three substituents independently selected from the group consisting of (C$_{1-3}$) alkyl, (C$_{1-3}$)alkoxy, phenyl(C$_{1-3}$)alkoxy, hydroxy, C$_{1-6}$alkylaminocarbonyl, and aminocarbonyl; provided that no more than one R$^{41}$ substituent is aminocarbonyl, C$_{1-6}$alkylaminocarbonyl, hydroxy, or a phenyl-containing substituent;
R$^5$ is hydrogen;
R$^a$ and R$^b$ are independently hydrogen or methyl;
and pharmaceutically acceptable enantiomers, diastereomers, racemates, and salts thereof.

32. A compound of Formula (Ia) wherein:
R$^1$ is selected from the group consisting of phenyl(C$_{1-3}$) alkyl, pyridinyl(C$_{1-3}$) alkyl, and furanyl(C$_{1-3}$)alkyl; wherein phenyl, pyridinyl, and furanyl are optionally substituted with one to three R$^{11}$ substituents independently selected from the group consisting of is C$_{1-3}$alkoxy; tetrazolyl; C$_{3-6}$cycloalkylaminocarbonyl; hydroxy(C$_{1-4}$)alkylaminocarbonyl; C$_{6-10}$arylaminocarbonyl wherein C$_{6-10}$aryl is optionally substituted with carboxy or C$_{1-4}$alkoxycarbonyl; morpholin-4-ylcarbonyl; chloro; fluoro; trifluoromethoxy; methoxycarbonyl; and carboxy; provided that no more than one R$^{11}$ is C$_{6-10}$arylaminocarbonyl;
R$^2$ is hydrogen or methyl;
R$^3$ is one to two substituents independently selected from the group consisting of methyl and phenyl; wherein phenyl is optionally substituted with one to three substituents independently selected from the group consisting of chloro and carboxy;
R$^4$ is phenyl substituted at the 4-position with hydroxy, C$_{1-3}$alkylaminocarbonyl, or aminocarbonyl, and optionally substituted with one to two substituents independently selected from the group consisting of methyl, methoxy, and benzyloxy;
R$^5$ is hydrogen;
R$^a$ and R$^b$ are each hydrogen;
and pharmaceutically acceptable enantiomers, diastereomers, racemates, and salts thereof.

33. A compound according to claim 32 wherein R$^1$ is phenylmethyl, pyridinylmethyl, or furanylmethyl; wherein phenyl, pyridinyl, and furanyl are optionally substituted with one to three R$^{11}$ substituents independently selected from is the group consisting of methoxy, tetrazolyl, cyclopropylaminocarbonyl, (2-hydroxyeth-1-yl)aminocarbonyl, phenylaminocarbonyl wherein phenyl is optionally substituted with carboxy, morpholin-4-ylcarbonyl, methoxycarbonyl, and carboxy; provided that no more than one R$^{11}$ is phenylaminocarbonyl.

34. A compound according to claim 32 wherein R$^4$ is phenyl substituted at the 4-position with hydroxy, C$_{1-3}$alkylaminocarbonyl, or aminocarbonyl, and optionally substituted with one to two methyl substituents.

35. A compound according to claim 32 wherein R$^4$ is phenyl substituted at the 4-position with hydroxy, C$_{1-3}$alkylaminocarbonyl, or aminocarbonyl, and substituted at the 2- and 6-positions with methyl substituents.

36. A compound of Formula (Ib)

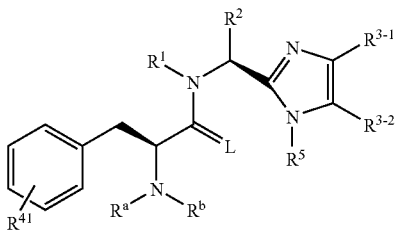

Formula (Ib)

wherein L is O and $R^1$, $R^2$, $R^{3-1}$, $R^{3-2}$, $R^5$, $R^a$, $R^b$, and $R^{41}$ are dependently selected from the group consisting of:

| $R^1$ | $R^2$ | $R^{3-1}$ | $R^{3-2}$ | $R^5$ | $R^{41}$ | $R^a/R^b$ |
|---|---|---|---|---|---|---|
| 2-Aminocarbonyl-phenylmethyl | methyl | phenyl | H | H | 2,6-dimethyl-4-aminocarbonyl | H |
| 2-Cyano-phenyl methyl | methyl | phenyl | H | H | 2,6-dimethyl-4-aminocarbonyl | H |
| 2-Bromo-phenyl methyl | methyl | phenyl | H | H | 2,6-dimethyl-4-aminocarbonyl | H |
| 3-Carboxy-4-methoxy-phenyl methyl | methyl | phenyl | H | H | 4-aminocarbonyl | H |
| 3-Carboxy-4-methoxy-phenyl methyl | H | phenyl | H | H | 4-aminocarbonyl | H |
| 3-Carboxy-4-methoxy-phenyl methyl | H | phenyl | H | H | 2,6-dimethyl-4-aminocarbonyl | H |
| 3-Methoxycarbonyl-4-methoxy-phenylmethyl | H | phenyl | H | H | 2,6-dimethyl-4-aminocarbonyl | H |
| 3-(1H-tetrazol-5-yl)-4-methoxy-phenylmethyl | methyl | phenyl | H | H | 2,6-dimethyl-4- | H |
| 3-Methoxycarbonyl-phenylmethyl | methyl | phenyl | H | H | 2,6-dimethyl-4-aminocarbonyl | H |
| 3-Methoxy carbonyl-phenylmethyl | methyl | naphthalen-1-yl | H | H | 2,6-dimethyl-4-aminocarbonyl | H |
| 3-Carboxy-phenylmethyl | methyl | naphthalen-1-yl | H | H | 2,6-dimethyl-4- | H |
| 3-Carboxy-phenylmethyl | methyl | 4-chloro-phenyl | Me | H | 2,6-dimethyl-4- | H |
| 4-Carboxy-phenylmethyl | methyl | naphthalen-1-yl | H | H | 2,6-dimethyl-4- | H |
| 3-Methoxy-4-carboxy-phenylmethyl | methyl | phenyl | H | H | 2,6-dimethyl-4-aminocarbonyl | H |
| 3,4-Dihydroxy-phenylmethyl | methyl | phenyl | H | H | 2,6-dimethyl-4-hydroxy | H |
| Piperidin-4-ylmethyl | methyl | phenyl | H | H | 2,6-dimethyl-4-hydroxy | H |
| 3-Methoxy carbonyl-4-methoxy-phenyl methyl | methyl | phenyl | H | H | 2,6-dimethyl-4-aminocarbonyl | H |
| 3-Carboxy-4-methoxy-phenylmethyl | methyl | phenyl | H | H | 2,6-dimethyl-4-aminocarbonyl | H |
| 3,4-Dimethoxy-phenylmethyl | methyl | 3-bromo phenyl | H | H | 2,6-dimethyl-4-aminocarbonyl | H |
| 3,4-Dimethoxy-phenylmethyl | methyl | 3-carboxy phenyl | H | H | 2,6-dimethyl-4-aminocarbonyl | H |
| 3,4-Dimethoxy-phenylmethyl | benzyl oxy methyl | phenyl | H | H | 2,6-dimethyl-4-hydroxy | H |
| 3,4-Dimethoxy-phenylmethyl | methyl | 3-amino carbonyl phenyl | H | H | 2,6-dimethyl-4-aminocarbonyl | H |

-continued

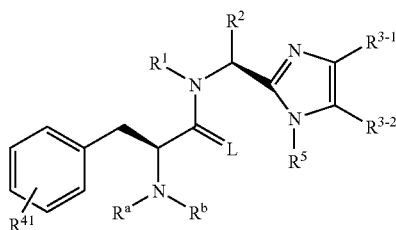

Formula (Ib)

wherein L is O and $R^1$, $R^2$, $R^{3-1}$, $R^{3-2}$, $R^5$, $R^a$, $R^b$, and $R^{41}$ are dependently selected from the group consisting of:

| $R^1$ | $R^2$ | $R^{3-1}$ | $R^{3-2}$ | $R^5$ | $R^{41}$ | $R^a/R^b$ |
|---|---|---|---|---|---|---|
| 3,4-Dimethoxy-phenylmethyl | methyl | 3-cyano phenyl | H | H | 2,6-dimethyl-4-aminocarbonyl | H |
| Isopropyl | H | quinoxalin-8-yl | Me | H | 2,6-dimethyl-4-hydroxy | H |
| 3,4-Dimethoxy-phenylmethyl | methyl | 2-bromo phenyl | H | H | 2,6-dimethyl-4-aminocarbonyl | H |
| 3,4-Dimethoxy-phenylmethyl | methyl | 2-cyano phenyl | H | H | 2,6-dimethyl-4-aminocarbonyl | H |
| 3,4-Dimethoxy-phenylmethyl | methyl | 2-amino carbonyl phenyl | | | 2,6-dimethyl-4-aminocarbonyl | H |
| 3,4-Dimethoxy-phenylmethyl | methyl | 2-carboxy phenyl | H | H | 2,6-dimethyl-4-aminocarbonyl | H |
| 3,4-Dibenzyloxy-phenylmethyl | methyl | phenyl | H | H | 2,6-dimethyl-4-hydroxy | H |
| [1,3]benzo dioxal-5-yl | methyl | phenyl | H | H | 2,6-dimethyl, 4-hydroxy | H |
| 4-Methoxy-phenylmethyl | methyl | phenyl | H | H | 2,6-dimethyl-4-hydroxy | H |
| 3-Methoxy-phenylmethyl | methyl | phenyl | H | H | 2,6-dimethyl-4-hydroxy | H |
| 2,4-Dimethoxy-phenylmethyl | methyl | phenyl | H | H | 2,6-dimethyl-4-hydroxy | H |
| 3,4-Dimethoxy-phenylmethyl | H | phenyl | H | H | 2,6-dimethyl-4-hydroxy | H |
| Isopropyl | H | 4-methyl carbonyl phenyl | H | H | 2,6-dimethyl-4-hydroxy | H |
| Isopropyl | H | 3-fluoro, 4-carboxy-phenyl | Me | H | 2,6-dimethyl-4-hydroxy | H |
| Isopropyl | H en-1-yl | 2-phenyl-ethyl | Me | H | 2,6-dimethyl-4-hydroxy | H |
| Isopropyl | H | 4-hydroxy methyl phenyl | Me | H | 2,6-dimethyl-4-hydroxy | H |
| Benzhydryl | H | phenyl | H | H | 2,6-dimethyl-4-hydroxy | H |
| Isopropyl | H | 4-cyano phenyl | Me | H | 2,6-dimethyl-4-hydroxy | H |
| Benzyl | methyl | 4-trifluoro methyl phenyl | H | H | 2,6-dimethyl-4-aminocarbonyl | H |
| Isopropyl | H | 3-trifluoro methoxy phenyl | Me | H | 2,6-dimethyl-4-hydroxy | H |
| Isopropyl | H | 4-trifluoro methoxy phenyl | Me | H | 2,6-dimethyl-4-hydroxy | H |
| Isopropyl | H | 3-methane sulfonyl amino phenyl | Me | H | 2,6-dimethyl-4-hydroxy | H |
| Isopropyl | H | 4-(2-carboxy ethyl) phenyl | Me | H | 2,6-dimethyl-4-hydroxy | H |
| Isopropyl | H | 3-amino-5-carboxy phenyl | Me | H | 2,6-dimethyl-4-hydroxy | H |

-continued

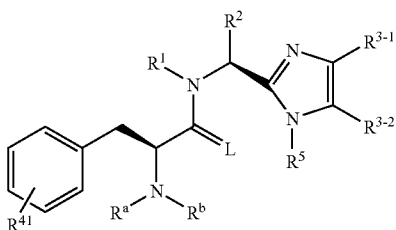

Formula (Ib)

wherein L is O and $R^1$, $R^2$, $R^{3-1}$, $R^{3-2}$, $R^5$, $R^a$, $R^b$, and $R^{41}$ are dependently selected from the group consisting of:

| $R^1$ | $R^2$ | $R^{3-1}$ | $R^{3-2}$ | $R^5$ | $R^{41}$ | $R^a/R^b$ |
|---|---|---|---|---|---|---|
| 3-Carboxy-phenylmethyl | methyl | phenyl | H | H | 2,6-dimethyl-4-hydroxy | H |
| 4-Carboxy-phenylmethyl | methyl | phenyl | H | H | 2,6-dimethyl-4-carboxy | H |
| 4-Carboxy-phenylmethyl | methyl | phenyl | H | H | 2,6-dimethyl-4-aminocarbonyl | H |
| 4-Methoxy carbonyl-phenylmethyl | methyl | phenyl | H | H | 2,6-dimethyl-4-aminocarbonyl | H |
| 3-Methoxy carbonyl-phenylmethyl | methyl | phenyl | H | H | 2,6-dimethyl-4-hydroxy | H |
| 1-Benzyloxy carbonyl-piperadin-4-ylmethyl | methyl | phenyl | H | H | 2,6-dimethyl-4-hydroxy | H |
| Furan-2-yl methyl | methyl | phenyl | H | H | 2,6-dimethyl-4-hydroxy | H |
| Furan-3-yl methyl | methyl | phenyl | H | H | 2,6-dimethyl-4-hydroxy | H |
| Cyclohexyl methyl | methyl | phenyl | H | H | 2,6-dimethyl-4-hydroxy | H |
| Pyridin-4-yl methyl | methyl | phenyl | H | H | 2,6-dimethyl-4-hydroxy | H |
| Benzyl | methyl | 4-chloro phenyl | Me | H | 2,6-dimethyl-4-aminocarbonyl | H |
| Benzyl | methyl | 3-fluoro phenyl | H | H | 2,6-dimethyl-4-aminocarbonyl | H |
| Isopropyl | H | 3-cyano phenyl | Me | H | 2,6-dimethyl-4-hydroxy | H |
| Isopropyl | H | 2,5-difluoro phenyl | Me | H | 2,6-dimethyl-4-hydroxy | H |
| Isopropyl | H | 4-methane sulfonyl phenyl | Me | H | 2,6-dimethyl-4-hydroxy | H |
| Benzyl | benzyl oxy methyl | phenyl | H | H | 2,6-dimethyl-4-aminocarbonyl | H |
| Isopropyl | H | Br | Me | H | 2,6-dimethyl-4-hydroxy | H |
| Isopropyl | H | 4-dimethyl amino phenyl | Me | H | 2,6-dimethyl-4-hydroxy | H |
| Isopropyl | H | 3-dimethyl amino carbonyl phenyl | Me | H | 2,6-dimethyl-4-hydroxy | H |
| Isopropyl | H | 3-hydroxy phenyl | Me | H | 2,6-dimethyl-4-hydroxy | H |
| Isopropyl | H | 4-amino carbonyl phenyl | Me | H | 2,6-dimethyl-4-hydroxy | H |
| Isopropyl | H | 3-chloro phenyl | Me | H | 2,6-dimethyl-4-hydroxy | H |
| Isopropyl | H | 2,4-difluoro phenyl | Me | H | 2,6-dimethyl-4-hydroxy | H |
| Isopropyl | H | 3-methane sulfonyl phenyl | Me | H | 2,6-dimethyl-4-hydroxy | H |

-continued

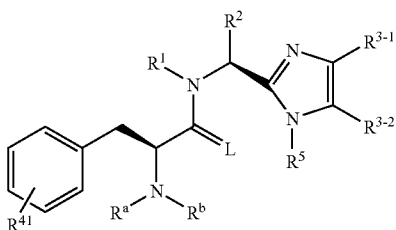

Formula (Ib)

wherein L is O and $R^1$, $R^2$, $R^{3-1}$, $R^{3-2}$, $R^5$, $R^a$, $R^b$, and $R^{41}$ are dependently selected from the group consisting of:

| $R^1$ | $R^2$ | $R^{3-1}$ | $R^{3-2}$ | $R^5$ | $R^{41}$ | $R^a/R^b$ |
|---|---|---|---|---|---|---|
| Isopropyl | H | 3-amino carbonyl phenyl | Me | H | 2,6-dimethyl-4-hydroxy | H |
| Benzyl | methyl | 4-trifluoro methyl phenyl | Me | H | 2,6-dimethyl-4-aminocarbonyl | H |
| 3,4-Dimethoxy-phenylmethyl | methyl | phenyl | H | H | 2,6-dimethyl-4-aminocarbonyl | H |
| Benzyl | methyl | 4-fluoro phenyl | H | H | 2,6-dimethyl-4-aminocarbonyl | H |
| 4-Dimethylamino-phenylmethyl | methyl | phenyl | H | Me | 2,6-dimethyl-4-hydroxy | H |
| 4-Methylamino-phenylmethyl | methyl | phenyl | H | H | 2,6-dimethyl-4-hydroxy | H |
| 4-Methylcarbonyl amino-phenyl methyl | methyl | phenyl | H | H | 2,6-dimethyl-4-hydroxy | H |
| 4-Carboxy-phenylmethyl | methyl | phenyl | H | H | 2,6-dimethyl-4-hydroxy | H |
| 4-Hydroxy-phenylmethyl | methyl | phenyl | H | H | 2,6-dimethyl-4-hydroxy | H |
| Benzyl | methyl | 4-fluoro phenyl | H | H | 2,6-dimethyl-4-hydroxy | H |
| Isopropyl | methyl | 4-fluoro phenyl | H | H | 2,6-dimethyl-4-hydroxy | H |
| Isopropyl | hydroxy methyl | phenyl | H | H | 2,6-dimethyl-4-aminocarbonyl | H |
| Isopropyl | H | phenyl | H | H | 2,6-dimethyl, 4-aminocarbonyl | H |
| 3,4-Dichloro-phenylmethyl | H | phenyl | H | H | 2,6-dimethyl-4-hydroxy | H |
| 4-Methylcarbonyl oxy-phenyl methyl | methyl | phenyl | H | H | 2,6-dimethyl-4-hydroxy | H |
| 4-Methoxy carbonyl-phenylmethyl | methyl | phenyl | H | H | 2,6-dimethyl-4-hydroxy | H |
| 3-Aminocarbonyl-phenylmethyl | methyl | phenyl | H | H | 2,6-dimethyl-4-hydroxy | H |
| 3-Cyano-phenyl methyl | methyl | phenyl | H | H | 2,6-dimethyl-4-hydroxy | H |
| Pyridin-3-yl methyl | methyl | phenyl | H | H | 2,6-dimethyl-4-hydroxy | H |
| Pyridin-2-yl methyl | methyl | phenyl | H | H | 2,6-dimethyl-4-hydroxy | H |
| 1-(R)-Phenylethyl | H | phenyl | H | H | 2,6-dimethyl-4-aminocarbonyl | H |
| 1-(R)-Phenylethyl | H | phenyl | H | H | 2,6-dimethyl-4-aminocarbonyl | H |
| 2-Methoxy-phenylmethyl | methyl | phenyl | H | H | 2,6-dimethyl-4-hydroxy | H |
| 2,6-Dichloro-phenylmethyl | methyl | phenyl | H | H | 2,6-dimethyl-4-hydroxy | H |
| 3-Phenoxy-phenylmethyl | methyl | phenyl | H | H | 2,6-dimethyl-4-hydroxy | H |
| Naphthalen-1-yl-methyl | methyl | phenyl | H | H | 2,6-dimethyl-4-hydroxy | H |
| Naphthalen-2-yl-methyl | methyl | phenyl | H | H | 2,6-dimethyl-4-hydroxy | H |
| 3-Bromo-phenyl methyl | methyl | phenyl | H | H | 2,6-dimethyl-4-hydroxy | H |

-continued

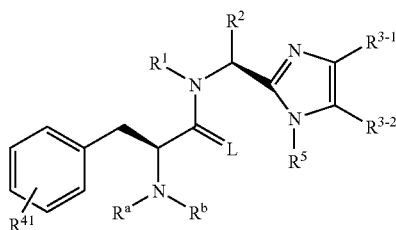

Formula (Ib)

wherein L is O and $R^1$, $R^2$, $R^{3-1}$, $R^{3-2}$, $R^5$, $R^a$, $R^b$, and $R^{41}$ are dependently selected from the group consisting of:

| $R^1$ | $R^2$ | $R^{3-1}$ | $R^{3-2}$ | $R^5$ | $R^{41}$ | $R^a/R^b$ |
|---|---|---|---|---|---|---|
| 3,4-Dimethoxy-phenylmethyl | methyl | phenyl | H | H | 2,6-dimethyl-4-hydroxy | H |
| 2,4-Dichloro-phenylmethyl | methyl | phenyl | H | H | 2,6-dimethyl-4-hydroxy | H |
| Benzyl | isobutyl | phenyl | H | H | 2,6-dimethyl-4-hydroxy | H |
| Benzyl | benzyl | phenyl | H | H | 2,6-dimethyl-4-hydroxy | H |
| Benzyl | isopropyl | phenyl | H | H | 2,6-dimethyl-4-hydroxy | H |
| Benzyl | H | phenyl | H | H | 2,6-dimethyl-4-aminocarbonyl | H |
| 3-Phenyl prop-1-yl | methyl | phenyl | H | H | 2,6-dimethyl-4-aminocarbonyl | H |
| 2-Phenylethyl | methyl | phenyl | H | H | 2,6-dimethyl-4-aminocarbonyl | H |
| 1-Phenylethyl diastereomer A | methyl | phenyl | H | H | 2,6-dimethyl-4-aminocarbonyl | H |
| 1-Phenylethyl diasteromer B | methyl | phenyl | H | H | 2,6-dimethyl-4-aminocarbonyl | H |
| Benzyl | methyl | phenyl | H | H | 2,6-dimethyl-4-aminocarbonyl | H |
| Isopropyl | H | 4-biphenyl | Me | H | 2,6-dimethyl-4-hydroxy | H |
| Isopropyl | H | 3-fluoro phenyl | Me | H | 2,6-dimethyl-4-hydroxy | H |
| Isopropyl | H | 2-fluoro phenyl | Me | H | 2,6-dimethyl-4-hydroxy | H |
| Isopropyl | hydroxy methyl | phenyl | H | H | 2,6-dimethyl-4-hydroxy | H |
| H | hydroxy methyl | phenyl | H | H | 2,6-dimethyl-4-hydroxy | H |
| Isopropyl | 3-(amino methyl) phenyl methyl | phenyl | H | H | 2,6-dimethyl-4-hydroxy | H |
| Isopropyl | 3-amino carbonyl phenyl methyl | phenyl | H | H | 2,6-dimethyl-4-hydroxy | H |
| Isopropyl | 3-cyano phenyl methyl | phenyl | H | H | 2,6-dimethyl-4-hydroxy | H |
| Isopropyl | H | 4-carboxy phenyl | Me | H | 2,6-dimethyl-4-hydroxy | H |
| Isopropyl | H | pyridin-3-yl | Me | H | 2,6-dimethyl-4-hydroxy | H |
| Isopropyl | H | 4-methoxy phenyl | Me | H | 2,6-dimethyl-4-hydroxy | H |
| Isopropyl | H | 3,5-difluoro phenyl | Me | H | 2,6-dimethyl-4-hydroxy | H |
| Cyclohexyl | methyl | phenyl | H | H | 2,6-dimethyl-4-aminocarbonyl | H |
| Carboxymethyl | H | phenyl | H | H | 2,6-dimethyl-4-hydroxy | H |
| Isopropyl | H | 3-hydroxy methyl phenyl | Me | H | 2,6-dimethyl-4-hydroxy | H |
| Isopropyl | H | pyrimidin-5-yl | Me | H | 2,6-dimethyl-4-hydroxy | H |

-continued

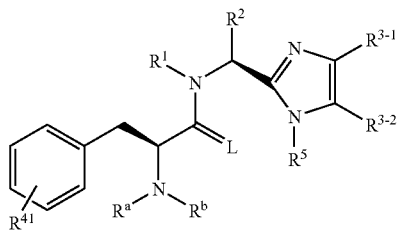

Formula (Ib)

wherein L is O and $R^1$, $R^2$, $R^{3-1}$, $R^{3-2}$, $R^5$, $R^a$, $R^b$, and $R^{41}$ are dependently selected from the group consisting of:

| $R^1$ | $R^2$ | $R^{3-1}$ | $R^{3-2}$ | $R^5$ | $R^{41}$ | $R^a/R^b$ |
|---|---|---|---|---|---|---|
| Isopropyl | H | pyrimidin-5-yl | Me | H | 4-hydroxy | H |
| Isopropyl | H | 3-carboxy phenyl | Me | H | 2,6-dimethyl-4-hydroxy | H |
| Isopropyl | H | 3-biphenyl | Me | H | 2,6-dimethyl-4-hydroxy | H |
| Isopropyl | H | 2-methoxy phenyl | Me | H | 2,6-dimethyl-4-hydroxy | H |
| Isopropyl | benzyl | phenyl | H | H | 3-aminocarbonyl | H |
| Isopropyl | isopropyl | phenyl | H | H | 3-aminocarbonyl | H |
| Isopropyl | benzyl oxy methyl | phenyl | H | H | 2,6-dimethyl-4-hydroxy | H |
| Isopropyl | isobutyl | phenyl | H | H | 2,6-dimethyl-4-[2-(2,6-dimethyl-4-hydroxyphenyl)-1-amino-ethylcarbonxyloxy] phenyl | H |
| Isopropyl | isobutyl | phenyl | H | H | 2,6-dimethyl-4-hydroxy | H |
| Isopropyl | H | 3,5-dichloro phenyl | Me | H | 2,6-dimethyl-4-hydroxy | H hydroxy |
| Isopropyl | H | 3-methoxy phenyl | Me | H | 2,6-dimethyl-4-hydroxy | H |
| Isopropyl | methyl | phenyl | H | H | 2,6-dimethyl-4-aminocarbonyl | H |
| Isopropyl | H | 2-biphenyl | Me | H | 2,6-dimethyl-4-hydroxy | H |
| Isopropyl | H | thiophen-3-yl | Me | H | 2,6-dimethyl-4-hydroxy | H |
| Isopropyl | H | 4-chloro phenyl | Me | H | 2,6-dimethyl-4-hydroxy | H |
| Isopropyl | H | 3-methyl carbonyl amino phenyl | Me | H | 2,6-dimethyl-4-hydroxy | H |
| Isopropyl | H | 4-trifluoro methyl phenyl | Me | H | 2,6-dimethyl-4-hydroxy | H |
| Isopropyl | H | naphthalen-2-yl | Me | H | 2,6-dimethyl-4-hydroxy | H |
| Isopropyl | H | 2-trifluoro methyl phenyl | Me | H | 2,6-dimethyl-4-hydroxy | H |
| Isopropyl | H | thiophen-3-yl | Me | H | 4-hydroxy | H |
| Isopropyl | H | pyridin-3-yl | Me | H | 4-hydroxy | H |
| Isopropyl | H | phenyl | Me | H | 4-hydroxy | H |
| Isopropyl | H | 2-chloro phenyl | Me | H | 2,6-dimethyl-4-hydroxy | H |
| Isopropyl | H | naphthalen-1-yl | Me | H | 2,6-dimethyl-4-hydroxy | H |
| Isopropyl | benzyl | phenyl | H | H | 3-cyano | H |
| Isopropyl | benzyl | phenyl | H | H | 4-hydroxy | H |
| Isopropyl | benzyl | phenyl | H | H | 2,6-dimethyl-4-hydroxy | H |
| Isopropyl | isopropyl | phenyl | H | H | 3-cyano | H |
| Isopropyl | isopropyl | phenyl | H | H | 4-hydroxy | H |
| Isopropyl | isopropyl | phenyl | H | H | 2,6-dimethyl-4-hydroxy | H |

-continued

Formula (Ib)

$$\text{Structure with } R^1, R^2, R^{3-1}, R^{3-2}, R^5, R^a, R^b, R^{41} \text{ substituents on imidazole-containing scaffold}$$

wherein L is O and $R^1$, $R^2$, $R^{3-1}$, $R^{3-2}$, $R^5$, $R^a$, $R^b$, and $R^{41}$ are dependently selected from the group consisting of:

| $R^1$ | $R^2$ | $R^{3-1}$ | $R^{3-2}$ | $R^5$ | $R^{41}$ | $R^a/R^b$ |
|---|---|---|---|---|---|---|
| Isopropyl | H | 4-fluoro phenyl | Me | H | 2,6-dimethyl-4-hydroxy | H |
| Isopropyl | H | 3,5-bis-trifluoro methyl phenyl | Me | H | 2,6-dimethyl-4-hydroxy | H |
| Isopropyl | H | 2-methyl phenyl | Me | H | 2,6-dimethyl-4-hydroxy | H |
| Isopropyl | H | phenyl | Me | H | 2,6-dimethyl-4-hydroxy | H |
| 2-Dimethylamino-1-methyl-eth-1-yl | H | phenyl | H | H | 2,6-dimethyl-4-hydroxy | H |
| Methyl | isobutyl | phenyl | H | H | 3-aminocarbonyl | H |
| Methyl | isobutyl | phenyl | H | H | 3-cyano | H |
| Ethyl | isopropyl | phenyl | H | H | 2,6-dimethyl-4-hydroxy | H |
| Methyl | isopropyl | phenyl | H | H | 4-hydroxy | H |
| H | 3-amino carbonyl phenyl methyl | phenyl | H | H | 2,6-dimethyl-4-hydroxy | H |
| H | 3-cyano phenyl methyl | phenyl | H | H | 2,6-dimethyl-4-hydroxy | H |
| Methyl | isobutyl | phenyl | H | H | 2,6-dimethyl-4-hydroxy | H |
| H | benzyl oxy methyl | phenyl | H | H | 2,6-dimethyl-4-hydroxy | H |
| H | isobutyl | phenyl | H | H | 2,6-dimethyl-4-hydroxy | H |
| H | benzyl | phenyl | H | H | 2,6-dimethyl-4-hydroxy | H |
| Isopropyl | H | phenyl | H | H | 2,6-dimethyl-4-aminocarbonyl | H |
| Methyl | methyl | phenyl | H | H | 2,6-dimethyl-4-morpholin-1-ylcarbonyl | H |
| Methyl | methyl | phenyl | H | H | 2,6-dimethyl-4-ethylamino carbonyl | H |
| Methyl | methyl | phenyl | H | H | 2,6-dimethyl-4-methylamino carbonyl | H |
| H | isopropyl | phenyl | H | H | 3-aminocarbonyl | H |
| H | isopropyl | phenyl | H | H | 3-cyano | H |
| H | isopropyl | phenyl | H | H | 2,6-dimethyl-4-hydroxy | H |
| H | isopropyl | phenyl | H | H | 4-hydroxy | H |
| Methyl | methyl | phenyl | H | H | 4-aminosulfonyl | H |
| Cyclohexyl | H | phenyl | H | H | 2,6-dimethyl-4-hydroxy | H |
| Cyclohexyl | H | phenyl | H | H | 2,6-dimethyl-4-4-hydroxy | H |
| Cyclopropyl methyl | H | phenyl | H | H | 2,6-dimethyl-4-hydroxy | H |
| Cyclopropyl methyl | H | phenyl | H | H | 4-hydroxy | H |
| Isopropyl | H | phenyl | H | H | 2,6-dimethyl-4-hydroxy | H |
| Isopropyl | H | phenyl | H | H | 4-hydroxy | H |

-continued

Formula (Ib)

wherein L is O and $R^1$, $R^2$, $R^{3-1}$, $R^{3-2}$, $R^5$, $R^a$, $R^b$, and $R^{41}$ are dependently selected from the group consisting of:

| $R^1$ | $R^2$ | $R^{3-1}$ | $R^{3-2}$ | $R^5$ | $R^{41}$ | $R^a/R^b$ |
|---|---|---|---|---|---|---|
| Methyl | methyl | phenyl | H | H | 2,6-dimethyl-4-aminocarbonyl | H |
| Ethyl | methyl | phenyl | H | H | 2,6-dimethyl-4-aminocarbonyl | H |
| Methyl | H | phenyl | H | H | 4-hydroxy | H |
| Methyl | H | phenyl | H | H | 2,6-dimethyl-4-hydroxy | H |
| Methyl | methyl | phenyl | H | H | 4-aminocarbonyl | H |
| Methyl | methyl | benzyl | H | H | 4-hydroxy | H |
| Methyl | methyl | benzyl | H | H | 2,6-dimethyl-4-hydroxy | H |
| Methyl | methyl | phenyl | H | H | 2,6-dimethyl-4-hydroxy | H |
| H | methyl | phenyl | H | H | 2,6-dimethyl-4-hydroxy | H |
| Methyl | methyl | phenyl | H | H | 4-hydroxy | H |
| H | methyl | phenyl | H | H | 4-hydroxy | H |
| Ethyl | methyl | phenyl | H | H | 4-hydroxy | H |
| Ethyl | methyl | phenyl | H | H | 2,6-dimethyl-4-hydroxy | H |
| Benzyl | methyl | phenyl | H | H | 2,6-dimethyl-4-hydroxy | H |
| Benzyl | methyl | phenyl | H | H | 4-hydroxy | H |
| Isopropyl | methyl | phenyl | H | H | 2,6-dimethyl-4-hydroxy | H |
| Isopropyl | methyl | phenyl | H | H | 4-hydroxy | H |
| 2-Carboxy-phenyl methyl | methyl | phenyl | H | H | 2,6-dimethyl-4-aminocarbonyl | H |
| 3-Carboxy-phenyl methyl | methyl | phenyl | H | H | 2,6-dimethyl-4-aminocarbonyl | H |
| 2-Bromo-4,5-dimethoxy-phenylmethyl | methyl | phenyl | H | H | 2,6-dimethyl-4-aminocarbonyl | H |
| 2-Carboxy-4,5-dimethoxy-phenylmethyl | methyl | phenyl | H | H | 2,6-dimethyl-4-aminocarbonyl | H |
| 3-Carboxy-4-methoxy-phenyl methyl | methyl | phenyl | H | H | H | H |
| 3-Carboxy-4-methoxy-phenyl methyl | methyl | phenyl | H | H | 2,6-dimethyl | H |
| 3-Methoxycarbonyl-4-methoxy-phenylmethyl | methyl | phenyl | H | H | 2,6-dimethyl | H |
| 3,4-Dimethoxy-phenylmethyl | methyl | phenyl | H | H | 2,6-dimethyl-4-imidazol-2-yl | H |
| 3,4-Dimethoxy-phenylmethyl | methyl | phenyl | H | H | 2,6-dimethyl | H |
| 3-Carboxy-4-methoxy-phenyl methyl | methyl | 4-chloro | H | H | 2,6-dimethyl-4-aminocarbonyl | H |
| 3-Carboxy-4-methoxy-phenyl methyl | methyl | 4-chloro | H | H | 2,6-dimethyl-4-aminocarbonyl | H |
| 3-Carboxy-4-methoxy-phenyl methyl | methyl | 4-chloro | H | H | 2,6-dimethyl-4-aminocarbonyl | H |
| 4-Carboxy- | methyl | 4-chloro | Me | H | 2,6-dimethyl-4- | H |

-continued

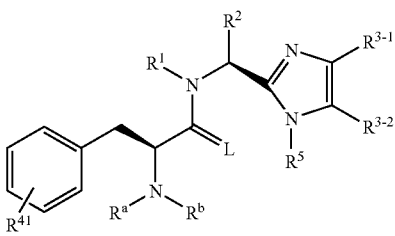

Formula (Ib)

wherein L is O and R$^1$, R$^2$, R$^{3-1}$, R$^{3-2}$, R$^5$, R$^a$, R$^b$, and R$^{41}$ are dependently selected from the group consisting of:

| R$^1$ | R$^2$ | R$^{3-1}$ | R$^{3-2}$ | R$^5$ | R$^{41}$ | R$^a$/R$^b$ |
|---|---|---|---|---|---|---|
| phenylmethyl | | phenyl | | | aminocarbonyl | |
| 3-Carboxy-4-methoxy-phenyl methyl | methyl | 4-chloro phenyl | Cl | H | 2,6-dimethyl-4-aminocarbonyl | H |
| 3-(1H-tetrazol-5-yl)-phenylmethyl | methyl | phenyl | H | H | 2,6-dimethyl-4-aminocarbonyl | H |
| 3-Carboxy-4-trifluoromethoxy-phenylmethyl | methyl | phenyl | H | H | 2,6-dimethyl-4-aminocarbonyl | H |
| Bis-3,4-trifluoromethoxy-phenylmethyl | methyl | phenyl | H | H | 2,6-dimethyl-4-aminocarbonyl | H |
| 3-Carboxy-phenylmethyl | methyl | phenyl | H | H | 2,6-dimethyl-4-aminocarbonyl | H |
| Quinolin-4-yl methyl | methyl | phenyl | H | H | 2,6-dimethyl-4-hydroxy | H |
| 4-Methoxy naphthalen-1-ylmethyl | methyl | phenyl | H | H | 2,6-dimethyl-4-hydroxy | H |
| 4-Trifluoromethoxy-phenylmethyl | methyl | phenyl | H | H | 2,6-dimethyl-4-hydroxy | H |
| 4-Trifluoromethyl-phenylmethyl | methyl | phenyl | H | H | 2,6-dimethyl-4-hydroxy | H |
| 4-Isopropyloxy-phenylmethyl | methyl | phenyl | H | H | 2,6-dimethyl-4-hydroxy | H |
| 3-Ethoxyphenyl-methyl | methyl | phenyl | H | H | 2,6-dimethyl-4-hydroxy | H |
| 5-Methoxycarbonyl-pyridin-2-yl methyl | methyl | phenyl | H | H | 2,6-dimethyl-4-aminocarbonyl | H |
| 5-Carboxy-pyridin-2-ylmethyl | methyl | phenyl | H | H | 2,6-dimethyl-4-aminocarbonyl | H |
| 6-Carboxy-pyridin-3-ylmethyl | methyl | phenyl | H | H | 2,6-dimethyl-4-aminocarbonyl | H |
| 6-Methoxycarbonyl-pyridin-3-ylmethyl | methyl | phenyl | H | H | 2,6-dimethyl-4-aminocarbonyl | H |
| 5-Carboxy-furan-2-ylmethyl | methyl | phenyl | H | H | 2,6-dimethyl-4-aminocarbonyl | H |
| 5-Methoxy carbonyl-furan-2-ylmethyl | methyl | phenyl | H | H | 2,6-dimethyl-4-aminocarbonyl | H |
| 3,4-Dimethoxy-phenylmethyl | hydroxy methyl | phenyl | H | H | 2,6-dimethyl-4-aminocarbonyl | H |
| Benzyl | hydroxy methyl | phenyl | H | H | 2,6-dimethyl-4-aminocarbonyl | H |
| 3-Carboxy-4-methoxy-phenyl methyl | methyl | phenyl | H | H | 2,6-dimethyl-4-hydroxy | H |
| 3-Carboxy-4-methoxy-phenyl methyl | methyl | phenyl | H | H | 4-hydroxy | H |
| 3-Carboxy-4-methoxy-phenyl methyl | methyl | phenyl | H | H | 4-hydroxy | H/Me |
| 3-Carboxy-4-methoxy-phenyl methyl | H | phenyl | H | H | 4-hydroxy | H |

-continued

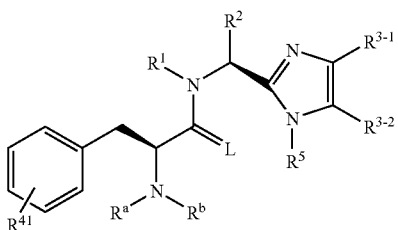

Formula (Ib)

wherein L is O and $R^1$, $R^2$, $R^{3-1}$, $R^{3-2}$, $R^5$, $R^a$, $R^b$, and $R^{41}$ are dependently selected from the group consisting of:

| $R^1$ | $R^2$ | $R^{3-1}$ | $R^{3-2}$ | $R^5$ | $R^{41}$ | $R^a/R^b$ |
|---|---|---|---|---|---|---|
| 3-Carboxy-4-methoxy-phenyl methyl | H | phenyl | H | H | 4-hydroxy | H/Me |
| 3-Carboxy-4-methoxy-phenyl methyl | H | phenyl | H | H | 2,6-dimethyl-4-hydroxy | H |
| 3-Methoxycarbonyl-4-methoxy-phenylmethyl | methyl | phenyl | H | H | H | H |
| 3-(1H-tetrazol-5-yl)-phenylmethyl | methyl | phenyl | H | H | 4-aminocarbonyl | H |
| 3-Methoxycarbonyl-4-methoxy-phenylmethyl | methyl | phenyl | H | H | 2,6-dimethyl-4-hydroxy | H |
| 3-Methoxycarbonyl | methyl | phenyl | H | H | 4-aminocarbonyl | H |
| 3-Carboxy | methyl | phenyl | H | H | 4-aminocarbonyl | H |
| 3-Methoxycarbonyl | H | phenyl | H | H | 2,6-dimethyl-4-aminocarbonyl | H |
| 3-Carboxy | H | phenyl | H | H | 2,6-dimethyl-4-aminocarbonyl | H |
| 3-Carboxy-4-methoxy-phenylmethyl | methyl | phenyl | H | H | 4-benzyloxy- | H/Me |
| 3-Carboxy-4-methoxy-phenylmethyl | methyl | phenyl | H | H | 4-aminocarbonyl | H |
| 3-Carboxy-phenyl | methyl | 4-chloro | Me | H | 4-aminocarbonyl | H |
| 3-Methoxycarbonyl-4-methoxy-phenylmethyl | methyl | phenyl | H | H | 4-hydroxy | H |
| 5-Methoxycarbonyl-furan-2-ylmethyl | methyl | phenyl | H | H | 2,6-dimethyl-4-hydroxy | H |
| 5-Carboxy-furan-2-ylmethyl | methyl | phenyl | H | H | 2,6-dimethyl-4-hydroxy | H |
| 3-Carboxy-4-methoxy-phenylmethyl | methyl | 3-bromo phenyl | H | H | 2,6-dimethyl-4-aminocarbonyl | H |
| 3-Carboxy-4-methoxy-phenylmethyl | methyl | 4-iodo | H | H | 2,6-dimethyl-4-aminocarbonyl | H |
| 3-Carboxy-4-methoxy-phenylmethyl | methyl | 2-bromo phenyl | H | H | 2,6-dimethyl-4-aminocarbonyl | H |
| 3-Carboxy-4-methoxy-phenylmethyl | methyl | 4-bromo | H | H | 2,6-dimethyl-4-aminocarbonyl | H |
| 3-Carboxy-4-methoxy-phenylmethyl | methyl | phenyl | H | H | 2,6-dimethyl | H |
| 3-Carboxy-4-methoxy-phenylmethyl | methyl | 4-chloro | methyl | H | 4-hydroxy | H |
| 3-Aminocarbonyl-4-methoxy phenylmethyl | methyl | phenyl | H | H | 2,6-dimethyl-4-aminocarbonyl | H |
| 3-(Morpholin-4-ylcarbonyl)-4-methoxy phenylmethyl | methyl | phenyl | H | H | 2,6-dimethyl-4-aminocarbonyl | H |
| -3-Aminocarbonyl- | methyl | phenyl | H | H | 4-hydroxy | H |

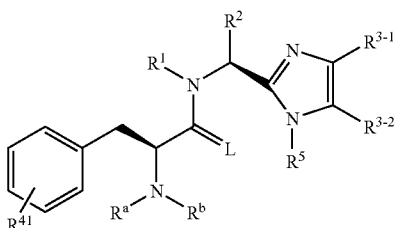

Formula (Ib)

wherein L is O and $R^1$, $R^2$, $R^{3-1}$, $R^{3-2}$, $R^5$, $R^a$, $R^b$, and $R^{41}$ are dependently selected from the group consisting of:

| $R^1$ | $R^2$ | $R^{3-1}$ | $R^{3-2}$ | $R^5$ | $R^{41}$ | $R^a/R^b$ |
|---|---|---|---|---|---|---|
| 4-methoxy-phenylmethyl | | | | | | |
| 3-(Morpholin-4-ylcarbonyl)-4-methoxy-phenylmethyl | methyl | phenyl | H | H | 4-hydroxy | H |
| 3-(2-Hydroxy eth-1-yl-aminocarbonyl)-4-methoxy phenylmethyl | methyl | phenyl | H | H | 2,6-dimethyl-4-aminocarbonyl | H |
| 3-(Cyclopropyl aminocarbonyl)-4-methoxy-phenylmethyl | methyl | phenyl | H | H | 2,6-dimethyl-4-aminocarbonyl | H |
| 3-(Phenylamino carbonyl)-4-methoxy-phenylmethyl | methyl | phenyl | H | H | 2,6-dimethyl-4-aminocarbonyl | H |
| 5-Methoxycarbonyl-furan-2-ylmethyl | methyl | phenyl | H | H | 4-aminocarbonyl | H |
| 5-Carboxy-furan-2-ylmethyl | methyl | phenyl | H | H | 4-aminocarbonyl | H |
| 3-(Phenylamino carbonyl)-4-methoxy-phenylmethyl | methyl | phenyl | H | H | 2,6-dimethyl-4-hydroxy | H |
| 3-(3-carboxyphenyl aminocarbonyl)-4-methoxy-phenylmethyl | methyl | phenyl | H | H | 2,6-dimethyl-4-hydroxy | H |
| 3-(1H-Tetrazol-5-yl)-4-methoxy-phenylmethyl | methyl | phenyl | H | H | 2,6-dimethyl-4-hydroxy | H |
| 3-(4-Carboxyphenyl aminocarbonyl)-4-methoxy-phenylmethyl | methyl | phenyl | H | H | 2,6-dimethyl-4-hydroxy | H |
| 3-(2-t-Butyl-tetrazol-5-yl)-4-methoxy-phenylmethyl | methyl | phenyl | H | H | 2,6-dimethyl-4-aminocarbonyl | H |
| 3-Methoxycarbonyl-4-methoxy-phenylmethyl | methyl | phenyl | H | H | 2,6-dimethyl-4-aminocarbonyl | Methoxy-carbonyl |
| 2-Methoxycarbonyl-pyridin-4-yl methyl | methyl | phenyl | H | H | 2,6-dimethyl-4-aminocarbonyl | H |
| 4-Methoxycarbonyl pyridin-2-yl methyl | methyl | phenyl | H | H | 2,6-dimethyl-4-aminocarbonyl | H |
| 6-Methoxycarbonyl-pyridin-2-ylmethyl | methyl | phenyl | H | H | 2,6-dimethyl-4-aminocarbonyl | H |
| 3-Methoxycarbonyl-4-methoxy-phenylmethyl | methyl | phenyl | H | H | 2,6-dimethyl-4-aminocarbonyl | Methoxy-carbonyl |
| 2-Carboxy-pyridin-4-ylmethyl | methyl | phenyl | H | H | 2,6-dimethyl-4-aminocarbonyl | H | and

-continued

Formula (Ib)

wherein L is O and $R^1$, $R^2$, $R^{3-1}$, $R^{3-2}$, $R^5$, $R^a$, $R^b$, and $R^{41}$ are dependently selected from the group consisting of:

| $R^1$ | $R^2$ | $R^{3-1}$ | $R^{3-2}$ | $R^5$ | $R^{41}$ | $R^a/R^b$ |
|---|---|---|---|---|---|---|
| 6-Carboxy-pyridin-2-ylmethyl | methyl | phenyl | H | H | 2,6-dimethyl-4-aminocarbonyl | H. |

37. A compound of Formula (Ic)

Formula (Ic)

wherein L is O and $R^1$, $R^2$, $R^{3-1}$, $R^{3-2}$, $R^5$, $R^a$, $R^b$, and $R^{41}$ are dependcently selected from the group consisting of:

| $R^1$ | $R^2$ | $R^{3-1}$ | $R^{3-2}$ | $R^5$ | $R^{41}$ | $R^a/R^b$ |
|---|---|---|---|---|---|---|
| 3,4-Dimethoxy-phenylmethyl | benzyloxy methyl | phenyl | H | H | 2,6-dimethyl-4-hydroxy | H |
| Isopropyl | hydroxy methyl | phenyl | H | H | 2,6-dimethyl-4-hydroxy | H |
| Isopropyl | methyl | 4-fluorophenyl | H | H | 2,6-dimethyl-4-hydroxy | H |
| 2-Phenylethyl | methyl | phenyl | H | H | 2,6-dimethyl-4-aminocarbonyl | H |
| Benzyl | methyl | phenyl | H | H | 2,6-dimethyl-4-aminocarbonyl | H |
| Cyclohexyl | methyl | phenyl | H | H | 2,6-dimethyl-4-aminocarbonyl | H |
| Methyl | methyl | phenyl | H | H | 2,6-dimethyl-4-aminocarbonyl | H |
| Methyl | methyl | phenyl | H | H | 2,6-dimethyl-4-(morpholin-4-carbonyl) | H |
| Methyl | methyl | phenyl | H | H | 2,6-dimethyl-4-ethylamino carbonyl | H |
| Methyl | methyl | phenyl | H | H | 2,6-dimethyl-4-methylamino carbonyl | H |
| Methyl | methyl | phenyl | H | H | 4-aminocarbonyl | H |
| Methyl | methyl | phenyl | H | H | 2,6-dimethyl-4-hydroxy | H |
| H | methyl | phenyl | H | H | 2,6-dimethyl-4-hydroxy | H |
| Methyl | methyl | phenyl | H | H | 4-hydroxy | H |
| H | methyl | phenyl | H | H | 4-hydroxy | H |
| Ethyl | methyl | phenyl | H | H | 4-hydroxy | H |
| Ethyl | methyl | phenyl | H | H | 2,6-dimethyl-4- | H |

-continued

Formula (Ic)

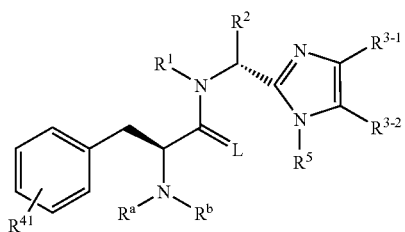

wherein L is O and $R^1$, $R^2$, $R^{3-1}$, $R^{3-2}$, $R^5$, $R^a$, $R^b$, and $R^{41}$ are dependcently selected from the group consisting of:

| $R^1$ | $R^2$ | $R^{3-1}$ | $R^{3-2}$ | $R^5$ | $R^{41}$ | $R^a/R^b$ |
|---|---|---|---|---|---|---|
| Benzyl | methyl | phenyl | H | H | 2,6-dimethyl-4-hydroxy | H |
| Benzyl | methyl | phenyl | H | H | 4-hydroxy | H |
| Isopropyl | methyl | phenyl | H | H | 4-hydroxy | H |
| Isopropyl | methyl | phenyl | H | H | 2,6-dimethyl-4-hydroxy | H |
| 3-Carboxy-phenyl methyl | methyl | 4-chlorophenyl | Me | H | 2,6-dimethyl-4-aminocarbonyl | H |
| 3-Carboxy-phenyl | methyl | 4-chlorophenyl | Me | H | 4-aminocarbonyl | H |
| 3-Carboxy-4-methoxy-phenylmethyl | methyl | 4-chlorophenyl | Me | H | 2,6-dimethyl-4-aminocarbonyl | H |
| 3-Methoxycarbonyl-4-methoxy-phenylmethyl | methyl | phenyl | H | H | 2,6-dimethyl-4-aminocarbonyl | H |
| 3-Methoxycarbonyl-4-methoxy-phenylmethyl | methyl | phenyl | H | H | 4-aminocarbonyl | H |
| 3-Carboxy-4-methoxy-phenylmethyl | methyl | phenyl | H | H | 2,6-dimethyl-4-aminocarbonyl | H |
| 3-Carboxy-4-methoxy-phenylmethyl | methyl | phenyl | H | H | 4-aminocarbonyl | H |
| 3-Carboxy-4-methoxy-phenylmethyl | methyl | 4-chlorophenyl | Me | H | 4-hydroxy | H |
| 6-Methoxy-carbonyl-pyridin-2-yl methyl | methyl | phenyl | H | H | 2,6-dimethyl-4-aminocarbonyl | H | and

| $R^1$ | $R^2$ | $R^{3-1}$ | $R^{3-2}$ | $R^5$ | $R^{41}$ | $R^a/R^b$ |
|---|---|---|---|---|---|---|
| 3-Carboxy-4-methoxy-phenylmethyl | methyl | 4-chlorophenyl | H | H | 4-aminocarbonyl | H. |

38. A compound of Formula (Id)

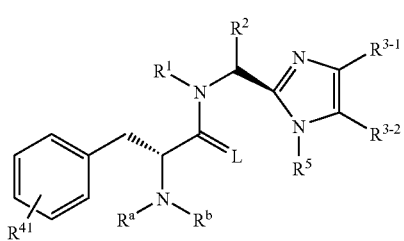
Formula (Id)

wherein L is O and $R^1$, $R^2$, $R^{3-1}$, $R^{3-2}$, $R^5$, $R^a$, $R^b$, and $R^{41}$ are dependently selected from the group consisting of:

| $R^1$ | $R^2$ | $R^{3-1}$ | $R^{3-2}$ | $R^5$ | $R^{41}$ | $R^a/R^b$ |
|---|---|---|---|---|---|---|
| 3-Carboxy-4-methoxyphenyl methyl | methyl | phenyl | H | H | 4-amino-carbonyl | H. |

39. A compound of Formula (Ie)

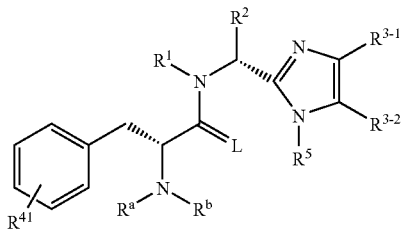
Formula (Ie)

wherein L is O and $R^1$, $R^2$, $R^{3-1}$, $R^{3-2}$, $R^5$, $R^a$, $R^b$, and $R^{41}$ are dependently selected from the group consisting of:

| $R^1$ | $R^2$ | $R^{3-1}$ | $R^{3-2}$ | $R^5$ | $R^{41}$ | $R^a/R^b$ |
|---|---|---|---|---|---|---|
| 3-Methoxycarbonyl-4-methoxy-phenylmethyl | methyl | phenyl | H | H | 4-amino-carbonyl | H |
| and | | | | | | |
| 3-Carboxy-4-methoxy-phenylmethyl | methyl | phenyl | H | H | 4-amino-carbonyl | H. |

40. A compound selected from the group consisting of

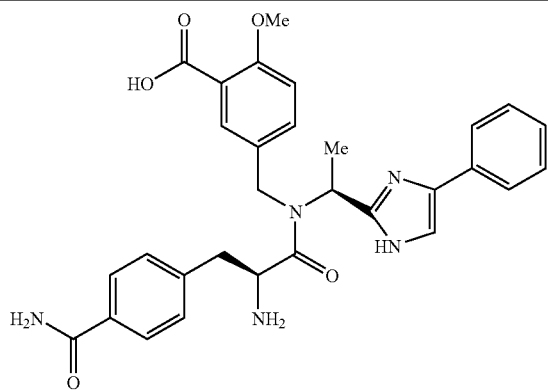

-continued

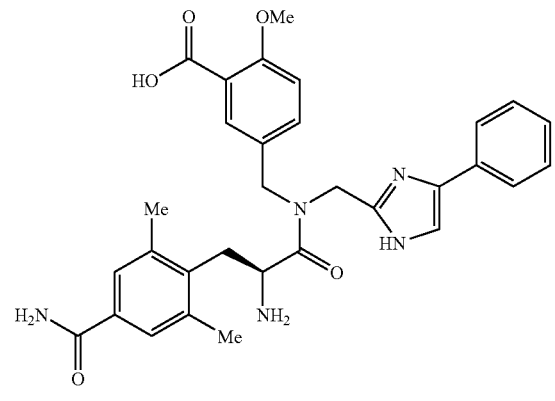

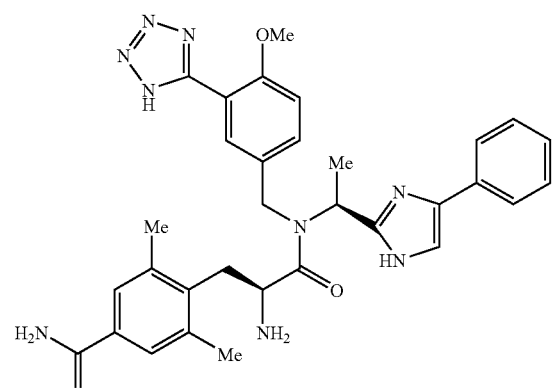

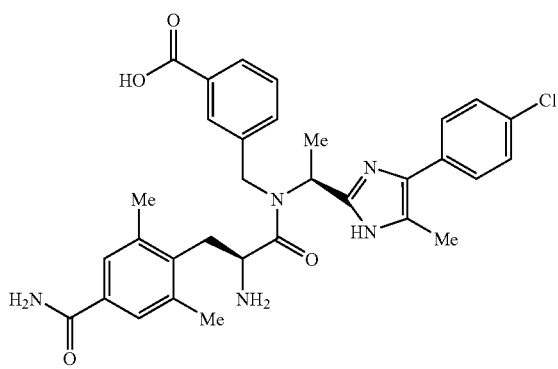

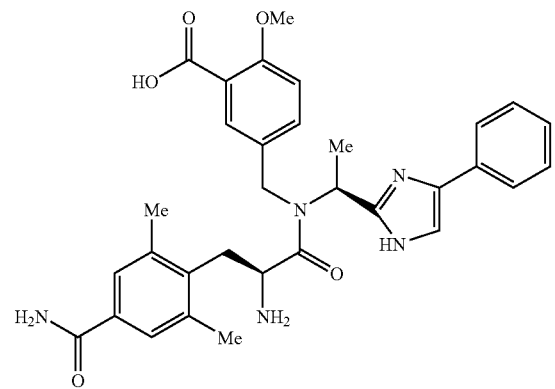

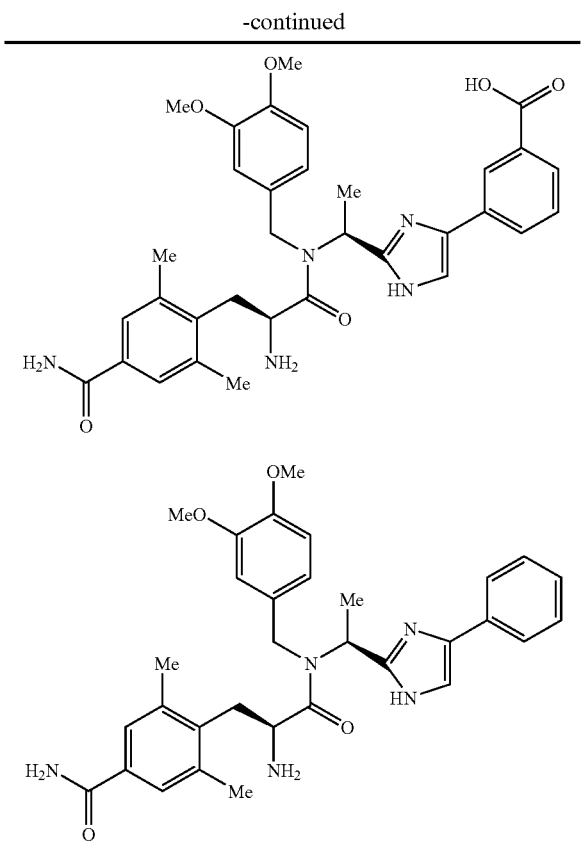

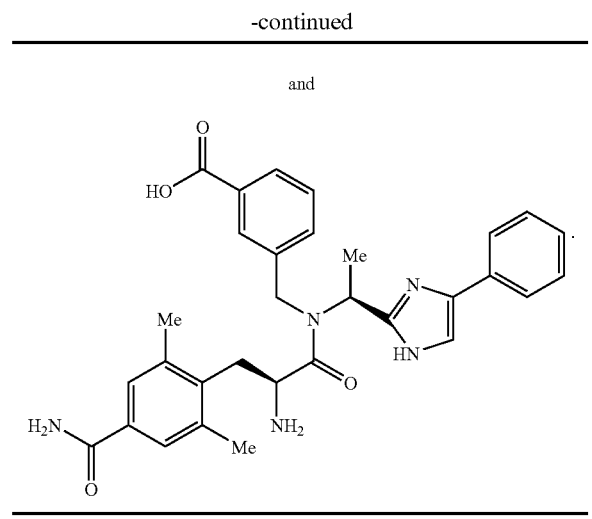

and

41. A composition comprising the compound of claim 1 and a pharmaceutically acceptable carrier.

42. The compound of claim 1 that is the hydrochloride salt of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid dihydrochloride.

43. The composition of claim 41 wherein the compound is the hydrochloride salt of 5-({[2-Amino-3-(4-carbamoyl-2,6-dimethyl-phenyl)-propionyl]-[1-(4-phenyl-1H-imidazol-2-yl)-ethyl]-amino}-methyl)-2-methoxy-benzoic acid.

* * * * *

UNITED STATES PATENT AND TRADEMARK OFFICE
CERTIFICATE OF CORRECTION

| | | |
|---|---|---|
| PATENT NO. | : 7,741,356 B2 | Page 1 of 1 |
| APPLICATION NO. | : 11/079647 | |
| DATED | : June 22, 2010 | |
| INVENTOR(S) | : Breslin et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1107 days.

Signed and Sealed this
Twenty-third Day of September, 2014

Michelle K. Lee
*Deputy Director of the United States Patent and Trademark Office*